US011236085B2

(12) United States Patent
Du et al.

(10) Patent No.: US 11,236,085 B2
(45) Date of Patent: Feb. 1, 2022

(54) PD-1/PD-L1 INHIBITORS

(71) Applicant: Gilead Sciences, Inc., Foster City, CA (US)

(72) Inventors: Zhimin Du, Belmont, CA (US); Michael Graupe, Pacifica, CA (US); Paulo A. Machicao Tello, Oakland, CA (US); Jonathan William Medley, San Mateo, CA (US); Samuel E. Metobo, Newark, CA (US); Eric Q. Parkhill, Union City, CA (US); Barton W. Phillips, San Mateo, CA (US); Scott P. Simonovich, San Francisco, CA (US); Peiyuan Wang, San Mateo, CA (US); Jie Xu, Foster City, CA (US); Christopher A. Ziebenhaus, San Francisco, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 16/660,219

(22) Filed: Oct. 22, 2019

(65) Prior Publication Data
US 2020/0157094 A1 May 21, 2020

Related U.S. Application Data

(60) Provisional application No. 62/750,209, filed on Oct. 24, 2018.

(51) Int. Cl.
*C07D 471/04* (2006.01)
*C07D 217/04* (2006.01)
*C07D 401/12* (2006.01)
*C07D 401/14* (2006.01)
*C07D 413/10* (2006.01)
*C07D 471/08* (2006.01)
*C07D 487/04* (2006.01)
*C07D 495/04* (2006.01)
*C07D 513/04* (2006.01)
*C07K 16/28* (2006.01)
*C07K 16/40* (2006.01)

(52) U.S. Cl.
CPC ......... *C07D 471/04* (2013.01); *C07D 217/04* (2013.01); *C07D 401/12* (2013.01); *C07D 401/14* (2013.01); *C07D 413/10* (2013.01); *C07D 471/08* (2013.01); *C07D 487/04* (2013.01); *C07D 495/04* (2013.01); *C07D 513/04* (2013.01); *C07K 16/2818* (2013.01); *C07K 16/2827* (2013.01); *C07K 16/40* (2013.01)

(58) Field of Classification Search
CPC .. C07D 471/04; C07D 217/04; C07D 401/14; C07D 401/12; C07D 413/10; C07D 487/04; C07D 495/04; C07D 471/08; C07D 513/04

USPC .......................................................... 514/221
See application file for complete search history.

(56) References Cited

U.S. PATENT DOCUMENTS

| | | |
|---|---|---|
| 7,687,522 B2 | 3/2010 | Bellon et al. |
| 7,750,048 B2 | 7/2010 | Kuo et al. |
| 8,273,341 B2 | 9/2012 | Guo et al. |
| 8,541,424 B2 | 9/2013 | Degoey et al. |
| 8,835,451 B2 | 9/2014 | Serrano-Wu et al. |
| 2002/0091116 A1 | 7/2002 | Zhu et al. |
| 2003/0013028 A1 | 1/2003 | Kaoru et al. |
| 2004/0209936 A1 | 10/2004 | Bratton et al. |
| 2004/0235877 A1 | 11/2004 | Natsuki et al. |
| 2006/0019967 A1 | 1/2006 | Wu et al. |
| 2007/0155726 A1 | 7/2007 | Arnaiz et al. |
| 2010/0249175 A1 | 9/2010 | Wilson et al. |
| 2012/0225851 A1 | 6/2012 | Cardone et al. |
| 2012/0189539 A1 | 7/2012 | Wang et al. |
| 2012/0289558 A1 | 11/2012 | Kounnas et al. |
| 2012/0309701 A1 | 12/2012 | Janetka et al. |
| 2013/0023495 A1 | 1/2013 | Meyers et al. |
| 2013/0310379 A1 | 11/2013 | Albrecht et al. |
| 2014/0064053 A1 | 3/2014 | Tsuyama et al. |
| 2014/0073631 A1 | 3/2014 | Shetty |
| 2015/0197538 A1 | 7/2015 | Janetka et al. |
| 2015/0352206 A1 | 12/2015 | Gajewsi et al. |
| 2016/0145304 A1 | 5/2016 | Baumann et al. |
| 2016/0166592 A1 | 6/2016 | Bae et al. |
| 2016/0194307 A1 | 7/2016 | Chupak et al. |
| 2016/0207923 A1 | 7/2016 | Youngman et al. |
| 2017/0088532 A1 | 3/2017 | Cohen et al. |
| 2017/0100414 A1 | 4/2017 | Dunman et al. |
| 2017/0107202 A1 | 4/2017 | Yeung et al. |
| 2017/0107216 A1 | 4/2017 | Wu et al. |
| 2017/0145025 A1 | 5/2017 | Li et al. |
| 2017/0174679 A1 | 6/2017 | Lajkiewicz et al. |
| 2017/0210715 A1 | 7/2017 | Shao et al. |

(Continued)

FOREIGN PATENT DOCUMENTS

| | | |
|---|---|---|
| CN | 104876912 | 9/2015 |
| DE | 10104279 | 8/2002 |

(Continued)

OTHER PUBLICATIONS

U.S. Appl. No. 16/551,550, filed Aug. 26, 2019, Aktoudianakis et al.
Gura, et al. Systems for Identifying New Drugs Are Often Faulty. Science. 1997; 278:1041-1042.
Johnson, et al. Relationships between drug activity in NCI preclinical in vitro and in vivo models and early clinical trials. British Journal of Cancer. 2001; 84:1424-1431.

(Continued)

Primary Examiner — Kahsay Habte
(74) Attorney, Agent, or Firm — Sheppard Mullin Richter & Hampton LLP

(57) ABSTRACT

Compounds and methods of using said compounds singly or in combination with additional agents and compositions of said compounds for the treatment of cancer are disclosed.

28 Claims, No Drawings

(56) References Cited

U.S. PATENT DOCUMENTS

| | | |
|---|---|---|
| 2017/0252432 A1 | 9/2017 | Allen et al. |
| 2017/0266211 A1 | 9/2017 | David et al. |
| 2017/0283462 A1 | 10/2017 | Miller et al. |
| 2017/0283463 A1 | 10/2017 | Miller et al. |
| 2017/0320875 A1 | 11/2017 | Li et al. |
| 2017/0331067 A1 | 11/2017 | Park et al. |
| 2017/0362253 A1 | 12/2017 | Xiao et al. |
| 2018/0008554 A1 | 1/2018 | Lange et al. |
| 2018/0044303 A1 | 2/2018 | Sasikumar et al. |
| 2018/0044304 A1 | 2/2018 | Sasikumar et al. |
| 2018/0044305 A1 | 2/2018 | Sasikumar et al. |
| 2018/0044329 A1 | 2/2018 | Sasikumar et al. |
| 2018/0044350 A1 | 2/2018 | Sasikumar et al. |
| 2018/0057455 A1 | 3/2018 | Yeung et al. |
| 2018/0057486 A1 | 3/2018 | Wu et al. |
| 2018/0065917 A1 | 3/2018 | Webber et al. |
| 2018/0086793 A1 | 3/2018 | Gillman et al. |
| 2018/0273519 A1 | 9/2018 | Wu et al. |
| 2018/0305315 A1 | 10/2018 | Aktoudianakis et al. |
| 2019/0040082 A1 | 2/2019 | Xiao et al. |
| 2019/0062345 A1 | 2/2019 | Xiao et al. |
| 2019/0071439 A1 | 3/2019 | Li et al. |
| 2019/0135745 A1 | 5/2019 | Lange et al. |
| 2019/0144402 A1 | 5/2019 | Sasikumar et al. |
| 2019/0144439 A1 | 5/2019 | Wu et al. |
| 2019/0202824 A1 | 7/2019 | Wu et al. |
| 2019/0270727 A1 | 9/2019 | Aktoudianakis et al. |
| 2019/0282555 A1 | 9/2019 | Lange et al. |
| 2019/0345131 A1 | 11/2019 | Aktoudianakis et al. |
| 2020/0017471 A1 | 1/2020 | Aktoudianakis et al. |
| 2021/0024494 A1 | 1/2021 | Aktoudianakis et al. |

FOREIGN PATENT DOCUMENTS

| | | |
|---|---|---|
| EP | 2002838 | 12/2008 |
| EP | 3363790 | 8/2018 |
| JP | 2001002661 | 1/2001 |
| JP | 2001335476 | 12/2001 |
| JP | 2012036168 | 2/2012 |
| UY | 35733 A | 4/2016 |
| WO | WO 97/31910 | 9/1997 |
| WO | WO 2001/019798 | 3/2001 |
| WO | WO 2001/056989 | 8/2001 |
| WO | WO 2002/000647 | 1/2002 |
| WO | WO 2002/020436 | 3/2002 |
| WO | WO 2002/051775 | 7/2002 |
| WO | WO 2004/052848 | 6/2004 |
| WO | WO 2004/054582 | 7/2004 |
| WO | WO 2004/084824 | 10/2004 |
| WO | WO 2005/044797 | 5/2005 |
| WO | WO 2005/051890 | 6/2005 |
| WO | WO 2005/086808 | 9/2005 |
| WO | WO 2005/095338 | 10/2005 |
| WO | WO 2006/011615 | 2/2006 |
| WO | WO 2006/038738 | 4/2006 |
| WO | WO 2006/052566 | 5/2006 |
| WO | WO 2006/083612 | 8/2006 |
| WO | WO 2006/083781 | 8/2006 |
| WO | WO 2006/091394 | 8/2006 |
| WO | WO 2006/123257 | 11/2006 |
| WO | WO 2006/127503 | 11/2006 |
| WO | WO 2007/013689 | 2/2007 |
| WO | WO 2007/033002 | 3/2007 |
| WO | WO 2007/047591 | 4/2007 |
| WO | WO 2007/049050 | 5/2007 |
| WO | WO 2007/052466 | 5/2007 |
| WO | WO 2007/096142 | 8/2007 |
| WO | WO 2007/104560 | 9/2007 |
| WO | WO 2007/106469 | 9/2007 |
| WO | WO 2007/109376 | 9/2007 |
| WO | WO 2007/123225 | 11/2007 |
| WO | WO 2007/128460 | 11/2007 |
| WO | WO 2007/131619 | 11/2007 |
| WO | WO 2007/131620 | 11/2007 |
| WO | WO 2007/131621 | 11/2007 |
| WO | WO 2007/131622 | 11/2007 |
| WO | WO 2007/132307 | 11/2007 |
| WO | WO 2007/136572 | 11/2007 |
| WO | WO 2008/001931 | 1/2008 |
| WO | WO 2008/014236 | 1/2008 |
| WO | WO 2008/021936 | 2/2008 |
| WO | WO 2008/030520 | 3/2008 |
| WO | WO 2008/037266 | 4/2008 |
| WO | WO 2008/054674 | 5/2008 |
| WO | WO 2008/054675 | 5/2008 |
| WO | WO 2008/063768 | 5/2008 |
| WO | WO 2008/065409 | 6/2008 |
| WO | WO 2008/066097 | 6/2008 |
| WO | WO 2008/067644 | 6/2008 |
| WO | WO 2008/073865 | 6/2008 |
| WO | WO 2008/079965 | 7/2008 |
| WO | WO 2008/083027 | 7/2008 |
| WO | WO 2008/090327 | 7/2008 |
| WO | WO 2008/090356 | 7/2008 |
| WO | WO 2008/106202 | 9/2008 |
| WO | WO 2008/130514 | 10/2008 |
| WO | WO 2008/139987 | 11/2008 |
| WO | WO 2008/144925 | 12/2008 |
| WO | WO 2008/147852 | 12/2008 |
| WO | WO 2008/156656 | 12/2008 |
| WO | WO 2009/017822 | 2/2009 |
| WO | WO 2009/025983 | 2/2009 |
| WO | WO 2009/038204 | 3/2009 |
| WO | WO 2009/039942 | 4/2009 |
| WO | WO 2009/039943 | 4/2009 |
| WO | WO 2009/047798 | 4/2009 |
| WO | WO 2009/048527 | 4/2009 |
| WO | WO 2009/054390 | 4/2009 |
| WO | WO 2009/054468 | 4/2009 |
| WO | WO 2009/054479 | 4/2009 |
| WO | WO 2009/058237 | 5/2009 |
| WO | WO 2009/102568 | 8/2009 |
| WO | WO 2009/102633 | 8/2009 |
| WO | WO 2009/111056 | 9/2009 |
| WO | WO 2009/112445 | 9/2009 |
| WO | WO 2010/012650 | 2/2010 |
| WO | WO 2010/017870 | 2/2010 |
| WO | WO 2010/039238 | 4/2010 |
| WO | WO 2010/045258 | 4/2010 |
| WO | WO 2010/066682 | 6/2010 |
| WO | WO 2010/082563 | 7/2010 |
| WO | WO 2010/085522 | 7/2010 |
| WO | WO 2010/085525 | 7/2010 |
| WO | WO 2010/085528 | 7/2010 |
| WO | WO 2010/091176 | 8/2010 |
| WO | WO 2010/091413 | 8/2010 |
| WO | WO 2010/096462 | 8/2010 |
| WO | WO 2010/099527 | 9/2010 |
| WO | WO 2010/111534 | 9/2010 |
| WO | WO 2010/123016 | 10/2010 |
| WO | WO 2010/123017 | 10/2010 |
| WO | WO 2010/132601 | 11/2010 |
| WO | WO 2010/143733 | 12/2010 |
| WO | WO 2010/144646 | 12/2010 |
| WO | WO 2011/008709 | 1/2011 |
| WO | WO 2011/024001 | 3/2011 |
| WO | WO 2011/031934 | 3/2011 |
| WO | WO 2011/031965 | 3/2011 |
| WO | WO 2011/044073 | 4/2011 |
| WO | WO 2011/046851 | 4/2011 |
| WO | WO 2011/049825 | 4/2011 |
| WO | WO 2011/052756 | 5/2011 |
| WO | WO 2011/066183 | 6/2011 |
| WO | WO 2011/066241 | 6/2011 |
| WO | WO 2011/073376 | 6/2011 |
| WO | WO 2011/076732 | 6/2011 |
| WO | WO 2011/076734 | 6/2011 |
| WO | WO 2011/078371 | 6/2011 |
| WO | WO 2011/080755 | 7/2011 |
| WO | WO 2011/082400 | 7/2011 |
| WO | WO 2011/092284 | 8/2011 |
| WO | WO 2011/119858 | 9/2011 |
| WO | WO 2011/119870 | 9/2011 |
| WO | WO 2011/138665 | 11/2011 |

(56) References Cited

FOREIGN PATENT DOCUMENTS

| | | |
|---|---|---|
| WO | WO 2011/143208 | 11/2011 |
| WO | WO 2011/143466 | 11/2011 |
| WO | WO 2011/151436 | 12/2011 |
| WO | WO 2011/161030 | 12/2011 |
| WO | WO 2012/004269 | 1/2012 |
| WO | WO 2012/004270 | 1/2012 |
| WO | WO 2012/010413 | 1/2012 |
| WO | WO 2012/011124 | 1/2012 |
| WO | WO 2012/012627 | 1/2012 |
| WO | WO 2012/036168 | 3/2012 |
| WO | WO 2012/046869 | 4/2012 |
| WO | WO 2012/050918 | 4/2012 |
| WO | WO 2012/065904 | 5/2012 |
| WO | WO 2012/068234 | 5/2012 |
| WO | WO 2012/072691 | 6/2012 |
| WO | WO 2012/078802 | 6/2012 |
| WO | WO 2012/083043 | 6/2012 |
| WO | WO 2012/083048 | 6/2012 |
| WO | WO 2012/083053 | 6/2012 |
| WO | WO 2012/083059 | 6/2012 |
| WO | WO 2012/083061 | 6/2012 |
| WO | WO 2012/098033 | 7/2012 |
| WO | WO 2012/111849 | 8/2012 |
| WO | WO 2012/129562 | 9/2012 |
| WO | WO 2012/136221 | 10/2012 |
| WO | WO 2012/147518 | 11/2012 |
| WO | WO 2012/154608 | 11/2012 |
| WO | WO 2013/009259 | 1/2013 |
| WO | WO 2013/025424 | 2/2013 |
| WO | WO 2013/057743 | 4/2013 |
| WO | WO 2013/102626 | 7/2013 |
| WO | WO 2013/104257 | 7/2013 |
| WO | WO 2013/106520 | 7/2013 |
| WO | WO 2013/109521 | 7/2013 |
| WO | WO 2013/122028 | 8/2013 |
| WO | WO 2013/122029 | 8/2013 |
| WO | WO 2013/128378 | 9/2013 |
| WO | WO 2013/144097 | 10/2013 |
| WO | WO 2013/154163 | 10/2013 |
| WO | WO 2013/164292 | 11/2013 |
| WO | WO 2013/170113 | 11/2013 |
| WO | WO 2013/170115 | 11/2013 |
| WO | WO 2013/178575 | 12/2013 |
| WO | WO 2014/014129 | 1/2014 |
| WO | WO 2014/014530 | 1/2014 |
| WO | WO 2014/019186 | 2/2014 |
| WO | WO 2014/035827 | 3/2014 |
| WO | WO 2014/073904 | 5/2014 |
| WO | WO 2014/078608 | 5/2014 |
| WO | WO 2014/078609 | 5/2014 |
| WO | WO 2014/078610 | 5/2014 |
| WO | WO 2014/081689 | 5/2014 |
| WO | WO 2014/082918 | 6/2014 |
| WO | WO 2014/086712 | 6/2014 |
| WO | WO 2014/122067 | 8/2014 |
| WO | WO 2014/130608 | 8/2014 |
| WO | WO 2014/133361 | 9/2014 |
| WO | WO 2014/134243 | 9/2014 |
| WO | WO 2014/145817 | 9/2014 |
| WO | WO 2014/146604 | 9/2014 |
| WO | WO 2014/169817 | 10/2014 |
| WO | WO 2014/170842 | 10/2014 |
| WO | WO 2014/171762 | 10/2014 |
| WO | WO 2014/187343 | 11/2014 |
| WO | WO 2015/000412 | 1/2015 |
| WO | WO 2015/010655 | 1/2015 |
| WO | WO 2015/020184 | 2/2015 |
| WO | WO 2015/024448 | 2/2015 |
| WO | WO 2015/024526 | 2/2015 |
| WO | WO 2015/028960 | 3/2015 |
| WO | WO 2015/032328 | 3/2015 |
| WO | WO 2015/034820 | 3/2015 |
| WO | WO 2015/044073 | 4/2015 |
| WO | WO 2015/051496 | 4/2015 |
| WO | WO 2015/062486 | 5/2015 |
| WO | WO 2015/065621 | 5/2015 |
| WO | WO 2015/073342 | 5/2015 |
| WO | WO 2015/076800 | 5/2015 |
| WO | WO 2015/078802 | 6/2015 |
| WO | WO 2015/078949 | 6/2015 |
| WO | WO 2015/084692 | 6/2015 |
| WO | WO 2015/088868 | 6/2015 |
| WO | WO 2015/089809 | 6/2015 |
| WO | WO 2015/097713 | 7/2015 |
| WO | WO 2015/105779 | 7/2015 |
| WO | WO 2015/105786 | 7/2015 |
| WO | WO 2018/121560 | 7/2015 |
| WO | WO 2015/119899 | 8/2015 |
| WO | WO 2015/140717 | 9/2015 |
| WO | WO 2015/150097 | 10/2015 |
| WO | WO 2015/160641 | 10/2015 |
| WO | WO 2015/171722 | 11/2015 |
| WO | WO 2015/171733 | 11/2015 |
| WO | WO 2015/171757 | 11/2015 |
| WO | WO 2015/176267 | 11/2015 |
| WO | WO 2015/198045 | 12/2015 |
| WO | WO 2015/198046 | 12/2015 |
| WO | WO 2016/007714 | 1/2016 |
| WO | WO 2016/019587 | 2/2016 |
| WO | WO 2016/022446 | 2/2016 |
| WO | WO 2016/022448 | 2/2016 |
| WO | WO 2016/022742 | 2/2016 |
| WO | WO 2016/026772 | 2/2016 |
| WO | WO 2016/032120 | 3/2016 |
| WO | WO 2016/039749 | 3/2016 |
| WO | WO 2016/041511 | 3/2016 |
| WO | WO 2016/060517 | 4/2016 |
| WO | WO 2016/060963 | 4/2016 |
| WO | WO 2016/071283 | 5/2016 |
| WO | WO 2016/071293 | 5/2016 |
| WO | WO 2016/073774 | 5/2016 |
| WO | WO 2016/110821 | 7/2016 |
| WO | WO 2016/128908 | 8/2016 |
| WO | WO 2016/142833 | 9/2016 |
| WO | WO 2016/142835 | 9/2016 |
| WO | WO 2016/142852 | 9/2016 |
| WO | WO 2016/142886 | 9/2016 |
| WO | WO 2016/142894 | 9/2016 |
| WO | WO 2016/195776 | 12/2016 |
| WO | WO 2016/197987 | 12/2016 |
| WO | WO 2017/011279 | 1/2017 |
| WO | WO 2017/025368 | 2/2017 |
| WO | WO 2017/027309 | 2/2017 |
| WO | WO 2017/027310 | 2/2017 |
| WO | WO 2017/027312 | 2/2017 |
| WO | WO 2017/031392 | 2/2017 |
| WO | WO 2017/042121 | 3/2017 |
| WO | WO 2017/066227 | 4/2017 |
| WO | WO 2017/070089 | 4/2017 |
| WO | WO 2017/079669 | 5/2017 |
| WO | WO 2017/087777 | 5/2017 |
| WO | WO 2017/099034 | 6/2017 |
| WO | WO 2017/106634 | 6/2017 |
| WO | WO 2017/107979 | 6/2017 |
| WO | WO 2017/112730 | 6/2017 |
| WO | WO 2017/118762 | 7/2017 |
| WO | WO 2017/143220 | 8/2017 |
| WO | WO 2017/151830 | 9/2017 |
| WO | WO 2017/162284 | 9/2017 |
| WO | WO 2017/172505 | 10/2017 |
| WO | WO 2017/176608 | 10/2017 |
| WO | WO 2017/180457 | 10/2017 |
| WO | WO 2017/180571 | 10/2017 |
| WO | WO 2017/180769 | 10/2017 |
| WO | WO 2017/192961 | 11/2017 |
| WO | WO 2017/201683 | 11/2017 |
| WO | WO 2017/202273 | 11/2017 |
| WO | WO 2017/202274 | 11/2017 |
| WO | WO 2017/202275 | 11/2017 |
| WO | WO 2017/202276 | 11/2017 |
| WO | WO 2017/202744 | 11/2017 |
| WO | WO 2017/205464 | 11/2017 |
| WO | WO 2017/222976 | 12/2017 |
| WO | WO 2018/005374 | 1/2018 |

(56) References Cited

FOREIGN PATENT DOCUMENTS

| | | |
|---|---|---|
| WO | WO 2018/009505 | 1/2018 |
| WO | WO 2018/026971 | 2/2018 |
| WO | WO 2018/029150 | 2/2018 |
| WO | WO 2018/044783 | 3/2018 |
| WO | WO 2018/044963 | 3/2018 |
| WO | WO 2018/045142 | 3/2018 |
| WO | WO 2018/051254 | 3/2018 |
| WO | WO 2018/051255 | 3/2018 |
| WO | WO 2018/053302 | 3/2018 |
| WO | WO 2018/077699 | 5/2018 |
| WO | WO 2018/081047 | 5/2018 |
| WO | WO 2018/095877 | 5/2018 |
| WO | WO 2018/106518 | 6/2018 |
| WO | WO 2018/111012 | 6/2018 |
| WO | WO 2018/118664 | 6/2018 |
| WO | WO 2018/118670 | 6/2018 |
| WO | WO 2018/118848 | 6/2018 |
| WO | WO 2018/119221 | 6/2018 |
| WO | WO 2018/119224 | 6/2018 |
| WO | WO 2018/119236 | 6/2018 |
| WO | WO 2018/119263 | 6/2018 |
| WO | WO 2018/119266 | 6/2018 |
| WO | WO 2018/119286 | 6/2018 |
| WO | WO 2018/138026 | 8/2018 |
| WO | WO 2018/138027 | 8/2018 |
| WO | WO 2018/138028 | 8/2018 |
| WO | WO 2018/138029 | 8/2018 |
| WO | WO 2018/138030 | 8/2018 |
| WO | WO 2018/146008 | 8/2018 |
| WO | WO 2018/172727 | 9/2018 |
| WO | WO 2018/181847 | 10/2018 |
| WO | WO 2018/182050 | 10/2018 |
| WO | WO 2018/183171 | 10/2018 |
| WO | WO 2018/195321 | 10/2018 |
| WO | WO 2018/196768 | 11/2018 |
| WO | WO 2019/008156 | 1/2019 |
| WO | WO 2019/023575 | 1/2019 |
| WO | WO 2019/032547 | 2/2019 |
| WO | WO 2019/034172 | 2/2019 |
| WO | WO 2019/059411 | 3/2019 |
| WO | WO 2019/070643 | 4/2019 |
| WO | WO 2019/074241 | 4/2019 |
| WO | WO 2019/076343 | 4/2019 |
| WO | WO 2019/128918 | 7/2019 |
| WO | WO 2019/160882 | 8/2019 |
| WO | WO 2019/165043 | 8/2019 |
| WO | WO 2019/174533 | 9/2019 |
| WO | WO 2019/175897 | 9/2019 |
| WO | WO 2019/191624 | 10/2019 |
| WO | WO 2019/191707 | 10/2019 |
| WO | WO 2019/192506 | 10/2019 |
| WO | WO 2019/204609 | 10/2019 |
| WO | WO 2019/217821 | 11/2019 |
| WO | WO 2020/011246 | 1/2020 |
| WO | WO 2020/014643 | 1/2020 |

OTHER PUBLICATIONS

Tryfon Zarganes-Tzitzikas et al., "Inhibitors of programmed cell death 1 (PD-1), a patent review, 2010-2015", expert Opinion on Therapeutic Patents, vol. 26, No. 9, Sep. 19, 2016, pp. 973-977, XP055394015.

U.S. Appl. No. 16/840,217, filed Apr. 3, 2020, Aktoudianakis et al.

U.S. Appl. No. 16/891,880, filed Jun. 3, 2020, Aktoudianakis et al.

International Search Report and Written Opinion for International Application No. PCT/US2018/028382 dated Sep. 11, 2018. (17 pages).

International Search Report and Written Opinion for International Application No. PCT/US2019/017721 dated Apr. 8, 2019. (15 pages).

International Search Report and Written Opinion for International Application No. PCT/US2019/028129 dated Jul. 22, 2019. (13 pages).

International Search Report and Written Opinion for International Application No. PCT/US2019/041657 dated Sep. 12, 2019. (12 pages).

International Search Report and Written Opinion for International Application No. PCT/US2019/057407 dated Feb. 18, 2020. (11 pages).

Office Action dated Aug. 4, 2020 for Taiwan Application No. 108138382. 9 pages.

Sham, K-C. et al.: Acid-induced formation of hydrogen-bonded double helix based on chiral polyphenyl-bridged bis(2,2'-bipyridine) ligands. RSC Advances, vol. 4, pp. 14513-14526, 2014.

Australian Examination Report dated Sep. 29, 2021 for AU 2019366355. 4 pages.

PD-1/PD-L1 INHIBITORS

CROSS REFERENCE TO RELATED APPLICATION

This patent application claims the benefit of priority of U.S. Provisional Patent Application 62/750,209 filed Oct. 24, 2018. The contents of this application is incorporated herein by reference in its entirety.

FIELD

The present disclosure generally relates to compounds useful as inhibitors of PD-1, PD-L1 or the PD-1/PD-L1 interaction. Provided herein are compounds, compositions comprising such compounds, and methods for their use.

BACKGROUND

Programmed death-1 (CD279) is a receptor on T cells that has been shown to suppress activating signals from the T cell receptor when bound by either of its ligands, Programmed death-ligand 1 (PD-L1, CD274, B7-H1) or PD-L2 (CD273, B7-DC). When PD-1 expressing T cells contact cells expressing its ligands, functional activities in response to antigenic stimuli, including proliferation, cytokine secretion, and cytotoxicity are reduced. PD-1/PD-Ligand interactions down regulate immune responses during resolution of an infection or tumor, or during the development of self-tolerance. Chronic antigen stimulation, such as that which occurs during tumor disease or chronic infections, results in T cells that express elevated levels of PD-1 and are dysfunctional with respect to activity towards the chronic antigen. This is termed "T cell exhaustion." B cells also display PD-1/PD-ligand suppression and "exhaustion."

Blockade of the PD-1/PD-L1 ligation using antibodies to PD-L1 has been shown to restore and augment T cell activation in many systems. Patients with advanced cancer benefit from therapy with a monoclonal antibody to PD-L1. Preclinical animal models of tumors and chronic infections have shown that blockade of the PD-1/PD-L1 pathway by monoclonal antibodies can enhance the immune response and result in tumor rejection or control of infection. Antitumor immunotherapy via PD-1/PD-L1 blockade may augment therapeutic immune response to a number of histologically distinct tumors.

Interference with the PD-1/PD-L1 interaction has also shown enhanced T cell activity in chronic infection systems. Chronic lymphocytic chorio meningitis virus infection of mice also exhibits improved virus clearance and restored immunity with blockade of PD-L1. Humanized mice infected with HIV-1 show enhanced protection against viremia and viral depletion of CD4+ T cells. Blockade of PD-1/PD-L1 through monoclonal antibodies to PD-L1 can restore in vitro antigen-specific functionality to T cells from H1V patients, HCV patients or HBV patients.

Accordingly, agents that block PD-1, PD-L1 and/or the PD-1/PD-L1 interaction are desired. Small molecule agents that block or inhibit PD-1, PD-L1 and/or the PD-1/PD-L1 interaction are particularly desired. Applicants have discovered small molecule compounds that have activity as inhibitors of PD-1, PD-L1 or inhibitors of the interaction of PD-1 with PD-L1, and thus may be useful for treating patients having cancer.

SUMMARY

The present disclosure provides a compound of Formula (X):

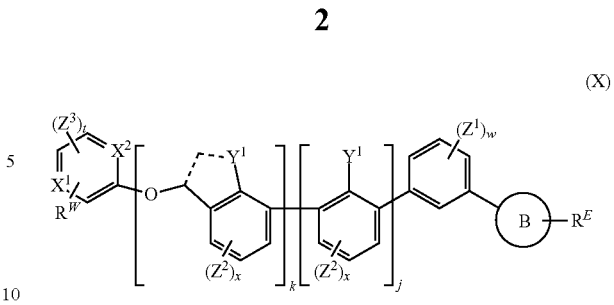

(X)

or a pharmaceutically acceptable salt, stereoisomer, mixture of stereoisomers, solvate, or tautomer thereof, wherein:

i) k is 1 and j is 0, and $Y^1$ is O, NH or $CH_2$ and the dashed lines ( --- ) are single bonds, or $Y^1$ is halo or $—C_{1-6}$ alkyl and the dashed lines ( --- ) are absent; or ii) k is 0 and j is 1, and $Y^1$ is halo or $—C_{1-6}$ alkyl;

$X^1$ is N, CH or $CZ^3$;

$X^2$ is N, CH or $CZ^3$;

ring B is a 9-, 10- or 11-membered fused bicyclic heterocyclyl or heteroaryl ring of the formula:

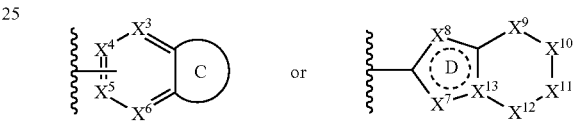

wherein $X^3$, $X^4$, $X^5$ and $X^6$ are each independently N or CH;

$X^7$ and $X^8$ are each independently S, N, NH, CH or $CH_2$;

$X^9$, $X^{10}$, $X^{11}$ and $X^{12}$ are each independently O, S, NH or $CH_2$;

$X^{13}$ is N or C;

ring C is cycloalkyl, heterocyclyl, aryl or heteroaryl; and ring D is heteroaryl;

w is 0, 1 or 2;

each $Z^1$ is independently halo, $—OR^a$, $—NO_2$, cyano, $—NR^aR^b$, $—N_3$, $—S(O)_2R^a$, $—C_{1-6}$ alkyl, $—C_{1-6}$ haloalkyl, $—C_{2-6}$ alkenyl, $—C_{2-6}$ alkynyl, $—O—C_{1-6}$ alkyl, $—O—C_{1-6}$ haloalkyl, $—C_{3-8}$ cycloalkyl, or $—C_{1-6}$ alkyl$C_{3-8}$ cycloalkyl; and wherein each alkyl, alkenyl, alkynyl, and cycloalkyl is optionally substituted with 1 to 4 groups independently selected from oxo, $—NO_2$, $—N_3$, $—OR^a$, halo, and cyano;

x is 0, 1 or 2;

each $Z^2$ is independently halo, $—OR^a$, $—NO_2$, cyano, $—NR^aR^b$, $—N_3$, $—S(O)_2R^a$, $—C_{1-6}$ alkyl, $—C_{1-6}$ haloalkyl, $—C_{2-6}$ alkenyl, $—C_{2-6}$ alkynyl, $—O—C_{1-6}$ alkyl, $—O—C_{1-6}$ haloalkyl, $—C_{3-8}$ cycloalkyl, or $—C_{1-6}$ alkyl$C_{3-8}$ cycloalkyl; and wherein each alkyl, alkenyl, alkynyl, and cycloalkyl is optionally substituted with 1 to 4 groups independently selected from oxo, $—NO_2$, $—N_3$, $—OR^a$, halo, and cyano;

t is 0, 1 or 2;

each $Z^3$ is independently halo, $—OR^a$, $—N_3$, $—NO_2$, cyano, $—NR^1R^2$, $—S(O)_2R^a$, $—S(O)_2NR^aR^b$, $—NR^aS(O)_2R^a$, $—NR^aC(O)R^a$, $—C(O)R^a$, $—C(O)OR^a$, $—C(O)NR^aR^b$, $—NR^aC(O)OR^a$, $—NR^aC(O)NR^1R^2$, $—OC(O)NR^aR^b$, $—NR^aS(O)_2NR^aR^b$, $—C(O)NR^aS(O)_2NR^aR^b$, $—C_{1-6}$ alkyl, $—C_{2-6}$ alkenyl, $—C_{2-6}$ alkynyl, $—O—C_{1-6}$ alkyl, $—C_{1-6}$ cyanoalkyl, $—C_{1-6}$ haloalkyl, $—O—C_{1-6}$ cyanoalkyl, —O—$C_{1-6}$ haloalkyl, —$C_{3-8}$ cycloalkyl, —$C_{1-6}$ alkyl$C_{3-8}$ cycloalkyl, aryl, heteroaryl, heterocyclyl, and $R^N$; and wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —O—$C_{1-6}$cyanoalkyl, —$C(O)NR^aR^b$, —$NR^aC(O)R^a$, —$NR^aC(O)OR^a$, —$S(O)_2R^a$, —$NR^aS(O)_2R^b$, —$SO_2NR^aR^b$, —$NR^aS(O)_2NR^aR^b$, —$C(O)NR^aS(O)_2NR^aR^b$ and —$C_{3-8}$ cycloalkyl;

$R^N$ is independently —$C_{1-6}$ alkyl$NR^1R^2$, —$OC_{1-6}$ alkyl$NR^1R^2$, —$C_{1-6}$ alkyl-O—$C_{1-6}$ alkyl$NR^1R^2$, —$NR^aC_{1-6}$ alkyl$NR^1R^2$, —$C_{1-6}$ alkyl$C(O)NR^1R^2$, —O—$C_{1-6}$ alkyl$C(O)NR^1R^2$, —O—$C_{1-6}$ alkyl$C(O)OR^1$, —$SC_{1-6}$ alkyl$NR^1R^2$, —$C_{1-6}$ alkyl$OR^a$, or

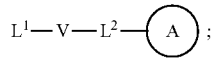;

wherein:
$L^1$ is independently a bond, —O—, —$NR^a$—, —S—, —S(O)—, or —$S(O)_2$—;
V is independently selected from a bond, $C_{1-6}$ alkyl, $C_{2-6}$ alkenyl, and $C_{2-6}$ alkynyl;
wherein each alkyl, alkenyl, or alkynyl is optionally independently substituted with —$OR^a$, halo, cyano, —$NR^aR^b$ or —$C_{3-8}$ cycloalkyl;
$L^2$ is independently a bond, —O—, —$NR^a$—, —S—, —S(O)—, or —$S(O)_2$—;
ring A is independently cycloalkyl, aryl, heteroaryl, or heterocyclyl;
wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$ alkenyl, —$C_{2-6}$ alkynyl, —O—$C_{1-6}$ haloalkyl, —$NR^aR^b$, —$C(O)R^a$, —$C(O)OR^a$, —O—$C_{1-6}$ cyanoalkyl, —$C(O)NR^aR^b$, —$NR^aC(O)R^a$, —$NR^aC(O)OR^a$, —$NR^aC(O)OR^a$, —$C(O)N(R^a)OR^b$, —$S(O)_2R^a$, —$S(O)_2NR^aR^b$, —$NR^aS(O)_2R^b$, —$NR^aS(O)_2NR^aR^b$, —$C(O)NR^aS(O)_2NR^aR^b$, —$C_{3-8}$ cycloalkyl, and —$C_{1-6}$ alkyl$C_{3-8}$ cycloalkyl; and
wherein the alkyl, alkenyl, or alkynyl group is optionally independently substituted with —$OR^a$, halo, cyano, —$NR^aR^b$ or —$C_{3-8}$ cycloalkyl;

$R^E$ is hydrogen, halo, —OH, —$NR^1C(O)NR^1R^2$, —$C_{1-6}$ alkyl$OC(O)NR^1R^2$, —$C_{1-6}$ alkyl$NR^1C(O)R^2$, —CN, —$C_{1-9}$ alkyl, —$C_{2-6}$ alkenyl, —$C_{2-6}$ alkynyl, —$C_{1-8}$ haloalkyl, $C_{1-8}$ alkoxy or $C_{3-15}$ cycloalkyl;

$R^W$ is —$NR^1R^2$, —$C_{1-6}$ alkyl$NR^1R^2$, —O—$C_{1-6}$ alkyl$NR^1R^2$, —$C_{1-6}$ alkyl-O—$C_{1-6}$ alkyl$NR^1R^2$, —$NR^a$—$C_{1-6}$ alkyl$NR^1R^2$, —$C_{1-6}$ alkyl$N^+R^1R^2R^3$, —S—$C_{1-6}$ alkyl$NR^1R^2$, —$C(O)NR^1R^2$, —$S(O)_2R^a$, —$(CH_2)_uS(O)_2NR^1R^2$, —$(CH_2)_uNR^aS(O)_2NR^aR^b$, —$S(O)_2NR^aC_{1-6}$ alkyl$NR^1R^2$, —$NR^aS(O)_2C_{1-6}$ alkyl$NR^1R^2$, —$(CH_2)_uC(O)NR^aS(O)_2NR^aR^b$, —$(CH_2)_uN^+R^1R^2O^-$, —$(CH_2)_uP^+R^bR^cR^d$, —$(CH_2)_uP^+R^cR^dO^-$, —$(CH_2)_uP^+O[NR^aR^b][NR^cR^d]$, —$(CH_2)_uNR^cP(O)(OR^c)_2$, —$(CH_2)_uCH_2OP(O)(OR^c)(OR^d)$, —$(CH_2)_uOP(O)(OR^c)(OR^d)$, —$(CH_2)_uOP(O)NR^aR^b)(OR^a)$, or

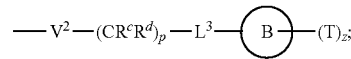;

wherein:
$V^2$ is independently a bond, —O—, —$NR^a$—, —S—, —SO—, —$SO_2$—, —$C(O)NR^a$—, —$NR^aC(O)$—, —$S(O)_2NR^1$—, or —$NR^aS(O)_2$—;
$L^3$ is independently a bond, —O—, —$NR^a$—, —S—, —SO—, —$SO_2$—, —$C(O)NR^a$—, —$NR^aC(O)$—, —$S(O)_2NR^1$—, or —$NR^aS(O)_2$—;
ring B is independently cycloalkyl, aryl, heteroaryl, or heterocyclyl;
T is independently hydrogen, —$OR^a$, —$(CH_2)_qNR^1R^2$, —$(CH_2)_qNR^aC(O)R^e$, or —$(CH_2)_qC(O)R^e$;
p is independently 0, 1, 2, 3, 4, or 5;
q is independently 0, 1, 2, 3, 4, or 5;
u is 0, 1, 2, 3, or 4;
z is 0, 1, 2, or 3; and
wherein the alkyl, cycloalkyl, aryl, heteroaryl, or heterocyclyl of $R^E$ or $R^W$ is optionally substituted with 1 to 3 substituents independently selected from the group consisting of —$NR^aR^b$, halo, cyano, oxo, —$OR^a$, —$C_{1-6}$ alkyl, —$C_{1-6}$ haloalkyl, —$C_{1-6}$ cyanoalkyl, —$C_{1-6}$ alkyl$NR^aR^b$, —$C_{1-6}$ hydroxyalkyl, —$C_{3-8}$ cycloalkyl, and —$C_{1-3}$ alkyl$C_{3-8}$cycloalkyl;
provided that at least one of $V^2$, $L^3$, ring B and T contains a nitrogen atom;

each $R^1$ is independently selected from hydrogen, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{1-6}$ alkyl$C(O)OR^a$, —$C_{2-6}$ alkenyl$C(O)OR^a$, —$S(O)_2R^a$, —$S(O)_2NR^aR^b$, —$C(O)NR^aS(O)_2R^a$, and —$C_{1-6}$ alkyl$C_{3-8}$cycloalkyl;

wherein each alkyl, alkenyl, cycloalkyl, aryl, heteroaryl, or heterocyclyl is optionally substituted with 1 to 4 groups independently selected from —$OR^a$, cyano, halo, $C_{1-6}$ alkyl, —$C_{1-6}$ alkyl$OR^a$, —$C_{1-6}$ cyanoalkyl, —$C_{1-6}$ haloalkyl, $C_{3-8}$ cycloalkyl, —$C_{1-3}$ alkyl$C_{3-8}$cycloalkyl, —$C(O)R^a$, —$C_{1-6}$ alkyl$C(O)R^a$, —$C(O)OR^a$, —$C_{1-6}$ alkyl$C(O)OR^a$, —$NR^aR^b$, —$OC(O)NR^aR^b$, $NR^aC(O)OR^b$, —$C_{1-6}$ alkyl$NR^aR^b$, —$C(O)NR^aR^b$, —$C_{1-6}$ alkyl$C(O)NR^aR^b$, —$S(O)_2R^a$, —$C_{1-6}$ alkyl$S(O)_2R^a$, —$S(O)_2NR^aR^b$, —$C_{1-6}$ alkyl$S(O)_2NR^aR^b$, —$C(O)NR^aS(O)_2R^b$, —$C_{1-6}$ alkyl$C(O)NR^aS(O)_2R^b$, —$NR^aC(O)R^b$, and —$C_{1-6}$ alkyl$NR^aC(O)R^b$;

each $R^2$ is independently selected from hydrogen, —$C_{1-6}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{2-6}$ alkyl-$OR^a$, —$C_{1-6}$ alkyl$C(O)OR^a$, and —$C_{2-6}$ alkenyl$C(O)OR^a$;

wherein each alkyl, alkenyl, alkynyl, cycloalkyl, aryl, heteroaryl, or heterocyclyl is optionally substituted with 1 to 4 groups independently selected from —$OR^a$, cyano, halo, $C_{1-6}$ alkyl, —$C_{1-6}$ alkyl$OR^a$, —$C_{1-6}$ cyanoalkyl, —$C_{1-6}$ haloalkyl, —$C_{3-8}$ cycloalkyl, —$C_{1-3}$ alkyl$C_{3-8}$cycloalkyl, —$C(O)R^a$, —$C_{1-6}$ alkyl$C(O)R^a$, —$C(O)OR^a$, —$C_{1-6}$ alkyl$C(O)OR^a$, —$NR^aR^b$, —$C_{1-6}$ alkyl$NR^aR^b$, —$C(O)NR^aR^b$, $C_{1-6}$ alkyl$C(O)NR^aR^b$, —$S(O)_2R^a$, —$C_{1-6}$ alkyl$S(O)_2R^a$, —$S(O)_2NR^aR^b$, —$C_{1-6}$ alkyl$S(O)_2NR^aR^b$, —$C(O)NR^aS(O)_2R^b$ and —$NR^aC(O)R^b$;

or $R^1$ and $R^2$ combine to form a heterocyclyl optionally substituted with 1 to 3 groups independently selected from oxo, —$C_{1-6}$ alkyl, —$C_{3-8}$ cycloalkyl, —$C_{2-6}$ alkenyl, —$C_{2-6}$ alkynyl, —$OR^a$, —$C(O)OR^a$, —$C_{1-6}$ cyanoalkyl, —$C_{1-6}$ alkylOR$^a$, —C$_{1-6}$ haloalkyl, —C$_{1-3}$ alkylC$_{3-8}$cycloalkyl, —C(O)R$^a$, C$_{1-6}$ alkylC(O)R$^a$, —C$_{1-6}$ alkylC(O)OR$^a$, —NR$^a$R$^b$, —C$_{1-6}$alkylNR$^a$R$^b$, —C(O)NR$^a$R$^b$, —C$_{1-6}$alkyl-C(O)NR$^a$R$^b$, —S(O)$_2$R$^a$, —C$_{1-6}$ alkylS(O)$_2$R$^a$, —S(O)$_2$NR$^a$R$^b$, —C(O)N=S(O)R$^a$NR$^a$R$^b$, —C(O)N=S(O)R$^a$N-R$^a$C(O)R$^b$, and —C$_{1-6}$ alkylS(O)$_2$NR$^a$R$^b$;

each R$^3$ is independently hydrogen, —C$_{1-6}$ alkyl, —C$_{2-6}$ alkenyl, —C$_{3-6}$ cycloalkyl, aryl, heteroaryl, heterocyclyl, —C$_{1-6}$alkylaryl, —C$_{1-6}$alkylheteroaryl, —C$_{1-6}$alkylheterocyclyl, —C$_{2-6}$ alkyl-OR$^a$, —C$_{1-6}$ alkylC(O)OR$^a$, or —C$_{2-6}$ alkenylC(O)OR$^a$;

each R$^a$ is independently selected from hydrogen, —C$_{1-6}$ alkyl, —C$_{1-6}$ cyanoalkyl, —C$_{1-6}$ haloalkyl, —C$_{3-8}$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;

each R$^b$ is independently selected from hydrogen, —C$_{1-6}$ alkyl, —C$_{1-6}$ cyanoalkyl, —C$_{1-6}$ haloalkyl, —C$_{3-8}$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;

or R$^a$ and R$^b$ may combine together to form a heterocyclyl optionally substituted with 1 to 4 groups independently selected from —OR$^f$, cyano, halo, —C$_{1-6}$ alkylOR$^f$, —C$_{1-6}$ cyanoalkyl, —C$_{1-6}$ haloalkyl, —C$_{3-8}$ cycloalkyl, —C$_{1-3}$ alkylC$_{3-8}$ cycloalkyl, —C(O)R$^f$, —C$_{1-6}$ alkylC(O)R$^f$, —C(O)OR$^f$, —C$_{1-6}$ alkylC(O)OR$^f$, —NR$^f$R$^g$, —C$_{1-6}$ alkylNR$^f$R$^g$, —C(O)NR$^f$R$^g$, —C$_{1-6}$ alkylC(O)NR$^f$R$^g$, —S(O)$_2$R$^f$, —C$_{1-6}$ alkylS(O)$_2$R$^f$, —S(O)$_2$NR$^f$R$^g$, —C$_{1-6}$ alkylS(O)$_2$NR$^f$R$^g$, —C(O)NR$^f$S(O)$_2$R$^g$ and —NR$^f$C(O)R$^g$;

each R$^c$ is independently selected from hydrogen, —OH, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl;

each R$^d$ is independently selected from hydrogen, —C$_{1-6}$ alkyl, —C$_3$-C$_8$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;

each R$^e$ is independently selected from hydrogen, —C$_{1-6}$ alkyl, —O—C$_{1-6}$ alkyl, —C$_{3-8}$ cycloalkyl, aryl, heteroaryl, heterocyclyl, —O—C$_{3-8}$ cycloalkyl, —O-aryl, —O-heteroaryl, —O-heterocyclyl, —C$_{1-3}$ alkylC$_{3-8}$cycloalkyl, —C$_{1-6}$ alkylaryl, —C$_{1-6}$ alkylheteroaryl, —NR$^f$R$^g$, —C$_{1-6}$ alkylNR$^f$R$^g$, —C(O)NR$^f$R$^g$, —C$_{1-6}$ alkylC(O)NR$^f$R$^g$, —NHS(O)$_2$R$^f$, —C$_{1-6}$ alkylS(O)$_2$R$^f$, and —C$_{1-6}$ alkylS(O)$_2$NR$^f$R$^g$;

each R$^f$ is independently selected from hydrogen, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl; and each R$^g$ is independently selected from hydrogen, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl.

Also provided herein are compounds of Formula (I) or (II) or a pharmaceutically acceptable salt, stereoisomer, mixture of stereoisomers, solvate, or tautomer thereof.

Also provided herein are compounds of Table 1 or a pharmaceutically acceptable salt, stereoisomer, mixture of stereoisomers, solvate, or tautomer thereof.

The present disclosure provides a method of inhibiting PD-1, PD-L1 and/or the PD-1/PD-L1 interaction comprising administering a compound of Formula (I) or (II), or any formula described herein, or a pharmaceutically acceptable salt, stereoisomer, mixture of stereoisomers, solvate, or tautomer thereof, to a patient in need thereof.

The present disclosure provides a method of treating cancer comprising administering a therapeutically effective amount of a compound Formula (I) or (II), or any formula described herein, or a pharmaceutically acceptable salt, stereoisomer, mixture of stereoisomers, solvate, or tautomer thereof, to a patient in need thereof.

One embodiment provides the use of a compound of Formula (I) or (II), or any formula described herein, or a pharmaceutically acceptable salt, stereoisomer, mixture of stereoisomers, solvate, or tautomer thereof, for the treatment of cancer or a condition in a patient that is amenable to treatment by inhibiting PD-1, PD-L1 or the PD-1/PD-L1 interaction comprising administering said compound of Formula (I) or (II), or any formula described herein, or a pharmaceutically acceptable salt, stereoisomer, mixture of stereoisomers, solvate, or tautomer thereof, to said patient in need thereof.

In one embodiment, provided is a method for treating a cancer wherein the cancer is pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, CNS cancer, brain cancer, bone cancer, soft tissue sarcoma, non-small cell lung cancer, small-cell lung cancer or colon cancer, comprising administering a therapeutically effective amount of Formula (I) or (II), or any formula described herein, or a pharmaceutically acceptable salt, stereoisomer, mixture of stereoisomers, solvate, or tautomer thereof, to a patient in need thereof.

In one embodiment, provided is a method for treating a cancer or a condition in a patient that is amenable to treatment by inhibiting PD-1, PD-L1 or the PD-1/PD-L1 interaction selected from pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, CNS cancer, brain cancer, bone cancer, soft tissue sarcoma, non-small cell lung cancer, small-cell lung cancer and colon cancer comprising administering a therapeutically effective amount of a compound of Formula (I) or (II), or any formula described herein, or a pharmaceutically acceptable salt, stereoisomer, mixture of stereoisomers, solvate, or tautomer thereof, to a patient in need thereof, further comprising administering at least one additional anticancer agent or therapy to a patient in need thereof. In certain embodiments, the additional anticancer agent or therapy is selected from nivolumab, pembrolizumab, atezolizumab, ipilimumab, chemotherapy, radiation therapy, and resection therapy, to a patient in need thereof.

In one embodiment, provided is a method for treating hepatitis B virus (HBV), comprising administering a therapeutically effective amount of Formula (I) or (II), or any formula described herein, or a pharmaceutically acceptable salt, stereoisomer, mixture of stereoisomers, solvate, or tautomer thereof, to a patient in need thereof.

In one embodiment, provided is a method for treating hepatitis D virus (HDV), comprising administering a therapeutically effective amount of Formula (I) or (II), or any formula described herein, or a pharmaceutically acceptable salt, stereoisomer, mixture of stereoisomers, solvate, or tautomer thereof, to a patient in need thereof.

In one embodiment, provided is a compound of Formula (I) or (II), or any formula described herein, or a pharmaceutically acceptable salt, stereoisomer, mixture of stereoisomers, solvate, or tautomer thereof, for the treatment of cancer or a condition in a patient selected from lymphoma, multiple myeloma, and leukemia. Additional diseases or conditions that may be treated include, but are not limited to acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), mantle cell lymphoma (MCL), follicular lymphoma, Waldestrom's macroglobulinemia (WM), T-cell lymphoma, B-cell lymphoma and diffuse large B-cell lymphoma (DLBCL).

In one embodiment, the present disclosure provides a compound of Formula (I) or (II), or any formula described herein, or a pharmaceutically acceptable salt, stereoisomer, mixture of stereoisomers, solvate, or tautomer thereof, in combination with at least one additional anti-cancer agent selected from rituxan, doxorubicin, gemcitabine, nivolumab, pembrolizumab, and ipilimumab.

In one embodiment, the present disclosure provides a compound of Formula (I) or (II), or any formula described herein, or a pharmaceutically acceptable salt, stereoisomer, mixture of stereoisomers, solvate, or tautomer thereof, in combination with at least one additional check-point inhibitor selected from nivolumab, pembrolizumab, atezolizumab, and ipilimumab.

In one embodiment, the present disclosure provides a pharmaceutical composition comprising a compound of Formula (I) or (II), or any formula described herein, or a pharmaceutically acceptable salt, stereoisomer, mixture of stereoisomers, solvate, or tautomer thereof, and a pharmaceutically acceptable carrier or excipient.

In one embodiment, the present disclosure provides a pharmaceutical composition comprising a compound of Formula (I) or (II), or any formula described herein, or a pharmaceutically acceptable salt, stereoisomer, mixture of stereoisomers, solvate, or tautomer thereof, and at least one additional anticancer agent and at least one pharmaceutically acceptable carrier or excipient.

In one embodiment, the present disclosure provides a pharmaceutical composition comprising a compound of Formula (I) or (II), or any formula described herein, or a pharmaceutically acceptable salt, stereoisomer, mixture of stereoisomers, solvate, or tautomer thereof, at least one additional therapeutic agent suitable for treating an hepatitis B virus (HBV) infection, and at least one pharmaceutically acceptable carrier or excipient.

In one embodiment, the present disclosure provides a pharmaceutical composition comprising a compound of Formula (I) or (II), or any formula described herein, or a pharmaceutically acceptable salt, stereoisomer, mixture of stereoisomers, solvate, or tautomer thereof, at least one additional therapeutic agent suitable for treating an hepatitis D virus (HDV) infection, and at least one pharmaceutically acceptable carrier or excipient.

In one embodiment, the present disclosure provides a kit that includes a compound of Formula (I) or (II), or any formula described herein, or a pharmaceutically acceptable salt, stereoisomer, mixture of stereoisomers, solvate, or tautomer thereof, a label and/or instructions for use of the compound in the treatment of cancer or a disease or condition mediated by PD-1, PD-L1 activity or the PD-1/PD-L1 interaction.

In one embodiment, the present disclosure provides a kit that includes a compound of Formula (I) or (II), or any formula described herein, or a pharmaceutically acceptable salt, stereoisomer, mixture of stereoisomers, solvate, or tautomer thereof, at least one additional anticancer agent, a label(s) and/or instructions for use of the compound(s) in the treatment of a disease or condition mediated by PD-1, PD-L1 activity or PD-1/PD-L1 interaction.

In one embodiment, the present disclosure provides articles of manufacture that include a compound of Formula (I) or (II), or any formula described herein, or a pharmaceutically acceptable salt, stereoisomer, mixture of stereoisomers, solvate, or tautomer thereof, and a container. In one embodiment, the container may be a vial, jar, ampoule, preloaded syringe, or an intravenous bag.

In one embodiment, the present disclosure provides a compound of Formula (I) or (II), or any formula described herein, or a pharmaceutically acceptable salt, stereoisomer, mixture of stereoisomers, solvate, or tautomer thereof, for use in therapy.

In another embodiment, the present disclosure provides a compound of Formula (I) or (II), or any formula described herein, or a pharmaceutically acceptable salt, stereoisomer, mixture of stereoisomers, solvate, or tautomer thereof, for use in the manufacture of a medicament for treating cancer.

DETAILED DESCRIPTION

Definitions

As used in the present disclosure, the following words and phrases are generally intended to have the meanings as set forth below unless expressly indicated otherwise or the context in which they are used indicates otherwise.

The following description sets forth exemplary methods, parameters and the like. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. Unless chemically or structurally required, no directionality is indicated or implied by the order in which a chemical group is written or named.

A squiggly line on a chemical group as shown below, for example,

indicates a point of attachment, i.e., it shows the broken bond by which the group is connected to another described group.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

The term "substituted" means that any one or more (e.g., one to three, or one to five) hydrogen atoms on the designated atom or group is replaced with one or more (e.g., one to three, or one to five) substituents other than hydrogen, provided that the designated atom's normal valence is not exceeded. The one or more (e.g., one to three, or one to five) substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocycloalkyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein, whether the substituents are the same or different. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

A "substituted" group also includes embodiments in which a monoradical substituent is bound to a single atom of the substituted group (e.g., forming a branch), and also includes embodiments in which the substituent may be a diradical bridging group bound to two adjacent atoms of the substituted group, thereby forming a fused ring on the substituted group.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., —$(CH_2)_3CH_3$), sec-butyl (i.e., —$CH(CH_3)CH_2CH_3$), isobutyl (i.e., —$CH_2CH(CH_3)_2$) and tert-butyl (i.e., —$C(CH_3)_3$); and "propyl" includes n-propyl (i.e., —$(CH_2)_2CH_3$) and isopropyl (i.e., —$CH(CH_3)_2$).

"Alkenyl" refers to an aliphatic group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl, and 1,3-butadienyl).

"Alkynyl" refers to an aliphatic group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—" or "—O-alkyl". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy.

"Haloalkoxy" refers to an alkoxy group as defined above, wherein one or more (e.g., one to three, or one to five) hydrogen atoms are replaced by a halogen.

"Amino" refers to the group —$NR^yR^z$ wherein $R^y$ and $R^z$ are independently selected from hydrogen, alkyl, haloalkyl, cycloalkyl, aryl, heterocyclyl, or heteroaryl; each of which may be optionally substituted.

"Aryl" refers to a monoradical or diradical aromatic carbocyclic group having a single ring (e.g., monocyclic) or multiple rings (e.g., bicyclic or tricyclic) including fused ring systems wherein one or more (e.g., one, two, or three) fused rings is/are fully or partially unsaturated. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Non-limiting examples of aryl groups as used herein include phenyl, naphthyl, fluorenyl, indanyl, tetrahydroindanuyl, and anthryl. Aryl, however, does not encompass or overlap in any way with heteroaryl defined below. If one or more aryl groups are fused with a heteroaryl ring, the resulting ring system is heteroaryl. The classification of mono or diradical indicates whether the aryl group terminates the chain (monoradical) or is within a chain (diradical). The above definition does not preclude additional substituents on the aryl group. For example, as used herein, the aryl group in "A-aryl-B" is a diradical whereas the aryl group in "A-B-aryl" is monoradical, though additional substituents may be present on each aryl group.

The term "alkylsulfinyl" refers to the group —S(O)-alkyl, where alkyl is as defined above, and includes optionally substituted alkyl groups as also defined above.

The term "alkylsulfonyl" refers to the group —$S(O)_2$-alkyl, where alkyl is as defined above, and includes optionally substituted alkyl groups as also defined above.

"Cycloalkyl" refers to a saturated or partially saturated cyclic alkyl group having a single ring or multiple rings including fused, bridged, and spiro ring systems. As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl. As used herein the term "cycloalkenyl" refers to the non-aromatic carbocyclic (partially saturated cyclic alkyl) group having at least one double bond.

"Cyanoalkyl" refers to an alkyl group substituted with cyano (CN).

"Halogen" or "halo" includes fluoro, chloro, bromo, and iodo.

The term "haloalkyl" refers to a monoradical or diradical having the indicated carbon atoms of the alkyl group wherein one or more (e.g., one to three, or one to five) hydrogen hydrogen atoms have been substituted by a halogen. Examples of haloalkyl groups include —CH$_2$F, —CHF$_2$, —CF$_3$, —CH$_2$CF$_3$, —CHFCH$_2$F, —CF$_2$—, —CHF—, and the like. Similarly, the term "haloalkoxy", e.g., —O—C$_{1-3}$haloalkyl, refers to an alkoxy group wherein one or more (e.g., one to three, or one to five) hydrogen hydrogen atoms of the alkyl group have been substituted by a halogen. Examples of haloalkoxy groups include —OCH$_2$F, —OCHF$_2$, —OCF$_3$, —OCH$_2$CF$_3$, —OCHFCH$_2$F, and the like. One of skill in the art is aware that similar definitions apply for the alkenyl and alkynyl analogs (e.g., C$_{2-4}$haloalkenyl, —O—C$_{2-4}$haloalkynyl).

"Heteroalkyl" refers to an alkyl group in which one or more (e.g., one to three, or one to five) hydrogen of the carbon atoms (and any associated hydrogen atoms) are each independently replaced with the same or different heteroatomic groups. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is H, alkyl, aryl, cycloalkyl, heteroalkyl, heteroaryl, or heterocycloalkyl, each of which may be optionally substituted. Examples of heteroalkyl groups include —OCH$_3$, —CH$_2$OCH$_3$, —SCH$_3$, —CH$_2$SCH$_3$, —NRCH$_3$, and —CH$_2$NRCH$_3$, where R is hydrogen, alkyl, cycloalkyl, aryl, arylalkyl, heteroalkyl, or heteroaryl, each of which may be optionally substituted. As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to a monoradical or diradical aromatic group having a single ring, multiple rings, or multiple fused rings, with one or more ring heteroatoms independently selected from nitrogen, oxygen, and sulfur. The term includes fused ring systems wherein one or more (e.g., one, two, or three) fused rings is/are fully or partially unsaturated. As used herein, heteroaryl include 1 to 20 ring carbon atoms (i.e., C$_{1-20}$ heteroaryl), 3 to 12 ring carbon atoms (i.e., C$_{3-12}$ heteroaryl), or 3 to 8 carbon ring atoms (i.e., C$_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Non-limiting examples of heteroaryl groups include pyrimidinyl, purinyl, pyridyl, pyridazinyl, benzothiazolyl, benzodioxanyl, indolinyl, and pyrazolyl. The classification of mono or diradical indicates whether the heteroaryl group terminates the chain (monoradical) or is within a chain (diradical). The above definition does not preclude additional substituents on the heteroaryl group. For example, the heteroaryl group in "A-heteroaryl-B" is a diradical whereas the heteroaryl group in "A-B-heteroaryl" is monoradical, though additional substituents may be present on each heteroaryl group. Heteroaryl does not encompass or overlap with aryl as defined above.

"Heterocyclyl," "heterocycle," or "heterocyclic" refer to a saturated or unsaturated cyclic alkyl group, with one or more ring heteroatoms independently selected from nitrogen, oxygen and sulfur. A heterocycloalkyl may be a single ring or multiple rings wherein the multiple rings may be fused, bridged, or spiro. As used herein, heterocyclyl has 2 to 20 ring carbon atoms (i.e., C$_{2-20}$ heterocyclyl), 2 to 12 ring carbon atoms (i.e., C$_{2-12}$ heterocyclyl), 2 to 10 ring carbon atoms (i.e., C$_{2-10}$ heterocyclyl), 2 to 8 ring carbon atoms (i.e., C$_{2-8}$ heterocyclyl), 3 to 12 ring carbon atoms (i.e., C$_{3-12}$ heterocyclyl), 3 to 8 ring carbon atoms (i.e., C$_{3-8}$ heterocyclyl), or 3 to 6 ring carbon atoms (i.e., C$_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include pyrrolidinyl, piperidinyl, piperazinyl, oxetanyl, dioxolanyl, azetidinyl, and morpholinyl. As used herein, the term "bridged-heterocyclyl" refers to a four- to ten-membered cyclic moiety connected at two non-adjacent atoms of the heterocyclyl with one or more (e.g., 1 or 2) four- to ten-membered cyclic moiety having at least one heteroatom where each heteroatom is independently selected from nitrogen, oxygen, and sulfur. As used herein, bridged-heterocycloalkyl includes bicyclic and tricyclic ring systems. Also used herein, the term "spiro-heterocyclyl" refers to a ring system in which a three- to ten-membered heterocycloalkyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of spiro-heterocyclyl include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl.

The term "heterocyclyl," "heterocycle," or "heterocyclic" includes monoradical or diradical saturated or unsaturated groups having a single ring or multiple condensed rings, having from 3 to 12 carbon atoms, from 1 to 6 heteroatoms, or from 1 to 4 heteroatoms, selected from nitrogen, sulfur, phosphorus, and/or oxygen within the ring. Where the group does not terminate the molecule, it is a diradical and is construed as such i.e., also referred to as heterocyclylene or heterocyclene.

The term "heterocyclyl" includes heterocycloalkenyl groups (i.e., the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. A heterocyclyl may contain one or more (e.g., one or two) oxo (=O or —O$^-$) and/or thioxo (=S) groups.

"Acyl" refers to a group —C(=O)R, wherein R is hydrogen, alkyl, cycloalkyl, heterocycloalkyl, aryl, heteroalkyl, or heteroaryl; each of which may be optionally substituted, as defined herein.

Examples of acyl include formyl, acetyl, cyclohexylcarbonyl, cyclohexylmethyl-carbonyl, and benzoyl.

The term "N-alkylated" means an alkyl group is substituted for one of the hydrogen atoms of a mono substituted amine, or a di-substituted amine group or a tri substituted amine group. When the alkylation is on a tri-substituted amine group an alkonium salt is generated i.e., a positive charge is generated on the nitrogen atom. N-alkylation is commonly associated with alkyl substitution on a ring nitrogen atom.

The term "cyano" refers to the group —CN.

The term "oxo" refers to a group =O.

The term "carboxy" refers to a group —C(O)—OH.

The term "ester" or "carboxyl ester" refers to the group —C(O)OR, where R is alkyl, cycloalkyl, aryl, heteroaryl, or heterocyclyl, which may be optionally further substituted, for example, by alkyl, alkoxy, halogen, $CF_3$, amino, substituted amino, cyano or —$S(O)_yR^z$, in which $R^z$ is alkyl, aryl, or heteroaryl, and y is 0, 1 or 2.

The term "substituted amino" refers to the group —NRR, where each R is independently hydrogen, alkyl, cycloalkyl, aryl, heteroaryl, or heterocyclyl, each of which may be optionally substituted, or a group as described or exemplified herein, or where both R groups are joined to form a heterocyclic group (e.g., morpholino) as described or exemplified herein, which also may be optionally substituted.

The term "amido" refers to the group —C(O)NRR where each R is independently hydrogen, alkyl, cycloalkyl, aryl, heteroaryl, or heterocyclyl, each of which may be optionally substituted, or a group as described or exemplified herein, or where both R groups are joined to form a heterocyclic group (e.g., morpholino) as described or exemplified herein, which also may be optionally substituted.

The term "sulfoxide" refers to a group —S(O)R, in which R is alkyl, cycloalkyl, heterocyclyl, aryl, or heteroaryl, each of which may be optionally substituted.

The term "sulfone" refers to a group —$S(O)_2R$, in which R is alkyl, cycloalkyl, heterocyclyl, aryl, or heteroaryl, each of which may be optionally substituted.

As used herein, the terms "alkylcycloalkyl," "alkylaryl," "alkylheteroaryl" and "alkylheterocyclyl" are intended to refer to a cycloalkyl, aryl, heteroaryl or heterocyclyl group which is bound to the remainder of the molecule via an alkyl moiety, where the terms "alkyl," "cycloalkyl," "aryl," "heteroaryl" and "heterocyclyl" are as defined herein. Exemplary alkylaryl groups include benzyl, phenethyl, and the like.

"Optional" or "optionally" means that the subsequently described event or circumstance may or may not occur, and that the description includes instances where said event or circumstance occurs and instances in which it does not.

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g., arylalkyl, the last mentioned group contains the atom by which the moiety is attached to the rest of the molecule.

Where a group is represented by a bond, multiple adjacent groups whether the same or different, when represented by bonds, constitute a single bond. For example the group "-$L^1$-$V^1$-$L^2$-" constitutes a single bond if each of $L^1$, $V^1$ and $L^2$ is a bond.

Where a given group (moiety) is described herein as being attached to a second group and the site of attachment is not explicit, the given group may be attached at any available site of the given group or to any available site of the second group. For example, an "alkyl-substituted phenyl," where the attachment sites are not explicit, may have any available site of the alkyl group attached to any available site of the phenyl group. In this regard, an "available site" is a site of the group at which hydrogen of the group may be replaced with a substituent.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The compounds of the disclosure may possess one or more asymmetric centers and may be produced as a racemic mixture or as individual enantiomers or diastereoisomers. The number of stereoisomers present in any given compound of a given formula depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis or by resolution of the compound by conventional means. The individual stereoisomers (including individual enantiomers and diastereoisomers) as well as racemic and non-racemic mixture of stereoisomers are encompassed within the scope of the present disclosure, all of which are intended to be depicted by the structures of this specification unless otherwise specifically indicated.

The absolute stereochemistry is specified according to the Cahn Ingold Prelog R S system. When the compound is a pure enantiomer the stereochemistry at each chiral carbon may be specified by either R or S. A resolved compound whose absolute configuration is unknown may be designated (+) or (−) depending on the direction (dextro- or laevorotary) that it rotates the plane of polarized light at the wavelength of the sodium D line.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The term "solvate" refers to a complex formed by combining a compound of Formula (I) or (II), or any other formula as disclosed herein, or a pharmaceutically acceptable salt, stereoisomer, mixture of stereoisomers, solvate, or tautomer thereof, and a solvent.

The term "hydrate" refers to the complex formed by the combining of a compound of Formula (I) or (II), or any formula disclosed herein, or a pharmaceutically acceptable salt, stereoisomer, mixture of stereoisomers, solvate, or tautomer thereof, and water.

The term "prodrug" refers to compounds of Formula (I) or (II), or derivatives of Formula (I) or (II) disclosed herein, that include chemical groups which, in vivo, can be converted and/or can be split off from the remainder of the molecule to provide for the active drug. Pharmaceutically acceptable salts or biologically active metabolites thereof of the prodrug of a compound of Formula (I) or (II), or any formula described herein, or a pharmaceutically acceptable salt, stereoisomer, mixture of stereoisomers, solvate, or tautomer thereof, are also within the ambit of the present disclosure.

Any formula or structure given herein, including Formula (I) or (II), or any formula disclosed herein, is intended to represent unlabeled forms as well as isotopically labeled forms of the compounds. Isotopically labeled compounds have structures depicted by the formulas given herein except that one or more (e.g., one to three, or one to five) atoms are replaced by an isotope having a selected atomic mass or mass number. Examples of isotopes that can be incorporated into compounds of the disclosure include isotopes of hydrogen, carbon, nitrogen, oxygen, phosphorus, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Various isotopically labeled compounds of the present disclosure, for example those into which radioactive isotopes such as $^3$H, $^{13}$C and $^{14}$C are incorporated, are within the ambit of the present disclosure. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in treatment of patients. Such isotopically labeled analogs of compounds of the present disclosure may also be useful for treatment of diseases disclosed herein because they may provide improved pharmacokinetic and/or pharmacodynamic properties over the unlabeled forms of the same compounds. Such isotopically leveled forms of or analogs of compounds herein are within the ambit of the present disclosure. One of skill in the art is able to prepare and use such isotopically labeled forms following procedures for isotopically labeling compounds or aspects of compounds to arrive at isotopic or radiolabeled analogs of compounds disclosed herein.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, di-substituted cycloalkyl amine, tri-substituted cycloalkyl amines, cycloalkenyl amines, di(cycloalkenyl) amines, tri(cycloalkenyl) amines, substituted cycloalkenyl amines, di-substituted cycloalkenyl amine, tri-substituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Amines are of general structure $N(R^{30})(R^{31})(R^{32})$, wherein mono-substituted amines have two of the three substituents on nitrogen ($R^{30}$, $R^{31}$, and $R^{32}$) as hydrogen, di-substituted amines have one of the three substituents on nitrogen ($R^{30}$, $R^{31}$, and $R^{32}$) as hydrogen, whereas tri-substituted amines have none of the three substituents on nitrogen ($R^{30}$, $R^{31}$, and $R^{32}$) as hydrogen. $R^{30}$, $R^{31}$, and $R^{32}$ are selected from a variety of substituents such as hydrogen, optionally substituted alkyl, aryl, heteroaryl, cycloalkyl, cycloalkenyl, heterocyclyl, and the like.

Specific examples of suitable amines include, by way of example only, isopropyl amine, trimethyl amine, diethyl amine, tri(iso-propyl) amine, tri(n-propyl) amine, ethanolamine, diethanolamine, 2-dimethylamino ethanol, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial, and antifungal agents, isotonic and absorption delaying agents and the like. The use of such media and agents for pharmaceutically active substances is well known in the art. Except insofar as any conventional media or agent is incompatible with the active ingredient, or unless otherwise indicated herein, its use in the therapeutic compositions is contemplated. Supplementary active ingredients can also be incorporated into the compositions.

The term "anticancer agent" is any drug that is effective in the treatment of a malignant, or cancerous disease. Effectiveness may mean inhibition, partial, or full remission, prolongation of life, improvement in quality of life, or cure. There are several major classes of anticancer drugs including chemical compositions as disclosed herein or known to one of skill in the art e.g., PD-1, PD-L1, PD-1/PD-L1 interaction inhibitors, alkylating agents, antimetabolites, natural products, and hormones.

The term "additional anticancer agent" as used herein means the use or combination of a second, third, fourth, fifth, etc., anticancer agent(s) in addition to a compound according to Formula (I) or (II) disclosed herein.

The term "anticancer therapy" means any currently known therapeutic methods for the treatment of cancer.

The term "blockade agent" or "check point inhibitors" are classes of immune oncology agents that inhibit PD-1, PD-L1, or the PD-1/PD-L1 interaction.

The term "treatment" or "treating" means any administration of a compound or compounds according to the present disclosure to a subject (e.g., a human) having or susceptible to a condition or disease disclosed herein for the purpose of: 1) preventing or protecting against the disease or condition, that is, causing the clinical symptoms not to develop; 2) inhibiting the disease or condition, that is, arresting or suppressing the development of clinical symptoms; or 3) relieving the disease or condition that is causing the regression of clinical symptoms. In some embodiments, the term "treatment" or "treating" refers to relieving the disease or condition or causing the regression of clinical symptoms.

As used herein, the term "preventing" refers to the prophylactic treatment of a patient in need thereof. The prophylactic treatment can be accomplished by providing an appropriate dose of a therapeutic agent to a subject at risk of suffering from an ailment, thereby substantially averting onset of the ailment. The presence of a genetic mutation or the predisposition to having a mutation may not be alterable. However, prophylactic treatment (prevention) as used herein has the potential to avoid/ameliorate the symptoms or clinical consequences of having the disease engendered by such genetic mutation or predisposition.

It will be understood by those of ordinary skill in the art that in human medicine, it is not always possible to distinguish between "preventing" and "suppressing" since the ultimate inductive event or events may be unknown, latent, or the patient is not ascertained until well after the occurrence of the event or events. Therefore, as used herein, the term "prophylaxis" is intended as an element of "treatment" to encompass both "preventing" and "suppressing" as defined herein. The term "protection," as used herein, is meant to include "prophylaxis."

The term "patient" typically refers to a "mammal" which includes, without limitation, human, monkeys, rabbits, mice, domestic animals, such as dogs and cats, farm animals, such as cows, horses, or pigs, and laboratory animals. In some embodiments, the term patient refers to a human in need of treatment as defined herein.

Compounds

Provided herein are compounds that function as PD-1 inhibitors, PD-L1 inhibitors, and/or PD-1/PD-L1 interaction inhibitors, methods of using such compounds and compositions comprising such compounds optionally in combination with one or more additional anticancer agents or therapies. In all embodiments discussed herein where there is more than one occurrence of a group or variable, it is intended that the group or variable is independently selected the list that follows. It is further contemplated that all embodiments directed to compounds include any pharmaceutically acceptable salt, stereoisomer, mixture of stereoisomers, solvate, prodrug or tautomer thereof.

The present disclosure provides a compound of Formula (X):

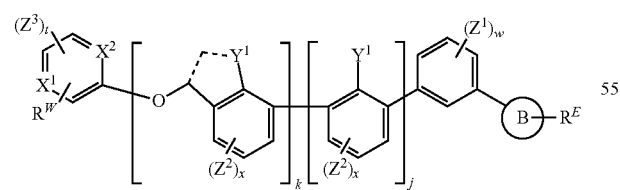

(X)

or a pharmaceutically acceptable salt, stereoisomer, mixture of stereoisomers, solvate, or tautomer thereof, wherein k is 1 and j is 0, or k is 0 and j is 1, and the remaining variables are as defined herein (e.g., Formula (I) and Formula (II)).

In one embodiment, provided is a compound of Formula (I):

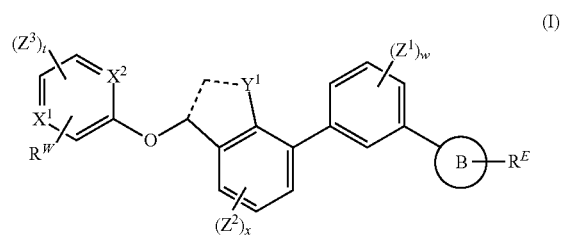

(I)

or a pharmaceutically acceptable salt, stereoisomer, mixture of stereoisomers, solvate, or tautomer thereof, wherein:

$X^1$ is N, CH or $CZ^3$;
$X^2$ is N, CH or $CZ^3$;
$Y^1$ is O, NH or $CH_2$ and the dashed lines ( --- ) are single bonds, or $Y^1$ is halo or $—C_{1-6}$ alkyl and the dashed lines ( --- ) are absent;
ring B is a 9-, 10- or 11-membered fused bicyclic heterocyclyl or heteroaryl ring of the formula:

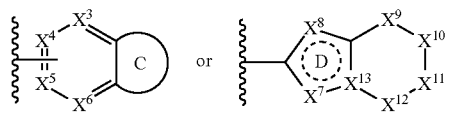

wherein $X^3$, $X^4$, $X^5$ and $X^6$ are each independently N or CH;
$X^7$ and $X^8$ are each independently S, N, NH, CH or $CH_2$;
$X^9$, $X^{10}$, $X^{11}$ and $X^{12}$ are each independently O, S, NH or $CH_2$;
$X^{13}$ is N or C;
ring C is cycloalkyl, heterocyclyl, aryl or heteroaryl; and
ring D is heteroaryl;
w is 0, 1 or 2;
each $Z^1$ is independently halo, $—OR^a$, $—NO_2$, cyano, $—NR^aR^b$, $—N_3$, $—S(O)_2R^a$, $—C_{1-6}$ alkyl, $—C_{1-6}$ haloalkyl, $—C_{2-6}$ alkenyl, $—C_{2-6}$ alkynyl, $—O—C_{1-6}$ alkyl, $—O—C_{1-6}$ haloalkyl, $—C_{3-8}$ cycloalkyl, or $—C_{1-6}$ alkyl$C_{3-8}$ cycloalkyl; and
  wherein each alkyl, alkenyl, alkynyl, and cycloalkyl is optionally substituted with 1 to 4 groups independently selected from oxo, $—NO_2$, $—N_3$, $—OR^a$, halo, and cyano;
x is 0, 1 or 2;
each $Z^2$ is independently halo, $—OR^a$, $—NO_2$, cyano, $—NR^aR^b$, $—N_3$, $—S(O)_2R^a$, $—C_{1-6}$ alkyl, $—C_{1-6}$ haloalkyl, $—C_{2-6}$ alkenyl, $—C_{2-6}$ alkynyl, $—O—C_{1-6}$ alkyl, $—O—C_{1-6}$ haloalkyl, $—C_{3-8}$ cycloalkyl, or $—C_{1-6}$ alkyl$C_{3-8}$ cycloalkyl; and
  wherein each alkyl, alkenyl, alkynyl, and cycloalkyl is optionally substituted with 1 to 4 groups independently selected from oxo, $—NO_2$, $—N_3$, $—OR^a$, halo, and cyano;
t is 0, 1 or 2;
each $Z^3$ is independently halo, $—OR^a$, $—N_3$, $—NO_2$, cyano, $—NR^1R^2$, $—S(O)_2R^a$, $—S(O)_2NR^aR^b$, $—NR^aS(O)_2R^a$, $—NR^aC(O)R^a$, $—C(O)R^a$, $—C(O)OR^a$, $—C(O)NR^aR^b$, $—NR^aC(O)OR^a$, $—NR^aC(O)NR^1R^2$, $—OC(O)NR^aR^b$, $—NR^aS(O)_2NR^aR^b$, $—C(O)NR^aS(O)_2NR^aR^b$, $—C_{1-6}$ alkyl, $—C_{2-6}$ alkenyl, $—C_{2-6}$ alkynyl, $—O—C_{1-6}$ alkyl, $—C_{1-6}$ cyanoalkyl, $—C_{1-6}$ haloalkyl, $—O—C_{1-6}$ cyanoalkyl, $—O—C_{1-6}$ haloalkyl, $—C_{3-8}$ cycloalkyl, $—C_{1-6}$ alkyl$C_{3-8}$ cycloalkyl, aryl, heteroaryl, heterocyclyl, and $R^N$; and

19 wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —O—$C_{1-6}$cyanoalkyl, —$C(O)NR^aR^b$, —$NR^aC(O)R^a$, —$NR^aC(O)OR^a$, —$S(O)_2R^a$, —$NR^aS(O)_2R^b$, —$SO_2NR^aR^b$, —$NR^aS(O)_2NR^aR^b$, —$C(O)NR^aS(O)_2NR^aR^b$ and —$C_{3-8}$ cycloalkyl;

$R^N$ is independently —$C_{1-6}$ alkyl$NR^1R^2$, —$OC_{1-6}$ alkyl$NR^1R^2$, —$C_{1-6}$ alkyl-O—$C_{1-6}$ alkyl$NR^1R^2$, —$NR^aC_{1-6}$ alkyl$NR^1R^2$, —$C_{1-6}$ alkylC(O)$NR^1R^2$, —O—$C_{1-6}$ alkylC(O)$NR^1R^2$, —O—$C_{1-6}$ alkylC(O)$OR^1$, —$SC_{1-6}$ alkyl$NR^1R^2$, —$C_{1-6}$ alkyl$OR^a$, or

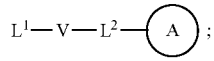

wherein:
L$^1$ is independently a bond, —O—, —$NR^a$—, —S—, —S(O)—, or —$S(O)_2$—; V is independently selected from a bond, $C_{1-6}$ alkyl, $C_{2-6}$ alkenyl, and $C_{2-6}$ alkynyl;
wherein each alkyl, alkenyl, or alkynyl is optionally independently substituted with —$OR^a$, halo, cyano, —$NR^aR^b$ or —$C_{3-8}$ cycloalkyl;
L$^2$ is independently a bond, —O—, —$NR^a$—, —S—, —S(O)—, or —$S(O)_2$—;
ring A is independently cycloalkyl, aryl, heteroaryl, or heterocyclyl;
wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$ alkenyl, —$C_{2-6}$ alkynyl, —O—$C_{1-6}$ haloalkyl, —$NR^aR^b$, —$C(O)R^a$, —$C(O)OR^a$, —O—$C_{1-6}$ cyanoalkyl, —$C(O)NR^aR^b$, —$NR^aC(O)R^a$, —$NR^aC(O)OR^a$, —$NR^aC(O)OR^a$, —$C(O)N(R^a)OR^b$, —$S(O)_2R^a$, —$S(O)_2NR^aR^b$, —$NR^aS(O)_2R^b$, —$NR^aS(O)_2NR^aR^b$, —$C(O)NR^aS(O)_2NR^aR^b$, —$C_{3-8}$ cycloalkyl, and —$C_{1-6}$ alkyl$C_{3-8}$ cycloalkyl; and
wherein the alkyl, alkenyl, or alkynyl group is optionally independently substituted with —$OR^a$, halo, cyano, —$NR^aR^b$ or —$C_{3-8}$ cycloalkyl;

$R^E$ is hydrogen, halo, —OH, —$NR^1C(O)NR^1R^2$, —$C_{1-6}$ alkyl$OC(O)NR^1R^2$, —$C_{1-6}$ alkyl$NR^1C(O)R^2$, —CN, —$C_{1-9}$ alkyl, —$C_{2-6}$ alkenyl, —$C_{2-6}$ alkynyl, —$C_{1-8}$ haloalkyl, $C_{1-8}$ alkoxy or $C_{3-15}$ cycloalkyl;

$R^W$ is —$NR^1R^2$, —$C_{1-6}$ alkyl$NR^1R^2$, —O—$C_{1-6}$ alkyl$NR^1R^2$, —$C_{1-6}$ alkyl-O—$C_{1-6}$ alkyl$NR^1R^2$, —$NR^a$—$C_{1-6}$ alkyl$NR^1R^2$, —$C_{1-6}$ alkyl$N^+R^1R^2R^3$, —S—$C_{1-6}$ alkyl$NR^1R^2$, —$C(O)NR^1R^2$, —$S(O)_2R^a$, —$(CH_2)S(O)_2NR^1R^2$, —$(CH_2)_uNR^aS(O)_2NR^aR^b$, —$S(O)_2NR^aC_{1-6}$ alkyl$NR^1R^2$, —$NR^aS(O)_2C_{1-6}$ alkyl$NR^1R^2$, —$(CH_2)_uC(O)NR^aS(O)_2NR^aR^b$, —$(CH_2)_uN^+R^1R^2O^-$, —$(CH_2)_uP^+R^bR^cR^d$, —$(CH_2)_uP^+R^cR^dO^-$, —$(CH_2)_uP^+O[NR^aR^b][NR^cR^d]$, —$(CH_2)_uNR^cP(O)(OR^c)_2$, —$(CH_2)_uCH_2OP(O)(OR^c)(OR^d)$, —$(CH_2)OP(O)(OR^c)(OR^d)$, —$(CH_2)_uOP(O)NR^aR^b)(OR^a)$, or

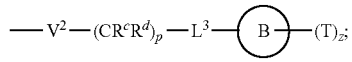

20 wherein:
V$^2$ is independently a bond, —O—, —$NR^a$—, —S—, —SO—, —$SO_2$—, —$C(O)NR^a$—, —$NR^aC(O)$—, —$S(O)_2NR^1$—, or —$NR^aS(O)_2$—;
L$^3$ is independently a bond, —O—, —$NR^a$—, —S—, —SO—, —$SO_2$—, —$C(O)NR^a$—, —$NR^aC(O)$—, —$S(O)_2NR^1$—, or —$NR^aS(O)_2$—;
ring B is independently cycloalkyl, aryl, heteroaryl, or heterocyclyl;
T is independently hydrogen, —$OR^a$, —$(CH_2)_qNR^1R^2$, —$(CH_2)_qNR^aC(O)R^e$, or —$(CH_2)_qC(O)R^e$;
p is independently 0, 1, 2, 3, 4, or 5;
q is independently 0, 1, 2, 3, 4, or 5;
u is 0, 1, 2, 3, or 4;
z is 0, 1, 2, or 3; and
wherein the alkyl, cycloalkyl, aryl, heteroaryl, or heterocyclyl of $R^E$ or $R^W$ is optionally substituted with 1 to 3 substituents independently selected from the group consisting of —$NR^aR^b$, halo, cyano, oxo, —$OR^a$, —$C_{1-6}$ alkyl, —$C_{1-6}$ haloalkyl, —$C_{1-6}$ cyanoalkyl, —$C_{1-6}$ alkyl$NR^aR^b$, —$C_{1-6}$ hydroxyalkyl, —$C_{3-8}$ cycloalkyl, and —$C_{1-3}$ alkyl$C_{3-8}$ cycloalkyl;
provided that at least one of V$^2$, L$^3$, ring B and T contains a nitrogen atom;
each R$^1$ is independently selected from hydrogen, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{1-6}$ alkylC(O)$OR^a$, —$C_{2-6}$ alkenylC(O)$OR^a$, —$S(O)_2R^a$, —$S(O)_2NR^aR^b$, —$C(O)NR^aS(O)_2R^a$, and —$C_{1-6}$ alkyl$C_{3-8}$cycloalkyl;
wherein each alkyl, alkenyl, cycloalkyl, aryl, heteroaryl, or heterocyclyl is optionally substituted with 1 to 4 groups independently selected from —$OR^a$, cyano, halo, $C_{1-6}$ alkyl, —$C_{1-6}$ alkyl$OR^a$, —$C_{1-6}$ cyanoalkyl, —$C_{1-6}$ haloalkyl, $C_{3-8}$ cycloalkyl, —$C_{1-3}$ alkyl$C_{3-8}$cycloalkyl, —$C(O)R^a$, —$C_{1-6}$ alkylC(O)$R^a$, —$C(O)OR^a$, —$C_{1-6}$ alkylC(O)$OR^a$, —$NR^aR^b$, —$OC(O)NR^aR^b$, $NR^aC(O)OR^b$, —$C_{1-6}$ alkyl$NR^aR^b$, —$C(O)NR^aR^b$, —$C_{1-6}$ alkylC(O)$NR^aR^b$, —$S(O)_2R^a$, —$C_{1-6}$ alkylS(O)$_2$ $R^a$, —$S(O)_2NR^aR^b$, —$C_{1-6}$ alkylS(O)$_2NR^aR^b$, —$C(O)NR^aS(O)_2R^b$, —$C_{1-6}$ alkylC(O)$NR^aS(O)_2R^b$, —$NR^aC(O)R^b$, and —$C_{1-6}$ alkyl$NR^aC(O)R^b$;
each R$^2$ is independently selected from hydrogen, —$C_{1-6}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{2-6}$ alkyl-$OR^a$, —$C_{1-6}$ alkylC(O)$OR^a$, and —$C_{2-6}$ alkenylC(O)$OR^a$;
wherein each alkyl, alkenyl, alkynyl, cycloalkyl, aryl, heteroaryl, or heterocyclyl is optionally substituted with 1 to 4 groups independently selected from —$OR^a$, cyano, halo, $C_{1-6}$ alkyl, —$C_{1-6}$ alkyl$OR^a$, —$C_{1-6}$ cyanoalkyl, —$C_{1-6}$ haloalkyl, —$C_{3-8}$ cycloalkyl, —$C_{1-3}$ alkyl$C_{3-8}$cycloalkyl, —$C(O)R^a$, —$C_{1-6}$ alkylC(O)$R^a$, —$C(O)OR^a$, —$C_{1-6}$ alkylC(O)$OR^a$, —$NR^aR^b$, —$C_{1-6}$ alkyl$NR^aR^b$, —$C(O)NR^aR^b$, $C_{1-6}$ alkylC(O)$NR^aR^b$, —$S(O)_2R^a$, —$C_{1-6}$ alkylS(O)$_2R^a$, —$S(O)_2NR^aR^b$, —$C_{1-6}$ alkylS(O)$_2NR^aR^b$, —$C(O)NR^aS(O)_2R^b$ and —$NR^aC(O)R^b$;
or R$^1$ and R$^2$ combine to form a heterocyclyl optionally substituted with 1 to 3 groups independently selected from oxo, —$C_{1-6}$ alkyl, —$C_{3-8}$ cycloalkyl, —$C_{2-6}$ alkenyl, —$C_{2-6}$ alkynyl, —$OR^a$, —$C(O)OR^a$, —$C_{1-6}$ cyanoalkyl, —$C_{1-6}$ alkyl$OR^a$, —$C_{1-6}$ haloalkyl, —$C_{1-3}$ alkyl$C_{3-8}$cycloalkyl, —$C(O)R^a$, $C_{1-6}$ alkylC(O)$R^a$, —$C_{1-6}$ alkylC(O)$OR^a$, —$NR^aR^b$, —$C_{1-6}$ alkyl$NR^aR^b$, —$C(O)NR^aR^b$, —$C_{1-6}$ alkyl-C(O)$NR^aR^b$, —$S(O)_2R^a$, —$C_{1-6}$ alkylS(O)$_2R^a$, —$S(O)_2$ —NR$^a$R$^b$, —C(O)N=S(O)R$^a$NR$^a$R$^b$, —C(O)N=S(O)R$^a$N-R$^a$C(O)R$^b$, and —C$_{1-6}$ alkylS(O)$_2$NR$^a$R$^b$;

each R$^3$ is independently hydrogen, —C$_{1-6}$ alkyl, —C$_{2-6}$ alkenyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{2-6}$ alkyl-OR$^a$, —C$_{1-6}$ alkylC(O)OR$^a$, or —C$_{2-6}$ alkenylC(O)OR$^a$;

each R$^a$ is independently selected from hydrogen, —C$_{1-6}$ alkyl, —C$_{1-6}$ cyanoalkyl, —C$_{1-6}$ haloalkyl, —C$_{3-8}$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;

each R$^b$ is independently selected from hydrogen, —C$_{1-6}$ alkyl, —C$_{1-6}$ cyanoalkyl, —C$_{1-6}$ haloalkyl, —C$_{3-8}$ cycloalkyl, aryl, heteroaryl, heterocyclyl, —C$_{1-3}$ alkylC$_{3-8}$cycloalkyl, —C$_{1-6}$ alkylaryl, —C$_{1-6}$ alkylheteroaryl, and —C$_{1-6}$ alkylheterocyclyl;

or R$^a$ and R$^b$ may combine together to form a heterocyclyl optionally substituted with 1 to 4 groups independently selected from —OR$^f$, cyano, halo, —C$_{1-6}$ alkylOR$^f$, —C$_{1-6}$ cyanoalkyl, —C$_{1-6}$ haloalkyl, —C$_{3-8}$ cycloalkyl, —C$_{1-3}$ alkylC$_{3-8}$ cycloalkyl, —C(O)R, —C$_{1-6}$ alkylC(O)R$^f$, —C(O)OR$^f$, —C$_{1-6}$ alkylC(O)OR$^f$, —NR$^f$R$^g$, —C$_{1-6}$ alkylNR$^f$R$^g$, —C(O)NR$^f$R$^g$, —C$_{1-6}$ alkylC(O)NR$^f$R$^g$, —S(O)$_2$R$^f$, —C$_{1-6}$ alkylS(O)$_2$R$^f$, —S(O)$_2$NR$^f$R$^g$, —C$_{1-6}$ alkylS(O)$_2$NR$^f$R$^g$, —C(O)NR$^f$S(O)$_2$R$^g$ and —NR$^f$C(O)R$^g$;

each R$^c$ is independently selected from hydrogen, —OH, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl;

each R$^d$ is independently selected from hydrogen, —C$_{1-6}$ alkyl, —C$_3$-C$_8$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl;

each R$^e$ is independently selected from hydrogen, —C$_{1-6}$ alkyl, —O—C$_{1-6}$ alkyl, —C$_{3-8}$ cycloalkyl, aryl, heteroaryl, heterocyclyl, —O—C$_{3-8}$ cycloalkyl, —O-aryl, —O-heteroaryl, —O-heterocyclyl, —C$_{1-3}$ alkylC$_{3-8}$ cycloalkyl, —C$_{1-6}$ alkylaryl, —C$_{1-6}$ alkylheteroaryl, —NR$^f$R$^g$, —C$_{1-6}$ alkylNR$^f$R$^g$, —C(O)NR$^f$R$^g$, —C$_{1-6}$ alkylC(O)NR$^f$R$^g$, —NHS(O)$_2$R$^f$, —C$_{1-6}$ alkylS(O)$_2$R$^f$, and —C$_{1-6}$ alkylS(O)$_2$NR$^f$R$^g$;

each R$^f$ is independently selected from hydrogen, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl; and each R$^g$ is independently selected from hydrogen, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl.

In one embodiment, provided is a compound of Formula (II):

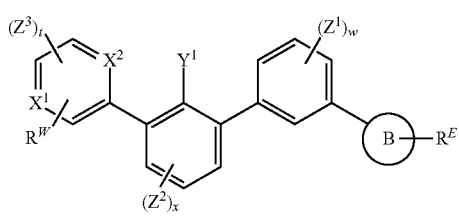

(II)

or a pharmaceutically acceptable salt, stereoisomer, mixture of stereoisomers, solvate, or tautomer thereof, wherein:

X$^1$ is N, CH or CZ$^3$;
X$^2$ is N, CH or CZ$^3$;
Y$^1$ is halo or —C$_{1-6}$ alkyl;
ring B is a 9-, 10- or 11-membered fused bicyclic heterocyclyl or heteroaryl ring of the formula:

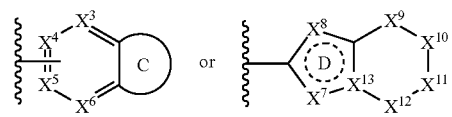

wherein X$^3$, X$^4$, X$^5$ and X$^6$ are each independently N or CH;
X$^7$ and X$^8$ are each independently S, N, NH, CH or CH$_2$;
X$^9$, X$^{10}$, X$^{11}$ and X$^{12}$ are each independently O, S, NH or CH$_2$;
X$^{13}$ is N or C;
ring C is cycloalkyl, heterocyclyl, aryl or heteroaryl; and
ring D is heteroaryl;
w is 0, 1 or 2;
each Z$^1$ is independently halo, —OR$^a$, —NO$_2$, cyano, —NR$^a$R$^b$, —N$_3$, —S(O)$_2$R$^a$, —C$_{1-6}$ alkyl, —C$_{1-6}$ haloalkyl, —C$_{2-6}$alkenyl, —C$_{2-6}$ alkynyl, —O—C$_{1-6}$ alkyl, —O—C$_{1-6}$ haloalkyl, —C$_{3-8}$ cycloalkyl, or —C$_{1-6}$ alkylC$_{3-8}$ cycloalkyl; and
wherein each alkyl, alkenyl, alkynyl, and cycloalkyl is optionally substituted with 1 to 4 groups independently selected from oxo, —NO$_2$, —N$_3$, —OR$^a$, halo, and cyano;

x is 0, 1 or 2;
each Z$^2$ is independently halo, —OR$^a$, —NO$_2$, cyano, —NR$^a$R$^b$, —N$_3$, —S(O)$_2$R$^a$, —C$_{1-6}$ alkyl, —C$_{1-6}$ haloalkyl, —C$_{2-6}$alkenyl, —C$_{2-6}$ alkynyl, —O—C$_{1-6}$ alkyl, —O—C$_{1-6}$ haloalkyl, —C$_{3-8}$ cycloalkyl, or —C$_{1-6}$ alkylC$_{3-8}$ cycloalkyl; and
wherein each alkyl, alkenyl, alkynyl, and cycloalkyl is optionally substituted with 1 to 4 groups independently selected from oxo, —NO$_2$, —N$_3$, —OR$^a$, halo, and cyano;

t is 0, 1 or 2;
each Z$^3$ is independently halo, —OR$^a$, —N$_3$, —NO$_2$, cyano, —NR$^1$R$^2$, —S(O)$_2$R$^a$, —S(O)$_2$NR$^a$R$^b$, —NR$^a$S(O)$_2$R$^a$, —NR$^a$C(O)R$^a$, —C(O)R$^a$, —C(O)OR$^a$, —C(O)NR$^a$R$^b$, —NR$^a$C(O)OR$^a$, —NR$^a$C(O)NR$^1$R$^2$, —OC(O)NR$^a$R$^b$, —NR$^a$S(O)$_2$NR$^a$R$^b$, —C(O)NR$^a$S(O)$_2$NR$^a$R$^b$, —C$_{1-6}$ alkyl, —C$_{2-6}$ alkenyl, —C$_{2-6}$ alkynyl, —O—C$_{1-6}$ alkyl, —C$_{1-6}$ cyanoalkyl, —C$_{1-6}$ haloalkyl, —O—C$_{1-6}$ cyanoalkyl, —O—C$_{1-6}$ haloalkyl, —C$_{3-8}$ cycloalkyl, —C$_{1-6}$ alkylC$_{3-8}$ cycloalkyl, aryl, heteroaryl, heterocyclyl, and R$^N$; and
wherein the alkyl, alkenyl, alkynyl, C$_{3-8}$ cycloalkyl, aryl, heteroaryl, or heterocyclyl group is optionally substituted with 1 to 4 groups independently selected from oxo, —NO$_2$, —N$_3$, —OR$^a$, halo, cyano, —NR$^a$R$^b$, —C(O)R$^a$, —C(O)OR$^a$, —O—C$_{1-6}$cyanoalkyl, —C(O)NR$^a$R$^b$, —NR$^a$C(O)R$^a$, —NR$^a$C(O)OR$^a$, —S(O)$_2$R$^a$, —NR$^a$S(O)$_2$R$^b$, —SO$_2$NR$^a$R$^b$, —NR$^a$S(O)$_2$NR$^a$R$^b$, —C(O)NR$^a$S(O)$_2$NR$^a$R$^b$ and —C$_{3-8}$ cycloalkyl;

R$^N$ is independently —C$_{1-6}$ alkylNR$^1$R$^2$, —OC$_{1-6}$ alkylNR$^1$R$^2$, —C$_{1-6}$ alkyl-O—C$_{1-6}$ alkylNR$^1$R$^2$, —NR$^a$C$_{1-6}$ alkylNR$^1$R$^2$, —C$_{1-6}$ alkylC(O)NR$^1$R$^2$, —O—C$_{1-6}$ alkylC(O)NR$^1$R$^2$, —O—C$_{1-6}$ alkylC(O)OR$^1$, —SC$_{1-6}$ alkylNR$^1$R$^2$, —C$_{1-6}$ alkylOR$^a$, or

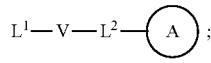

wherein:

L¹ is independently a bond, —O—, —NR$^a$—, —S—, —S(O)—, or —S(O)$_2$—;

V is independently selected from a bond, $C_{1-6}$ alkyl, $C_{2-6}$ alkenyl, and $C_{2-6}$ alkynyl;

wherein each alkyl, alkenyl, or alkynyl is optionally independently substituted with —OR$^a$, halo, cyano, —NR$^a$R$^b$ or —C$_{3-8}$ cycloalkyl;

L² is independently a bond, —O—, —NR$^a$—, —S—, —S(O)—, or —S(O)$_2$—;

ring A is independently cycloalkyl, aryl, heteroaryl, or heterocyclyl;

wherein each cycloalkyl, aryl, heteroaryl, or heterocyclyl is optionally substituted with 1 to 4 groups independently selected from oxo, —NO$_2$, —N$_3$, —OR$^a$, halo, cyano, —C$_{1-6}$ alkyl, —C$_{1-6}$ haloalkyl, —C$_{2-6}$ alkenyl, —C$_{2-6}$ alkynyl, —O—C$_{1-6}$ haloalkyl, —NR$^a$R$^b$, —C(O)R$^a$, —C(O)OR$^a$, —O—C$_{1-6}$ cyanoalkyl, —C(O)NR$^a$R$^b$, —NR$^a$C(O)R$^a$, —NR$^a$C(O)OR$^a$, —NR$^a$C(O)OR$^a$, —C(O)N(R$^a$)OR$^b$, —S(O)$_2$R$^a$, —S(O)$_2$NR$^a$R$^b$, —NR$^a$S(O)$_2$R$^b$, —NR$^a$S(O)$_2$NR$^a$R$^b$, —C(O)NR$^a$S(O)$_2$NR$^a$R$^b$, —C$_{3-8}$ cycloalkyl, and —C$_{1-6}$ alkylC$_{3-8}$ cycloalkyl; and wherein the alkyl, alkenyl, or alkynyl group is optionally independently substituted with —OR$^a$, halo, cyano, —NR$^a$R$^b$ or —C$_{3-8}$ cycloalkyl;

R$^E$ is hydrogen, halo, —OH, —NR$^1$C(O)NR$^1$R$^2$, —C$_{1-6}$ alkylOC(O)NR$^1$R$^2$, —C$_{1-6}$ alkylNR$^1$C(O)R$^2$, —CN, —C$_{1-9}$ alkyl, —C$_{2-6}$ alkenyl, —C$_{2-6}$ alkynyl, —C$_{1-8}$ haloalkyl, C$_{1-8}$ alkoxy or C$_{3-15}$ cycloalkyl;

R$^W$ is —NR$^1$R$^2$, —C$_{1-6}$ alkylNR$^1$R$^2$, —O—C$_{1-6}$ alkylNR$^1$R$^2$, —C$_{1-6}$ alkyl-O—C$_{1-6}$ alkylNR$^1$R$^2$, —NR$^a$—C$_{1-6}$ alkylNR$^1$R$^2$, —C$_{1-6}$ alkylN$^+$R$^1$R$^2$R$^3$, —S—C$_{1-6}$ alkylNR$^1$R$^2$, —C(O)NR$^1$R$^2$, —S(O)$_2$R$^a$, —(CH$_2$)$_u$S(O)$_2$NR$^1$R$^2$, —(CH$_2$)$_u$NR$^a$S(O)$_2$NR$^a$R$^b$, —S(O)$_2$NR$^a$C$_{1-6}$ alkylNR$^1$R$^2$, —NR$^a$S(O)$_2$C$_{1-6}$ alkylNR$^1$R$^2$, —(CH$_2$)$_u$C(O)NR$^a$S(O)$_2$NR$^a$R$^b$, —(CH$_2$)N$^+$R$^1$R$^2$O$^-$, —(CH$_2$)$_u$P$^+$R$^b$R$^c$R$^d$, —(CH$_2$)$_u$P$^+$R$^c$R$^d$O$^-$, —(CH$_2$)$_u$P$^+$O[NR$^a$R$^b$][NR$^c$R$^d$], —(CH$_2$)$_u$NR$^a$P(O)(OR$^c$)$_2$, —(CH$_2$)CH$_2$OP(O)(OR$^c$)(OR$^d$), —(CH$_2$)$_u$OP(O)(OR$^c$)(OR$^d$), —(CH$_2$)$_u$OP(O)NR$^a$R$^b$)(OR$^a$), or

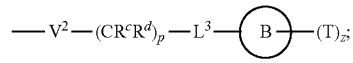

wherein:

V² is independently a bond, —O—, —NR$^a$—, —S—, —SO—, —SO$_2$—, —C(O)NR$^a$—, —NR$^a$C(O)—, —S(O)$_2$NR$^1$—, or —NR$^a$S(O)$_2$—;

L³ is independently a bond, —O—, —NR$^a$—, —S—, —SO—, —SO$_2$—, —C(O)NR$^a$—, —NR$^a$C(O)—, —S(O)$_2$NR$^1$—, or —NR$^a$S(O)$_2$—;

ring B is independently cycloalkyl, aryl, heteroaryl, or heterocyclyl;

T is independently hydrogen, —OR$^a$, —(CH$_2$)$_q$NR$^1$R$^2$, —(CH$_2$)$_q$NR$^a$C(O)R$^e$, or —(CH$_2$)$_q$C(O)R$^e$;

p is independently 0, 1, 2, 3, 4, or 5;

q is independently 0, 1, 2, 3, 4, or 5;

u is 0, 1, 2, 3, or 4;

z is 0, 1, 2, or 3; and wherein the alkyl, cycloalkyl, aryl, heteroaryl, or heterocyclyl of R$^E$ or R$^W$ is optionally substituted with 1 to 3 substituents independently selected from the group consisting of —NR$^a$R$^b$, halo, cyano, oxo, —OR$^a$, —C$_{1-6}$ alkyl, —C$_{1-6}$ haloalkyl, —C$_{1-6}$ cyanoalkyl, —C$_{1-6}$ alkylNR$^a$R$^b$, —C$_{1-6}$ hydroxyalkyl, —C$_{3-8}$ cycloalkyl, and —C$_{1-3}$ alkylC$_{3-8}$ cycloalkyl;

provided that at least one of V², L³, ring B and T contains a nitrogen atom;

each R¹ is independently selected from hydrogen, —C$_{1-8}$ alkyl, —C$_{2-6}$ alkenyl, —C$_{2-6}$ alkynyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{1-6}$ alkylC(O)OR$^a$, —C$_{2-6}$ alkenylC(O)OR$^a$, —S(O)$_2$R$^a$, —S(O)$_2$NR$^a$R$^b$, —C(O)NR$^a$S(O)$_2$R$^a$, and —C$_{1-6}$ alkylC$_{3-8}$ cycloalkyl;

wherein each alkyl, alkenyl, cycloalkyl, aryl, heteroaryl, or heterocyclyl is optionally substituted with 1 to 4 groups independently selected from —OR$^a$, cyano, halo, C$_{1-6}$ alkyl, —C$_{1-6}$ alkylOR$^a$, —C$_{1-6}$ cyanoalkyl, —C$_{1-6}$ haloalkyl, C$_{3-8}$ cycloalkyl, —C$_{1-3}$ alkylC$_{3-8}$ cycloalkyl, —C(O)R$^a$, —C$_{1-6}$ alkylC(O)R$^a$, —C(O)OR$^a$, —C$_{1-6}$ alkylC(O)OR$^a$, —NR$^a$R$^b$, —OC(O)NR$^a$R$^b$, NR$^a$C(O)OR$^b$, —C$_{1-6}$ alkylNR$^a$R$^b$, —C(O)NR$^a$R$^b$, —C$_{1-6}$ alkylC(O)NR$^a$R$^b$, —S(O)$_2$R$^a$, —C$_{1-6}$ alkylS(O)$_2$R$^a$, —S(O)$_2$NR$^a$R$^b$, —C$_{1-6}$ alkylS(O)$_2$NR$^a$R$^b$, —C(O)NR$^a$S(O)$_2$R$^b$, —C$_{1-6}$ alkylC(O)NR$^a$S(O)$_2$R$^b$, —NR$^a$C(O)R$^b$, and —C$_{1-6}$ alkylNR$^a$C(O)R$^b$;

each R² is independently selected from hydrogen, —C$_{1-6}$ alkyl, —C$_{2-6}$ alkenyl, —C$_{2-6}$ alkynyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{2-6}$ alkyl-OR$^a$, —C$_{1-6}$ alkylC(O)OR$^a$, and —C$_{2-6}$ alkenylC(O)OR$^a$;

wherein each alkyl, alkenyl, alkynyl, cycloalkyl, aryl, heteroaryl, or heterocyclyl is optionally substituted with 1 to 4 groups independently selected from —OR$^a$, cyano, halo, C$_{1-6}$ alkyl, —C$_{1-6}$ alkylOR$^a$, —C$_{1-6}$ cyanoalkyl, —C$_{1-6}$ haloalkyl, —C$_{3-8}$ cycloalkyl, —C$_{1-3}$ alkylC$_{3-8}$ cycloalkyl, —C(O)R$^a$, —C$_{1-6}$ alkylC(O)R$^a$, —C(O)OR$^a$, —C$_{1-6}$ alkylC(O)OR$^a$, —NR$^a$R$^b$, —C$_{1-6}$ alkylNR$^a$R$^b$, —C(O)NR$^a$R$^b$, C$_{1-6}$ alkylC(O)NR$^a$R$^b$, —S(O)$_2$R$^a$, —C$_{1-6}$ alkylS(O)$_2$R$^a$, —S(O)$_2$NR$^a$R$^b$, —C$_{1-6}$ alkylS(O)$_2$NR$^a$R$^b$, —C(O)NR$^a$S(O)$_2$R$^b$ and —NR$^a$C(O)R$^b$;

or R¹ and R² combine to form a heterocyclyl optionally substituted with 1 to 3 groups independently selected from oxo, —C$_{1-6}$ alkyl, —C$_{3-8}$ cycloalkyl, —C$_{2-6}$ alkenyl, —C$_{2-6}$ alkynyl, —OR$^a$, —C(O)OR$^a$, —C$_{1-6}$ cyanoalkyl, —C$_{1-6}$ alkylOR$^a$, —C$_{1-6}$ haloalkyl, —C$_{1-3}$ alkylC$_{3-8}$ cycloalkyl, —C(O)R$^a$, C$_{1-6}$ alkylC(O)R$^a$, —C$_{1-6}$ alkylC(O)OR$^a$, —NR$^a$R$^b$, —C$_{1-6}$ alkylNR$^a$R$^b$, —C(O)NR$^a$R$^b$, —C$_{1-6}$ alkylC(O)NR$^a$R$^b$, —S(O)$_2$R$^a$, —C$_{1-6}$ alkylS(O)$_2$R$^a$, —S(O)$_2$NR$^a$R$^b$, —C(O)N=S(O)R$^a$NR$^a$R$^b$, —C(O)N=S(O)R$^a$NR$^a$C(O)R$^b$, and —C$_{1-6}$ alkylS(O)$_2$NR$^a$R$^b$;

each R³ is independently hydrogen, —C$_{1-6}$ alkyl, —C$_{2-6}$ alkenyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{2-6}$ alkyl-OR$^a$, —C$_{1-6}$ alkylC(O)OR$^a$, or —C$_{2-6}$ alkenylC(O)OR$^a$;

each R$^a$ is independently selected from hydrogen, —C$_{1-6}$ alkyl, —C$_{1-6}$ cyanoalkyl, —C$_{1-6}$ haloalkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl;

each $R^b$ is independently selected from hydrogen, —$C_{1-6}$ alkyl, —$C_{1-6}$ cyanoalkyl, —$C_{1-6}$ haloalkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$ alkylheterocyclyl;

or $R^a$ and $R^b$ may combine together to form a heterocyclyl optionally substituted with 1 to 4 groups independently selected from —$OR^f$, cyano, halo, —$C_{1-6}$ alkyl$OR^f$, —$C_{1-6}$ cyanoalkyl, —$C_{1-6}$ haloalkyl, —$C_{3-8}$ cycloalkyl, —$C_{1-3}$ alkyl$C_{3-8}$ cycloalkyl, —C(O)$R^f$, —$C_{1-6}$ alkylC(O)$R^f$, —C(O)O$R^f$, —$C_{1-6}$ alkylC(O)O$R^f$, —N$R^fR^g$, —$C_{1-6}$ alkylN$R^fR^g$, —C(O)N$R^fR^g$, —$C_{1-6}$ alkylC(O)N$R^fR^g$, —S(O)$_2R^f$, —$C_{1-6}$ alkylS(O)$_2R^f$, —S(O)$_2$N$R^fR^g$, —$C_{1-6}$ alkylS(O)$_2$N$R^fR^g$, —C(O)N$R^f$S(O)$_2R^g$ and —N$R^f$C(O)$R^g$;

each $R^c$ is independently selected from hydrogen, —OH, —$C_{1-6}$ alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$ alkylheterocyclyl;

each $R^d$ is independently selected from hydrogen, —$C_{1-6}$ alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$ alkylheterocyclyl;

each $R^e$ is independently selected from hydrogen, —$C_{1-6}$ alkyl, —O—$C_{1-6}$ alkyl, —$C_{3-8}$ cycloalkyl, aryl, heteroaryl, heterocyclyl, —O—$C_{3-8}$ cycloalkyl, —O-aryl, —O-heteroaryl, —O-heterocyclyl, —$C_{1-3}$ alkyl$C_{3-8}$ cycloalkyl, —$C_{1-6}$ alkylaryl, —$C_{1-6}$ alkylheteroaryl, —N$R^fR^g$, —$C_{1-6}$ alkylN$R^fR^g$, —C(O)N$R^fR^g$, —$C_{1-6}$ alkylC(O)N$R^fR^g$, —NHS(O)$_2R^f$, —$C_{1-6}$ alkylS(O)$_2R^f$, and —$C_{1-6}$ alkylS(O)$_2$N$R^fR^g$;

each $R^f$ is independently selected from hydrogen, —$C_{1-6}$ alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$ alkylheterocyclyl; and each $R^g$ is independently selected from hydrogen, —$C_{1-6}$ alkyl, —$C_{3-8}$ cycloalkyl, aryl, heteroaryl, heterocyclyl, —$C_{1-3}$ alkyl$C_{3-8}$ cycloalkyl, —$C_{1-6}$ alkylaryl, —$C_{1-6}$ alkylheteroaryl, and —$C_{1-6}$ alkylheterocyclyl.

In certain embodiments, $Z^1$ and $Z^2$ are each independently hydrogen, halo, —NH$_2$, —OH, —CN, $C_{1-9}$ alkyl, $C_{2-6}$ alkenyl, $C_{2-6}$ alkynyl, $C_{1-8}$ haloalkyl or $C_{1-8}$ alkoxy.

In certain embodiments, $Z^1$ and $Z^2$ are each independently hydrogen, halo, or —$C_{1-9}$ alkyl.

Also provided is a compound of Formula (IA):

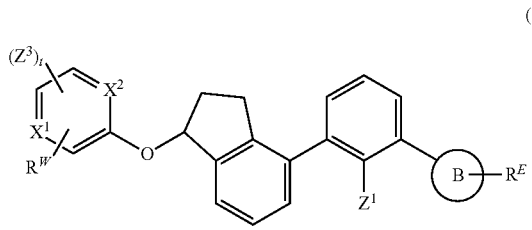

(IA)

or a pharmaceutically acceptable salt, stereoisomer, mixture of stereoisomers, solvate, or tautomer thereof, wherein t, $X^1$, $X^2$, $Z^1$, $Z^3$, $R^W$, $R^E$ and ring B are as defined herein.

Also provided is a compound of Formula (IA-a):

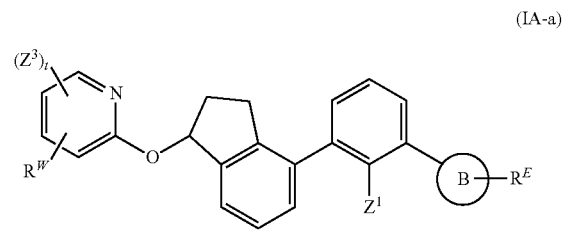

(IA-a)

or a pharmaceutically acceptable salt, stereoisomer, mixture of stereoisomers, solvate, or tautomer thereof, wherein t, $Z^1$, $Z^3$, $R^W$, $R^E$ and ring B are as defined herein.

Also provided is a compound of Formula (IA-b):

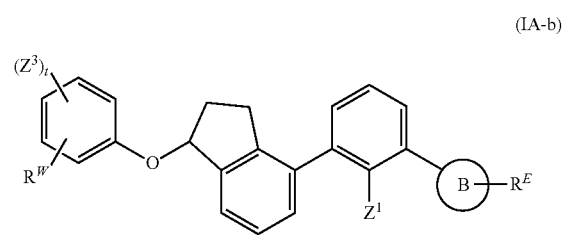

(IA-b)

or a pharmaceutically acceptable salt, stereoisomer, mixture of stereoisomers, solvate, or tautomer thereof, wherein t, $Z^1$, $Z^3$, $R^W$, $R^E$ and ring B are as defined herein.

Also provided is a compound of Formula (IA-c):

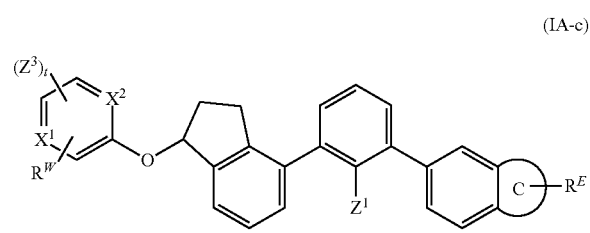

(IA-c)

or a pharmaceutically acceptable salt, stereoisomer, mixture of stereoisomers, solvate, or tautomer thereof, wherein t, $X^1$, $X^2$, $Z^1$, $Z^3$, $R^W$, $R^E$ and ring C are as defined herein.

Also provided is a compound of Formula (IA-d):

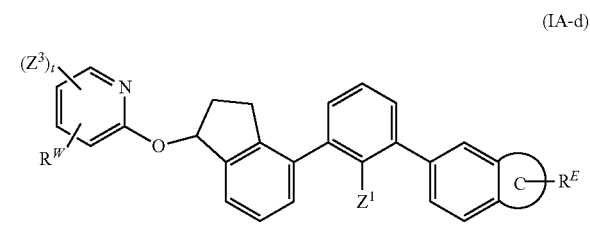

(IA-d)

or a pharmaceutically acceptable salt, stereoisomer, mixture of stereoisomers, solvate, or tautomer thereof, wherein t, $Z^1$, $Z^3$, $R^W$, $R^E$ and ring C are as defined herein.

Also provided is a compound of Formula (IA-e):

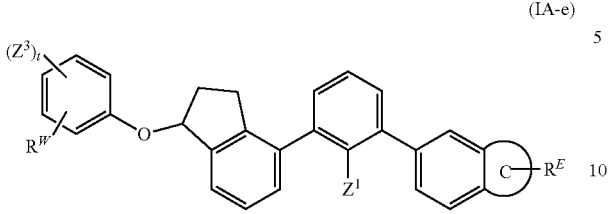
(IA-e)

or a pharmaceutically acceptable salt, stereoisomer, mixture of stereoisomers, solvate, or tautomer thereof, wherein t, $Z^1$, $Z^3$, $R^W$, $R^E$ and ring C are as defined herein.

Also provided is a compound of Formula (IA-f):

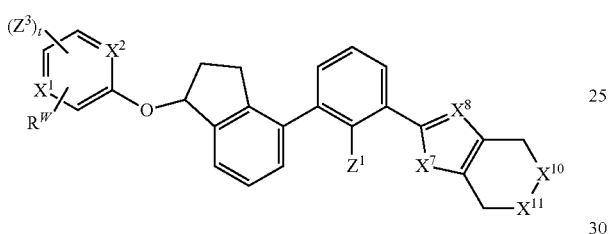
(IA-f)

or a pharmaceutically acceptable salt, stereoisomer, mixture of stereoisomers, solvate, or tautomer thereof, wherein t, $X^1$, $X^2$, $X^7$, $X^8$, $X^{10}$, $X^{11}$, $Z^1$, $Z^3$, $R^W$ and $R^E$ are as defined herein.

Also provided is a compound of Formula (IA-g):

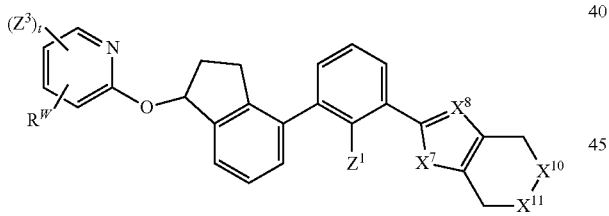
(IA-g)

or a pharmaceutically acceptable salt, stereoisomer, mixture of stereoisomers, solvate, or tautomer thereof, wherein t, $X^7$, $X^8$, $X^{10}$, $X^{11}$, $Z^1$, $Z^3$, $R^W$ and $R^E$ are as defined herein.

Also provided is a compound of Formula (IA-h):

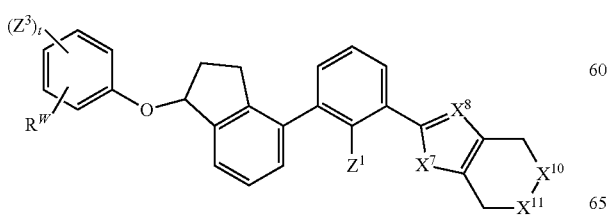
(IA-h)

or a pharmaceutically acceptable salt, stereoisomer, mixture of stereoisomers, solvate, or tautomer thereof, wherein t, $X^7$, $X^8$, $X^{10}$, $X^{11}$, $Z^1$, $Z^3$, $R^W$ and $R^E$ are as defined herein.

Also provided is a compound of Formula (IB):

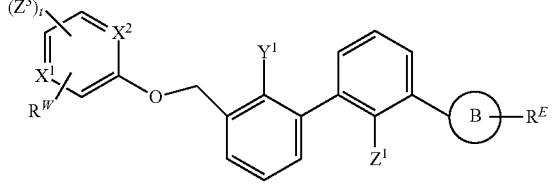
(IB)

or a pharmaceutically acceptable salt, stereoisomer, mixture of stereoisomers, solvate, or tautomer thereof, wherein t, $Y^1$, $X^1$, $X^2$, $Z^1$, $Z^3$, $R^W$, $R^E$ and ring B are as defined herein.

Also provided is a compound of Formula (IB-a):

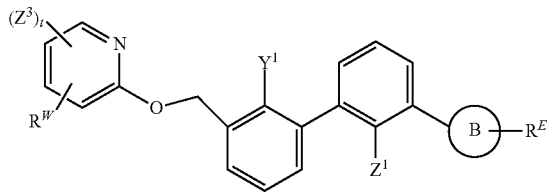
(IB-a)

or a pharmaceutically acceptable salt, stereoisomer, mixture of stereoisomers, solvate, or tautomer thereof, wherein t, $Y^1$, $Z^1$, $Z^3$, $R^W$, $R^E$ and ring B are as defined herein.

Also provided is a compound of Formula (IB-b):

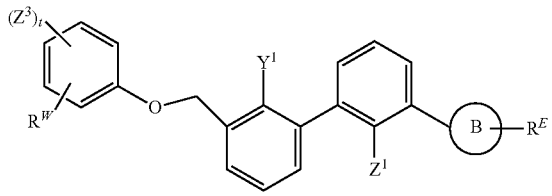
(IB-b)

or a pharmaceutically acceptable salt, stereoisomer, mixture of stereoisomers, solvate, or tautomer thereof, wherein t, $Y^1$, $Z^1$, $Z^3$, $R^W$, $R^E$ and ring B are as defined herein.

Also provided is a compound of Formula (IB-c):

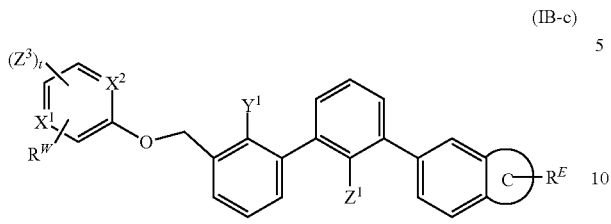

or a pharmaceutically acceptable salt, stereoisomer, mixture of stereoisomers, solvate, or tautomer thereof, wherein t, $Y^1$, $X^1$, $X^2$, $Z^1$, $Z^3$, $R^W$, $R^E$ and ring C are as defined herein.

Also provided is a compound of Formula (IB-d):

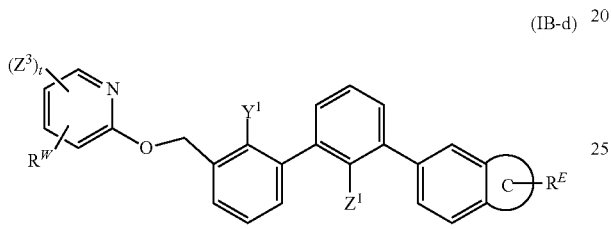

or a pharmaceutically acceptable salt, stereoisomer, mixture of stereoisomers, solvate, or tautomer thereof, wherein t, $Y^1$, $Z^1$, $Z^3$, $R^W$, $R^E$ and ring C are as defined herein.

Also provided is a compound of Formula (IB-e):

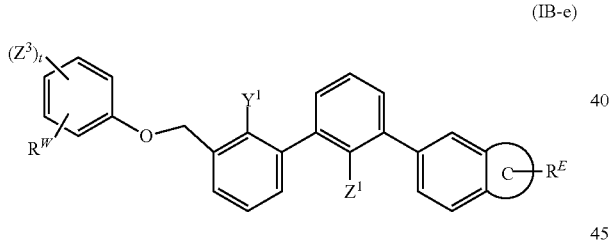

or a pharmaceutically acceptable salt, stereoisomer, mixture of stereoisomers, solvate, or tautomer thereof, wherein t, $Y^1$, $Z^1$, $Z^3$, $R^W$, $R^E$ and ring C are as defined herein.

Also provided is a compound of Formula (IB-f):

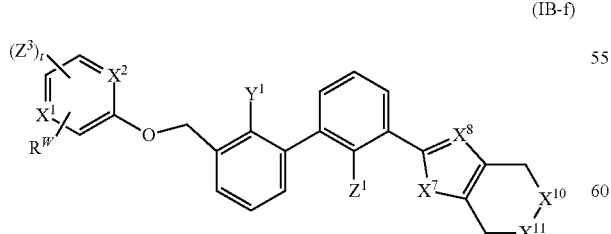

or a pharmaceutically acceptable salt, stereoisomer, mixture of stereoisomers, solvate, or tautomer thereof, wherein t, $Y^1$, $X^1$, $X^2$, $X^7$, $X^8$, $X^{10}$, $X^{11}$, $Z^1$, $Z^3$, $R^W$ and $R^E$ are as defined herein.

Also provided is a compound of Formula (IB-g):

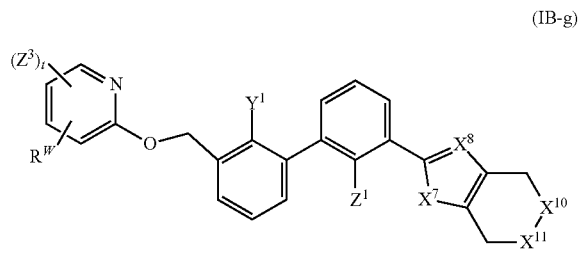

or a pharmaceutically acceptable salt, stereoisomer, mixture of stereoisomers, solvate, or tautomer thereof, wherein t, $Y^1$, $X^7$, $X^8$, $X^{10}$, $X^{11}$, $Z^1$, $Z^3$, $R^W$ and $R^E$ are as defined herein.

Also provided is a compound of Formula (IB-h):

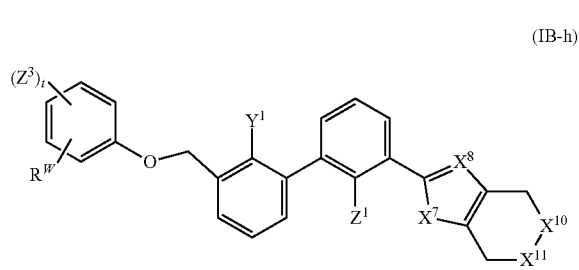

or a pharmaceutically acceptable salt, stereoisomer, mixture of stereoisomers, solvate, or tautomer thereof, wherein t, $Y^1$, $X^7$, $X^8$, $X^{10}$, $X^{11}$, $Z^1$, $Z^3$, $R^W$ and $R^E$ are as defined herein.

Also provided is a compound of Formula (IIA):

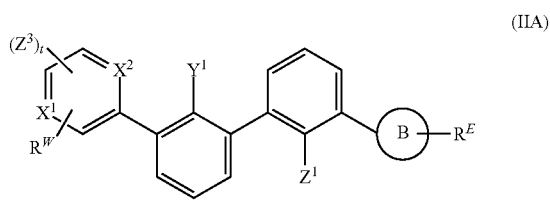

or a pharmaceutically acceptable salt, stereoisomer, mixture of stereoisomers, solvate, or tautomer thereof, wherein t, $Y^1$, $X^1$, $X^2$, $Z^1$, $Z^3$, $R^W$, $R^E$ and ring B are as defined herein.

Also provided is a compound of Formula (IIA-a):

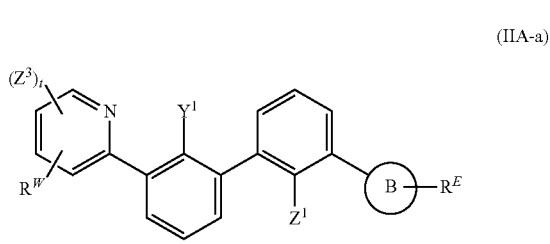

or a pharmaceutically acceptable salt, stereoisomer, mixture of stereoisomers, solvate, or tautomer thereof, wherein t, $Y^1$, $Z^1$, $Z^3$, $R^W$, $R^E$ and ring B are as defined herein.

Also provided is a compound of Formula (IIA-b):

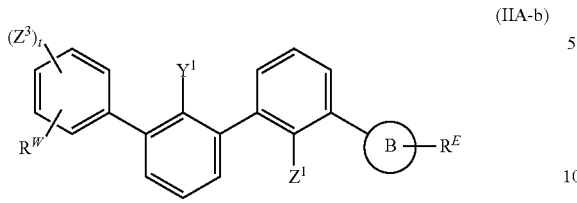

(IIA-b)

or a pharmaceutically acceptable salt, stereoisomer, mixture of stereoisomers, solvate, or tautomer thereof, wherein t, $Y^1$, $Z^1$, $Z^3$, $R^W$, $R^E$ and ring B are as defined herein.

Also provided is a compound of Formula (IIA-c):

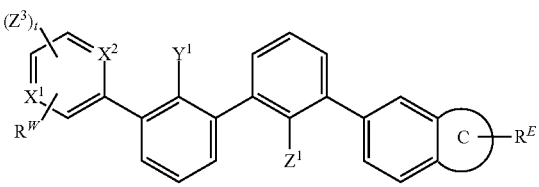

(IIA-c)

or a pharmaceutically acceptable salt, stereoisomer, mixture of stereoisomers, solvate, or tautomer thereof, wherein t, $Y^1$, $X^1$, $X^2$, $Z^1$, $Z^3$, $R^W$, $R^E$ and ring C are as defined herein.

Also provided is a compound of Formula (IIA-d):

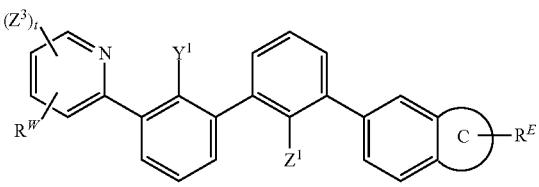

(IIA-d)

or a pharmaceutically acceptable salt, stereoisomer, mixture of stereoisomers, solvate, or tautomer thereof, wherein t, $Y^1$, $Z^1$, $Z^3$, $R^W$, $R^E$ and ring C are as defined herein.

Also provided is a compound of Formula (IIA-e):

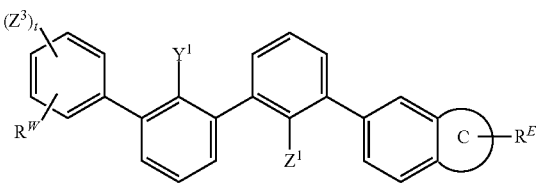

(IIA-e)

or a pharmaceutically acceptable salt, stereoisomer, mixture of stereoisomers, solvate, or tautomer thereof, wherein t, $Y^1$, $Z^1$, $Z^3$, $R^W$, $R^E$ and ring C are as defined herein.

Also provided is a compound of Formula (IIA-f):

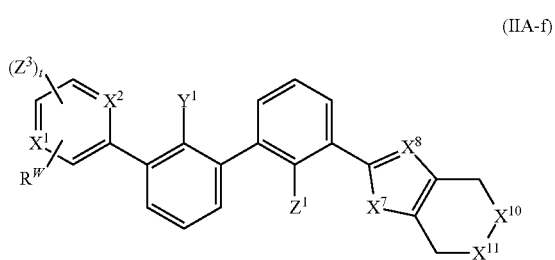

(IIA-f)

or a pharmaceutically acceptable salt, stereoisomer, mixture of stereoisomers, solvate, or tautomer thereof, wherein t, $Y^1$, $X^1$, $X^2$, $X^7$, $X^8$, $X^{10}$, $X^{11}$, $Z^1$, $Z^3$, $R^W$ and $R^E$ are as defined herein.

Also provided is a compound of Formula (IIA-g):

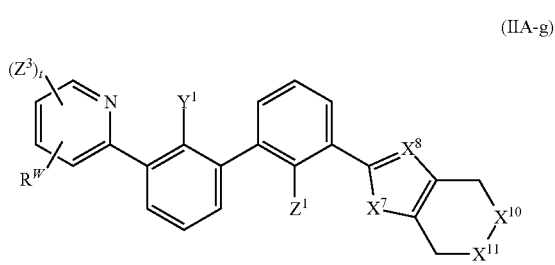

(IIA-g)

or a pharmaceutically acceptable salt, stereoisomer, mixture of stereoisomers, solvate, or tautomer thereof, wherein t, $Y^1$, $X^7$, $X^8$, $X^{10}$, $X^{11}$, $Z^1$, $Z^3$, $R^W$ and $R^E$ are as defined herein.

Also provided is a compound of Formula (IIA-h):

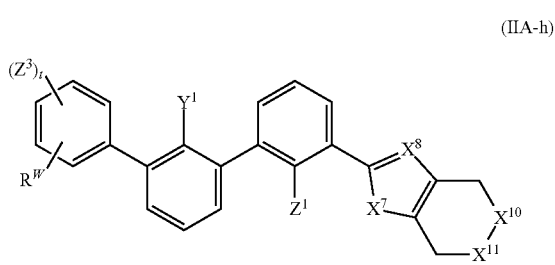

(IIA-h)

or a pharmaceutically acceptable salt, stereoisomer, mixture of stereoisomers, solvate, or tautomer thereof, wherein t, $Y^1$, $X^7$, $X^8$, $X^{10}$, $X^{11}$, $Z^1$, $Z^3$, $R^W$ and $R^E$ are as defined herein.

In certain embodiments, $Z^1$ is hydrogen, halo, or —$C_{1-9}$ alkyl.

In certain embodiments, t is 1.

In certain embodiments, $Z^3$ is hydrogen, halo, —OH, —CN, —$C_{1-9}$ alkyl, $C_{2-6}$ alkenyl, —$C_{2-6}$ alkynyl, —$C_{1-8}$ haloalkyl, —$C_{1-8}$ alkoxy or —$C_{3-15}$ cycloalkyl.

In certain embodiments, $R^E$ is hydrogen, —OH, —$NR^1C(O)NR^1R^2$, —$C_{1-6}$ alkylOC(O)$NR^1R^2$, or —$C_{1-6}$ alkyl$NR^1C(O)R^2$.

In certain embodiments, $R^E$ is hydrogen.

In certain embodiments, $X^7$ is N or S and $X^8$ is N or CH.

In certain embodiments, $X^7$ is S and $X^8$ is N.

In certain embodiments, $X^7$ is S and $X^8$ is CH.

In certain embodiments, $X^7$ is N and $X^8$ is N.

In certain embodiments, each $Z^1$ is independently halo.

In certain embodiments, $Z^3$ is halo, —$C_{1-9}$ alkyl, $C_{1-8}$ haloalkyl, —O—$C_{1-8}$ cyanoalkyl, —O—$C_{1-8}$ haloalkyl, or $C_{1-8}$ alkoxy.

In certain embodiments, $Z^3$ is of the formula:

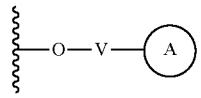

V is independently selected from a bond, $C_{1-6}$ alkyl, $C_{2-6}$ alkenyl, and $C_{2-6}$ alkynyl;
  wherein each alkyl, alkenyl, or alkynyl is optionally independently substituted with —OR$^a$, halo, cyano, —NR$^a$R$^b$ or —$C_{3-8}$ cycloalkyl;
ring A is independently cycloalkyl, aryl, heteroaryl, or heterocyclyl;
  wherein each cycloalkyl, aryl, heteroaryl, or heterocyclyl is optionally substituted with 1 to 4 groups independently selected from oxo, —NO$_2$, —N$_3$, —OR$^a$, halo, cyano, —$C_{1-6}$ alkyl, —$C_{1-6}$ haloalkyl, —$C_{2-6}$ alkenyl, —$C_{2-6}$ alkynyl, —O—$C_{1-6}$ haloalkyl, NR$^a$R$^b$, —C(O)R$^a$, —C(O)OR$^a$, —OC$_{1-6}$ alkylCN, —C(O)NR$^a$R$^b$, —NR$^a$C(O)R$^a$, NR$^a$C(O)OR$^a$, —NR$^a$C(O)OR$^a$, —C(O)N(R$^a$)OR$^b$, —S(O)$_2$R$^a$, —S(O)$_2$NR$^a$R$^b$, —NR$^a$S(O)$_2$R$^b$, —NR$^a$S(O)$_2$NR$^a$R$^b$, —C(O)NR$^a$S(O)$_2$NR$^a$R$^b$, —$C_{3-8}$ cycloalkyl, heteroaryl, and —$C_{1-6}$ alkyl$C_{3-8}$ cycloalkyl.

In certain embodiments, R$^W$ is —$C_{1-6}$ alkylNR$^1$R$^2$, where R$^1$ and R$^2$ combine to form a heterocyclyl optionally substituted with 1 to 3 groups independently selected from oxo, —$C_{1-6}$ alkyl, —$C_{3-8}$ cycloalkyl, —$C_{2-6}$ alkenyl, —$C_{2-6}$ alkynyl, —OR$^a$, —C(O)OR$^a$, —$C_{1-6}$ cyanoalkyl, —$C_{1-6}$ alkylOR$^a$, —$C_{1-6}$ haloalkyl, —$C_{1-3}$ alkyl$C_{3-8}$ cycloalkyl, —C(O)R$^a$, —$C_{1-6}$ alkylC(O)R$^a$, —$C_{1-6}$ alkylC(O)OR$^a$, —NR$^a$R$^b$, —$C_{1-6}$ alkylNR$^a$R$^b$, —C(O)NR$^a$R$^b$, —$C_{1-6}$ alkylC(O)NR$^a$R$^b$, —S(O)$_2$R$^a$, —$C_{1-6}$ alkylS(O)$_2$R$^a$, —S(O)$_2$NR$^a$R$^b$, —C(O)N=S(O)R$^a$NR$^a$R$^b$, —C(O)N=S(O)R$^a$NR$^a$C(O)R$^b$, and —$C_{1-6}$ alkylS(O)$_2$NR$^a$R$^b$; or
  —$C_{1-6}$ alkylNR$^1$R$^2$, where R$^1$ is hydrogen and R$^2$ is —$C_{1-6}$ alkylheteroaryl or —$C_{1-6}$ alkylheterocyclyl.

In certain embodiments, R$^W$ is —$C_{1-6}$ alkylNR$^1$R$^2$.

In certain embodiments, R$^E$ is hydrogen and R$^W$ is —$C_{1-6}$ alkylNR$^1$R$^2$.

In certain embodiments, R$^1$ and R$^2$ combine to form a heterocyclyl optionally substituted with 1 to 3 groups independently selected from oxo, —$C_{1-6}$ alkyl, —$C_{3-8}$ cycloalkyl, —$C_{2-6}$ alkenyl, —$C_{2-6}$ alkynyl, —OR$^a$, —C(O)OR$^a$, —$C_{1-6}$ cyanoalkyl, —$C_{1-6}$ alkylOR$^a$, —$C_{1-6}$ haloalkyl, —$C_{1-3}$ alkyl$C_{3-8}$ cycloalkyl, —C(O)R$^a$, —$C_{1-6}$ alkylC(O)R$^a$, —$C_{1-6}$ alkylC(O)OR$^a$, —NR$^a$R$^b$, —$C_{1-6}$ alkylNR$^a$R$^b$, —C(O)NR$^a$R$^b$, —$C_{1-6}$ alkylC(O)NR$^a$R$^b$, —S(O)$_2$R$^a$, —$C_{1-6}$ alkylS(O)$_2$R$^a$, —S(O)$_2$NR$^a$R$^b$, —C(O)N=S(O)R$^a$NR$^a$R$^b$, —C(O)N=S(O)R$^a$NR$^a$C(O)R$^b$, and —$C_{1-6}$ alkylS(O)$_2$NR$^a$R$^b$.

In certain embodiments, R$^1$ is hydrogen and R$^2$ is —$C_{1-6}$ alkylheteroaryl.

In certain embodiments, R$^1$ is hydrogen and R$^2$ is —$C_{1-6}$ alkylheterocyclyl.

In certain embodiments, provided is a compound as shown in Table 1, or a pharmaceutically acceptable salt, stereoisomer, mixture of stereoisomers, solvate, or tautomer thereof.

In certain embodiments, the compound as provided herein has a molecular weight of less than about 850 g/mol, or less than about 800 g/mol, or less than about 750 g/mol, or less than about 700 g/mol, or between about 500 to about 850 g/mol, or between about 500 to about 600 g/mol, or between about 550 to about 650 g/mol, or between about 600 to about 700 g/mol, or between about 650 to about 750 g/mol, or between about 700 to about 800 g/mol, or between about 750 to about 850 g/mol.

One of skill in the art is aware that each and every embodiment of a group (e.g., R$^E$) disclosed herein may be combined with any other embodiment of each of the remaining groups (e.g., R$^W$, Z$^1$, Z$^3$, etc.) to generate a complete compound of Formula (I) or (II), or any formula described herein or a pharmaceutically acceptable salt, stereoisomer, mixture of stereoisomers, solvate, or tautomer thereof, each of which is deemed within the ambit of the present disclosure.

Formulations and Methods

PD-1 and its ligand, PD-L1, are monomeric type I transmembrane proteins that play critical roles in T cell inhibition and exhaustion. PD-L1 is composed of two extracellular immunoglobulin (Ig)-like domains whereas PD-1 is composed of a single extracellular Ig like domain and an intracellular tail. The crystal structure of the PD-1/PD-L1 complex reveals that PD-1 binds to PD-L1 with a 1:1 stoichiometry to form a monomeric complex (see, e.g., Cheng et al. *J Biol Chem*, 2013; 288(17); 11771-85, Lin et al. *Proc Natl Acad Sci USA*, 2008; 105(8); 3011-6, Zak et al. *Structure*, 2015; 23(12); 2341-8). This arrangement represents a distinct ligand-binding mode and signaling mechanism that differs from other co-inhibitory receptor/ligand interactions such as CTLA-4/B7, where oligomerization plays an important role in signaling (see, e.g., Schwartz et al. *Nature*, 2001; 410(6828); 604-8). Engagement of PD-1 to PD-L1, along with TCR signaling, leads to phosphorylation of the cytoplasmic domain tyrosines on PD-1 and recruitment of Src-homology 2-containing tyrosine phosphatases (SHP-1 and SHP-2). These phosphatases dephosphorylate TCR-associated proteins, resulting in alteration of downstream signaling including blocking phosphoinositide 3 kinase (PI3K) and Akt kinase activation, disrupting glucose metabolism, and inhibiting IL-2 and IFN-γ secretion (see, e.g., Hofmeyer et al. *J Biomed Biotechnol*, 2011; 2011; 451694, Latchman et al. Nature immunology, 2001; 2(3); 261-8).

Monoclonal antibodies developed for cancer immunotherapy binding to either PD-1 or PD-L1 have demonstrated significant response rates in patients, particularly for melanoma, non-small cell lung cancer (NSCLC), renal cell carcinoma (RCC) and bladder cancer. Many of these studies have shown that blockade of the PD-1/PD-L1 axis leads to an enhancement in T cell cytotoxic activity at the tumor site (see, e.g., Wherry E J. *Nat Immunol*, 2011; 12(6); 492-9). In addition to cancer, inhibition of this pathway has also shown promise for the control or elimination of chronic viral infections, such as HBV (see, e.g., Bengsch et al. *J Hepatol*, 2014; 61(6); 1212-9, Fisicaro et al. *Gastroenterology*, 2010; 138(2), 682-93, 93 e1-4, Fisicaro et al. *Gastroenterology*, 2012; 143(6), 1576-85 e4).

Methods

In one embodiment, the present disclosure provides a compound of Formula (I) or (II), or any formula described herein, or a pharmaceutically acceptable salt, stereoisomer, mixture of stereoisomers, solvate, or tautomer thereof, useful as an inhibitor of PD-1, PD-L1 and/or the PD-1/PD-L1 interaction.

In some embodiments, compounds disclosed herein inhibit the PD-1/PD-L1 interaction by dimerizing PD-L1, or by inducing or stabilizing PD-L1 dimer formation.

In one embodiment, the present disclosure provides a pharmaceutical composition comprising a compound of Formula (I) or (II) or a pharmaceutically acceptable salt, stereoisomer, mixture of stereoisomers or tautomer thereof, at least one additional therapeutic agent suitable for treating an HBV infection, and at least one pharmaceutically acceptable carrier or excipient.

In one embodiment, provided is a compound of Formula (I) or (II) or a pharmaceutically acceptable salt, stereoisomer, mixture of stereoisomers or tautomer thereof, useful for treating an HBV infection or a condition in a patient that is amenable to treatment by inhibiting PD-1, PD-L1 or the PD-1/PD-L1 interaction.

In another embodiment, the present disclosure provides a compound of Formula (I) or (II) for use in the manufacture of a medicament for treating or eliminating HBV. Elimination of HBV during acute infection is associated with the emergence of functional HBV-specific $CD8^+$ T cells. In contrast, chronic infection is marked by the presence of dysfunctional HBV-specific $CD8^+$ T cells that are unable to control viral infection (see, e.g., Boni et al. *J Virol,* 2007; 81(8); 4215-4225, Ferrari, *Liver Int,* 2015; 35; Suppl 1:121-8, Fisicaro et al., *Gastroenterology,* 2010; 138(2); 682-693, 93 e1-4, Guidotti et al. *Cell,* 2015; 161(3); 486-500). Mechanisms that may contribute to the dysfunction of HBV-specific T cells in CHB include upregulation of inhibitory T cell receptors (e.g. PD-1, CTLA-4 and TIM-3), due to persistent high viral load and antigen levels (see, e.g., Boni et al. *J Virol,* 2007; 81(8); 4215-4225, Franzese et al. *J Virol,* 2005; 79(6); 3322-3328, Peppa et al. *J Exp Med,* 2013; 210(1); 99-114, Wherry E J. Nature immunology 2011; 12(6); 492-499). Among all inhibitory immune receptors, PD-1 is most frequently upregulated on HBV-specific T cells. Furthermore, multiple studies have confirmed that the majority of circulating and intrahepatic HBV-specific $CD8^+$ T cells in CHB patients are exhausted and express high levels of PD-1 (see, e.g., Bengsch et al. *J Hepatol,* 2014; 61(6); 1212-1219, Fisicaro et al., *Gastroenterology,* 2010; 138(2); 682-693, 93 e1-4). Notably, the defects in effector cytokine production by HBV-specific $CD4^+$ and $CD8^+$ T cells were partially reversed by blocking the PD-1/PD-L1 interaction with an anti-PD-L1 antibody in PBMCs isolated from CHB patients (see, e.g., Bengsch et al. *J Hepatol,* 2014; 61(6); 1212-1219, Fisicaro et al., *Gastroenterology,* 2010; 138(2); 682-693, 93 e1-4, Fisicaro et al. *Gastroenterology,* 2012; 143(6); 1576-1585 e4). Consistent with these preclinical data, a clinical study evaluating α-PD-1 therapy in CHB subjects showed significant reductions in HBsAg levels in the majority of subjects which includes three out of twenty patients with reduction in HBsAg levels of over 0.5 $log_{10}$ and one subject that experienced a functional cure (sustained HBsAg loss and appearance of anti-HBsAb) (see, e.g., Gane et al. "A phase 1 study evaluating anti-PD-1 treatment with or without GS-4774 in HBeAg negative chronic hepatitis B patients", Abstract PS-044, European Association for the Study of the Liver (EASL); 2017; Apr. 19-23; Amsterdam, The Netherlands). Taken together, these findings demonstrate that inhibiting the PD-1/PD-L1 axis may improve T cell function in CHB patients and increase the rates of functional cure. Disclosed herein are selective and potent PD-L1 small molecule inhibitors that bind specifically to PD-L1 and inhibit the PD-1/PD-L1 interaction by inducing PD-L1 dimerization.

In one embodiment, the present disclosure provides a method of treating infectious diseases in a patient in need thereof, comprising administering a compound of Formula (I) or (II), or any formula described herein, or a pharmaceutically acceptable salt, stereoisomer, mixture of stereoisomers, solvate, or tautomer thereof. In some embodiments, infectious diseases include diseases such as hepatitis A, hepatitis B (HBV), hepatitis C (HCV), hepatitis D (HDV), HIV, human papillomavirus (HPV), respiratory syncytial virus (RSV), severe acute respiratory syndrome (SARS), influenza, parainfluenza, cytomegalovirus, dengue, herpes simplex virus-1, herpes simplex virus-2, leishmania infection, and respiratory syncytial virus as well as coinfections thereof, including HDV/HBV coinfection. In certain embodiments, infectious diseases include diseases such as hepatitis A, hepatitis B (HBV), hepatitis D (HDV), HIV, human papillomavirus (HPV), respiratory syncytial virus (RSV), severe acute respiratory syndrome (SARS), influenza, parainfluenza, cytomegalovirus, dengue, herpes simplex virus-1, herpes simplex virus-2, leishmania infection, and respiratory syncytial virus.

In one embodiment, the present disclosure provides a method of treating cancer in a patient in need thereof, comprising administering a compound of Formula (I) or (II), or any formula described herein, or a pharmaceutically acceptable salt, stereoisomer, mixture of stereoisomers, solvate, or tautomer thereof, in combination with one or more check-point inhibitors selected from nivolumab, pembrolizumab, and artezolizumab.

In one embodiment, the present disclosure provides a pharmaceutical composition comprising a compound of Formula (I) or (II), or any formula described herein, or a pharmaceutically acceptable salt, stereoisomer, mixture of stereoisomers, solvate, or tautomer thereof, and a pharmaceutically acceptable carrier.

In one embodiment, the present disclosure provides a pharmaceutical composition comprising a compound of Formula (I) or (II), or any formula described herein, or a pharmaceutically acceptable salt, stereoisomer, mixture of stereoisomers, solvate, or tautomer thereof, and at least one additional anticancer agent and at least one pharmaceutically acceptable excipient.

The present disclosure provides a compound of Formula (I) or (II), or any formula described herein, or a pharmaceutically acceptable salt, stereoisomer, mixture of stereoisomers, solvate, or tautomer thereof, for use in therapy. In another embodiment, the present disclosure provides a compound of Formula (I) or (II), or any formula described herein, or a pharmaceutically acceptable salt, stereoisomer, mixture of stereoisomers, solvate, or tautomer thereof, for use in the manufacture of a medicament for treating cancer.

In one embodiment, provided is a compound of Formula (I) or (II), or any formula described herein, or a pharmaceutically acceptable salt, stereoisomer, mixture of stereoisomers, solvate, or tautomer thereof, useful for the treatment of cancer or a condition in a patient that is amenable to treatment by inhibiting PD-1, PD-L1 or the PD-1/PD-L1 interaction. Cancers that may be treated with the compounds of Formula (I) or (II) disclosed herein include pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, CNS cancer, brain cancer, bone cancer, soft tissue sarcoma, non-small cell lung cancer, small-cell lung cancer and colon cancer.

In one embodiment, provided is a compound of Formula (I) or (II), or any formula described herein, or a pharmaceutically acceptable salt, stereoisomer, mixture of stereoisomers, solvate, or tautomer thereof, useful for the treatment of cancer or a condition in a patient that is amenable to treatment by inhibiting PD-1, PD-L1 or the PD-1/PD-L1 interaction including, but not limited to, lymphoma, multiple myeloma, and leukemia. Additional diseases or conditions that may be treated include, but are not limited to acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), mantle cell lymphoma (MCL), follicular lymphoma, Waldestrom's macroglobulinemia (WM), T-cell lymphoma, B-cell lymphoma and diffuse large B-cell lymphoma (DLBCL).

"Administering" or "administration" refers to the delivery of one or more therapeutic agents to a patient. In one embodiment, the administration is a monotherapy wherein a compound of Formula (I) or (II), or any formula described herein, or a pharmaceutically acceptable salt, stereoisomer, mixture of stereoisomers, solvate, or tautomer thereof, is the only active ingredient administered to the patient in need of therapy. In another embodiment, the administration is co-administration such that two or more therapeutic agents are delivered together during the course of the treatment. In one embodiment, two or more therapeutic agents may be co-formulated into a single dosage form or "combined dosage unit", or formulated separately and subsequently combined into a combined dosage unit, as is typically for intravenous administration or oral administration as a mono or bilayer tablet or capsule.

In one embodiment, the compound of Formula (I) or (II), or any formula described herein, or a pharmaceutically acceptable salt, stereoisomer, mixture of stereoisomers, solvate, or tautomer thereof, in an effective amount, such as, from about 0.1 mg to about 1000 mg per day of said compound. In one embodiment, the effective amount is from about 0.1 mg to about 200 mg per day. In one embodiment, the effective amount is from about 1 mg to about 100 mg per day. In other embodiments, the effective amount is about 1 mg, about 3 mg, about 5 mg, about 10 mg, about 15 mg, about 18 mg, about 20 mg, about 30 mg, about 40 mg, about 60 mg, about 80 mg, or about 100 mg per day.

In one embodiment, the compound of Formula (I) or (II), or any formula described herein, or a pharmaceutically acceptable salt, stereoisomer, mixture of stereoisomers, solvate, or tautomer thereof, and at least one additional anticancer agent is administered to a human patient in need thereof in an effective amount of each agent, independently from about 0.1 mg to about 1000 mg per compound or formulation per day per compounds. In one embodiment, the effective amount of the combination treatment of a compound of Formula (I) or (II), or any formula described herein, or a pharmaceutically acceptable salt, stereoisomer, mixture of stereoisomers, solvate, or tautomer thereof, and an additional compound is independently from about 0.1 mg to about 200 mg per compound per day. In one embodiment, the effective amount of the combination treatment of a compound of Formula (I) or (II), or any formula described herein, or a pharmaceutically acceptable salt, stereoisomer, mixture of stereoisomers, solvate, or tautomer thereof, and an additional compound is independently from about 1 mg to about 100 mg per compound per day. In other embodiments, the effective amount of the combination treatment of a compound of Formula (I) or (II), or any formula described herein, or a pharmaceutically acceptable salt, stereoisomer, mixture of stereoisomers, solvate, or tautomer thereof, and an additional compound is for each component, about 1 mg, about 3 mg, about 5 mg, about 10 mg, about 15 mg, about 18 mg, about 20 mg, about 30 mg, about 40 mg, about 60 mg, about 80 mg, about 100 mg, about 200 mg, or about 500 mg each per day.

In one embodiment, the compound of Formula (I) or (II), or any formula described herein, or a pharmaceutically acceptable salt, stereoisomer, mixture of stereoisomers, solvate, or tautomer thereof, and/or a combination of the compound of Formula (I) or (II), or any formula described herein, or a pharmaceutically acceptable salt, stereoisomer, mixture of stereoisomers, solvate, or tautomer thereof, and an additional anticancer agent or a pharmaceutically acceptable salt thereof is administered once a day. In yet another embodiment, the compound of Formula (I) or (II), or any formula described herein, or a pharmaceutically acceptable salt, stereoisomer, mixture of stereoisomers, solvate, or tautomer thereof, and/or an additional anticancer agent or a pharmaceutically acceptable salt thereof is administered as a loading dose of from about 10 mg to about 500 mg per compound on the first day and each day or on alternate days or weekly for up to a month followed by a regular regimen of a compound of Formula (I) or (II), or any formula described herein, or a pharmaceutically acceptable salt, stereoisomer, mixture of stereoisomers, solvate, or tautomer thereof, and/or one or more additional anticancer agents or therapies. The maintenance dose may be 1-500 mg daily or weekly for each component of a multi component drug regimen. A qualified care giver or treating physician is aware of what dose regimen is best for a particular patient or particular presenting conditions and will make appropriate treating regimen decisions for that patient. Thus, in another embodiment, the qualified caregiver is able to tailor a dose regimen of the compound of Formula (I) or (II), or any formula described herein, or a pharmaceutically acceptable salt, stereoisomer, mixture of stereoisomers, solvate, or tautomer thereof, and/or an additional agent(s) as disclosed herein to fit with the particular needs of the patient. Thus, it will be understood that the amount of the compound of Formula (I) or (II), or any formula described herein, or a pharmaceutically acceptable salt, stereoisomer, mixture of stereoisomers, solvate, or tautomer thereof, and the amount of an additional agent actually administered will usually be determined by a physician, in light of the relevant circumstances, including the condition(s) to be treated, the chosen route of administration, the actual compound (e.g., salt or free base) administered and its relative activity, the age, weight, and response of the individual patient, the severity of the patient's symptoms, and the like.

Co-administration may also include administering component drugs e.g., one on more compounds of Formula (I) or (II), or any formula described herein, and one or more additional (e.g., a second, third, fourth or fifth) anticancer or other therapeutic agent(s). Such combination of one on more compounds of Formula (I) or (II), or any formula described herein, and one or more additional anticancer or other therapeutic agent(s) may be administered simultaneously or in sequence (one after the other) within a reasonable period of time of each administration (e.g., about 1 minute to 24 hours) depending on the pharmacokinetic and/or pharmacodynamics properties of each agent or the combination. Co-administration may also involve treatment with a fixed combination wherein agents of the treatment regimen are combinable in a fixed dosage or combined dosage medium e.g., solid, liquid or aerosol. In one embodiment, a kit may be used to administer the drug or drug components.

Thus, one embodiment of the present disclosure is a method of treating a disease amenable to treatment with a PD-1, PD-L1 inhibitor or a PD-1/PD-L1 interaction inhibitor e.g., cancer comprising administering therapeutically effective amounts of formulations of one on more compounds of Formula (I) or (II), or any formula described herein, and one or more additional anticancer agents, including for example, via a kit to a patient in need thereof. It will be understood that a qualified care giver will administer or direct the administration of a therapeutically effective amount of any of the compound(s) or combinations of compounds of the present disclosure.

"Intravenous administration" is the administration of substances directly into a vein, or "intravenously." Compared with other routes of administration, the intravenous (IV) route is a faster way to deliver fluids and medications throughout the body. An infusion pump can allow precise control over the flow rate and total amount of medication delivered. However, in cases where a change in the flow rate would not have serious consequences, or if pumps are not available, the drip is often left to flow simply by placing the bag above the level of the patient and using the clamp to regulate the rate. Alternatively, a rapid infuser can be used if the patient requires a high flow rate and the IV access device is of a large enough diameter to accommodate it. This is either an inflatable cuff placed around the fluid bag to force the fluid into the patient or a similar electrical device that may also heat the fluid being infused. When a patient requires medications only at certain times, intermittent infusion is used which does not require additional fluid. It can use the same techniques as an intravenous drip (pump or gravity drip), but after the complete dose of medication has been given, the tubing is disconnected from the IV access device. Some medications are also given by IV push or bolus, meaning that a syringe is connected to the IV access device and the medication is injected directly (slowly, if it might irritate the vein or cause a too-rapid effect). Once a medicine has been injected into the fluid stream of the IV tubing there must be some means of ensuring that it gets from the tubing to the patient. Usually this is accomplished by allowing the fluid stream to flow normally and thereby carry the medicine into the bloodstream; however, a second fluid injection is sometimes used, as a "flush", following the injection to push the medicine into the bloodstream more quickly. Thus in one embodiment, compound(s) or combination of compounds described herein may be administered by IV administration alone or in combination with administration of certain components of the treatment regimen by oral or parenteral routes.

"Oral administration" is a route of administration where a substance is taken through the mouth, and includes buccal, sub labial, and sublingual administration, as well as enteral administration and that through the respiratory tract, unless made through e.g., tubing so the medication is not in direct contact with any of the oral mucosa. Typical form for the oral administration of therapeutic agents includes the use of tablets or capsules. Thus in one embodiment, compound(s) or combination of compounds described herein may be administered by oral route alone or in combination with administration of certain components of the treatment regimen by IV or parenteral routes.

Pharmaceutical Formulations

The compound(s) of Formula (I) or (II), or any formula described herein, or a pharmaceutically acceptable salt, stereoisomer, mixture of stereoisomers, solvate, or tautomer thereof, may be administered in a pharmaceutical formulation. Pharmaceutical formulations/compositions contemplated by the present disclosure comprise, in addition to a carrier, the compound of Formula (I) or (II), or any formula described herein, or a pharmaceutically acceptable salt, stereoisomer, mixture of stereoisomers, solvate, or tautomer thereof, or a combination of compound of Formula (I) or (II), or any formula described herein, or a pharmaceutically acceptable salt, stereoisomer, mixture of stereoisomers, solvate, or tautomer thereof, optionally in combination with an additional agent such as for example, ipilimumab, or a pharmaceutically acceptable salt thereof.

Pharmaceutical formulations/compositions contemplated by the present disclosure may also be intended for administration by injection and include aqueous solutions, oil suspensions, emulsions (with sesame oil, corn oil, cottonseed oil, or peanut oil) as well as elixirs, mannitol, dextrose, or a sterile aqueous solution, and similar pharmaceutical vehicles. Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and/or by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the component compound(s) in the required amount in the appropriate solvent with various other ingredients as enumerated above or as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient(s) plus any additional desired ingredient from a previously sterile-filtered solution thereof.

In making pharmaceutical compositions that comprise compound of Formula (I) or (II), or any formula described herein, or a pharmaceutically acceptable salt, stereoisomer, mixture of stereoisomers, solvate, or tautomer thereof, optionally in combination with an additional agent/therapy useful for the purpose or pharmaceutically acceptable salt thereof, the active ingredient is usually diluted by an excipient or carrier and/or enclosed or mixed with such a carrier that may be in the form of a capsule, sachet, paper or other container. When the excipient serves as a diluent, it can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 20% by weight of the active compounds, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the disclosure may be formulated so as to provide quick, sustained or delayed release of the active ingredient after administration to the patient by employing procedures known in the art. In one embodiment, sustained release formulations are used. Controlled release drug delivery systems for oral administration include osmotic pump systems and dissolutional systems containing polymer-coated reservoirs or drug-polymer matrix formulations.

Certain compositions are preferably formulated in a unit dosage form. The term "unit dosage forms" or "combined dosage unit" refers to physically discrete units suitable as unitary dosages for human subjects and other mammals, each unit containing a predetermined quantity of one or more of the active materials (e.g., compound (I), optionally in combination with an additional agent calculated to produce the desired effect, in association with a suitable pharmaceutical excipient in for example, a tablet, capsule, ampoule or vial for injection. It will be understood, however, that the amount of each active agent actually administered will be determined by a physician, in the light of the relevant circumstances, including the condition to be treated, the chosen route of administration, the actual compounds administered and their relative activity, the age, weight, and response of the individual patient, the severity of the patient's symptoms, and the like.

For preparing solid compositions such as tablets, the principal active ingredient(s) is/are mixed with a pharmaceutical excipient to form a solid pre-formulation composition containing a homogeneous mixture of a compound of the present disclosure. When referring to these pre-formulation compositions as homogeneous, it is meant that the active ingredient(s) are dispersed evenly throughout the composition so that the composition may be readily subdivided into equally effective unit dosage forms such as tablets, pills and capsules.

The tablets or pills comprising compound of Formula (I) or (II), or any formula described herein, or a pharmaceutically acceptable salt, stereoisomer, mixture of stereoisomers, solvate, or tautomer thereof, of the present disclosure optionally in combination with the second agent may be coated or otherwise compounded to provide a dosage form affording the advantage of prolonged action, or to protect from the acidic conditions of the stomach. For example, the tablet or pill can comprise an inner dosage and an outer dosage element, the latter being in the form of an envelope over the former. In one embodiment, the inner dosage element may comprise the compound (I) and the outer dosage element may comprise the second or additional agent or vice versa. Alternatively, the combined dosage unit may be side by side configuration as in a capsule or tablet where one portion or half of the tablet or capsule is filled with a formulation of the compound of Formula (I) or (II), or any formula described herein, or a pharmaceutically acceptable salt, stereoisomer, mixture of stereoisomers, solvate, or tautomer thereof, while the other portion or half of the table or capsule comprises the additional agent.

A variety of materials may be used for such enteric layers or coatings, such materials including a number of polymeric acids and mixtures of polymeric acids with such materials as shellac, cetyl alcohol, and cellulose acetate. One of ordinary skill in the art is aware of techniques and materials used in the manufacture of dosages of formulations disclosed herein.

A "sustained release formulation" or "extended release formulation" is a formulation which is designed to slowly release a therapeutic agent into the body over an extended period of time, whereas an "immediate release formulation" is a formulation which is designed to quickly release a therapeutic agent into the body over a shortened period of time. In some cases the immediate release formulation may be coated such that the therapeutic agent is only released once it reaches the desired target in the body (e.g., the stomach). One of ordinary skill in the art is able to develop sustained release formulations of the presently disclosed compounds without undue experimentation. Thus in one embodiment, compound(s) or combination of compounds described herein may be delivered via sustained released formulations alone or in combination with administration of certain components of the treatment regimen by oral, IV or parenteral routes.

A lyophilized formulation may also be used to administer a compound of Formula (I) or (II), or any formula described herein, singly or in combination with an additional anticancer agent. One of skill in the art is aware of how to make and use lyophilized formulations of drug substances amenable to lyophilization.

Spray-dried formulation may also be used to administer a compound of Formula (I) or (II), or any formula described herein, or a pharmaceutically acceptable salt, stereoisomer, mixture of stereoisomers, solvate, or tautomer thereof, singly or in combination with an additional anti-cancer agent. One of skill in the art is aware of how to make and use spray-dried formulations of drug substances amenable to spray-drying. Other known formulation techniques may also be employed to formulate a compound or combination of compounds disclosed herein.

In one embodiment, the instructions are directed to use of the pharmaceutical composition for the treatment of cancer, including for example, leukemia or lymphoma. In specific embodiments, the cancer is acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), indolent non-Hodgkin's lymphoma (iNHL), refractory iNHL, non-Hodgkin's lymphoma (NHL), mantle cell lymphoma (MCL), follicular lymphoma, Waldestrom's macroglobulinemia (WM), T-cell lymphoma, B-cell lymphoma, and diffuse large B-cell lymphoma (DLBCL). In one embodiment, the cancer is T-cell acute lymphoblastic leukemia (T-ALL), or B-cell acute lymphoblastic leukemia (B-ALL). The non-Hodgkin lymphoma encompasses the indolent B-cell diseases that include, for example, follicular lymphoma, lymphoplasmacytic lymphoma, Waldenstrom macroglobulinemia, and marginal zone lymphoma, as well as the aggressive lymphomas that include, for example, Burkitt lymphoma, diffuse large B-cell lymphoma (DLBCL) and mantle cell lymphoma (MCL). In one embodiment, the cancer is indolent non-Hodgkin's lymphoma (iNHL)

In a particular variation, the instructions are directed to use of the pharmaceutical composition for the treatment of an autoimmune disease. Specific embodiments of an autoimmune disease include asthma, rheumatoid arthritis, multiple sclerosis, and lupus.

Articles of Manufacture

Articles of manufacture comprising a container in which a compound of Formula (I) or (II), or any formula described herein, or a pharmaceutically acceptable salt, stereoisomer, mixture of stereoisomers, solvate, or tautomer thereof, and at least one pharmaceutically acceptable carrier are contained are provided. The article of manufacture may be a bottle, vial, ampoule, single-use disposable applicator, or the like, containing the pharmaceutical composition provided in the present disclosure. The container may be formed from a variety of materials, such as glass or plastic and in one aspect also contains a label on, or associated with, the container which indicates directions for use in the treatment of cancer or inflammatory conditions.

It should be understood that the active ingredient may be packaged in any material capable of providing reasonable chemical and physical stability, such as an aluminum foil bag.

Unit dosage forms of the pharmaceutical composition comprising a compound of Formula (I) or (II), or any formula described herein, or a pharmaceutically acceptable salt, stereoisomer, mixture of stereoisomers, solvate, or tautomer thereof, and at least one pharmaceutically acceptable carrier are also provided.

Any pharmaceutical composition provided in the present disclosure may be used in the articles of manufacture, the same as if each and every composition were specifically and individually listed for use an article of manufacture.

Also provided is a kit that includes a compound of Formula (I) or (II), or any formula described herein, or a pharmaceutically acceptable salt, stereoisomer, mixture of stereoisomers, solvate, or tautomer thereof, a label, and/or instructions for use of the compound in the treatment of a disease or condition mediated by PD-1, PD-L1 activity or PD-1/PD-L1 interaction.

Also provided is an article of manufacture which includes a compound of Formula (I) or (II), or any formula described herein, or a pharmaceutically acceptable salt, stereoisomer, mixture of stereoisomers, solvate, or tautomer thereof, and a container. In one embodiment, the container may be a vial, jar, ampoule, preloaded syringe, or an intravenous bag.

Formulations of compound(s) of the present disclosure i.e., a compound of Formula (I) or (II), or any formula described herein, or a pharmaceutically acceptable salt, stereoisomer, mixture of stereoisomers, solvate, or tautomer thereof, or the combination of a compound of Formula (I) or (II), or any formula described herein, or a pharmaceutically acceptable salt, stereoisomer, mixture of stereoisomers, solvate, or tautomer thereof, and an additional agent may be accomplished by admixing said compounds or salt thereof with one or more non-toxic, pharmaceutically acceptable vehicles, carriers and/or diluents and/or adjuvants collectively referred to herein as excipients or carrier materials. The compounds of the disclosure may be administered by any suitable route, preferably in the form of a pharmaceutical composition adapted to such route, and in a therapeutically effective dose. The compounds or the combination of compounds for the disclosure may be delivered orally, mucosally, parenterally, including intravascularly, intravenously, intraperitoneally, subcutaneously, intramuscularly, and intranasally in dosage formulations containing conventional pharmaceutical excipients.

In one embodiment, the combination of a compound Formula (I) or (II), or any formula described herein, or a pharmaceutically acceptable salt, stereoisomer, mixture of stereoisomers, solvate, or tautomer thereof, and an additional agent useful for the treatment of cancer may be formulated in a fixed dose or combined dose formulation in a tablet, capsule or premixed IV solution. In another embodiment, the fixed dose combination preferably comprises of compound Formula (I) or (II), or any formula described herein, and an additional anticancer agent. Other fixed dose formulations may include premixed liquids, suspensions, elixirs, aerosolized sprays or patch presentations. As used herein fixed dose or combined dose formulations are synonymous with simultaneous co-administration of the active ingredients of the compound of Formula (I) or (II), or any formula described herein, or a pharmaceutically acceptable salt, stereoisomer, mixture of stereoisomers, solvate, or tautomer thereof, and at least one additional agent.

Combination Therapy

Also provided are methods of treatment in which a compound of Formula (I) or (II), or any formula described herein, or a pharmaceutically acceptable salt, stereoisomer, mixture of stereoisomers, solvate, or tautomer thereof, is given to a patient in combination with one or more additional active agents or therapy.

Thus in one embodiment, a method of treating cancer and/or diseases or symptoms that co-present or are exacerbated or triggered by the cancer e.g., an allergic disorder and/or an autoimmune and/or inflammatory disease, and/or an acute inflammatory reaction, comprises administering to a patient in need thereof an effective amount of a compound of Formula (I) or (II), or any formula described herein, or a pharmaceutically acceptable salt, stereoisomer, mixture of stereoisomers, solvate, or tautomer thereof, optionally in combination with an additional agent (e.g., a second, third, fourth or fifth active agent) which can be useful for treating a cancer, an allergic disorder and/or an autoimmune and/or inflammatory disease, and/or an acute inflammatory reaction incident to or co-presenting with a cancer. Treatment with the second, third, fourth or fifth active agent may be prior to, concomitant with, or following treatment with a compound of Formula (I) or (II), or any formula described herein, or a pharmaceutically acceptable salt, stereoisomer, mixture of stereoisomers, solvate, or tautomer thereof. In one embodiment, a compound of Formula (I) or (II), or any formula described herein, or a pharmaceutically acceptable salt, stereoisomer, mixture of stereoisomers, solvate, or tautomer thereof, is combined with another active agent in a single dosage form. Suitable antitumor or anticancer therapeutics that may be used in combination with a compound of Formula (I) or (II), or any formula described herein, or a pharmaceutically acceptable salt, stereoisomer, mixture of stereoisomers, solvate, or tautomer thereof, include, but are not limited to, chemotherapeutic agents, for example mitomycin C, carboplatin, taxol, cisplatin, paclitaxel, etoposide, doxorubicin, or a combination comprising at least one of the foregoing chemotherapeutic agents. Radiotherapeutic antitumor agents may also be used, alone or in combination with chemotherapeutic agents.

A compound of Formula (I) or (II), or any formula described herein, or a pharmaceutically acceptable salt, stereoisomer, mixture of stereoisomers, solvate, or tautomer thereof, an be useful as chemo-sensitizing agents, and thus, can be useful in combination with other chemotherapeutic drugs, in particular, drugs that induce apoptosis. Thus, in one embodiment, the present disclosure provides a method for increasing sensitivity of cancer cells to chemotherapy, comprising administering to a patient in need of or undergoing chemotherapy, a chemotherapeutic agent together with a compound of Formula (I) or (II), or a pharmaceutically acceptable salt, stereoisomer, mixture of stereoisomers, solvate, or tautomer thereof, in an amount sufficient to increase the sensitivity of cancer cells to the chemotherapeutic agent.

Examples of other chemotherapeutic drugs that can be used in combination with compounds of Formula (I) or (II), or any or a pharmaceutically acceptable salt, stereoisomer, mixture of stereoisomers, solvate, or tautomer thereof, include topoisomerase I inhibitors (camptothesin or topotecan), topoisomerase II inhibitors (e.g., daunomycin and etoposide), alkylating agents (e.g., cyclophosphamide, melphalan and BCNU), tubulin directed agents (e.g., taxol and vinblastine), and biological agents (e.g., antibodies such as anti CD20 antibody, IDEC 8, immunotoxins, and cytokines).

In some embodiments, the compound(s) of Formula (I) or (II), or any formula described herein, or a pharmaceutically acceptable salt, stereoisomer, mixture of stereoisomers, solvate, or tautomer thereof, is used in combination with Rituxan® (Rituximab) and/or other agents that work by selectively depleting CD20+ B-cells.

Included herein are methods of treatment in which a compound of Formula (I) or (II), or any formula described herein, or a pharmaceutically acceptable salt, stereoisomer, mixture of stereoisomers, solvate, or tautomer thereof, is administered in combination with an anti-inflammatory agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate.

Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an $IC_{50}$ that is at least 50-fold lower than the $IC_{50}$ for COX-1) such as celecoxib, valdecoxib, lumiracoxib, etoricoxib and/or rofecoxib.

In a further embodiment, the anti-inflammatory agent is a salicylate. Salicylates include but are not limited to acetylsalicylic acid or aspirin, sodium salicylate, and choline and magnesium salicylates.

The anti-inflammatory agent may also be a corticosteroid. For example, the corticosteroid may be chosen from cortisone, dexamethasone, methylprednisolone, prednisolone, prednisolone sodium phosphate, and prednisone.

In some embodiments, the anti-inflammatory therapeutic agent is a gold compound such as gold sodium thiomalate or auranofin.

In some embodiments, the anti-inflammatory agent is a metabolic inhibitor such as a dihydrofolate reductase inhibitor, such as methotrexate or a dihydroorotate dehydrogenase inhibitor, such as leflunomide.

In one embodiment, the compound(s) of Formula (I) or (II), or any formula described herein, or a pharmaceutically acceptable salt, stereoisomer, mixture of stereoisomers, solvate, or tautomer thereof, is used in combination with at least one anti-inflammatory compound that is an anti-C5 monoclonal antibody (such as eculizumab or pexelizumab), a TNF antagonist, such as entanercept, or infliximab, which is an anti-TNF alpha monoclonal antibody.

In one embodiment, the compound(s) of Formula (I) or (II), or any formula described herein, or a pharmaceutically acceptable salt, stereoisomer, mixture of stereoisomers, solvate, or tautomer thereof, is used in combination with at least one active agent that is an immunosuppressant compound such as methotrexate, leflunomide, cyclosporine, tacrolimus, azathioprine, or mycophenolate mofetil.

In other embodiments, the compound(s) of Formula (I) or (II), or any formula described herein, or a pharmaceutically acceptable salt, stereoisomer, mixture of stereoisomers, solvate, or tautomer thereof, is used in combination with one or more phosphatidylinositol 3-kinase (PI3K) inhibitors, including for example, Compounds A, B and C (whose structures are provided below), or a pharmaceutically acceptable salt thereof.

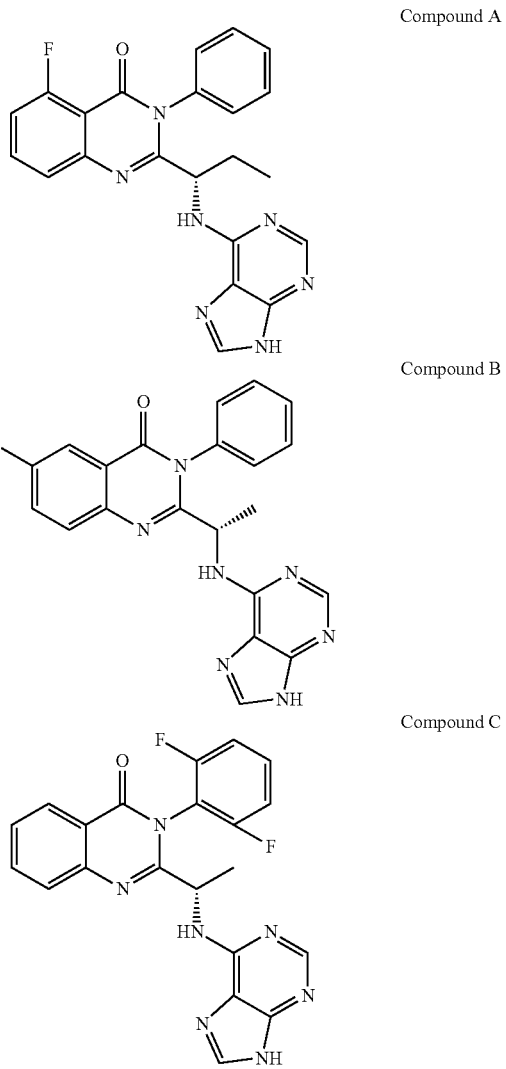

Compound A

Compound B

Compound C

Compounds A, B and C are disclosed in WO2015/017460 and WO2015/100217. Additional examples of PI3K inhibitors include, but are not limited to, ACP-319, AEZA-129, AMG-319, AS252424, AZD8186, BAY 10824391, BEZ$^{235}$, buparlisib (BKM120), BYL719 (alpelisib), CH5132799, copanlisib (BAY 80-6946), duvelisib, GDC-0941, GDC-0980, GSK2636771, GSK2269557, idelalisib (Zydelig®), IPI-145, IPI-443, IPI-549, KAR4141, LY294002, LY3023414, MLN1117, OXY111A, PA799, PX-866, RG7604, rigosertib, RP5090, taselisib, TG100115, TGR-1202, TGX221, WX-037, X-339, X-414, XL147 (SAR245408), XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences).

In yet another embodiment, the compound(s) of Formula (I) or (II) may be used in combination with Spleen Tyrosine Kinase (SYK) Inhibitors. Examples of SYK inhibitors include, but are not limited to, 6-(1H-indazol-6-yl)-N-(4-morpholinophenyl)imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), and those described in U.S. Pat. No. 8,450,321 (Gilead Conn.) and those described in U.S. 2015/0175616.

In yet another embodiment, the compounds of Formula (I) or (II) may be used in combination with Tyrosine-kinase Inhibitors (TKIs). TKIs may target epidermal growth factor receptors (EGFRs) and receptors for fibroblast growth factor (FGF), platelet-derived growth factor (PDGF), and vascular endothelial growth factor (VEGF). Examples of TKIs include, but are not limited to, afatinib, ARQ-087, asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, midostaurin, nintedanib, ODM-203, osimertinib (AZD-9291), ponatinib, poziotinib, quizartinib, radotinib, rociletinib, sulfatinib (HMPL-012), sunitinib, and TH-4000.

In yet other embodiments, the compound(s) of Formula (I) or (II), or any formula described herein, or a pharmaceutically acceptable salt, stereoisomer, mixture of stereoisomers, solvate, or tautomer thereof, is used in combination with one or more inhibitors of lysyl oxidase-like 2 (LOXL) or a substance that binds to LOXL, including for example, a humanized monoclonal antibody (mAb) with an immunoglobulin IgG4 isotype directed against human LOXL2. Examples of LOXL inhibitors include, but are not limited to, the antibodies described in WO 2009/017833 (Arresto Biosciences). Examples of LOXL2 inhibitors include, but are not limited to, the antibodies described in WO 2009/017833 (Arresto Biosciences), WO 2009/035791 (Arresto Biosciences), and WO 2011/097513 (Gilead Biologics).

In yet another embodiment, the compounds of Formula (I) or (II) may be used in combination with Toll-like receptor 8 (TLR8) inhibitors. Examples of TLR8 inhibitors include, but are not limited to, E-6887, IMO-4200, IMO-8400, IMO-9200, MCT-465, MEDI-9197, motolimod, resiquimod, VTX-1463, and VTX-763.

In yet another embodiment, the compounds of Formula (I) or (II) may be used in combination with Toll-like receptor (TLR9) inhibitors. Examples of TLR9 inhibitors include, but are not limited to, IMO-2055, IMO-2125, lefitolimod, litenimod, MGN-1601, and PUL-042.

In one embodiment, the compound of Formula (I) or (II), or any formula described herein, or a pharmaceutically acceptable salt, stereoisomer, mixture of stereoisomers, solvate, or tautomer thereof, is useful for the treatment of cancer in combination with a BTK (Bruting's Tyrosine kinase) inhibitor. An example of such BTK inhibitor is a compound disclosed in U.S. Pat. No. 7,405,295. Additional examples of BTK inhibitors include, but are not limited to, (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, HM71224, ibrutinib, M-2951, tirabrutinib (ONO-4059), PRN-1008, spebrutinib (CC-292), and TAK-020.

In one embodiment, the compound of Formula (I) or (II), or any formula described herein, or a pharmaceutically acceptable salt, stereoisomer, mixture of stereoisomers, solvate, or tautomer thereof, is useful for the treatment of cancer in combination with a BET inhibitor. An example of such BET inhibitor is a compound disclosed in WO2014/182929, the entire contents of which are incorporated herein by reference.

In one embodiment, the compound of Formula (I) or (II), or any formula described herein, or a pharmaceutically acceptable salt, stereoisomer, mixture of stereoisomers, solvate, or tautomer thereof, is useful for the treatment of cancer in combination with a TBK (Tank Binding kinase) inhibitor. An example of such TBK inhibitor is a compound disclosed in WO2016/049211.

In one embodiment, the compound of Formula (I) or (II), or any formula described herein, or a pharmaceutically acceptable salt, stereoisomer, mixture of stereoisomers, solvate, or tautomer thereof, is useful for the treatment of cancer in combination with a OX40 inhibitor. An example of such OX40 inhibitor is a compound disclosed in U.S. Pat. No. 8,450,460, the entire contents of which are incorporated herein by reference.

In one embodiment, the compound of Formula (I) or (II), or any formula described herein, or a pharmaceutically acceptable salt, stereoisomer, mixture of stereoisomers, solvate, or tautomer thereof, is useful for the treatment of cancer in combination with a JAK-1 inhibitor. An example of such JAK-1 inhibitor is a compound disclosed in WO2008/109943. Examples of other JAK inhibitors include, but are not limited to, AT9283, AZD 1480, baricitinib, BMS-911543, fedratinib, filgotinib (GLPG0634), gandotinib (LY2784544), INCB039110, lestaurtinib, momelotinib (CYT0387), NS-018, pacritinib (SB1518), peficitinib (ASP015K), ruxolitinib, tofacitinib (formerly tasocitinib), and XL019.

In one embodiment, the compound of Formula (I) or (II), or any formula described herein, or a pharmaceutically acceptable salt, stereoisomer, mixture of stereoisomers, solvate, or tautomer thereof, is useful for the treatment of cancer in combination with an Indoleamine-pyrrole-2,3-dioxygenase (IDO) inhibitors. An example of such IDO inhibitor is a compound disclosed in WO2016/186967. In one embodiment, the compounds of Formula (I) or (II) are useful for the treatment of cancer in combination with IDO1 inhibitors including but not limited to BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, and shIDO-ST.

In one embodiment, the compound of Formula (I) or (II), or any formula described herein, or a pharmaceutically acceptable salt, stereoisomer, mixture of stereoisomers, solvate, or tautomer thereof, is useful for the treatment of cancer in combination with a Mitogen-activated Protein Kinase (MEK) Inhibitors. MEK inhibitors useful for combination treatment with a compound(s) of Formula (I) or (II) includes antroquinonol, binimetinib, cobimetinib (GDC-0973, XL-518), MT-144, selumetinib (AZD6244), sorafenib, trametinib (GSK1120212), uprosertib and trametinib.

In one embodiment, the compound of Formula (I) or (II), or any formula described herein, or a pharmaceutically acceptable salt, stereoisomer, mixture of stereoisomers, solvate, or tautomer thereof, is useful for the treatment of cancer in combination with an Apoptosis Signal-Regulating Kinase (ASK) Inhibitors: ASK inhibitors include but are not limited to those described in WO 2011/008709 (Gilead Sciences) and WO 2013/112741 (Gilead Sciences) including, for example, selonsertib.

In one embodiment, the compounds of Formula (I) or (II) may be combined with Cluster of Differentiation 47 (CD47) inhibitors. Examples of CD47 inhibitors include, but are not limited to anti-CD47 mAbs (Vx-1004), anti-human CD47 mAbs (CNTO-7108), CC-90002, CC-90002-ST-001, humanized anti-CD47 antibody (Hu5F9-G4), NI-1701, NI-1801, RCT-1938, and TTI-621.

In one embodiment, the compounds of Formula (I) or (II) may be combined with Cyclin-dependent Kinase (CDK) Inhibitors. CDK inhibitors include inhibitors of CDK 1, 2, 3, 4, 6 and 9, such as abemaciclib, alvocidib (HMR-1275, flavopiridol), AT-7519, FLX-925, LEE001, palbociclib, ribociclib, rigosertib, selinexor, UCN-01, and TG-02.

In one embodiment, the compounds of Formula (I) or (II) may be combined with Discoidin Domain Receptor (DDR) Inhibitors for the treatment of cancer. DDR inhibitors include inhibitors of DDR1 and/or DDR2. Examples of DDR inhibitors include, but are not limited to, those disclosed in WO 2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO 2013/034933 (Imperial Innovations).

In one embodiment, the compounds of Formula (I) or (II) may be combined with Histone Deacetylase (HDAC) Inhibitors such as those disclosed in U.S. Pat. No. 8,575,353 and equivalents thereof. Additional examples of HDAC inhibitors include, but are not limited to, abexinostat, ACY-241, AR-42, BEBT-908, belinostat, CKD-581, CS-055 (HBI-8000), CUDC-907, entinostat, givinostat, mocetinostat, panobinostat, pracinostat, quisinostat (JNJ-26481585), resminostat, ricolinostat, SHP-141, valproic acid (VAL-001), vorinostat.

In one embodiment, the compound of Formula (I) or (II), or any formula described herein, or a pharmaceutically acceptable salt, stereoisomer, mixture of stereoisomers, solvate, or tautomer thereof, is useful for the treatment of cancer in combination with a standard of care in the treatment of the respective cancer. One of skill in the art is aware of the standard of care as of a given date in the particular field of cancer therapy or with respect to a given cancer.

Certain embodiments of the present application include or use one or more additional therapeutic agent. The one or more additional therapeutic agent may be an agent useful for the treatment of cancer, inflammation, autoimmune disease and/or related conditions. The one or more additional therapeutic agent may be a chemotherapeutic agent, an anti-angiogenic agent, an antifibrotic agent, an anti-inflammatory agent, an immune modulating agent, an immunotherapeutic agent, a therapeutic antibody, a radiotherapeutic agent, an anti-neoplastic agent, an anti-cancer agent, an anti-proliferation agent, or any combination thereof. In some embodiments, the compound(s) described herein may be used or combined with a chemotherapeutic agent, an anti-angiogenic agent, an anti-fibrotic agent, an anti-inflammatory agent, an immune modulating agent, an immunotherapeutic agent, a therapeutic antibody, a radiotherapeutic agent, an antineoplastic agent or an anti-cancer agent, an anti-proliferation agent, or any combination thereof.

In one embodiment, a compound(s) of Formula (I) or (II) optionally in combination with an additional anticancer agent described herein, may be used or combined with an anti-neoplastic agent or an anti-cancer agent, anti-fibrotic agent, an anti-anti-inflammatory agent, or an immune modulating agent.

In one embodiment, provided are kits comprising a pharmaceutical composition comprising a compound of Formula (I) or (II), or any formula described herein, or a pharmaceutically acceptable salt, stereoisomer, mixture of stereoisomers, solvate, or tautomer thereof, or a compound of Formula (I) or (II), or any formula described herein, or a pharmaceutically acceptable salt, stereoisomer, mixture of stereoisomers, solvate, or tautomer thereof, and at least one additional anticancer agent, or a pharmaceutically acceptable salt thereof, and at least one pharmaceutically acceptable carrier. In one embodiment, the kit comprises instructions for use in the treatment of cancer or inflammatory conditions. In one embodiment, the instructions in the kit are directed to use of the pharmaceutical composition for the treatment of cancer selected from pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, CNS cancer, brain cancer, bone cancer, soft tissue sarcoma, non-small cell lung cancer, small-cell lung cancer and colon cancer.

The application also provides method for treating a subject who is undergoing one or more standard therapies, such as chemotherapy, radiotherapy, immunotherapy, surgery, or combination thereof comprising administering or co-administering a compound of Formula (I) or (II), or any formula described herein, or a pharmaceutically acceptable salt, stereoisomer, mixture of stereoisomers, solvate, or tautomer thereof, said subject. Accordingly, one or more compound (S) of Formula (I) or (II), or any formula described herein, or pharmaceutically acceptable salt thereof, may be administered before, during, or after administration of a chemotherapy, radiotherapy, immunotherapy, surgery or combination thereof.

In one embodiment, the subject may be a human who is (i) substantially refractory to at least one chemotherapy treatment, or (ii) in relapse after treatment with chemotherapy, or both (i) and (ii). In some of embodiments, the subject is refractory to at least two, at least three, or at least four chemotherapy treatments (including standard or experimental chemotherapies).

In one embodiment, the subject is refractory to at least one, at least two, at least three, or at least four chemotherapy treatment (including standard or experimental chemotherapy) selected from fludarabine, rituximab, obinutuzumab, alkylating agents, alemtuzumab and other chemotherapy treatments such as CHOP (cyclophosphamide, doxorubicin, vincristine, prednisone); R-CHOP (rituximab-CHOP); hyperCVAD (hyperfractionated cyclophosphamide, vincristine, doxorubicin, dexamethasone, methotrexate, cytarabine); R-hyperCVAD (rituximab-hyperCVAD); FCM (fludarabine, cyclophosphamide, mitoxantrone); R-FCM (rituximab, fludarabine, cyclophosphamide, mitoxantrone); bortezomib and rituximab; temsirolimus and rituximab; temsirolimus and Velcade®; Iodine-131 tositumomab (Bexxar®) and CHOP; CVP (cyclophosphamide, vincristine, prednisone); R-CVP (rituximab-CVP); ICE (iphosphamide, carboplatin, etoposide); R-ICE (rituximab-ICE); FCR (fludarabine, cyclophosphamide, rituximab); FR (fludarabine, rituximab); and D. T. PACE (dexamethasone, thalidomide, cisplatin, Adriamycin®, cyclophosphamide, etoposide).

Other examples of chemotherapy treatments (including standard or experimental chemotherapies) are described below. In addition, treatment of certain lymphomas is reviewed in Cheson, B. D., Leonard, J. P., "Monoclonal Antibody Therapy for B-Cell Non-Hodgkin's Lymphoma" *The New England Journal of Medicine* 2008, 359(6), p. 613-626; and Wierda, W. G., "Current and Investigational Therapies for Patients with CLL" *Hematology* 2006, p. 285-294. Lymphoma incidence patterns in the United States is profiled in Morton, L. M., et al. "*Lymphoma Incidence Patterns by WHO Subtype in the United States, 1992-2001*" *Blood* 2006, 107(1), p. 265-276.

Examples of immunotherapeutic agents treating lymphoma or leukemia include, but are not limited to, rituximab (such as Rituxan), alemtuzumab (such as Campath, Mab-Campath), anti-CD19 antibodies, anti-CD20 antibodies, anti-MN-14 antibodies, anti-TRAIL, Anti-TRAIL DR4 and DR5 antibodies, anti-CD74 antibodies, apolizumab, bevacizumab, CHIR-12.12, epratuzumab (hLL2-anti-CD22 humanized antibody), galiximab, ha20, ibritumomab tiuxetan, lumiliximab, milatuzumab, ofatumumab, PRO131921, SGN-40, WT-1 analog peptide vaccine, WT1 126-134 peptide vaccine, tositumomab, autologous human tumor-derived HSPPC-96, and veltuzumab. Additional immunotherapy agents includes using cancer vaccines based upon the genetic makeup of an individual patient's tumor, such as lymphoma vaccine example is GTOP-99 (MyVax®).

Examples of chemotherapy agents for treating lymphoma or leukemia include aldesleukin, alvocidib, antineoplaston AS2-1, antineoplaston A10, anti-thymocyte globulin, amifostine trihydrate, aminocamptothecin, arsenic trioxide, beta alethine, Bcl-2 family protein inhibitor ABT-263, BMS-345541, bortezomib (Velcade®), bryostatin 1, busulfan, carboplatin, campath-1H, CC-5103, carmustine, caspofungin acetate, clofarabine, cisplatin, Cladribine (Leustarin), Chlorambucil (Leukeran), Curcumin, cyclosporine, Cyclophosphamide (Cyloxan, Endoxan, Endoxana, Cyclostin), cytarabine, denileukin diftitox, dexamethasone, DT PACE, docetaxel, dolastatin 10, Doxorubicin (Adriamycin®, Adriblastine), doxorubicin hydrochloride, enzastaurin, epoetin alfa, etoposide, Everolimus (RAD001), fenretinide, filgrastim, melphalan, mesna, Flavopiridol, Fludarabine (Fludara), Geldanamycin (17-AAG), ifosfamide, irinotecan hydrochloride, ixabepilone, Lenalidomide (Revlimid®, CC-5013), lymphokine-activated killer cells, melphalan, methotrexate, mitoxantrone hydrochloride, motexafin gadolinium, mycophenolate mofetil, nelarabine, oblimersen (Genasense) Obatoclax (GX15-070), oblimersen, octreotide acetate, omega-3 fatty acids, oxaliplatin, paclitaxel, PD0332991, PEGylated liposomal doxorubicin hydrochloride, pegfilgrastim, Pentstatin (Nipent), perifosine, Prednisolone, Prednisone, R-roscovitine (Selicilib, CYC202), recombinant interferon alfa, recombinant interleukin-12, recombinant interleukin-11, recombinant flt3 ligand, recombinant human thrombopoietin, rituximab, sargramostim, sildenafil citrate, simvastatin, sirolimus, Styryl sulphones, tacrolimus, tanespimycin, Temsirolimus (CCI-779), Thalidomide, therapeutic allogeneic lymphocytes, thiotepa, tipifarnib, Velcade® (bortezomib or PS-341), Vincristine (Oncovin), vincristine sulfate, vinorelbine ditartrate, Vorinostat (SAHA), vorinostat, and FR (fludarabine, rituximab), CHOP (cyclophosphamide, doxorubicin, vincristine, prednisone), CVP (cyclophosphamide, vincristine and prednisone), FCM (fludarabine, cyclophosphamide, mitoxantrone), FCR (fludarabine, cyclophosphamide, rituximab), hyperCVAD (hyperfractionated cyclophosphamide, vincristine, doxorubicin, dexamethasone, methotrexate, cytarabine), ICE (iphosphamide, carboplatin and etoposide), MCP (mitoxantrone, chlorambucil, and prednisolone), R-CHOP (rituximab plus CHOP), R-CVP (rituximab plus CVP), R-FCM (rituximab plus FCM), R-ICE (rituximab-ICE), and R-MCP (Rituximab-MCP).

In some embodiments, the cancer is melanoma. Suitable agents for use in combination with the compounds described herein include, without limitation, dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC, temozolomide or YERVOY™. Compounds disclosed herein may also be combined with immunotherapy drugs, including cytokines such as interferon alpha, interleukin 2, and tumor necrosis factor (TNF) in the treatment of melanoma.

Compounds described here may also be used in combination with vaccine therapy in the treatment of melanoma. Anti-melanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds described herein, using for example, a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF) and optionally in combination with a compound of Formula (I) or (II), or any formula described herein or a pharmaceutically acceptable salt, stereoisomer, mixture of stereoisomers, solvate, or tautomer thereof.

The therapeutic treatments can be supplemented or combined with any of the aforementioned therapies with stem cell transplantation or treatment. One example of modified approach is radioimmunotherapy, wherein a monoclonal antibody is combined with a radioisotope particle, such as indium In 111, yttrium Y 90, iodine I-131. Examples of combination therapies include, but are not limited to, Iodine-131 tositumomab (Bexxar®), Yttrium-90 ibritumomab tiuxetan (Zevalin®), Bexxar® with CHOP.

Other therapeutic procedures useful in combination with treatment with a compound of Formula (I) or (II), or any formula described herein, or a pharmaceutically acceptable salt, stereoisomer, mixture of stereoisomers, solvate, or tautomer thereof, include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, pharmacological study, low-LET cobalt-60 gamma ray therapy, bleomycin, conventional surgery, radiation therapy, and nonmyeloablative allogeneic hematopoietic stem cell transplantation.

In some embodiments, the application provides pharmaceutical compositions comprising a compound of Formula (I) or (II), or any formula described herein, or a pharmaceutically acceptable salt, stereoisomer, mixture of stereoisomers, solvate, or tautomer thereof, in combination with an MMP9 binding protein and/or one or more additional therapeutic agent, and a pharmaceutically acceptable diluent, carrier or excipient. In one embodiment, the pharmaceutical compositions comprise an MMP9 binding protein, one or more additional therapeutic agent, and a pharmaceutically acceptable excipient, carrier or diluent. In some embodiments, the pharmaceutical compositions comprise the compound of Formula (I) or (II), or any formula described herein, or a pharmaceutically acceptable salt, stereoisomer, mixture of stereoisomers, solvate, or tautomer thereof, and anti-MMP9 antibody AB0045.

In one embodiment, the pharmaceutical compositions comprise the compound of Formula (I) or (II), or any formula described herein, or a pharmaceutically acceptable salt, stereoisomer, mixture of stereoisomers, solvate, or tautomer thereof, anti-MMP9 antibody AB0045, at least one additional therapeutic agent that is an immunomodulating agent, and a pharmaceutically acceptable diluent, carrier or excipient. In certain other embodiments, the pharmaceutical compositions comprise the anti-MMP9 antibody AB0045, at least one additional therapeutic agent that is an anti-inflammatory agent, and a pharmaceutically acceptable diluent, carrier or excipient. In certain other embodiments, the pharmaceutical compositions comprise compound of Formula (I) or (II), or any formula described herein, or a pharmaceutically acceptable salt, stereoisomer, mixture of stereoisomers, solvate, or tautomer thereof, the anti-MMP9 antibody AB0045, at least one additional therapeutic agent that is an antineoplastic agent or anti-cancer agent, and a pharmaceutically acceptable diluent, carrier or excipient. In one embodiment, MMP9 compounds useful for combination treatment with a compound of Formula (I) or (II), or any formula described herein, or a pharmaceutically acceptable salt, stereoisomer, mixture of stereoisomers, solvate, or tautomer thereof, include but are not limited to marimastat (BB-2516), cipemastat (Ro 32-3555) and those described in WO 2012/027721 (Gilead Biologics).

In one embodiment, the one or more additional therapeutic agent is an immune modulating agent, e.g., an immunostimulant or an immunosuppressant. In certain other embodiments, an immune modulating agent is an agent capable of altering the function of immune checkpoints, including the CTLA-4, LAG-3, B7-H3, B7-H4, Tim3, BTLA, KIR, A2aR, CD200 and/or PD-1 pathways. In other embodiments, the immune modulating agent is immune checkpoint modulating agents. Exemplary immune checkpoint modulating agents include anti-CTLA-4 antibody (e.g., ipilimumab), anti-LAG-3 antibody, anti-B7-H3 antibody, anti-B7-H4 antibody, anti-Tim3 antibody, anti-BTLA antibody, anti-KIR antibody, anti-A2aR antibody, anti CD200 antibody, anti-PD-1 antibody, anti-PD-L1 antibody, anti-CD28 antibody, anti-CD80 or -CD86 antibody, anti-B7RP1 antibody, anti-B7-H3 antibody, anti-HVEM antibody, anti-CD137 or -CD137L antibody, anti-OX40 or —OX40L antibody, anti-CD40 or -CD40L antibody, anti-GAL9 antibody, anti-IL-10 antibody and A2aR drug. For certain such immune pathway gene products, the use of either antagonists or agonists of such gene products is contemplated, as are small molecule modulators of such gene products. In one embodiment, the immune modulatory agent is an anti-PD-1 or anti-PD-L1 antibody. In some embodiments, immune modulating agents include those agents capable of altering the function of mediators in cytokine mediated signaling pathways.

In some embodiments, the one or more additional therapy or anti-cancer agent is cancer gene therapy or cell therapy. Cancer gene therapy and cell therapy include the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; genetic approaches to modify cellular activity to further alter endogenous immune responsiveness against cancer. Non limiting examples are Algenpantucel-L (2 pancreatic cell lines), Sipuleucel-T, SGT-53 liposomal nanodelivery (scL) of gene p53; T-cell therapy, such as CD19 CAR-T tisagenlecleucel-T (CTL019) WO2012079000, WO2017049166, axicabtagene ciloleucel (KTE-C19) U.S. Pat. Nos. 7,741,465, 6,319,494, JCAR-015 U.S. Pat. No. 7,446,190, JCAR-014, JCAR-020, JCAR-024, JCAR-023, JTCR-016, JCAR-018 WO2016090190, JCAR-017, (WO2016196388, WO2016033570, WO2015157386), BPX-501 U.S. Pat. No. 9,089,520, WO2016100236, AU-105, UCART-22, ACTR-087, P-BCMA-101; activated allogeneic natural killer cells CNDO-109-AANK, FATE-NK100, LFU-835 hematopoietic stem cells.

In one embodiment, the one or more additional therapeutic agent is an immune checkpoint inhibitor. Tumors subvert the immune system by taking advantage of a mechanism known as T-cell exhaustion, which results from chronic exposure to antigens and is characterized by the up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular determinants to influence whether cell cycle progression and other intracellular signaling processes should proceed based upon extracellular information.

In addition to specific antigen recognition through the T-cell receptor (TCR), T-cell activation is regulated through a balance of positive and negative signals provided by costimulatory receptors. These surface proteins are typically members of either the TNF receptor or B7 superfamilies. Agonistic antibodies directed against activating co-stimulatory molecules and blocking antibodies against negative co-stimulatory molecules may enhance T-cell stimulation to promote tumor destruction.

Programmed Cell Death Protein 1, (PD-1 or CD279), a 55-kD type 1 transmembrane protein, is a member of the CD28 family of T cell co-stimulatory receptors that include immunoglobulin superfamily member CD28, CTLA-4, inducible co-stimulator (ICOS), and BTLA. PD-1 is highly expressed on activated T cells and B cells. PD-1 expression can also be detected on memory T-cell subsets with variable levels of expression. Two ligands specific for PD-1 have been identified: programmed death-ligand 1 (PD-L1, also known as B7-H1 or CD274) and PD-L2 (also known as B7-DC or CD273). PD-L1 and PD-L2 have been shown to down-regulate T cell activation upon binding to PD-1 in both mouse and human systems (Okazaki et al., Int. Immunol., 2007; 19: 813-824). The interaction of PD-1 with its ligands, PD-L1 and PD-L2, which are expressed on antigen-presenting, cells (APCs) and dendritic cells (DCs), transmits negative regulatory stimuli to down-modulate the activated T cell immune response. Blockade of PD-1 suppresses this negative signal and amplifies T cell responses. Numerous studies indicate that the cancer microenvironment manipulates the PD-L1/PD-1 signaling pathway and that induction of PD-L1 expression is associated with inhibition of immune responses against cancer, thus permitting cancer progression and metastasis. The PD-L1/PD-1 signaling pathway is a primary mechanism of cancer immune evasion for several reasons. This pathway is involved in negative regulation of immune responses of activated T effector cells found in the periphery. PD-L1 is up-regulated in cancer microenvironments, while PD-1 is also up-regulated on activated tumor infiltrating T cells, thus possibly potentiating a vicious cycle of inhibition. This pathway is also intricately involved in both innate and adaptive immune regulation through bi-directional signaling. These factors make the PD-1/PD-L1 complex a central point through which cancer can manipulate immune responses and promote its own progression.

The first immune-checkpoint inhibitor to be tested in a clinical trial was ipilimumab (Yervoy, Bristol-Myers Squibb), a CTLA-4 mAb. CTLA-4 belongs to the immunoglobulin superfamily of receptors, which also includes PD-1, BTLA, TIM-3, and V-domain immunoglobulin suppressor of T cell activation (VISTA). Anti-CTLA-4 mAb is a powerful checkpoint inhibitor which removes "the break" from both naive and antigen-experienced cells.

Therapy enhances the antitumor function of CD8+ T cells, increases the ratio of CD8+ T cells to Foxp3+ T regulatory cells, and inhibits the suppressive function of T regulatory cells. TIM-3 has been identified as another important inhibitory receptor expressed by exhausted CD8+ T cells. In mouse models of cancer, it has been shown that the most dysfunctional tumor-infiltrating CD8+ T cells actually co-express PD-1 and LAG-3. LAG-3 is another recently identified inhibitory receptor that acts to limit effector T-cell function and augment the suppressive activity of T regulatory cells. It has recently been revealed that PD-1 and LAG-3 are extensively co-expressed by tumor-infiltrating T cells in mice, and that combined blockade of PD-1 and LAG-3 provokes potent synergistic antitumor immune responses in mouse models of cancer.

Thus in one embodiment, the present disclosure provides the use of immune checkpoint inhibitors of Formula (I) or (II) disclosed herein in combination with one or more additional immune checkpoint inhibitors. In one embodiment, the present disclosure provides the use of immune checkpoint inhibitors of Formula (I) or (II) disclosed herein in combination with one or more additional immune checkpoint inhibitors and an anti-MMP9 antibody or antigen binding fragment thereof to treat or prevent cancer. In some embodiments, the immune checkpoint inhibitors may be an anti-PD-1 and/or an anti-PD-L1 antibody or an anti PD-1/PD-L1 interaction inhibitor. In some embodiments, the anti-PD-L1 antibody may be B7-H1 antibody, BMS 936559 antibody, MPDL3280A (atezolizumab) antibody, MEDI-4736 antibody, MSB0010718C antibody or combinations thereof. According to another embodiment, the anti-PD-1 antibody may be nivolumab antibody, pembrolizumab antibody, pidilizumab antibody or combinations thereof.

In addition, PD-1 may also be targeted with AMP-224, which is a PD-L2-IgG recombinant fusion protein. Additional antagonists of inhibitory pathways in the immune response include IMP321, a soluble LAG-3 Ig fusion protein and MHC class II agonist, which is used to increase an immune response to tumors. Lirilumab is an antagonist to the KIR receptor and BMS 986016 is an antagonist of LAG3. The TIM-3-Galectin-9 pathway is another inhibitory checkpoint pathway that is also a promising target for checkpoint inhibition. RX518 targets and activates the glucocorticoid-induced tumor necrosis factor receptor (GITR), a member of the TNF receptor superfamily that is expressed on the surface of multiple types of immune cells, including regulatory T cells, effector T cells, B cells, natural killer (NK) cells, and activated dendritic cells. Thus, in one embodiment, the compound(s) of Formula (I) or (II) may be used in combination with IMP321, Lirilumab and/or BMS 986016.

Anti-PD-1 antibodies that may be used in the compositions and methods described herein include but are not limited to: Nivolumab/MDX-1106/BMS-936558/ONO 1152, a fully human lgG4 anti-PD-1 monoclonal antibody; pidilizumab (MDV9300/CT-011), a humanized lgG1 monoclonal antibody; pembrolizumab (MK-3475/pembrolizumab/lambrolizumab), a humanized monoclonal IgG4 antibody; durvalumab (MEDI-4736) and atezolizumab. Anti-PD-L1 antibodies that may be used in compositions and methods described herein include but are not limited to: avelumab; BMS-936559, a fully human IgG4 antibody; atezolizumab (MPDL3280A/RG-7446), a human monoclonal antibody; MEDI4736; MSB0010718C, and MDX1105-01.

In one embodiment, the compound of Formula (I) or (II), or any formula described herein, or a pharmaceutically acceptable salt, stereoisomer, mixture of stereoisomers, solvate, or tautomer thereof, is administered in combination with the anti-PD-1 antibody nivolumab, pembrolizumab, and/or pidilizumab to a patient in need thereof. In one embodiment, the anti-PD-L1 antibody useful for combination treatment with a compound of Formula (I) or (II), or any formula described herein, or a pharmaceutically acceptable salt, stereoisomer, mixture of stereoisomers, solvate, or tautomer thereof, is BMS-936559, atezolizumab, or avelumab. In one embodiment, the immune modulating agent inhibits an immune checkpoint pathway. In another embodiment, the immune checkpoint pathway is selected from CTLA-4, LAG-3, B7-H3, B7-H4, Tim3, BTLA, KIR, A2aR, CD200 and PD-1. Additional antibodies that may be used in combination with a compound of Formula (I) or (II), or any formula described herein, or a pharmaceutically acceptable salt, stereoisomer, mixture of stereoisomers, solvate, or tautomer thereof, in compositions and methods described herein include the anti-PD-1 and anti-PD-L1 antibodies disclosed in U.S. Pat. Nos. 8,008,449 and 7,943,743, respectively.

In one embodiment, the one or more additional therapeutic agent is an anti-inflammatory agent.

In certain other embodiments, the anti-inflammatory agent is a tumor necrosis factor alpha (TNF-α) inhibitor. As used herein, the terms "TNF alpha," "TNF-α," and "TNFα," are interchangeable. TNF-α is a pro-inflammatory cytokine secreted primarily by macrophages but also by a variety of other cell types including lymphoid cells, mast cells, endothelial cells, cardiac myocytes, adipose tissue, fibroblasts, and neuronal tissue. TNF-α is also known as endotoxin-induced factor in serum, cachectin, and differentiation inducing factor. The tumor necrosis factor (TNF) family includes TNF alpha, TNF beta, CD40 ligand (CD40L), Fas ligand (FasL), TNF-related apoptosis inducing ligand (TRAIL), and LIGHT (homologous to lymphotoxins, exhibits inducible expression, and competes with HSV glycoprotein D for HVEM, a receptor expressed by T lymphocytes), some of the most important cytokines involved in, among other physiological processes, systematic inflammation, tumor lysis, apoptosis and initiation of the acute phase reaction.

The above therapeutic agents when employed in combination with a compound(s) disclosed herein, may be used, for example, in those amounts indicated in the referenced manuals e.g., Physicians Desk Reference or in amounts generally known to a qualified care giver, i.e., one of ordinary skill in the art. In the methods of the present disclosure, such other therapeutic agent(s) may be administered prior to, simultaneously with, or following the administration of the compound(s) of Formula (I) or (II). Certain other therapeutic agents may be combined into a single formulation or kit when amenable to such. For example, tablet, capsule or liquid formulations may be combined with other tablet, capsule or liquid formulations into one fixed or combined dose formulation or regimen. Other combinations may be given separately, contemporaneously or otherwise.

Combination Therapy for HBV In certain embodiments, a method for treating or preventing an HBV infection in a human having or at risk of having the infection is provided, comprising administering to the human a therapeutically effective amount of a compound disclosed herein, or any formula described herein, or a pharmaceutically acceptable salt, stereoisomer, mixture of stereoisomers, solvate, or tautomer thereof, in combination with a therapeutically effective amount of one or more (e.g., one, two, three, four, one or two, one to three, or one to four) additional therapeutic agents. In one embodiment, a method for treating an HBV infection in a human having or at risk of having the infection is provided, comprising administering to the human a therapeutically effective amount of a compound disclosed herein, or any formula described herein, or a pharmaceutically acceptable salt, stereoisomer, mixture of stereoisomers, solvate, or tautomer thereof, in combination with a therapeutically effective amount of one or more (e.g., one, two, three, four, one or two, one to three, or one to four) additional therapeutic agents.

In certain embodiments, the present disclosure provides a method for treating an HBV infection, comprising administering to a patient in need thereof a therapeutically effective amount of a compound disclosed herein or any formula described herein, or a pharmaceutically acceptable salt, stereoisomer, mixture of stereoisomers, solvate, or tautomer thereof, in combination with a therapeutically effective amount of one or more (e.g., one, two, three, four, one or two, one to three, or one to four) additional therapeutic agents which are suitable for treating an HBV infection.

In certain embodiments, a compound disclosed herein, or any formula described herein, or a pharmaceutically acceptable salt, stereoisomer, mixture of stereoisomers, solvate, or tautomer thereof, is combined with one, two, three, four, or more additional therapeutic agents. In certain embodiments, a compound disclosed herein, or any formula described herein, or a pharmaceutically acceptable salt, stereoisomer, mixture of stereoisomers, solvate, or tautomer thereof, is combined with two additional therapeutic agents. In other embodiments, a compound disclosed herein, or any formula described herein, or a pharmaceutically acceptable salt, stereoisomer, mixture of stereoisomers, solvate, or tautomer thereof, is combined with three additional therapeutic agents. In further embodiments, a compound disclosed herein, or any formula described herein, or a pharmaceutically acceptable salt, stereoisomer, mixture of stereoisomers, solvate, or tautomer thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of HBV Combination Therapy

In certain embodiments, when a compound disclosed herein is combined with one or more additional therapeutic agents as described above, the components of the composition are administered as a simultaneous or sequential regimen. When administered sequentially, the combination may be administered in two or more administrations.

Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the patient.

Co-administration includes administration of unit dosages of the compounds disclosed herein before or after administration of unit dosages of one or more additional therapeutic agents. The compound disclosed herein may be administered within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

In certain embodiments, a compound disclosed herein is combined with one or more additional therapeutic agents in a unitary dosage form for simultaneous administration to a patient, for example as a solid dosage form for oral administration.

In certain embodiments a compound of Formula (I) or (II), or any formula described herein, or a pharmaceutically acceptable salt, stereoisomer, mixture of stereoisomers, solvate, or tautomer thereof, is formulated as a tablet, which may optionally contain one or more other compounds useful for treating hepatitis B virus (HBV). In certain embodiments, the tablet can contain another active ingredient for treating hepatitis B virus (HBV).

In certain embodiments, such tablets are suitable for once daily dosing.

The compounds described herein may be used or combined with one or more of a chemotherapeutic agent, an immunomodulator, an immunotherapeutic agent, a therapeutic antibody, a therapeutic vaccine, a bispecific antibody and "antibody-like" therapeutic protein (such as DARTs®, Duobodies®, Bites®, XmAbs®, TandAbs®, Fab derivatives), an antibody-drug conjugate (ADC), gene modifiers or gene editors (such as CRISPR Cas9, zinc finger nucleases, homing endonucleases, synthetic nucleases, TALENs), cell therapies such as CAR-T (chimeric antigen receptor T-cell), and TCR-T (an engineered T cell receptor) agent or any combination thereof.

In the above embodiments, the additional therapeutic agent may be an anti-HBV agent. For example, the additional therapeutic agent may be selected from the group consisting of HBV combination drugs, other drugs for treating hepatitis B virus (HBV), 3-dioxygenase (IDO) inhibitors, antisense oligonucleotide targeting viral mRNA, Apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), covalently closed circular DNA (cccDNA) inhibitors, cyclophilin inhibitors, cytokines, cytotoxic T-lymphocyte-associated protein 4 (ipi4) inhibitors, DNA polymerase inhibitor, Endonuclease modulator, epigenetic modifiers, Farnesoid X receptor agonist, gene modifiers or editors, HBsAg inhibitors, HBsAg secretion or assembly inhibitors, HBV antibodies, HBV DNA polymerase inhibitors, HBV replication inhibitors, HBV RNAse inhibitors, HBV vaccines, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, IAPs inhibitors, IL-2 agonist, IL-7 agonist, Immunoglobulin agonist, Immunoglobulin G modulator, immunomodulators, indoleamine-2, inhibitors of ribonucleotide reductase, Interferon agonist, Interferon alpha 1 ligand, Interferon alpha 2 ligand, Interferon alpha 5 ligand modulator, Interferon alpha ligand, Interferon alpha ligand modulator, interferon alpha receptor ligands, Interferon beta ligand, Interferon ligand, Interferon receptor modulator, Interleukin-2 ligand, ipi4 inhibitors, lysine demethylase inhibitors, histone demethylase inhibitors, KDM5 inhibitors, KDM1 inhibitors, killer cell lectin-like receptor subfamily G member 1 inhibitors, lymphocyte-activation gene 3 inhibitors, lymphotoxin beta receptor activators, microRNA (miRNA) gene therapy agents, modulators of Axl, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, PD-1 inhibitors, PD-L1 inhibitors, PEG-Interferon Lambda, Peptidylprolyl isomerase inhibitor, phosphatidylinositol-3 kinase (PI3K) inhibitors, recombinant scavenger receptor A (SRA) proteins, recombinant thymosin alpha-1, Retinoic acid-inducible gene 1 stimulator, Reverse transcriptase inhibitor, Ribonuclease inhibitor, RNA DNA polymerase inhibitor, short interfering RNAs (siRNA), short synthetic hairpin RNAs (sshRNAs), SLC 10A1 gene inhibitor, SMAC mimetics, Src tyrosine kinase inhibitor, stimulator of interferon gene (STING) agonists, stimulators of NOD 1, T cell surface glycoprotein CD28 inhibitor, T-cell surface glycoprotein CD8 modulator, Thymosin agonist, Thymosin alpha 1 ligand, Tim-3 inhibitors, TLR-3 agonist, TLR-7 agonist, TLR-9 agonist, TLR9 gene stimulator, toll-like receptor (TLR) modulators, Viral ribonucleotide reductase inhibitor, zinc finger nucleases or synthetic nucleases (TALENs), and combinations thereof.

In some embodiments, provided herein is a method for treating hepatitis B virus (HBV) in a patient in need thereof, comprising administering an effective amount of a compound described herein in combination with an effective amount of one or more anti-HCV agents, such as a NS5A inhibitor, a NS5B inhibitor, a NS3 inhibitor, or a combination thereof.

In some embodiments, provided is a method of treating a hepatitis B virus (HBV) infection in a human in need thereof, comprising administering to the patient an effective amount of a compound described herein in combination with an effective amount of a NS5A inhibitor. In some embodiments, the NS5A inhibitor is ledipasvir or velpatasvir. In some embodiments, is provided a method of treating a hepatitis B virus (HBV) infection in a human in need thereof, comprising administering to the patient an effective amount of a compound described herein in combination with an effective amount of a NS5B inhibitor. In some embodiments, the NS5B inhibitor is sofosbuvir or mericitabine. In some embodiments, is provided a method of treating a hepatitis B virus (HBV) infection in a human in need thereof, comprising administering to the patient an effective amount of a compound described herein in combination with an effective amount of a NS3 inhibitor. In some embodiments, the NS3 inhibitor is voxilaprevir.

In some embodiments, the patient is administered an effective amount of a compound described herein in combination with an effective amount of both an effective amount of a NS5A inhibitor and an effective amount of a NS5B inhibitor. In some embodiments, the NS5A inhibitor is ledipasvir and the NS5B inhibitor is sofosbuvir. In some embodiments, the patient is administered an effective amount of a compound described herein in combination with an effective amount of a fixed dose combination of a NS5A inhibitor and a NS5B inhibitor. In some embodiments, the patient is administered an effective amount of a compound described herein in combination with an effective amount of a fixed dose combination of ledipasvir and sofosbuvir (e.g., ledipasvir 90 mg/sofosbuvir 400 mg). In some embodiments, the patient is administered an effective amount of a compound described herein in combination with an effective amount of Harvoni®. In some embodiments, the patient is administered an effective amount of a compound described herein in combination with an effective amount of a fixed dose combination of velpatasvir and sofosbuvir (e.g., velpatasvir 100 mg/sofosbuvir 400 mg). In some embodiments, the patient is administered an effective amount of a compound described herein in combination with an effective amount of Epclusa®.

In some embodiments, the patient is administered an effective amount of a compound of Table 1 in combination with an effective amount of both an effective amount of a NS5A inhibitor and an effective amount of a NS5B inhibitor. In some embodiments, the NS5A inhibitor is ledipasvir and the NS5B inhibitor is sofosbuvir. In some embodiments, the patient is administered an effective amount of a compound of Table 1 in combination with an effective amount of a fixed dose combination of a NS5A inhibitor and a NS5B inhibitor. In some embodiments, the patient is administered an effective amount of a compound of Table 1 in combination with an effective amount of a fixed dose combination of ledipasvir and sofosbuvir (e.g., ledipasvir 90 mg/sofosbuvir 400 mg). In some embodiments, the patient is administered an effective amount of a compound of Table 1 in combination with an effective amount of Harvoni®. In some embodiments, the patient is administered an effective amount of a compound of Table 1 in combination with an effective amount of a fixed dose combination of velpatasvir and sofosbuvir (e.g., velpatasvir 100 mg/sofosbuvir 400 mg). In some embodiments, the patient is administered an effective amount of a compound of Table 1 in combination with an effective amount of Epclusa®.

In some embodiments, the patient is administered an effective amount of a compound described herein in combination with an effective amount of both an effective amount of a NS5A inhibitor and an effective amount of a NS5B inhibitor, and optionally a NS3 inhibitor. In some embodiments, the patient is administered an effective amount of a compound described herein in combination with an effective amount of sofosbuvir, velpatasvir, and voxilaprevir (e.g., sofosbuvir 400 mg/velpatasvir 100 mg/voxilaprevir 100 mg). In some embodiments, the patient is administered an effective amount of a compound described herein (e.g., compound 139) in combination with an effective amount of Vosevi™.

In certain embodiments, a compound of Formula (I) or (II), or any formula described herein, or a pharmaceutically acceptable salt, stereoisomer, mixture of stereoisomers, solvate, or tautomer thereof, is formulated as a tablet, which may optionally contain one or more other compounds useful for treating hepatitis B virus (HBV). In certain embodiments, the tablet can contain another active ingredient for treating hepatitis B virus (HBV), such as 3-dioxygenase (IDO) inhibitors, Apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), core protein allosteric modulators, covalently closed circular DNA (cccDNA) inhibitors, cyclophilin inhibitors, cytotoxic T-lymphocyte-associated protein 4 (ipi4) inhibitors, DNA polymerase inhibitor, Endonuclease modulator, epigenetic modifiers, Farnesoid X receptor agonist, HBsAg inhibitors, HBsAg secretion or assembly inhibitors, HBV DNA polymerase inhibitors, HBV replication inhibitors, HBV RNAse inhibitors, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, IAPs inhibitors, IL-2 agonist, IL-7 agonist, immunomodulators, indoleamine-2 inhibitors, inhibitors of ribonucleotide reductase, Interleukin-2 ligand, ipi4 inhibitors, lysine demethylase inhibitors, histone demethylase inhibitors, KDM1 inhibitors, KDM5 inhibitors, killer cell lectin-like receptor subfamily G member 1 inhibitors, lymphocyte-activation gene 3 inhibitors, lymphotoxin beta receptor activators, modulators of Axl, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, PD-1 inhibitors, PD-L1 inhibitors, Peptidylprolyl isomerase inhibitor, phosphatidylinositol-3 kinase (PI3K) inhibitors, Retinoic acid-inducible gene 1 stimulator, Reverse transcriptase inhibitor, Ribonuclease inhibitor, RNA DNA polymerase inhibitor, SLC 1 OA 1 gene inhibitor, SMAC mimetics, Src tyrosine kinase inhibitor, stimulator of interferon gene (STING) agonists, stimulators of NOD 1, T cell surface glycoprotein CD28 inhibitor, T-cell surface glycoprotein CD8 modulator, Thymosin agonist, Thymosin alpha 1 ligand, Tim-3 inhibitors, TLR-3 agonist, TLR-7 agonist, TLR-9 agonist, TLR9 gene stimulator, toll-like receptor (TLR) modulators, Viral ribonucleotide reductase inhibitor, and combinations thereof.

In certain embodiments, a compound of the present disclosure, or any formula described herein, or a pharmaceutically acceptable salt, stereoisomer, mixture of stereoisomers, solvate, or tautomer thereof, is combined with one, two, three, four or more additional therapeutic agents selected from hepatitis B virus (HBV) combination drugs, HBV vaccines, HBV DNA polymerase inhibitors, immunomodulators toll-like receptor (TLR) modulators, interferon alpha receptor ligands, hyaluronidase inhibitors, hepatitis b surface antigen (HBsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA) and ddRNAi endonuclease modulators, ribonucelotide reductase inhibitors, HBV E antigen inhibitors, covalently closed circular DNA (cccDNA) inhibitors, farnesoid X receptor agonists, HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2,3-dioxygenase (IDO) pathway inhibitors, PD-1 inhibitors, PD-L1 inhibitors, recombinant thymosin alpha-1, bruton's tyrosine kinase (BTK) inhibitors, KDM inhibitors, HBV replication inhibitors, arginase inhibitors, and other HBV drugs.

HBV Combination Drugs

Examples of combination drugs for the treatment of HBV include TRUVADA® (tenofovir disoproxil fumarate and emtricitabine); ABX-203, lamivudine, and PEG-IFN-alpha; ABX-203 adefovir, and PEG-IFNalpha; and INO-1800 (INO-9112 and RG7944).

Other HBV Drugs

Examples of other drugs for the treatment of HBV include alpha-hydroxytropolones, amdoxovir, beta-hydroxycytosine nucleosides, AL-034, CCC-0975, elvucitabine, ezetimibe, cyclosporin A, gentiopicrin (gentiopicroside), JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-006IA, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, UB-551, and ZH-2N, and the compounds disclosed in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO 16102438A1 (Roche), WO16012470A1 (Roche), US2016220586A (Roche), and US2015031687A (Roche).

HBV Vaccines

HBV vaccines include both prophylactic and therapeutic vaccines. Examples of HBV prophylactic vaccines include Vaxelis, Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, ENGERIX B®, recombinant hepatitis B vaccine (intramuscular, Kangtai Biological Products), recombinant hepatitis B vaccine (Hansenual polymorpha yeast, intramuscular, Hualan Biological Engineering), recombinant hepatitis B surface antigen vaccine, Bimmugen, Euforavac, Eutravac, anrix-DTaP—IPV-Hep B, HBAI-20, Infanrix-DTaP—IPV-Hep B-Hib, Pentabio Vaksin DTP—HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan5, Shan6, rhHBsAG vaccine, HBI pentavalent vaccine, LBVD, Infanrix HeXa, and DTaP-rHB-Hib vaccine.

Examples of HBV therapeutic vaccines include HBsAG-HBIG complex, ARB-1598, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2, TG-1050, NU-500, HBVax, im/TriGrid/antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, and Lm HBV.

HBV DNA Polymerase Inhibitors

Examples of HBV DNA polymerase inhibitors include adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, besifovir, entecavir (BARACLUDE®), entecavir maleate, telbivudine (TYZEKA®), pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234.

Immunomodulators

Examples of immunomodulators include rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), WF-10, ribavirin, IL-12, INO-9112, polymer polyethyleneimine (PEI), Gepon, VGV-1, MOR-22, BMS-936559, RO-7011785, RO-6871765, AIC-649, and IR-103.

Toll-Like Receptor (TLR) Modulators

TLR modulators include modulators of TLR1, TLR2, TLR3, TLR4, TLR5, TLR6, TLR7, TLR8, TLR9, TLR10, TLR11, TLR12, and TLR13. Examples of TLR3 modulators include rintatolimod, poly-ICLC, RIBOXXON®, Apoxxim, RIBOXXIM®, IPH-33, MCT-465, MCT-475, GS-9688 and ND-1.1.

Examples of TLR7 modulators include GS-9620, GSK-2245035, imiquimod, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, RG-7854, and the compounds disclosed in US20100143301 (Gilead Sciences), US20110098248 (Gilead Sciences), and US20090047249 (Gilead Sciences).

Examples of TLR8 modulators include motolimod, resiquimod, 3M-051, 3M-052, MCT-465, IMO-4200, VTX-763, VTX-1463, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics).

Examples of TLR9 modulators include BB-001, BB-006, CYT-003, IMO-2055, IMO-2125, IMO-3100, IMO-8400, IR-103, IMO-9200, agatolimod, DIMS-9054, DV-1079, DV-1179, AZD-1419, leftolimod (MGN-1703), litenimod, and CYT-003-QbG10.

Interferon Alpha Receptor Ligands

Examples of interferon alpha receptor ligands include interferon alpha-2b (INTRON A®), pegylated interferon alpha-2a (PEGASYS®), PEGylated interferon alpha-lb, interferon alpha 1b (HAPGEN®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-INTRON®), Bioferon, Novaferon, Inmutag (Inferon), MULTIFERON®, interferon alfa-n1 (HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B PDferon-B, interferon alfa-2b (IFN, Laboratorios Biprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin intereferon alpha 2a fusion protein), rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b, SFR-9216, and Interapo (Interapa).

Hyaluronidase Inhibitors

Examples of hyaluronidase inhibitors include astodrimer.

Hepatitis B Surface Antigen (HBsAg) Inhibitors

Examples of HBsAg inhibitors include HBF-0259, PBHBV-001, PBHBV-2-15, PBHBV-2-1, REP-9AC, REP-9C, REP-9, REP-2139, REP-2139-Ca, REP-2165, REP-2055, REP-2163, REP-2165, REP-2053, REP-2031 and REP-006, and REP-9AC'.

Examples of HBsAg secretion inhibitors include BM601.

Cytotoxic T-Lymphocyte-Associated Protein 4 (Ipi4) Inhibitors

Examples of Cytotoxic T-lymphocyte-associated protein 4 (ipi4) inhibitors include AGEN-2041, AGEN-1884, ipilumimab, belatacept, PSI-001, PRS-010, Probody mAbs, tremelimumab, and JHL-1155.

Cyclophilin Inhibitors

Examples of cyclophilin inhibitors include CPI-431-32, EDP-494, OCB-030, SCY-635, NVP-015, NVP-018, NVP-019, STG-175, and the compounds disclosed in U.S. Pat. No. 8,513,184 (Gilead Sciences), US20140030221 (Gilead Sciences), US20130344030 (Gilead Sciences), and US20130344029 (Gilead Sciences).

HBV Viral Entry Inhibitors

Examples of HBV viral entry inhibitors include Myrcludex B.

Antisense Oligonucleotide Targeting Viral mRNA

Examples of antisense oligonucleotide targeting viral mRNA include ISIS-HBVRx, IONIS-HBVRx, IONIS-GSK6-LRx, GSK-3389404, RG-6004.

Short Interfering RNAs (siRNA) and ddRNAi.

Examples of siRNA include TKM-HBV (TKM-HepB), ALN-HBV, SR-008, HepB-nRNA, and ARC-520, ARC-521, ARB-1740, ARB-1467.

Examples of DNA-directed RNA interference (ddRNAi) include BB-HB-331.

Endonuclease Modulators

Examples of endonuclease modulators include PGN-514.

Ribonucleotide Reductase Inhibitors

Examples of inhibitors of ribonucleotide reductase include Trimidox.

HBVE Antigen Inhibitors

Examples of HBV E antigen inhibitors include wogonin.

Covalently Closed Circular DNA (cccDNA) Inhibitors

Examples of cccDNA inhibitors include BSBI-25, and CHR-101.

Farnesoid X Receptor Agonist

Example of farnesoid x receptor agonist such as EYP-001.

HBV Antibodies

Examples of HBV antibodies targeting the surface antigens of the hepatitis B virus include GC-1102, XTL-17, XTL-19, KN-003, IV Hepabulin SN, and fully human monoclonal antibody therapy (hepatitis B virus infection, Humabs BioMed). Examples of HBV antibodies, including monoclonal antibodies and polyclonal antibodies, include Zutectra, Shang Sheng Gan Di, Uman Big (Hepatitis B Hyperimmune), Omri-Hep-B, Nabi-HB, Hepatect CP, Hepa-Gam B, igantibe, Niuliva, CT-P24, hepatitis B immunoglobulin (intravenous, pH4, HBV infection, Shanghai RAAS Blood Products), and Fovepta (BT-088). Fully human monoclonal antibodies such as HBC-34.

CCR2 Chemokine Antagonists

Examples of CCR2 chemokine antagonists include propagermanium.

Thymosin Agonists

Examples of thymosin agonists include Thymalfasin, recombinant thymosin alpha 1 (GeneScience).

Cytokines

Examples of cytokines include recombinant IL-7, CYT-107, interleukin-2 (IL-2, Immunex), recombinant human interleukin-2 (Shenzhen Neptunus), IL-15, IL-21, IL-24, and celmoleukin.

Nucleoprotein Modulators

Nucleoprotein modulators may be either HBV core or capsid protein inhibitors. Examples of nucleoprotein modulators include AB-423, AT-130, GLS4, NVR-1221, NVR-3778, BAY 41-4109, morphothiadine mesilate, JNJ-379, RG-7907, ABI-H0731, ABI-H2158 and DVR-23.

Examples of capsid inhibitors include the compounds disclosed in US20140275167 (Novira Therapeutics), US20130251673 (Novira Therapeutics), US20140343032 (Roche), WO2014037480 (Roche), US20130267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche).

Retinoic Acid-Inducible Gene 1 Stimulators

Examples of stimulators of retinoic acid-inducible gene 1 include SB-9200, SB-40, SB-44, ORI-7246, ORI-9350, ORI-7537, ORI-9020, ORI-9198, and ORI-7170, RGT-100.

NOD2 Stimulators

Examples of stimulators of NOD2 include SB-9200.

Phosphatidylinositol 3-kinase (PI3K) Inhibitors

Examples of PI3K inhibitors include idelalisib, ACP-319, AZD-8186, AZD-8835, buparlisib, CDZ-173, CLR-457, pictilisib, neratinib, rigosertib, rigosertib sodium, EN-3342, TGR-1202, alpelisib, duvelisib, IPI-549, UCB-5857, taselisib, XL-765, gedatolisib, ME-401, VS-5584, copanlisib, CAI orotate, perifosine, RG-7666, GSK-2636771, DS-7423, panulisib, GSK-2269557, GSK-2126458, CUDC-907, PQR-309, INCB-40093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301, TAK-117, HMPL-689, tenalisib, voxtalisib, and CLR-1401.

Indoleamine-2,3-dioxygenase (IDO) Pathway Inhibitors

Examples of IDO inhibitors include epacadostat (INCB24360), resminostat (4SC-201), indoximod, F-001287, SN-35837, NLG-919, GDC-0919, GBV-1028, GBV-1012, NKTR-218, and the compounds disclosed in US20100015178 (Incyte), US2016137652 (Flexus Biosciences, Inc.), WO2014073738 (Flexus Biosciences, Inc.), and WO2015188085 (Flexus Biosciences, Inc.).

PD-1 Inhibitors

Examples of PD-1 inhibitors include nivolumab, pembrolizumab, pidilizumab, BGB-108, SHR-1210, PDR-001, PF-06801591, IBI-308, GB-226, STI-1110, and mDX-400.

PD-L1 Inhibitors

Examples of PD-L1 inhibitors include atezolizumab, avelumab, AMP-224, MEDI-0680, RG-7446, GX-P2, durvalumab, KY-1003, KD-033, MSB-0010718C, TSR-042, ALN-PDL, STI-A1014, CX-072, and BMS-936559.

In a particular embodiment, a compound disclosed herein, or any formula described herein, or a pharmaceutically acceptable salt, stereoisomer, mixture of stereoisomers, solvate, or tautomer thereof, is combined with compounds such as those disclosed in WO2018026971, US20180044329, US20180044305, US20180044304, US20180044303, US20180044350, US20180057455, US20180057486, US20180045142, WO20180044963, WO2018044783, WO2018009505, WO20180044329, WO2017066227, WO2017087777, US20170145025, WO2017079669, WO2017070089, US2017107216, WO2017222976, US20170262253, WO2017205464, US20170320875, WO2017192961, WO2017112730, US20170174679, WO2017106634, WO2017202744, WO2017202275, WO2017202273, WO2017202274, WO2017202276, WO2017180769, WO2017118762, WO2016041511, WO2016039749, WO2016142835, WO2016142852, WO2016142886, WO2016142894, and WO2016142833.

Recombinant Thymosin Alpha-1

Examples of recombinant thymosin alpha-1 include NL-004 and PEGylated thymosin alpha-1.

Bruton's Tyrosine Kinase (BTK) Inhibitors

Examples of BTK inhibitors include ABBV-105, acalabrutinib (ACP-196), ARQ-531, BMS-986142, dasatinib, ibrutinib, GDC-0853, PRN-1008, SNS-062, ONO-4059, BGB-3111, ML-319, MSC-2364447, RDX-022, X-022, AC-058, RG-7845, spebrutinib, TAS-5315, TP-0158, TP-4207, HM-71224, KBP-7536, M-2951, TAK-020, AC-0025, and the compounds disclosed in US20140330015 (Ono Pharmaceutical), US20130079327 (Ono Pharmaceutical), and US20130217880 (Ono Pharmaceutical).

KDM Inhibitors

Examples of KDM5 inhibitors include the compounds disclosed in WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel).

Examples of KDM1 inhibitors include the compounds disclosed in U.S. Pat. No. 9,186,337B2 (Oryzon Genomics), and GSK-2879552, RG-6016, ORY-2001.

HBV Replication Inhibitors

Examples of hepatitis B virus replication inhibitors include isothiafludine, IQP-HBV, RM-5038, and Xingantie.

Arginase Inhibitors

Examples of Arginase inhibitors include CB-1158, C-201, and resminostat.

Gene Therapy and Cell Therapy

Gene Therapy and Cell Therapy including the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection.

Gene Editors

The genome editing system is selected from the group consisting of: a CRISPR/Cas9 system, a zinc finger nuclease system, a TALEN system, a homing endonucleases system, and a meganuclease system; e.g., cccDNA elimination via targeted cleavage, and altering one or more of the hepatitis B virus (HBV) viral genes. Altering (e.g., knocking out and/or knocking down) the PreC, C, X, PreS1, PreS2, S, P or SP gene refers to (1) reducing or eliminating PreC, C, X, PreS1, PreS2, S, P or SP gene expression, (2) interfering with Precore, Core, X protein, Long surface protein, middle surface protein, S protein (also known as HBs antigen and HBsAg), polymerase protein, and/or Hepatitis B spliced protein function (HBe, HBc, HBx, PreS1, PreS2, S, Pol, and/or HBSP or (3) reducing or eliminating the intracellular, serum and/or intraparenchymal levels of HBe, HBc, HBx, LHBs, MHBs, SHBs, Pol, and/or HBSP proteins. Knockdown of one or more of the PreC, C, X, PreS1, PreS2, S, P and/or SP gene(s) is performed by targeting the gene(s) within HBV cccDNA and/or integrated HBV DNA.

CAR-T Cell Therapy

A population of immune effector cells engineered to express a chimeric antigen receptor (CAR), wherein the CAR comprises an HBV antigen-binding domain. The immune effector cell is a T cell or an NK cell. In some embodiments, the T cell is a CD4+ T cell, a CD8+ T cell, or a combination thereof. Cells can be autologous or allogeneic.

TCR-T Cell Therapy

T cells expressing HBV-specific T cell receptors. TCR-T cells are engineered to target HBV derived peptides presented on the surface of virus-infected cells.

T-Cells expressing HBV surface antigen (HBsAg)-specific TCR.

TCR-T therapy directed to treatment of HBV, such as LTCR-H2-1

HBV Combination Therapy

In a particular embodiment, a compound disclosed herein, or any formula described herein, or a pharmaceutically acceptable salt, stereoisomer, mixture of stereoisomers, solvate, or tautomer thereof, is combined with one, two, three, or four additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®). In a particular embodiment, a compound disclosed herein, or any formula described herein, or a pharmaceutically acceptable salt, stereoisomer, mixture of stereoisomers, solvate, or tautomer thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®). In one embodiment, pharmaceutical compositions comprising a compound disclosed herein, or any formula described herein, or a pharmaceutically acceptable salt, stereoisomer, mixture of stereoisomers, solvate, or tautomer thereof, in combination with one or more (e.g., one, two, three, four, one or two, or one to three, or one to four) additional therapeutic agents and a pharmaceutically acceptable carrier, diluent, or excipient are provided.

HBV DNA Polymerase Inhibitor Combination Therapy

In a specific embodiment, a compound disclosed herein, or any formula described herein, or a pharmaceutically acceptable salt, stereoisomer, mixture of stereoisomers, solvate, or tautomer thereof, is combined with an HBV DNA polymerase inhibitor. In another specific embodiment, a compound disclosed herein, or any formula described herein, or a pharmaceutically acceptable salt, stereoisomer, mixture of stereoisomers, solvate, or tautomer thereof, is combined with an HBV DNA polymerase inhibitor and at least one additional therapeutic agent selected from the group consisting of: immunomodulators, TLR modulators, interferon alpha receptor ligands, hyaluronidase inhibitors, recombinant IL-7, HBsAg inhibitors, HBsAg secretion or assembly inhibitors, compounds targeting HBcAg, cyclophilin inhibitors, HBV vaccines, HBV viral entry inhibitors, NTCP inhibitors, antisense oligonucleotide targeting viral mRNA, siRNA, miRNA gene therapy agents, endonuclease modulators, inhibitors of ribonucleotide reductase, hepatitis B virus E antigen inhibitors, recombinant SRA proteins, src kinase inhibitors, HBx inhibitors, cccDNA inhibitors, sshRNAs, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), CCR2 chemokine antagonists, thymosin agonists, cytokines, nucleoprotein modulators (HBV core or capsid protein modulators), stimulators of retinoic acid-inducible gene 1, stimulators of RIG-I like receptors, stimulators of NOD2, stimulators of NOD1, Arginase inhibitors, STING agonists, PI3K inhibitors, lymphotoxin beta receptor activators, natural killer cell receptor 2B4 inhibitors, Lymphocyte-activation gene 3 inhibitors, CD160 inhibitors, cytotoxic T-lymphocyte-associated protein 4 (ipi4) inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambda, recombinant thymosin alpha-1, BTK inhibitors, modulators of TIGIT, modulators of CD47, modulators of SIRPalpha, modulators of ICOS, modulators of CD27, modulators of CD70, modulators of OX40, epigenetic modifiers, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), IAPs inhibitors, SMAC mimetics, KDM5 inhibitors, IDO inhibitors, and hepatitis B virus replication inhibitors.

In another specific embodiment, a compound disclosed herein, or any formula described herein, or a pharmaceutically acceptable salt, stereoisomer, mixture of stereoisomers, solvate, or tautomer thereof, is combined with an HBV DNA polymerase inhibitor, one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2, and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In another specific embodiment, a compound disclosed herein, or any formula described herein, or a pharmaceutically acceptable salt, stereoisomer, mixture of stereoisomers, solvate, or tautomer thereof, is combined with an HBV DNA polymerase inhibitor and at least a second additional therapeutic agent selected from the group consisting of: immunomodulators, TLR modulators, HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2.

In another specific embodiment, a compound disclosed herein, or any formula described herein, or a pharmaceutically acceptable salt, stereoisomer, mixture of stereoisomers, solvate, or tautomer thereof, is combined with an HBV DNA polymerase inhibitor and at least a second additional therapeutic agent selected from the group consisting of: HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein inhibitors).

HBV Drug Combination Therapy

In a particular embodiment, a compound disclosed herein, or any formula described herein, or a pharmaceutically acceptable salt, stereoisomer, mixture of stereoisomers, solvate, or tautomer thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®), and at least a second additional therapeutic agent selected from the group consisting of immunomodulators, TLR modulators, interferon alpha receptor ligands, hyaluronidase inhibitors, recombinant IL-7, HBsAg inhibitors, HBsAg secretion or assembly inhibitors, compounds targeting HBcAg, cyclophilin inhibitors, HBV vaccines, HBV viral entry inhibitors, NTCP inhibitors, antisense oligonucleotide targeting viral mRNA, siRNA, miRNA gene therapy agents, endonuclease modulators, inhibitors of ribonucleotide reductase, hepatitis B virus E antigen inhibitors, recombinant SRA proteins, src kinase inhibitors, HBx inhibitors, cccDNA inhibitors, sshRNAs, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, and TCR-like antibodies), CCR2 chemokine antagonists, thymosin agonists, cytokines, nucleoprotein modulators (HBV core or capsid protein modulators), stimulators of retinoic acid-inducible gene 1, stimulators of RIG-I like receptors, stimulators of NOD2, stimulators of NOD1, IDO inhibitors, recombinant thymosin alpha-1, Arginase inhibitors, STING agonists, PI3K inhibitors, lymphotoxin beta receptor activators, natural killer cell receptor 2B4 inhibitors, Lymphocyte-activation gene 3 inhibitors, CD160 inhibitors, ipi4 inhibitors, CD137 inhibitors, killer cell lectin-like receptor subfamily G member 1 inhibitors, TIM-3 inhibitors, B- and T-lymphocyte attenuator inhibitors, epigenetic modifiers, CD305 inhibitors, PD-1 inhibitors, PD-L1 inhibitors, PEG-Interferon Lambd, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), IAPs inhibitors, SMAC mimetics, KDM5 inhibitors, and hepatitis B virus replication inhibitors.

In a particular embodiment, a compound disclosed herein, or any formula described herein, or a pharmaceutically acceptable salt, stereoisomer, mixture of stereoisomers, solvate, or tautomer thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®) or lamivudine (EPIVIR-HBV®) and at least a second additional therapeutic agent selected from the group consisting of peginterferon alfa-2b (PEG-INTRON®), MULTIFERON®, interferon alpha 1b (HAPGEN®), interferon alpha-2b (INTRON A®), pegylated interferon alpha-2a (PEGASYS®), interferon alfa-n1 (HUMOFERON®), ribavirin, interferon beta-1a (AVONEX®), Bioferon, Ingaron, Inmutag (Inferon), Algeron, Roferon-A, Oligotide, Zutectra, Shaferon, interferon alfa-2b (AXXO), Alfaferone, interferon alfa-2b (BioGeneric Pharma), Feron, interferon-alpha 2 (CJ), BEVAC, Laferonum, VIPEG, BLAUFERON-B, BLAUFERON-A, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2, Immunex), recombinant human interleukin-2 (Shenzhen Neptunus), Layfferon, Ka Shu Ning, Shang Sheng Lei Tai, INTEFEN, SINOGEN, Fukangtai, Alloferon, and celmoleukin.

In a particular embodiment, a compound disclosed herein, or any formula described herein, or a pharmaceutically acceptable salt, stereoisomer, mixture of stereoisomers, solvate, or tautomer thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®), and at least a second additional therapeutic agent selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, Arginase inhibitors, PI3K inhibitors, PD-1 inhibitors, PD-L1 inhibitors, IDO inhibitors, and stimulators of NOD2.

In a particular embodiment, a compound disclosed herein, or any formula described herein, or a pharmaceutically acceptable salt, stereoisomer, mixture of stereoisomers, solvate, or tautomer thereof, is combined with a first additional therapeutic agent selected from the group consisting of: adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®), and at least a second additional therapeutic agent selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or any formula described herein, or a pharmaceutically acceptable salt, stereoisomer, mixture of stereoisomers, solvate, or tautomer thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); one, two, or three additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2; and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or any formula described herein, or a pharmaceutically acceptable salt, stereoisomer, mixture of stereoisomers, solvate, or tautomer thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2; and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or any formula described herein, or a pharmaceutically acceptable salt, stereoisomer, mixture of stereoisomers, solvate, or tautomer thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); and one, two, three, or four additional therapeutic agents selected from the group consisting of immunomodulators, TLR7 modulators, TLR8 modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, stimulators of NOD2 HBV viral entry inhibitors, NTCP inhibitors, HBx inhibitors, cccDNA inhibitors, siRNA, miRNA gene therapy agents, sshRNAs, KDM5 inhibitors, and nucleoprotein modulators (HBV core or capsid protein modulators).

In a particular embodiment, a compound disclosed herein, or any formula described herein, or a pharmaceutically acceptable salt, stereoisomer, mixture of stereoisomers, solvate, or tautomer thereof, is combined with compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics), U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (Flexus Biosciences, Inc.), WO2014073738 (Flexus Biosciences, Inc.), WO2015188085 (Flexus Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel), U.S. Pat. No. 9,186,337B2 (Oryzon Genomics), and other drugs for treating hepatitis B virus (HBV), and combinations thereof.

In certain embodiments, a compound as disclosed herein (e.g., any compound of Formula I) may be combined with one or more (e.g., one, two, three, four, one or two, one to three, or one to four) additional therapeutic agents in any dosage amount of the compound of Formula (I) or (II), or any formula described herein, or a pharmaceutically acceptable salt, stereoisomer, mixture of stereoisomers, solvate, or tautomer thereof, (e.g., from 10 mg to 1000 mg of compound).

In certain embodiments, a compound disclosed herein, or any formula described herein, or a pharmaceutically acceptable salt, stereoisomer, mixture of stereoisomers, solvate, or tautomer thereof, is combined with 5-30 mg tenofovir alafenamide fumarate, tenofovir alafenamide hemifumarate, or tenofovir alafenamide. In certain embodiments, a compound disclosed herein, or a pharmaceutically acceptable salt, stereoisomer, mixture of stereoisomers, solvate, or tautomer thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide. In certain embodiments, a compound disclosed herein, or a pharmaceutically acceptable salt, stereoisomer, mixture of stereoisomers, solvate, or tautomer thereof, is combined with 10 mg tenofovir alafenamide fumarate, tenofovir alafenamide hemifumarate, or tenofovir alafenamide. In certain embodiments, a compound disclosed herein, or a pharmaceutically acceptable salt, stereoisomer, mixture of stereoisomers, solvate, or tautomer thereof, is combined with 25 mg tenofovir alafenamide fumarate, tenofovir alafenamide hemifumarate, or tenofovir alafenamide. A compound as disclosed herein (e.g., a compound of Formula I) may be combined with the agents provided herein in any dosage amount of the compound (e.g., from 50 mg to 500 mg of compound) the same as if each combination of dosages were specifically and individually listed.

In certain embodiments, a compound disclosed herein, or a pharmaceutically acceptable salt, stereoisomer, mixture of stereoisomers, solvate, or tautomer thereof, is combined with 100-400 mg tenofovir disoproxil fumarate, tenofovir disoproxil hemifumarate, or tenofovir disoproxil. In certain embodiments, a compound disclosed herein, or a pharmaceutically acceptable salt, stereoisomer, mixture of stereoisomers, solvate, or tautomer thereof, is combined with 100 mg to 150 mg; 100 mg to 200 mg; 100 mg to 250 mg; 100 mg to 300 mg; 100 mg to 350 mg; 150 mg to 200 mg; 150 mg to 250 mg; 150 mg to 300 mg; 150 mg to 350 mg; 150 mg to 400 mg; 200 mg to 250 mg; 200 mg to 300 mg; 200 mg to 350 mg; 200 mg to 400 mg; 250 mg to 350 mg; 250 mg to 400 mg; 350 mg to 400 or 300 mg to 400 mg tenofovir disoproxil fumarate, tenofovir disoproxil hemifumarate, or tenofovir disoproxil. In certain embodiments, a compound disclosed herein, or a pharmaceutically acceptable salt, stereoisomer, mixture of stereoisomers, solvate, or tautomer thereof, is combined with 300 mg tenofovir disoproxil fumarate, tenofovir disoproxil hemifumarate, or tenofovir disoproxil. In certain embodiments, a compound disclosed herein, or a pharmaceutically acceptable salt, stereoisomer, mixture of stereoisomers, solvate, or tautomer thereof, is combined with 250 mg tenofovir disoproxil fumarate, tenofovir disoproxil hemifumarate, or tenofovir disoproxil. In certain embodiments, a compound disclosed herein, or a pharmaceutically acceptable salt, stereoisomer, mixture of stereoisomers, solvate, or tautomer thereof, is combined with 150 mg tenofovir disoproxil fumarate, tenofovir disoproxil hemifumarate, or tenofovir disoproxil. A compound as disclosed herein (e.g., a compound of Formula I) may be combined with the agents provided herein in any dosage amount of the compound (e.g., from 50 mg to 500 mg of compound) the same as if each combination of dosages were specifically and individually listed.

In one embodiment, kits comprising a compound disclosed herein, or a pharmaceutically acceptable salt, stereoisomer, mixture of stereoisomers, solvate, or tautomer thereof, in combination with one or more (e.g., one, two, three, four, one or two, or one to three, or one to four) additional therapeutic agents are provided.

Any pharmaceutical composition provided in the present disclosure may be used in the kits, the same as if each and every composition were specifically and individually listed for use in a kit.

Synthesis

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of typical compounds of Formula (I) or (II), e.g., compounds having structures described by one or more of Formula (I) or (II), or other formulas or compounds disclosed herein, or a pharmaceutically acceptable salt, stereoisomer, mixture of stereoisomers, solvate, or tautomer thereof, may be accomplished as described in the following examples.

General Syntheses

Typical embodiments of compounds in accordance with the present disclosure may be synthesized using the general reaction schemes and/or examples described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Starting materials are typically obtained from commercial sources or synthesized using published methods for synthesizing compounds which are embodiments of the present disclosure, inspection of the structure of the compound to be synthesized will provide the identity of each substituent group. The identity of the final product will generally render apparent the identity of the necessary starting materials by a simple process of inspection, given the examples herein. Group labels (e.g., $R^1$, $R^a$, $R^b$) used in the reaction schemes herein are for illustrative purposes only and unless otherwise specified do not necessarily match by name or function the labels used elsewhere to describe compounds of Formula (I) or (II), or any formula described herein, or aspects or fragments thereof.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, $5^{th}$ Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient to achieve a stated function, e.g., to bring a solution to the desired volume (i.e., 100%).

Compounds as provided herein may be synthesized according to the general schemes provided below. In the Schemes below, it should be appreciated that each of the compounds shown therein may have protecting groups as required present at any step. Standard protecting groups are well within the pervue of one skilled in the art.

Scheme 1 shows an exemplary synthetic route for the synthesis of compounds provided herein (e.g., compounds of Formula I). In Scheme 1, t, x, w, $R^E$, $R^W$, $Z^1$, $Z^2$, $Z^3$, $X^1$, $X^2$, $X^3$ and $X^4$ are as defined herein, $R^{50}$ is a functional group capable of forming a covalent bond with compound 108 (e.g., —C(O)H), R⁵⁴ is hydrogen, a suitable protecting group and/or a leaving group with the oxygen atom to which it is bound, and each R⁵² is independently C$_{1-6}$ alkyl or two R⁵² together with the atom to which they are attached form a ring, each X is independently halo (e.g., bromo), R⁵⁵ is a leaving group (e.g., halo).

catalyst) in a suitable solvent (e.g., dioxane, water, etc.), optionally under an inert atmosphere, to provide compound 107. Compound 107 is then reacted with compound 108 under conditions suitable to provide compound 109. Exemplary conditions include, but are not limited to, reductive amination when R⁵⁰ is an aldehyde and compound 108 comprises a primary or secondary amine.

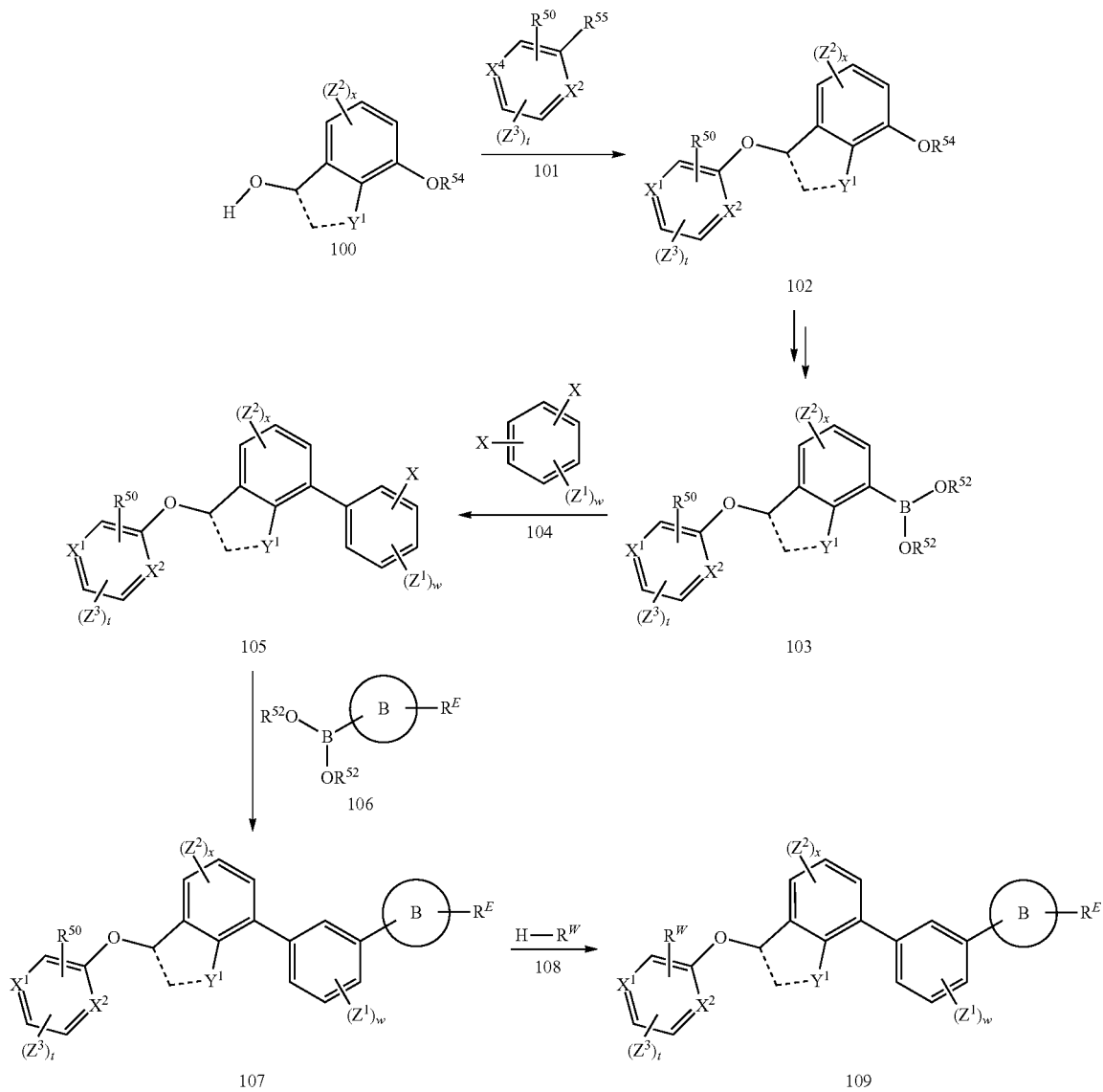

Scheme 1

In Scheme 1, suitably compound 100 is reacted with compound 101 under standard coupling conditions. Compound 102 is converted to compound 103 by converting —OR⁵⁴ to a leaving group (e.g., —OTf) and a suitable borate or borane reagent (e.g., 4,4,4',4',5,5,5',5'-octamethyl-2,2'-bi(1,3,2-dioxaborolane). Compound 103 is coupled with compound 104 under standard metal-catalyzed coupling conditions (e.g., using a palladium catalyst) in a suitable solvent (e.g., dioxane, water, etc.), optionally under an inert atmosphere, to provide compound 105. Compound 105 is then coupled with compound 106 under standard metal-catalyzed coupling conditions (e.g., using a palladium Suitably substituted compounds 100, 101, 104, 106 and 108 for use in the methods provided herein can be purchased from commercial sources or synthesized by known methods. Resolution of isomers can be performed as needed using standard chiral separation/resolution conditions (e.g., chromatography, crystallization, etc.).

Scheme 2 shows an exemplary synthetic route for the synthesis of compounds provided herein (e.g., compounds of Formula II). In Scheme 2, t, w, x, R$^E$, R$^W$, Z¹, Z², Z³, Y¹, X¹, X² and ring B are as defined herein, R⁵⁰ is a functional group capable of forming a covalent bond with compound 108 (e.g., —C(O)H), each R⁵² is independently C$_{1-6}$ alkyl or two R$^{52}$ together with the atom to which they are attached form a ring, each R$^{55}$ is a leaving group (e.g., halo, such as bromo).

described herein, and that other known methods and variants of methods described herein may be used. The methods or features described in various Examples may be combined or

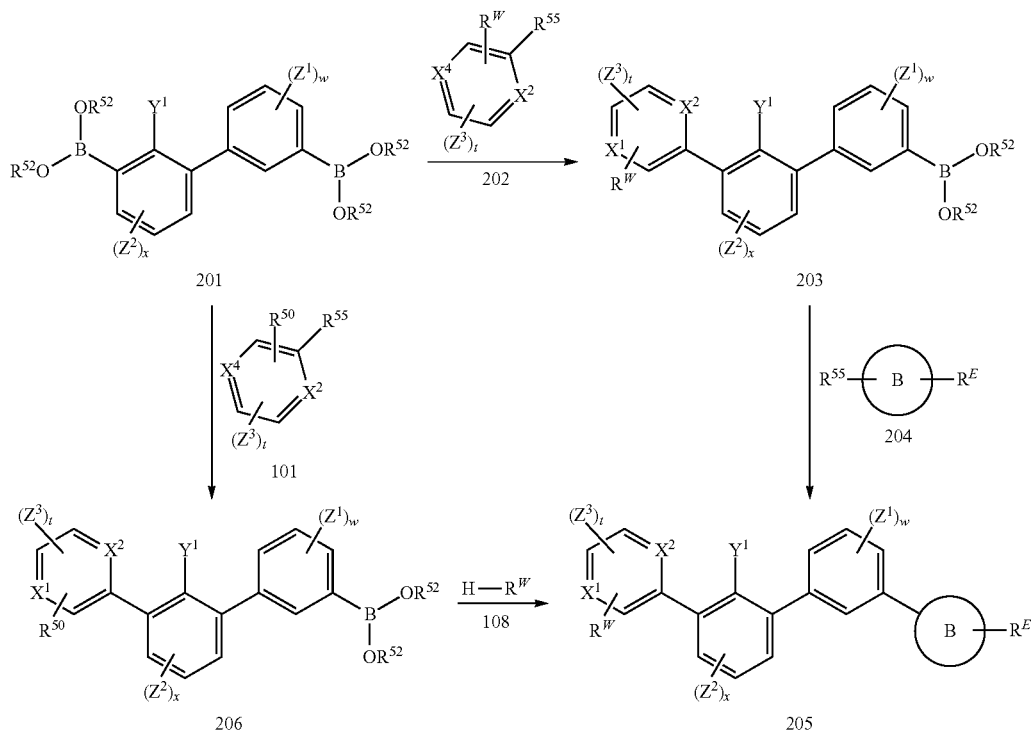

In Scheme 1, compound 201 is coupled with compound 202 under standard metal-catalyzed coupling conditions (e.g., using a palladium(O) catalyst) in a suitable solvent (e.g., DMF) under an inert atmosphere to provide compound 203. Compound 205 are then provided by contacting compound 204 with compound 203 under standard metal-catalyzed coupling conditions. Alternatively, compound 201 is contacted with compound 101 under standard metal-catalyzed coupling conditions to provide compound 206. Compound 206 is then reacted with compound 108 under conditions suitable to provide compound 205. Exemplary conditions include, but are not limited to, reductive amination.

Suitably substituted compounds 201, 202, 204, and 108 for use in the methods provided herein can be purchased from commercial sources or synthesized by known methods. Resolution of the isomers of Formula (II) can be performed as needed using standard chiral separation/resolution conditions (e.g., chromatography, crystallization, etc.).

EXAMPLES

The compounds were named using the IUPAC naming convention or using ChemBioDraw Ultra Version 14.0. Structures are drawn ChemBioDraw.

When production of starting materials is not particularly described, the compounds are known or may be prepared analogously to methods known in the art or as disclosed in the Examples. One of skill in the art will appreciate that synthetic methodologies described herein are only representative of methods for preparation of the compounds adapted in various ways to provide additional ways of making the compounds described herein.

Example A: (R)-1-((6-(((S)-4-(2-chloro-3-(5,6,7,8-tetrahydro-1,6-naphthyridin-2-yl)phenyl)-2,3-di-hydro-1H-inden-1-yl)oxy)-2-methoxy-5-(trifluoromethyl)pyridin-3-yl)methyl)pyrrolidine-3-carboxylic acid (1)

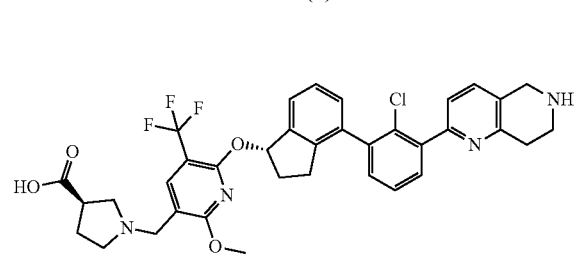

Step 1: A solution of tert-butyl 2-chloro-7,8-dihydro-1,6-naphthyridine-6(5H)-carboxylate (714 mg, 3 mmol) in DCM (10 mL) and TFA (10 mL) was stirred for 1 h at rt, then concentrated to provide 2-chloro-5,6,7,8-tetrahydro-1,6-naphthyridine.

Step 2: To a solution of 2-chloro-5,6,7,8-tetrahydro-1,6-naphthyridine (187 mg, 0.567 mmol) in DCM (10 mL) and TEA (1.29 mL, 3 mmol) was added 1-[(2-trimethylsilyl) ethoxycarbonyloxy]pyrrolidin-2,5-dione (758 mg, 3 mmol) and the mixture stirred for 1 h. After 1 h, the reaction mixture was diluted with CH$_2$Cl$_2$ and brine solution. The organic layer was then separated and the aqueous layer was back extracted with CH₂Cl₂ and the combined organic layers were dried (MgSO₄). Filtration, concentration, followed by purification by column chromatography (SiO₂, 0% EtOAc/hexanes to 100% EtOAc/hexanes) gave 2-(trimethylsilyl) ethyl 2-chloro-7,8-dihydro-1,6-naphthyridine-6(5H)-carboxylate.

Step 3: To a mixture of 2-(trimethylsilyl)ethyl 2-chloro-7,8-dihydro-1,6-naphthyridine-6(5H)-carboxylate (0.92 g, 0.29 mol), (S)-6-((4-(2-chloro-3-(4,4,5,5-tetramethyl-1,3,2-dioxaborolan-2-yl)phenyl)-2,3-dihydro-1H-inden-1-yl) oxy)-2-methoxy-5-(trifluoromethyl)nicotinaldehyde (140 mg, 0.244 mmol) in 1,4-Dioxane/water (3 mL, 9:1) was added K₂CO₃ (67 mg, 0.49 mmol) and Tetrakis(triphenylphosphine)palladium(O) (114 mg, 0.098 mmol) and the reaction mixture was heated at 85° C. for 4 h. After cooling to room temperature, the reaction mixture was diluted with EtOAc and water. The organic layer was then separated and the aqueous layer was back extracted with EtOAc and the combined organic layers were dried (MgSO₄). Filtration and concentration followed by purification by column chromatography (SiO₂, 0% EtOAc/hexanes to 100% EtOAc/hexanes) gave 2-(trimethylsilyl)ethyl (S)-2-(2-chloro-3-(1-((5-formyl-6-methoxy-3-(trifluoromethyl)pyridin-2-yl)oxy)-2,3-dihydro-1H-inden-4-yl)phenyl)-7,8-dihydro-1,6-naphthyridine-6(5H)-carboxylate.

Step 4: To a solution of 2-(trimethylsilyl)ethyl (S)-2-(2-chloro-3-(1-((5-formyl-6-methoxy-3-(trifluoromethyl)pyridin-2-yl)oxy)-2,3-dihydro-1H-inden-4-yl)phenyl)-7,8-dihydro-1,6-naphthyridine-6(5H)-carboxylate (100 mg, 0.137 mmol) in DMF (1.0 mL) was added TASF (226 mg, 0.822 mmol) and the mixture was stirred at 45° C. After 0.5 h, the reaction mixture was diluted with EtOAc and 1N K₂CO₃ solution. Organic layer was separated, dried sodium sulfate, filtered and concentrated to (S)-6-((4-(2-chloro-3-(5,6,7,8-tetrahydro-1,6-naphthyridin-2-yl)phenyl)-2,3-dihydro-1H-inden-1-yl)oxy)-2-methoxy-5-(trifluoromethyl)nicotinaldehyde.

Step 5: To a solution of (S)-6-((4-(2-chloro-3-(5,6,7,8-tetrahydro-1,6-naphthyridin-2-yl)phenyl)-2,3-dihydro-1H-inden-1-yl)oxy)-2-methoxy-5-(trifluoromethyl)nicotinaldehyde (25 mg, 0.043 mmol) in DMSO (2.0 mL) was added (R)-pyrrolidine-3-carboxylic acid (50 mg, 0.43 mmol) and the misture stirred for 1h. Sodium triacetoxyborohydride (64 mg, 0.30 mmol) and the mixture was stirred at rt for 45 min. The mixture was acidified with TFA (23 µL, 0.30 mmol) and stirred for 15 min, then purified by reverse phase chromatography to give the title compound as the TFA salt. LCMS-ESI⁺ (m/z): [M+H]⁺ calcd for C₃₆H₃₄ClF₃N₄O₄: 679.22; found: 679.06. ¹H NMR (400 MHz, DMSO-d₆) δ 12.89 (s, 1H), 9.87 (s, 1H), 9.09 (s, 2H), 8.21 (s, 1H), 7.77 (d, J=8.1 Hz, 1H), 7.63-7.48 (m, 3H), 7.48-7.33 (m, 2H), 7.27 (dd, J=7.5, 1.1 Hz, 1H), 6.67 (s, 1H), 4.39 (s, 2H), 4.33 (d, J=18.1 Hz, 2H), 4.07 (s, 3H), 3.69 (s, 3H), 3.39 (s, 2H), 3.23-3.10 (m, 4H), 2.87 (d, J=13.6 Hz, 1H), 2.80-2.71 (m, 1H), 2.25-2.15 (m, 1H), 2.06 (s, 2H).

Example B: (R)-1-((6-(((S)-4-(2-chloro-3-(4,5,6,7-tetrahydrothiazolo[4,5-c]pyridin-2-yl)phenyl)-2,3-dihydro-1H-inden-1-yl)oxy)-2-methoxy-5-(trifluoromethyl)pyridin-3-yl)methyl)pyrrolidine-3-carboxylic acid (2)

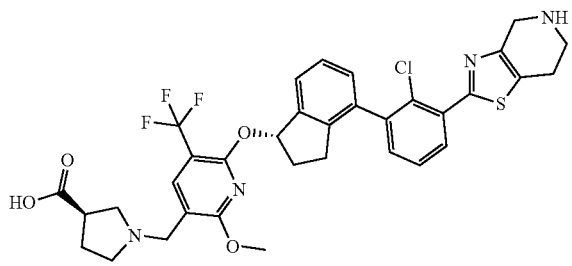 [SMILES: COc1nc(O[C@H]2CCc3c(-c4cccc(-c5nc6c(s5)CCNC6)c4Cl)cccc32)c(C(F)(F)F)cc1CN1CC[C@@H](C(=O)O)C1]

Step 1: A solution of tert-butyl 2-bromo-6,7-dihydrothiazolo[4,5-c]pyridine-5(4H)-carboxylate (181 mg, 0.567 mmol) in DCM (6 mL) and TFA (6 mL) was stirred for 1h at rt, then concentrated to provide 2-bromo-4,5,6,7-tetrahydrothiazolo[4,5-c]pyridine as a light brown oil. LCMS-ESI⁺ (m/z): [M+H]⁺ calcd for C₁₁H₁₅BrN₂O₂S: 319.0; found: 318.73.

Step 2: To a solution of 2-bromo-4,5,6,7-tetrahydrothiazolo[4,5-c]pyridine (187 mg, 0.567 mmol) in DCM (3 mL) and TEA (0.277 mL, 2 mmol) was added 1-[(2-trimethylsilyl)ethoxycarbonyloxy]pyrrolidin-2,5-dione (172 mg, 0.624 mmol) and the mixture stirred for 1 h. After 1 h, the reaction mixture was diluted with CH₂Cl₂ and brine solution. The organic layer was then separated and the aqueous layer was back extracted with CH₂Cl₂ and the combined organic layers were dried (MgSO₄). Filtration, concentration and followed by purification by column chromatography (SiO₂, 0% EtOAc/hexanes to 100% EtOAc/hexanes) gave 2-(trimethylsilyl)ethyl 2-bromo-6,7-dihydrothiazolo[4,5-c]pyridine-5(4H)-carboxylate.

Step 3: To a mixture 2-methoxy-6-[rac-(1S)-4-[2-chloro-3-(4,4,5,5-tetramethyl-1,3,2-dioxaborolan-2-yl)phenyl]indan-1-yl]oxy-5-(trifluoromethyl)pyridine-3-carbaldehyde (0.14 g, 0 mol) (140 mg, 0.244 mmol) and 2-(trimethylsilyl) ethyl 2-bromo-6,7-dihydrothiazolo[4,5-c]pyridine-5(4H)-carboxylate (106 mg, 0.293 mmol) in 1,4-Dioxane/water (3 mL, 9:1) was added K₂CO₃ (67 mg, 0.49 mmol) and Tetrakis(triphenylphosphine)palladium(O) (114 mg, 0.098 mmol) and the reaction mixture was heated at 85° C. for 16 h. After cooling to room temperature, the reaction mixture was diluted with EtOAc and water. The organic layer was then separated and the aqueous layer was back extracted with EtOAc and the combined organic layers were dried (MgSO₄). Filtration, concentration and followed by purification by column chromatography (SiO₂, 0% EtOAc/hexanes to 100% EtOAc/hexanes) gave 2-(trimethylsilyl) ethyl (S)-2-(2-chloro-3-(1-((5-formyl-6-methoxy-3-(trifluoromethyl)pyridin-2-yl)oxy)-2,3-dihydro-1H-inden-4-yl)phenyl)-6,7-dihydrothiazolo[4,5-c]pyridine-5 (4H)-carboxylate.

Step 4: To a solution of gave 2-(trimethylsilyl)ethyl (S)-2-(2-chloro-3-(1-((5-formyl-6-methoxy-3-(trifluoromethyl)pyridin-2-yl)oxy)-2,3-dihydro-1H-inden-4-yl)phenyl)-6,7-dihydrothiazolo[4,5-c]pyridine-5(4H)-carboxylate. (100 mg, 0.137 mmol) in DMF (1.0 mL) was added TASF (226 mg, 0.822 mmol and the mixture was stirred at 45° C. After 0.5 h, the reaction mixture was Diluted with EtOAc and 1N K₂CO₃ solution. Organic layer was separated, dried sodium sulfate, filtered and concentrated to provide (S)-6-((4-(2-chloro-3-(4,5,6,7-tetrahydrothiazolo[4,5-c]pyridin-2-yl)phenyl)-2,3-dihydro-1H-inden-1-yl)oxy)-2-methoxy-5-(trifluoromethyl)nicotinaldehyde.

Step 5: To a solution of (S)-6-((4-(2-chloro-3-(4,5,6,7-tetrahydrothiazolo[4,5-c]pyridin-2-yl)phenyl)-2,3-dihydro-1H-inden-1-yl)oxy)-2-methoxy-5-(trifluoromethyl)nicotinaldehyde (20 mg, 0.034 mmol) was added (R)-pyrrolidine-3-carboxylic acid (39 mg, 0.434 mmol) in DMSO (2.0 mL) and the mixture stirred for 1h. Sodium triacetoxyborohydride (51 mg, 0.24 mmol) and the mixture was stirred at rt for 45 min. The mixture was acidified with TFA (18 µL, 0.24 mmol) and stirred 15 min, then purified by reverse phase chromatography to give the title compound as the TFA salt.

LCMS-ESI⁺ (m/z): [M+H]⁺ calcd for $C_{34}H_{32}ClF_3N_4O_4S$: 685.18; found: 684.98. ¹H NMR (400 MHz, DMSO-d₆) δ 12.90 (s, 1H), 9.90 (s, 1H), 9.28 (s, 2H), 8.22 (s, 1H), 8.08 (dd, J=7.7, 1.9 Hz, 1H), 7.57 (q, J=6.6, 5.6 Hz, 1H), 7.47 (d, J=7.6 Hz, 1H), 7.39 (t, J=7.8 Hz, 1H), 7.28 (d, J=7.1 Hz, 1H), 6.67 (s, 1H), 4.42 (s, 2H), 4.35 (s, 2H), 4.07 (s, 3H), 3.68 (s, 3H), 3.50 (s, 4H), 3.39 (s, 2H), 3.16 (t, J=6.1 Hz, 2H), 3.00 (s, OH), 2.81 (d, J=11.2 Hz, 1H), 2.77-2.67 (m, 1H), 2.52 (s, OH), 2.36 (s, OH), 2.20 (s, 1H), 2.13-2.03 (m, 1H).

The following compounds of Table 1 were prepared according to the general procedures described herein using the appropriate starting material(s) and appropriate protecting group chemistry as needed.

TABLE 1

| No | Structure | LC/MS |
|----|-----------|-------|
| 1 | 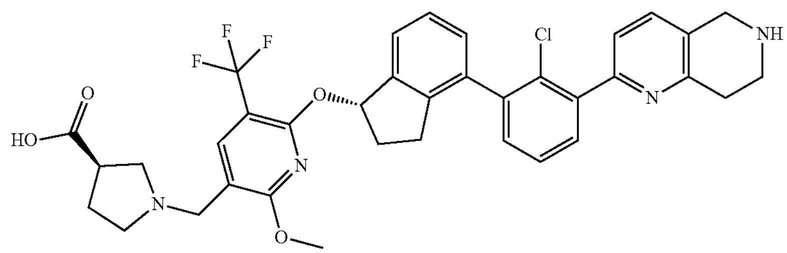 [SMILES: COc1nc(O[C@H]2CCc3c(-c4cccc(-c5ccc6c(n5)CCNC6)c4Cl)cccc32)c(C(F)(F)F)cc1CN1CC[C@@H](C(=O)O)C1] | 679.06 |
| 2 | 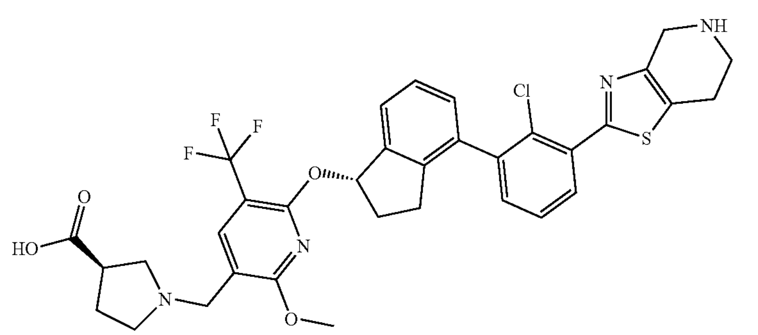 [SMILES: COc1nc(O[C@H]2CCc3c(-c4cccc(-c5nc6c(s5)CCNC6)c4Cl)cccc32)c(C(F)(F)F)cc1CN1CC[C@@H](C(=O)O)C1] | 684.98 |
| 3 | 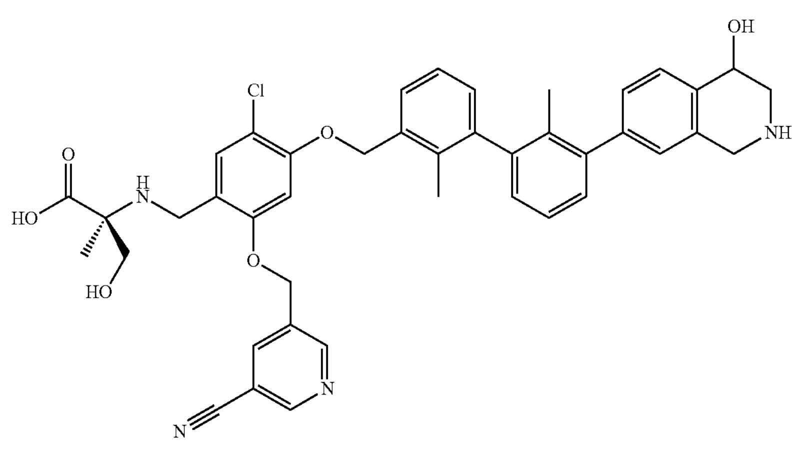 [SMILES: Cc1c(COc2cc(OCc3cncc(C#N)c3)c(CN[C@@](C)(CO)C(=O)O)cc2Cl)cccc1-c1cccc(-c2ccc3c(c2)CNCC3O)c1C] | 733.9 |

TABLE 1-continued

| No | Structure | LC/MS |
|---|---|---|
| 4 | 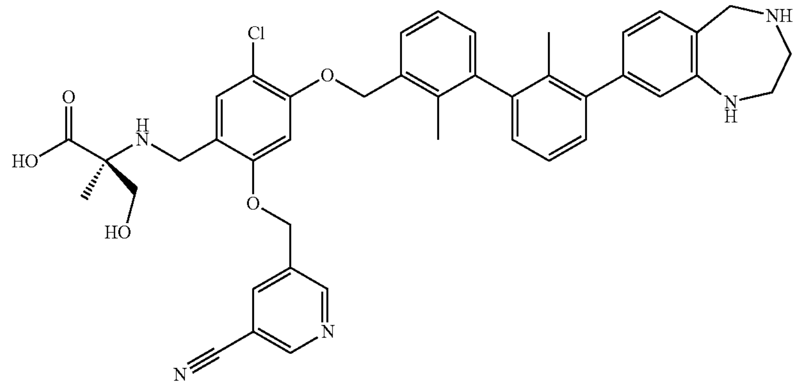 [SMILES: Cc1c(COc2cc(OCc3cncc(C#N)c3)c(CN[C@@](C)(CO)C(=O)O)cc2Cl)cccc1-c1cccc(-c2ccc3c(c2)NCCNC3)c1C] | 732.9 |
| 5 | 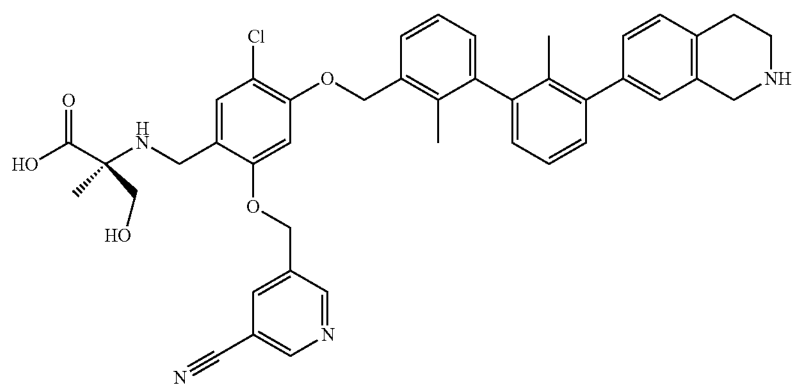 [SMILES: Cc1c(COc2cc(OCc3cncc(C#N)c3)c(CN[C@@](C)(CO)C(=O)O)cc2Cl)cccc1-c1cccc(-c2ccc3c(c2)CNCC3)c1C] | 717.6 |
| 6 | 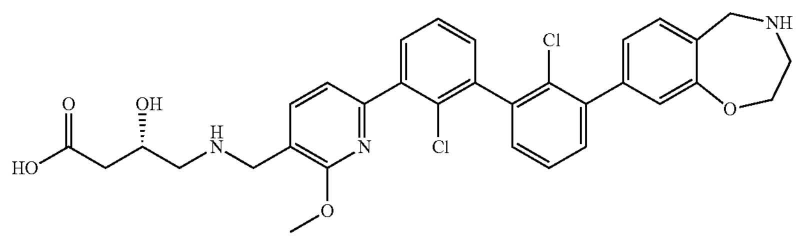 [SMILES: COc1nc(-c2cccc(-c3cccc(-c4ccc5c(c4)OCCNC5)c3Cl)c2Cl)ccc1CNC[C@@H](O)CC(=O)O] | 608.1 |
| 7 | 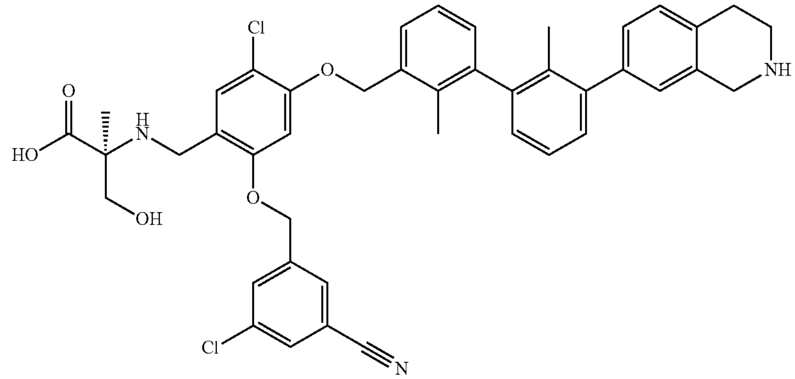 [SMILES: Cc1c(COc2cc(OCc3cc(Cl)cc(C#N)c3)c(CN[C@@](C)(CO)C(=O)O)cc2Cl)cccc1-c1cccc(-c2ccc3c(c2)CNCC3)c1C] | 750.1 |

TABLE 1-continued

| No | Structure | LC/MS |
|---|---|---|
| 8 | 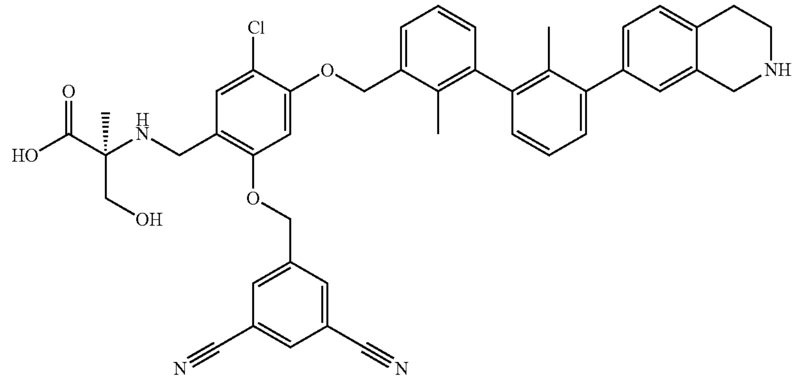 [SMILES: Cc1c(COc2cc(OCc3cc(C#N)cc(C#N)c3)c(CN[C@@](C)(CO)C(=O)O)cc2Cl)cccc1-c1cccc(-c2ccc3c(c2)CNCC3)c1C] | 741.1 |
| 9 | 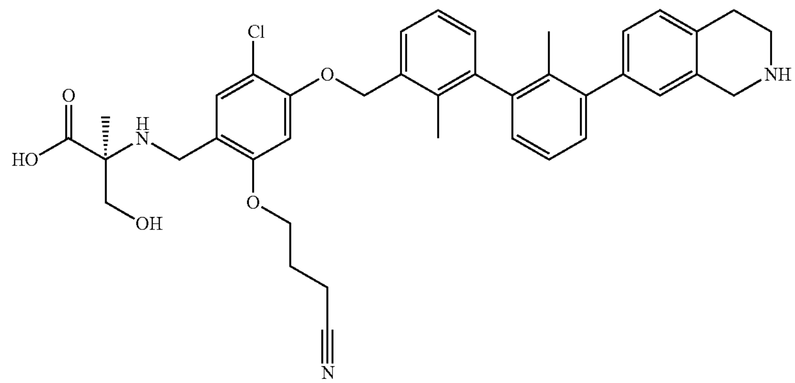 [SMILES: Cc1c(COc2cc(OCCCC#N)c(CN[C@@](C)(CO)C(=O)O)cc2Cl)cccc1-c1cccc(-c2ccc3c(c2)CNCC3)c1C] | 668.1 |
| 10 | 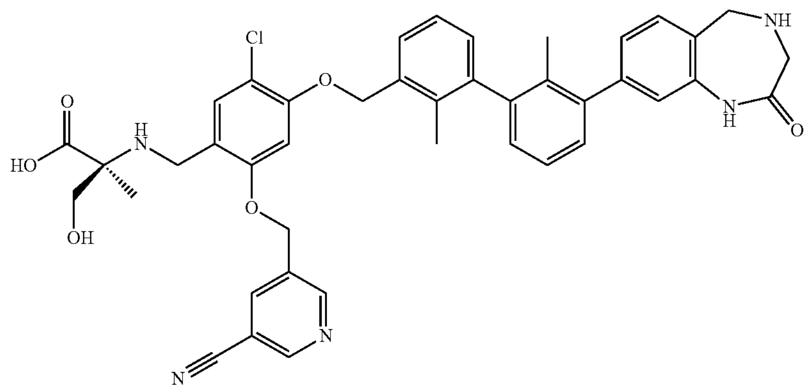 [SMILES: Cc1c(COc2cc(OCc3cncc(C#N)c3)c(CN[C@@](C)(CO)C(=O)O)cc2Cl)cccc1-c1cccc(-c2ccc3c(c2)NC(=O)CNC3)c1C] | 746.001 |
| 11 | 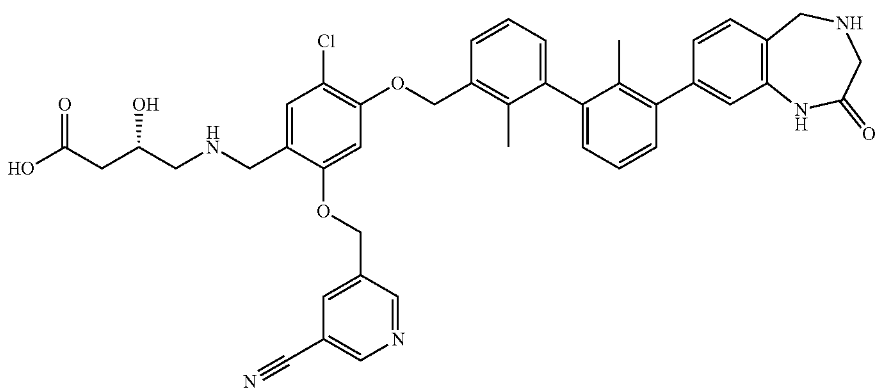 [SMILES: Cc1c(COc2cc(OCc3cncc(C#N)c3)c(CNC[C@@H](O)CC(=O)O)cc2Cl)cccc1-c1cccc(-c2ccc3c(c2)NC(=O)CNC3)c1C] | 746.047 |

TABLE 1-continued

| No | Structure | LC/MS |
|---|---|---|
| 12 | 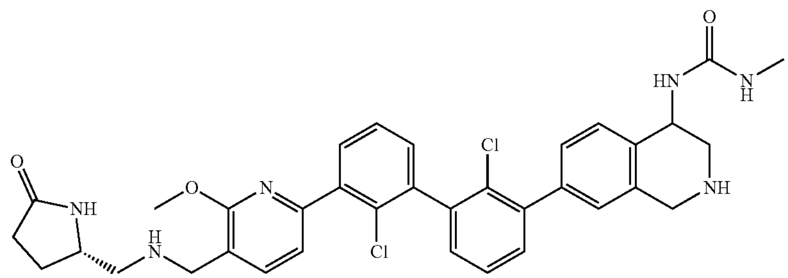 [SMILES: CNC(=O)NC1CNCc2cc(-c3cccc(-c4cccc(-c5ccc(CNC[C@@H]6CCC(=O)N6)c(OC)n5)c4Cl)c3Cl)ccc21] | 659.23 |
| 13 | 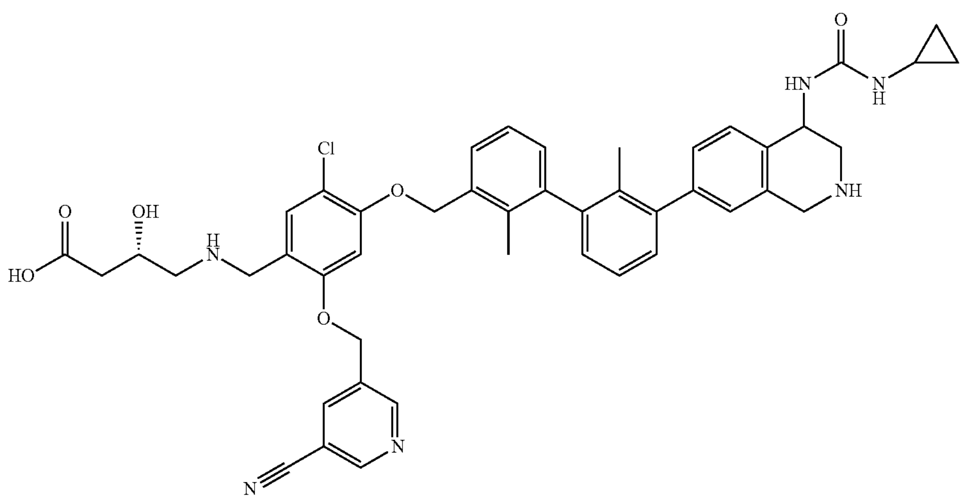 [SMILES: Cc1c(COc2cc(OCc3cncc(C#N)c3)c(CNC[C@@H](O)CC(=O)O)cc2Cl)cccc1-c1cccc(-c2ccc3c(c2)CNCC3NC(=O)NC2CC2)c1C] | 815.33 |
| 14 | 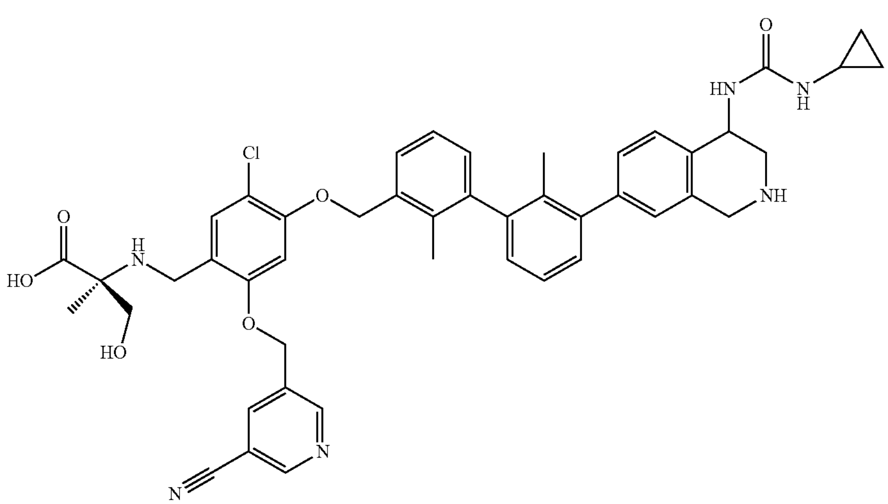 [SMILES: Cc1c(COc2cc(OCc3cncc(C#N)c3)c(CN[C@@](C)(CO)C(=O)O)cc2Cl)cccc1-c1cccc(-c2ccc3c(c2)CNCC3NC(=O)NC2CC2)c1C] | 815.33 |

TABLE 1-continued

| No | Structure | LC/MS |
|----|-----------|-------|
| 15 | 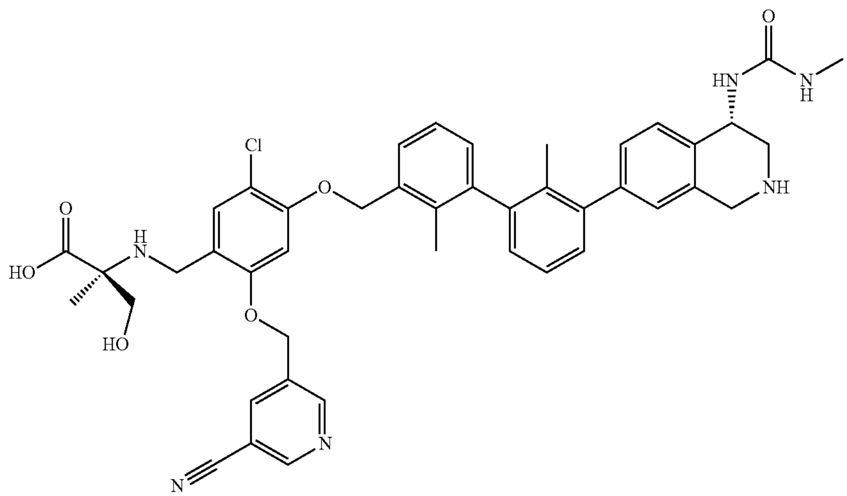 [SMILES: CNC(=O)N[C@@H]1CNCc2cc(-c3cccc(-c4cccc(COc5cc(OCc6cncc(C#N)c6)c(CN[C@@](C)(CO)C(=O)O)cc5Cl)c4C)c3C)ccc21] | 789.32 |
| 16 | 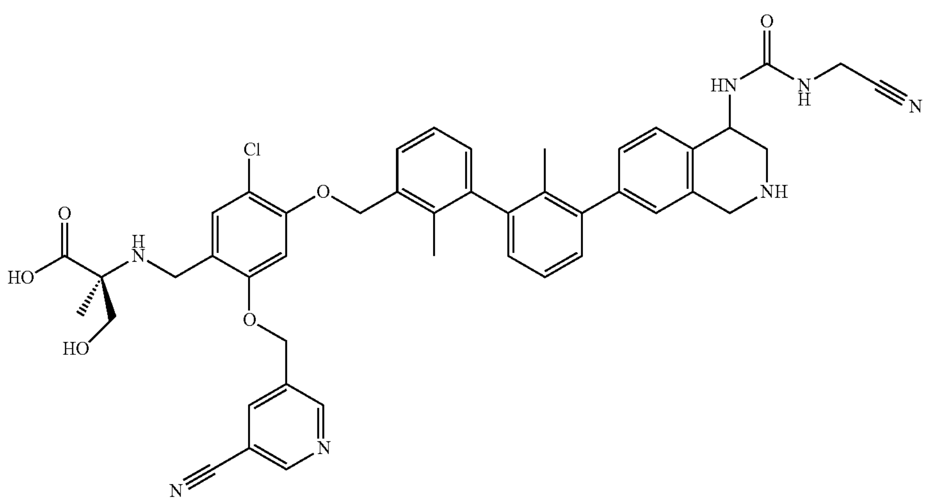 [SMILES: Cc1c(COc2cc(OCc3cncc(C#N)c3)c(CN[C@@](C)(CO)C(=O)O)cc2Cl)cccc1-c1cccc(-c2ccc3c(c2)CNCC3NC(=O)NCC#N)c1C] | 814.31 |
| 17 | 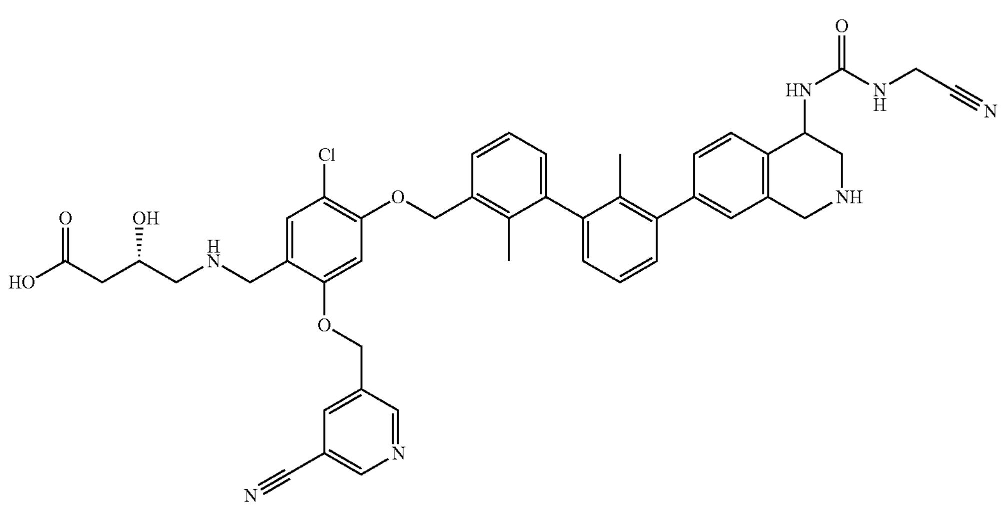 [SMILES: Cc1c(COc2cc(OCc3cncc(C#N)c3)c(CNC[C@@H](O)CC(=O)O)cc2Cl)cccc1-c1cccc(-c2ccc3c(c2)CNCC3NC(=O)NCC#N)c1C] | 814.31 |

TABLE 1-continued

| No | Structure | LC/MS |
|---|---|---|
| 18 | 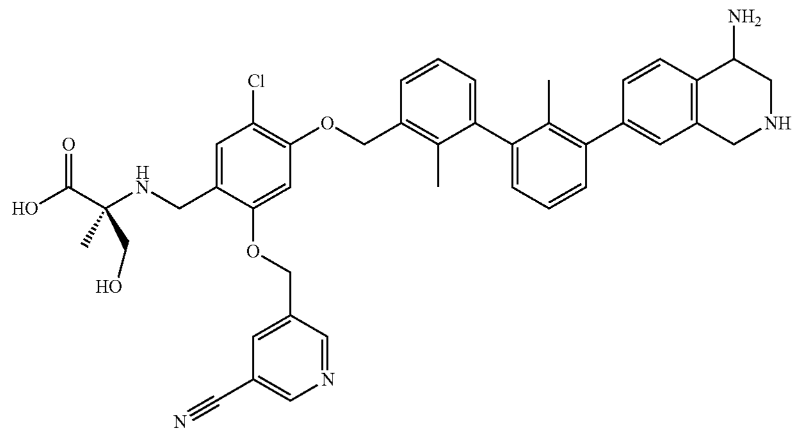 [SMILES: Cc1c(COc2cc(OCc3cncc(C#N)c3)c(CN[C@@](C)(CO)C(=O)O)cc2Cl)cccc1-c1cccc(-c2ccc3c(c2)CNCC3N)c1C] | 732.3 |
| 19 | 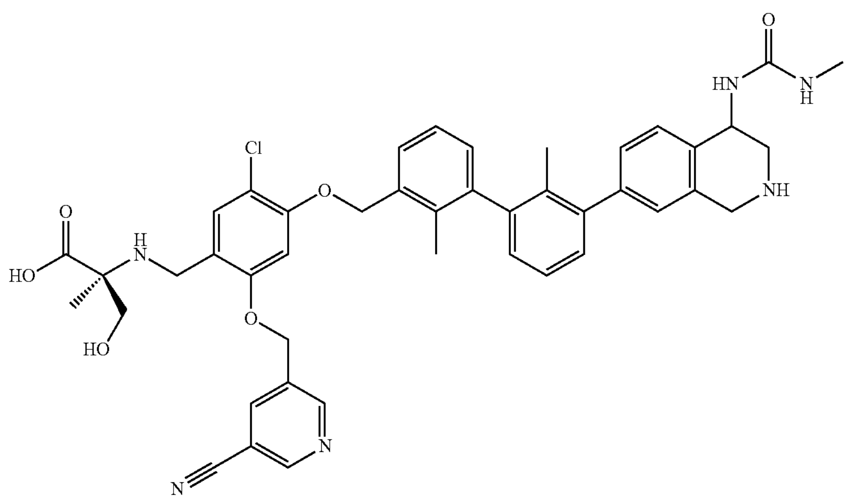 [SMILES: CNC(=O)NC1CNCc2cc(-c3cccc(-c4cccc(COc5cc(OCc6cncc(C#N)c6)c(CN[C@@](C)(CO)C(=O)O)cc5Cl)c4C)c3C)ccc21] | 774.31 |
| 20 | 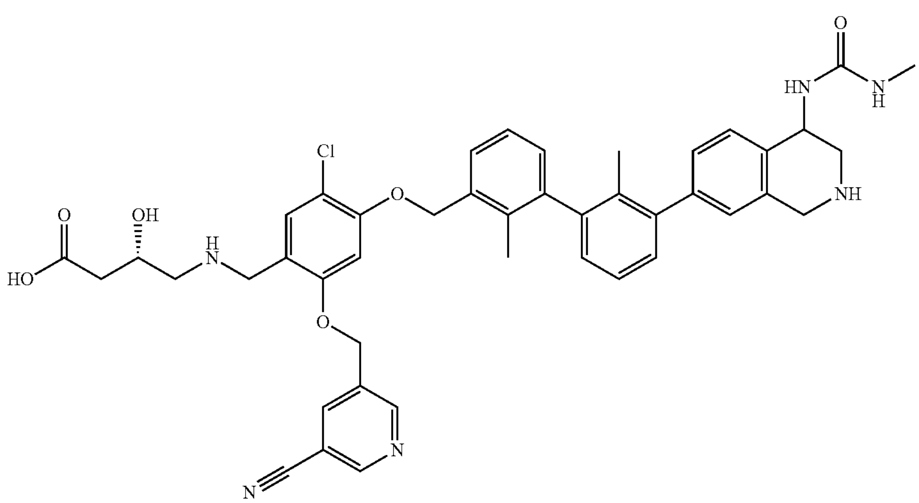 [SMILES: CNC(=O)NC1CNCc2cc(-c3cccc(-c4cccc(COc5cc(OCc6cncc(C#N)c6)c(CNC[C@@H](O)CC(=O)O)cc5Cl)c4C)c3C)ccc21] | 789.32 |

| No | Structure | LC/MS |
|---|---|---|
| 21 | 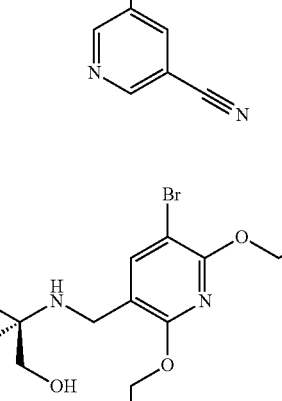 | 804 |
| 22 | 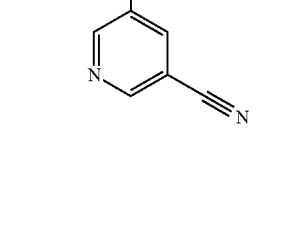 | 803.92 |
| 23 | 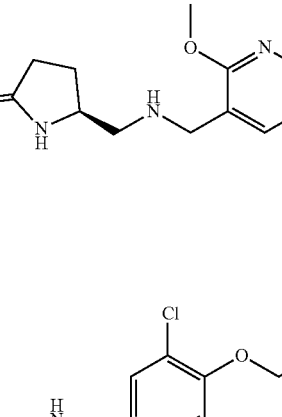 | 574.13 |
| 24 | 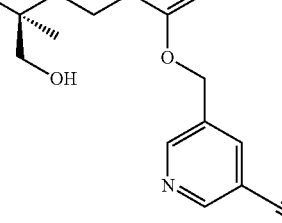 | 743.3 |

TABLE 1-continued

| No | Structure | LC/MS |
|---|---|---|
| 25 | 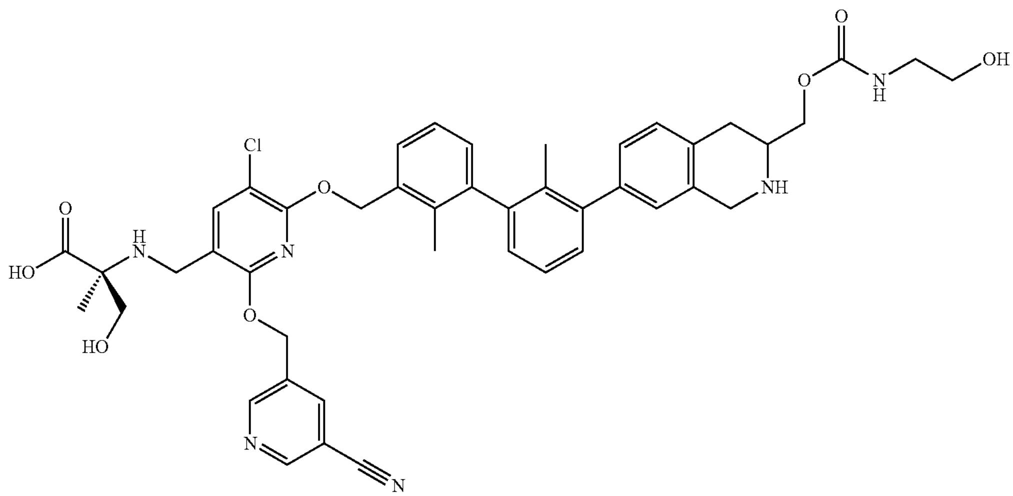 [SMILES: Cc1c(COc2nc(OCc3cncc(C#N)c3)c(CN[C@@](C)(CO)C(=O)O)cc2Cl)cccc1-c1cccc(-c2ccc3c(c2)CNC(COC(=O)NCCO)C3)c1C] | 834.3 |
| 26 | 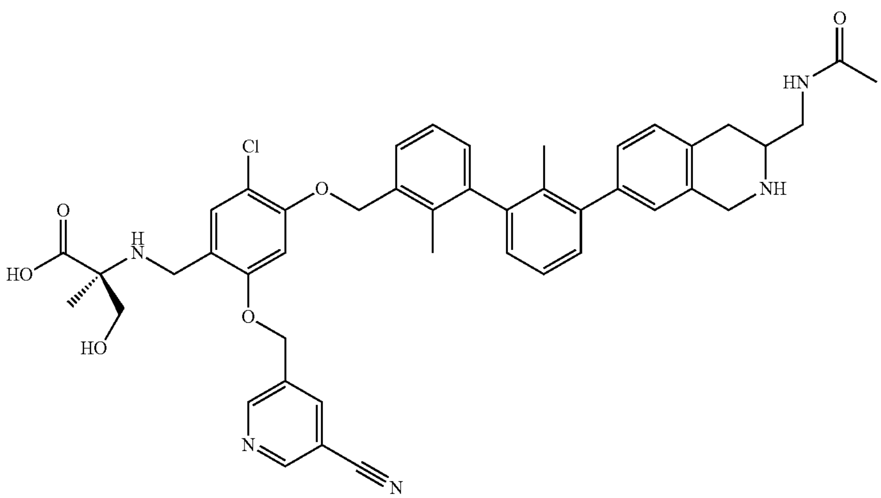 [SMILES: CC(=O)NCC1Cc2ccc(-c3cccc(-c4cccc(COc5cc(OCc6cncc(C#N)c6)c(CN[C@@](C)(CO)C(=O)O)cc5Cl)c4C)c3C)cc2CN1] | 788.3 |
| 27 | 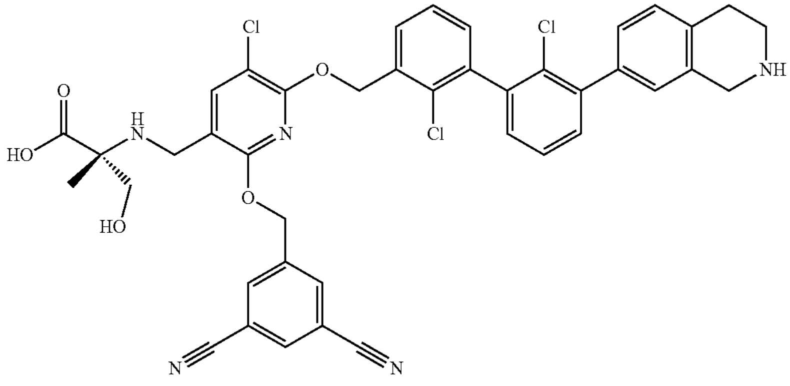 [SMILES: C[C@](CO)(NCc1cc(Cl)c(OCc2cccc(-c3cccc(-c4ccc5c(c4)CNCC5)c3Cl)c2Cl)nc1OCc1cc(C#N)cc(C#N)c1)C(=O)O] | 782.2 |

TABLE 1-continued

| No | Structure | LC/MS |
|---|---|---|
| 28 | 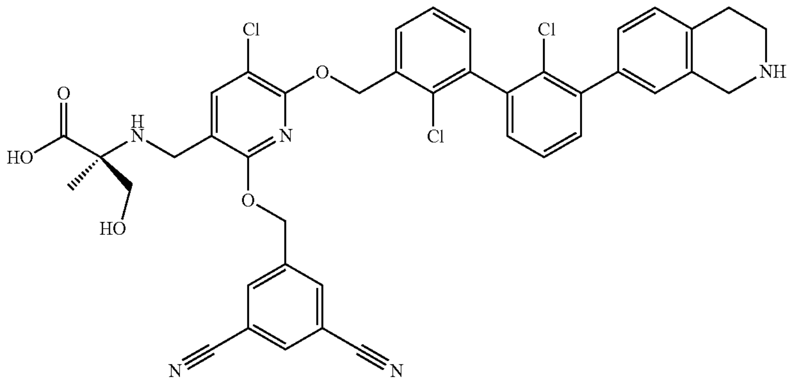 [SMILES: C[C@@](CO)(NCc1cc(Cl)c(OCc2cccc(-c3cccc(-c4ccc5c(c4)CNCC5)c3Cl)c2Cl)nc1OCc1cc(C#N)cc(C#N)c1)C(=O)O] | 782.2 |
| 29 | 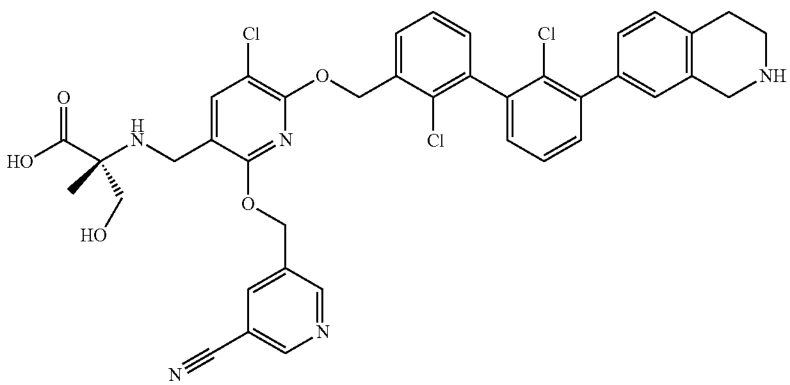 [SMILES: C[C@](CO)(NCc1cc(Cl)c(OCc2cccc(-c3cccc(-c4ccc5c(c4)CNCC5)c3Cl)c2Cl)nc1OCc1cncc(C#N)c1)C(=O)O] | 758.2 |
| 30 | 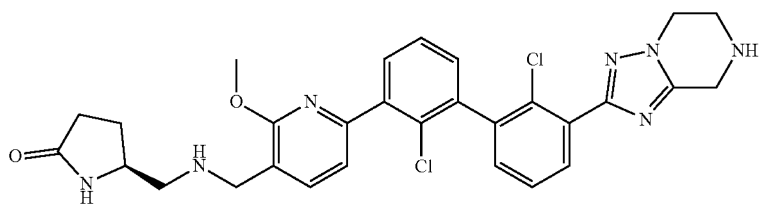 [SMILES: COc1nc(-c2cccc(-c3cccc(-c4nc5n(n4)CCNC5)c3Cl)c2Cl)ccc1CNC[C@@H]1CCC(=O)N1] | 578.1 |
| 31 | 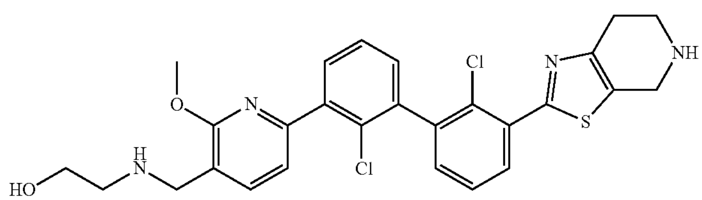 [SMILES: COc1nc(-c2cccc(-c3cccc(-c4nc5c(s4)CNCC5)c3Cl)c2Cl)ccc1CNCCO] | 540.9 |
| 32 | 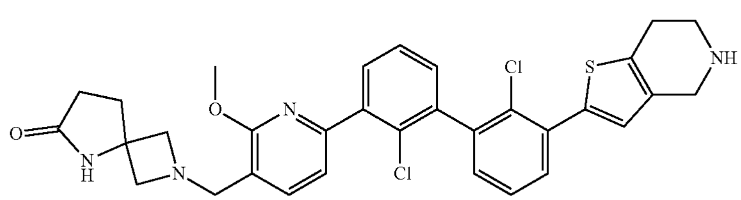 [SMILES: COc1nc(-c2cccc(-c3cccc(-c4cc5c(s4)CCNC5)c3Cl)c2Cl)ccc1CN1CC2(CCC(=O)N2)C1] | 605.0 |
| 33 | 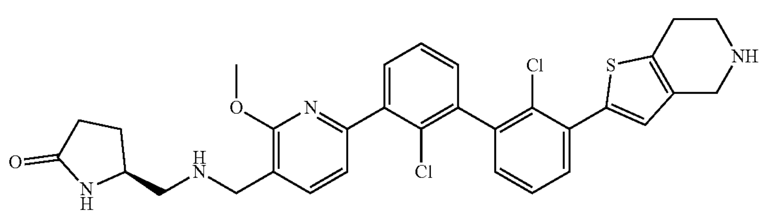 [SMILES: COc1nc(-c2cccc(-c3cccc(-c4cc5c(s4)CCNC5)c3Cl)c2Cl)ccc1CNC[C@@H]1CCC(=O)N1] | 595.1 |

TABLE 1-continued

| No | Structure | LC/MS |
|---|---|---|
| 34 | 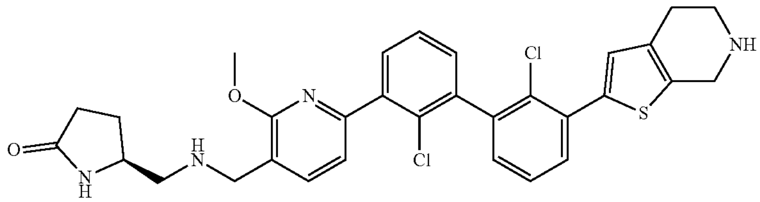 [SMILES: COc1nc(-c2cccc(-c3cccc(-c4cc5c(s4)CNCC5)c3Cl)c2Cl)ccc1CNC[C@@H]1CCC(=O)N1] | 593.0 |
| 35 | 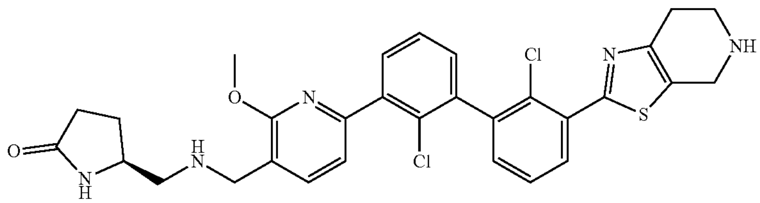 [SMILES: COc1nc(-c2cccc(-c3cccc(-c4nc5c(s4)CNCC5)c3Cl)c2Cl)ccc1CNC[C@@H]1CCC(=O)N1] | 594.1 |
| 36 | 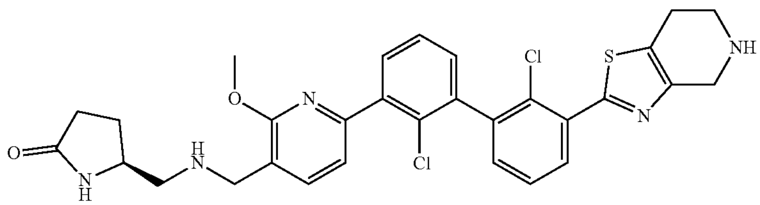 [SMILES: COc1nc(-c2cccc(-c3cccc(-c4nc5c(s4)CCNC5)c3Cl)c2Cl)ccc1CNC[C@@H]1CCC(=O)N1] | 594.2 |

NMR data for select compounds is shown below in Table 2.

TABLE 2A

| No | NMR |
|---|---|
| 1 | 1H NMR (400 MHz, DMSO-d6) δ 12.89 (s, 1H), 9.87 (s, 1H), 9.09 (s, 2H), 8.21 (s, 1H), 7.77 (d, J = 8.1 Hz, 1H), 7.63-7.48 (m, 3H), 7.48-7.33 (m, 2H), 7.27 (dd, J = 7.5, 1.1 Hz, 1H), 6.67 (s, 1H), 4.39 (s, 2H), 4.33 (d, J = 18.1 Hz, 2H), 4.07 (s, 3H), 3.69 (s, 3H), 3.39 (s, 2H), 3.23-3.10 (m, 4H), 2.87 (d, J = 13.6 Hz, 1H), 2.80-2.71 (m, 1H), 2.25-2.15 (m, 1H), 2.06 (s, 2H) |
| 2 | 1H NMR (400 MHz, DMSO-d6) δ 12.90 (s, 1H), 9.90 (s, 1H), 9.28 (s, 2H), 8.22 (s, 1H), 8.08 (dd, J = 7.7, 1.9 Hz, 1H), 7.57 (q, J = 6.6, 5.6 Hz, 1H), 7.47 (d, J = 7.6 Hz, 1H), 7.39 (t, J = 7.8 Hz, 1H), 7.28 (d, J = 7.1 Hz, 1H), 6.67 (s, 1H), 4.42 (s, 2H), 4.35 (s, 2H), 4.07 (s, 3H), 3.68 (s, 3H), 3.50 (s, 4H), 3.39 (s, 2H), 3.16 (t, J = 6.1 Hz, 2H), 3.00 (s, 0H), 2.81 (d, J = 11.2 Hz, 1H), 2.77-2.67 (m, 1H), 2.52 (s, 0H), 2.36 (s, 0H), 2.20 (s, 1H), 2.13-2.03 (m, 1H) |
| 3 | 1H NMR (400 MHz, Methanol-d4) δ 8.99 (d, J = 2.1 Hz, 1H), 8.92 (d, J = 2.0 Hz, 1H), 8.43 (s, 1H), 7.60-7.54 (m, 2H), 7.48 (d, J = 7.5 Hz, 1H), 7.39 (d, J = 8.3 Hz, 1H), 7.35-7.24 (m, 3H), 7.21 (d, J = 7.4 Hz, 1H), 7.18-7.11 (m, 2H), 7.09 (s, 1H), 5.38 (s, 2H), 5.33 (s, 2H), 5.01 (t, J = 3.3 Hz, 1H), 4.53-4.37 (m, 2H), 4.29 (s, 2H), 4.02 (d, J = 12.1 Hz, 1H), 3.81 (d, J = 12.2 Hz, 1H), 3.57-3.52 (m, 2H), 2.15 (s, 3H), 1.89 (s, 3H), 1.53 (s, 3H). |
| 4 | $^1$H NMR (400 MHz, Methanol-d$_4$) δ 8.99 (d, J = 2.1 Hz, 1H), 8.92 (d, J = 1.9 Hz, 1H), 8.43 (t, J = 2.1 Hz, 1H), 7.56 (s, 1H), 7.48 (d, J = 7.5 Hz, 1H), 7.35 (d, J = 7.8 Hz, 1H), 7.33-7.24 (m, 2H), 7.19 (dd, J = 7.7, 1.5 Hz, 1H), 7.15 (dd, J = 7.7, 1.4 Hz, 1H), 7.12-7.08 (m, 2H), 6.97 (d, J = 1.6 Hz, 1H), 6.91 (dd, J = 7.7, 1.7 Hz, 1H), 5.38 (s, 2H), 5.33 (s, 2H), 4.31 (s, 2H), 4.29 (s, 2H), 4.02 (d, J = 12.1 Hz, 1H), 3.81 (d, J = 12.2 Hz, 1H), 3.39 (d, J = 5.7 Hz, 2H), 3.34 (d, J = 6.0 Hz, 2H), 2.15 (s, 3H), 1.88 (s, 3H), 1.54 (s, 3H). |
| 5 | $^1$H NMR(400 MHz, Methanol-d$_4$) δ 8.99 (d, J = 2.1 Hz, 1H), 8.92 (d, J = 1.9 Hz, 1H), 8.43 (t, J = 2.1 Hz, 1H), 7.56 (s, 1H), 7.51-7.44 (m, 1H), 7.36-7.24 (m, 4H). 7.24-7.18 (m, 2H), 7.15 (dd, J = 7.3, 1.1 Hz, 1H), 7.12-7.07 (m, 2H), 5.37 (s, 2H), 5.33 (s, 2H), 4.42 (s, 2H). 4.29 (s, 2H), 4.02 (d, J = 12.1 Hz, 1H), 3.82 (d, J = 12.2 Hz, 1H). 3.56 (t, J = 6.4 Hz, 2H), 3.19 (t, J = 6.4 Hz, 2H), 2.15 (s, 3H), 1.88 (s, 3H), 1.54 (s, 3H). |
| 6 | $^1$H NMR (400 MHz, Methanol-d$_4$) δ 7.90 (d, J = 7.6 Hz, 1H), 7.67 (dd, J = 7.7, 1.7 Hz, 1H), 7.60-7.47 (m, 3H), 7.47-7.34 (m, 4H), 7.29 (dd, J = 7.7, 1.7 Hz, 1H), 7.26 (d, J = 1.7 Hz, 1H), 4.49 (s, 2H), 4.43-4.25 (m, 5H), 4.11 (s, 3H), 3.71-3.60 (m, 2H), 3.29 (d, J = 3.1 Hz, 1H), 3.10 (dd, J = 12.7, 9.8 Hz, 1H), 2.60 (d, J = 6.4 Hz, 2H). |
| 7 | 1H NMR (400 MHz, Methanol-d4) δ 7.92 (t, J = 1.8 Hz, 1H), 7.88 (d, J = 1.5 Hz, 1H), 7.80 (t, J = 1.7 Hz, 1H), 7.55 (s, 1H), 7.43 (d, J = 7.5 Hz, 1H), 7.33-7.22 (m, 4H), 7.21-7.15 (m, 2H), 7.11 (ddd, J = 16.2, 7.6, 1.4 Hz, 2H), 7.00 (s, 1H), 5.29 (d, J = 6.6 Hz. 4H), 4.41 (s, 2H), 4.33-4.21 (m, 2H), 4.02 (d, J = 12.1 Hz, 1H), 3.82 (d, J = 12.2 Hz. 1H), 3.55 (t, J = 6.4 Hz, 2H), 3.17 (t, J = 6.4 Hz, 2H), 2.13 (s, 3H), 1.86 (s, 3H), 1.53 (s, 3H). |

TABLE 2A-continued

| No | NMR |
|---|---|
| 8 | 1H NMR (400 MHz, Methanol-d4) δ 8.23 (d, J = 1.5 Hz, 2H), 8.18 (d, J = 1.6 Hz, 1H), 7.55 (s, 1H), 7.45 (d, J = 7.5 Hz, 1H), 7.37-7.16 (m, 6H), 7.11 (ddd, J = 17.8, 7.6, 1.5 Hz, 2H), 7.02 (s, 1H), 5.33 (d, J = 18.1 Hz, 5H), 4.41 (s, 2H), 4.30 (s, 2H), 4.03 (d, J = 12.1 Hz, 1H), 3.82 (d, J = 12.2 Hz, 1H), 3.55 (t, J = 6.4 Hz, 2H), 3.18 (t, J = 6.4 Hz, 2H), 2.13 (s, 3H), 1.87 (s, 3H), 1.55 (s, 3H). |
| 9 | 1H NMR (400 MHz, Methanol-d4) δ 7.57-6.86 (m, 11H), 5.32 (s, 2H), 4.41 (s, 2H), 4.24 (t, J = 5.1 Hz, 4H), 3.94 (dd, J = 80.5, 12.1 Hz, 2H), 3.54 (t, J = 6.4 Hz. 2H), 3.17 (t, J = 6.4 Hz, 2H), 2.84-2.68 (m, 2H), 2.29-2.15 (m, 2H), 2.14 (s, 3H), 1.87 (s, 3H), 1.58 (s, 3H). |
| 10 | 1H NMR (400 MHz, Methanol-d4) δ 8.98 (d, 2.0 Hz, 1H), 8.90 (d, 2.0 Hz. 1H), 8.42 (s, 1H), 7.71-6.99 (m, 11H), 5.37 (s, 2H), 5.32 (s, 2H), 4.38 (s, 2H), 4.26 (s, 2H), 3.98 (d, J = 12.1 Hz, 1H), 3.87-3.73 (m, 3H), 2.14 (s, 3H), 1.90 (s, 3H), 1.50 (s, 3H). |
| 11 | 1H NMR (400 MHz, Methanol-d4) δ 8.96 (d, J = 2.0 Hz, 1H), 8.93 (d. J = 2.0 Hz. 1H), 8.38 (t, J = 2.1 Hz, 1H), 7.62-6.99 (m, 11H), 5.38 (s, 2H), 5.31 (s, 2H), 4.38 (s, 2H), 4.28-4.15 (m, 1H), 4.23 (s, 2H), 3.78 (s, 2H), 3.20 (dd, J = 12.8, 3.1 Hz, 1H), 3.05-2.87 (m, 1H), 2.51 (dd, J = 6.3, 0.9 Hz, 2H), 2.14 (s, 3H), 1.90 (s, 3H). |
| 12 | 1H NMR (400 MHz, Methanol-d4) δ 7.91 (d, J = 7.7 Hz, 1H), 7.67 (d. J = 7.7 Hz, 1H), 7.53 (q, J = 8.0 Hz, 4H), 7.42 (dd, J = 17.5, 7.7 Hz, 5H), 5.04 (s, 1H), 4.61-4.39 (m, 2H), 4.37 (s, 2H), 4.13 (s, 3H), 4.08 (s, 1H), 3.74-3.63 (m, 2H), 3.65-3.53 (m, 1H), 3.29 (s, 2H), 2.74 (s, 3H), 2.54-2.33 (m, 2H), 1.94 (s, 3H). |
| 13 | 1H NMR (400 MHz, Methanol-d4) δ 8.97 (dd, J = 10.5, 1.9 Hz, 2H), 8.41 (s, 1H), 7.58-7.46 (m, 3H), 7.42 (d, J = 8.2 Hz, 1H), 7.38-7.08 (m, 7H), 5.41 (s, 2H), 5.34 (s, 2H), 5.10 (s, 1H), 4.52 (d, J = 15.8 Hz, 1H), 4.43 (d, J = 15.8 Hz, 1H), 4.26 (s, 3H), 3.70 (dd, J = 12.9, 5.6 Hz, 1H), 3.66-3.57 (m, 1H), 3.23 (d, J = 10.3 Hz, 1H), 3.05-2.95 (m, 1H), 2.55 (d, J = 6.4 Hz, 2H), 2.16 (s, 3H), 1.91 (s, 3H), 0.76 (d, J = 5.3 Hz, 2H), 0.52 (s, 2H). |
| 14 | 1H NMR (400 MHz, Methanol-d4) δ 9.01 (d, J = 2.1 Hz, 1H), 8.94 (d, J = 2.0 Hz, 1H), 8.45 (d, J = 2.1 Hz, 1H), 7.61-7.46 (m, 3H), 7.45-7.08 (m, 8H), 5.40 (s, 2H), 5.35 (s, 2H), 5.16-5.08 (m, 1H), 4.52 (d, J = 15.9 Hz, 1H), 4.43 (d, J = 15.8 Hz, 1H), 4.30 (s, 2H), 4.03 (d, J = 12.1 Hz, 1H), 3.82 (d, J = 12.1 Hz, 1H), 3.70 (dd, J = 12.9, 5.5 Hz, 1H), 3.61 (dd, J = 12.8, 5.1 Hz, 1H), 2.51 (td, J = 6.8, 3.5 Hz, 1H), 2.17 (s, 3H), 1.90 (s, 3H), 1.54 (s, 3H), 0.81-0.68 (m, 2H), 0.52 (s, 2H). |
| 15 | 1H NMR (400 MHz, Methanol-d4) δ 9.01 (d, J = 2.1 Hz, 1H), 8.94 (d. J = 1.9 Hz, 1H), 8.45 (s, 1H), 7.58 (s, 1H), 7.52 (t, J = 9.1 Hz, 2H), 7.41 (d. J = 8.2 Hz, 1H), 7.38-7.25 (m, 3H), 7.23 (d, J = 7.8 Hz, 1H), 7.20-7.09 (m, 3H), 5.40 (s, 2H), 5.35 (s, 2H), 5.04 (s, 1H), 4.52 (d, J = 15.9 Hz, 1H), 4.43 (d, J = 15.8 Hz, 1H), 4.31 (s, 2H), 4.04 (d, J = 12.1 Hz. 1H), 3.83 (d, J = 12.2 Hz, 1H), 3.68 (dd, J = 12.7, 5.4 Hz, 1H), 3.58 (dd, J = 12.7, 5.2 Hz. 1H), 2.74 (s, 3H), 2.17 (s, 3H), 1.91 (s, 3H), 1.56 (s, 3H). |
| 16 | 1H NMR (400 MHz, Methanol-d4) δ 9.01 (s, 1H), 8.94 (s, 1H), 8.45 (s, 1H), 7.61-7.46 (m, 3H), 7.41 (d, J = 8.8 Hz. 1H), 7.38-7.21 (m, 4H), 7.14 (dd, J = 17.4, 9.7 Hz, 3H), 5.37 (d, J = 16.2 Hz, 4H), 5.12 (s, 1H), 4.66-4.34 (m, 1H), 4.31 (s, 2H), 4.14 (d, J = 7.0 Hz, 2H), 4.04 (d, J = 12.1 Hz, 1H), 3.83 (d, J = 12.2 Hz, 1H), 3.70 (s, 1H), 3.60 (d, J = 16.3 Hz, 1H), 2.17 (s, 3H), 1.90 (s, 3H), 1.55 (s, 3H),. |
| 17 | 1H NMR (400 MHz, Methanol-d4) δ 9.01-8.93 (m, 2H), 8.40 (s, 1H), 7.57-7.47 (m, 3H), 7.41 (d, J = 8.8 Hz, 1H), 7.37-7.08 (m, 7H), 5.40 (s, 2H), 5.34 (s, 2H), 4.53 (d. J = 16.2 Hz, 1H), 4.44 (d, J = 16.2 Hz, 1H), 4.26 (s, 3H), 4.14 (d, J = 6.6 Hz, 2H), 4.00-3.83 (m, 1H), 3.71 (dd, J = 12.8, 5.3 Hz, 1H), 3.60 (dd, J = 12.7, 5.6 Hz, 1H), 3.22 (dd, J = 12.7, 2.9 Hz, 1H), 3.05-2.95 (m, 1H), 2.54 (d, J = 6.3 Hz, 2H), 2.16 (s, 2H), 1.90 (s, 3H). |
| 18 | 1H NMR (400 MHz, Methanol-d4) δ 9.01 (d, J = 2.0 Hz, 1H), 8.94 (d, J = 1.9 Hz, 1H), 8.46 (d, J = 2.0 Hz, 1H), 7.71 (d, J = 8.1 Hz, 1H), 7.58 (s, 1H), 7.55-7.47 (m, 2H), 7.40 (s, 1H), 7.40-7.13 (m, 6H), 7.12 (s, 1H), 5.38 (d, J = 18.2 Hz, 4H), 5.04 (t, J = 5.7 Hz, 1H), 4.60 (d, J = 16.0 Hz, 1H), 4.52 (d. J = 16.0 Hz, 1H), 4.31 (s, 2H), 4.08-3.96 (m, 2H), 3.84 (d, J = 12.2 Hz, 1H), 3.81-3.71 (m, 1H), 2.17 (s, 3H), 1.90 (s, 3H), 1.56 (s, 3H) |
| 19 | 1H NMR (400 MHz, Methanol-d4) δ 8.98 (d, J = 2.1 Hzm 1H), 8.91 (d, J = 1.9 Hz, 1H), 8.42 (t, J = 2.1 Hz, 1H), 7.55 (s, 1H), 7.50-7.43 (m, 2H), 7.38 (dd, J = 8.1, 1.7 Hz, 1H), 7.35-7.22 (m, 3H), 7.19 (dd, J = 7.8, 1.5 Hz, 1H), 7.12 (ddd, J = 9.1, 7.5, 1.4 Hz, 2H), 7.08 (s, 1H), 5.34 (d, J = 17.5 Hz, 4H), 5.26 (t, J = 5.7 Hz, 1H), 4.51 (d, J = 15.9 Hz, 1H), 4.42 (d, J = 15.9 Hz, 1H), 4.28 (s, 2H), 4.01 (d, J = 12.1 Hz, 1H), 3.81 (d, J = 12.2 Hz, 1H), 3.67 (dd, J = 12.9, 5.5 Hz, 1H), 3.52 (dd, J = 12.8, 5.9 Hz, 1H), 2.14 (s, 3H), 2.04 (s, 3H), 1.87 (s, 3H), 1.53 (s, 3H). |
| 20 | 1H NMR (400 MHz, Methanol-d4) δ 8.94 (dd, J = 15.6, 2.0 Hz, 2H), 8.38 (t, J = 2.1 Hz, 1H), 7.53-7.42 (m, 3H), 7.40-7.05 (m, 9H), 5.34 (d, J = 27.0 Hz, 4H), 5.03 (t, J = 5.2 Hz, 1H), 4.49 (d, J = 15.8 Hz, 1H), 4.39 (d, J = 15.8 Hz, 1H), 4.24 (s, 2H), 4.23 (td, J = 9.5, 6.3 Hz, 1H), 3.64 (dd, J = 12.8, 5.3 Hz, 1H), 3.56 (dd, J = 12.8, 5.0 Hz, 1H), 3.20 (dd, J = 12.8, 3.1 Hz, 1H), 2.98 (dd, J = 12.8, 9.8 Hz, 1H), 2.71 (s, 3H), 2.51 (d, J = 6.4 Hz, 2H), 2.13 (s, 3H), 1.87 (s, 3H). |
| 21 | 1H NMR (400 MHz, Methanol-d4) δ 8.90 (d, 1H), 8.83 (d, 1H), 8.29 (t, 1H), 8.10 (s, 1H), 7.58-7.51 (m, 1H), 7.48-7.25 (m, 9H), 5.74-5.39 (m, 4H), 4.43 (s, 2H), 4.28 (s, 2H), 4.04 (d, 1H), 3.84 (d, 1H), 3.55 (t, 2H), 3.19 (t, 2H), 1.57 (s, 3H). |
| 22 | 1H NMR (400 MHz, Methanol-d4) δ 8.90 (d, 1H), 8.83 (d, 1H), 8.29 (t, 1H), 8.10 (s, 1H), 7.60-7.51 (m, 1H), 7.49-7.24 (m, 9H), 5.74-5.40 (m, 4H), 4.43 (s, 2H), 4.27 (s, 2H), 4.04 (d, 1H), 3.83 (d, 1H), 3.55 (t, 3H), 3.19 (t, J = 6.4 Hz, 2H), 1.56 (s, 3H). |
| 23 | 1H NMR (400 MHz, Methanol-d4) δ 8.73 (d, J = 1.2 Hz, 1H), 7.88 (d, J = 7.6 Hz, 1H), 7.77 (s, 1H), 7.65 (dd, J = 7.7, 1.8 Hz, 1H), 7.54 (dtd, J = 17.9, 7.6, 1.9 Hz, 2H), 7.48-7.25 (m, 3H), 4.78 (d, J = 8.9 Hz, 3H), 4.34 (d, J = 2.7 Hz, 2H), 4.10 (d, J = 1.9 Hz, 2H), 4.05 (q, J = 6.7 Hz, 1H), 3.25 (dd, J = 6.1, 3.8 Hz, 2H), 2.56-2.27 (m, 3H), 1.91 (q, J = 7.1, 6.4 Hz, 2H), 1.36 (dd, J = 6.7, 3.5 Hz, 1H). 19F NMR (376 MHz, Methanol-d4) δ -77.77. |
| 24 | 1H NMR (400 MHz, Methanol-d4) δ 8.99 (d, J = 2.1 Hz, 1H), 8.91 (d, J = 1.9 Hz, 1H), 8.43 (t, J = 2.1 Hz, 1H), 7.55 (s, 1H), 7.50-7.45 (m, 1H), 7.41-7.18 (m, 6H), 7.15-7.05 (m, 3H), 5.37 (s, 2H), 5.33 (s, 2H), 4.41 (t, J = 5.3 Hz, 1H), 4.29 (s, 2H), 4.02 (d, J = 12.1 Hz, |

TABLE 2A-continued

No NMR

1H), 3.82 (d, J = 12.2 Hz, 1H), 3.53 (dd, J = 17.7, 5.0 Hz, 1H), 3.02 (dd, J = 17.8, 1.3 Hz, 1H), 2.45-2.35 (m, 2H), 2.22 (td, J = 10.0, 2.3 Hz, 1H), 2.14 (s, 3H), 2.02-1.95 (m, 1H), 1.88 (s, 3H), 1.54 (s, 3H).

25 $^1$H NMR (400 MHz, Methanol-d$_4$) δ 8.94 (dd, J = 27.5, 2.1 Hz, 2H), 8.42 (s, 1H), 7.55 (s, 1H), 7.46 (d, J = 7.4 Hz, 1H), 7.40-6.95 (m, 7H), 5.48 (s, 2H), 5.34 (d, J = 18.6 Hz, 2H). 4.50 (s, 2H), 4.36-4.28 (m, 4H), 4.25 (s, 1H), 4.01-3.69 (m, 6H), 3.61 (t, J = 5.6 Hz, 3H), 3.15 (dd, J = 19.8, 6.6 Hz, 4H), 2.13 (s, 2H), 1.86 (s, 2H), 1.48 (s, 2H).

26 1H NMR (400 MHz, Methanol-d4) δ 8.96 (dd, J = 27.5, 2.0 Hz, 2H), 8.42 (s, 1H), 7.55 (s, 1H), 7.48 (d, J = 7.4 Hz, 1H), 7.40-6.95 (m, 7H), 5.45 (s, 2H), 5.34 (d, J = 18.6 Hz, 2H), 4.50 (s, 2H), 4.36-4.28 (m, 4H), 4.25 (s, 1H), 4.009-3.71 (m, 6H), 3.61 (t, J = 5.6 Hz, 3H), 3.13 (dd, J = 19.8, 6.6 Hz, 3H), 2.13 (s, 2H), 1.86 (s, 2H), 1.48 (s, 2H).

27 $^1$H NMR (400 MHz, Methanol-d$_4$) δ 8.92-8.77 (m, 2H), 8.28 (s, 1H), 7.96 (s, 1H), 7.61-7.17 (m, 7H), 5.55 (dd, J = 42.3, 8.6 Hz, 3H), 4.43 (s, 2H), 4.27 (s, 2H), 4.14-3.97 (m, 2H), 3.82 (d, J = 12.0 Hz, 1H), 3.60-3.43 (m, 3H), 3.24-3.07 (m, 2H), 2.00 (s, 2H), 1.55 (s, 2H).

28 $^1$H NMR (400 MHz, Methanol-d$_4$) δ 8.92-8.77 (m, 2H), 8.28 (s, 1H), 7.96 (s, 1H), 7.61-7.17 (m, 7H), 5.55 (dd, J = 42.3, 8.6 Hz, 3H), 4.43 (s, 2H), 4.27 (s, 2H), 4.14-3.97 (m, 2H), 3.82 (d, J = 12.0 Hz, 1H), 3.60-3.43 (m, 3H), 3.24-3.07 (m, 2H), 2.00 (s, 2H), 1.55 (s, 2H).

29 $^1$H NMR(400 MHz, Methanol-d$_4$) δ 8.91-8.74 (m, 2H), 8.28 (s, 1H), 7.96 (s, 1H), 7.61-7.17 (m, 7H), 5.55 (dd, J = 42.3, 8.6 Hz, 3H), 4.43 (s, 2H), 4.27 (s, 2H), 4.14-3.96 (m, 2H), 3.82 (d, J = 12.1 Hz, 1H), 3.60-3.43 (m, 3H), 3.19-3.07 (m, 2H), 1.98 (s, 2H), 1.55 (s, 2H).

30 1H NMR (400 MHz, DMSO-d6) δ 9.59 (s, 2H), 8.90 (s, 1H), 8.67 (s, 1H), 7.97 (d, J = 7.6 Hz, 1H), 7.85 (dd, J = 7.7, 1.8 Hz, 1H), 7.69 (dd, J = 7.7, 1.8 Hz, 1H), 7.64-7.55 (m, 3H), 7.50 (ddd, J = 11.7, 7.5, 1.8 Hz, 2H), 7.41 (d, J = 7.6 Hz, 1H), 4.63 (s, 2H), 4.46 (t, J = 5.7 Hz, 2H), 4.24 (s, 2H), 3.90 (d, J = 6.1 Hz, 2H), 3.78 (t, J = 5.8 Hz, 2H), 3.13 (d, J = 29.0 Hz, 3H), 2.27-2.14 (m, 3H), 1.80 (tdd, J = 9.7, 6.3, 3.9 Hz, 1H).

31 1H NMR (400 MHz, DMSO-d6) δ 9.33 (s, 2H), 8.83 (s, 2H), 8.17 (dd, J = 7.8, 1.8 Hz, 1H), 7.96 (d, J = 7.7 Hz, 1H), 7.71 (dd, J = 7.7, 1.7 Hz, 1H), 7.66-7.55 (m, 3H), 7.51 (dd, J = 7.6, 1.8 Hz, 1H), 7.39 (d, J = 7.5 Hz, 1H), 5.30 (s, 1H), 4.53 (s, 2H), 3.98 (s, 3H), 3.71 (t, J = 5.3 Hz, 2H), 3.56 (t, J = 6.2 Hz, 3H), 3.11 (dd, J = 14.0, 7.5 Hz, 4H).

32 1H NMR (400 MHz, DMSO-d6) δ 9.15 (s, 2H), 8.25 (s, 1H), 7.91 (d, J = 7.6 Hz, 1H), 7.69 (dd, J = 7.7, 1.8 Hz, 1H), 7.64 (dd, J = 7.8, 1.7 Hz, 1H), 7.59 (d, J = 7.6 Hz, 1H), 7.57-7.51 (m, 1H), 7.49 (dd, J = 7.6, 1.8 Hz, 1H), 7.45-7.38 (m, 2H), 7.27 (s, 1H), 4.43 (s, 2H), 4.33 (s, 2H), 4.25 (s, 3H), 3.99 (s, 3H), 3.10 (t, J = 6.1 Hz, 2H), 2.33 (t, J = 7.7 Hz, 2H), 2.25-2.17 (m, 2H).

33 1H NMR (400 MHz, DMSO-d6) δ 9.14 (s, 2H), 8.96 (s, 1H), 8.72 (s, 1H), 7.97 (d, J = 7.6 Hz, 1H), 7.69 (dd, J = 7.7, 1.8 Hz, 1H), 7.66-7.60 (m, 2H), 7.60-7.55 (m, 1H), 7.53 (d, J = 7.7 Hz, 1H), 7.49 (dd, J = 7.6, 1.8 Hz, 1H), 7.45-7.38 (m, 2H), 7.27 (s, 1H), 4.25 (s, 4H), 3.99 (s, 3H), 3.90 (q, J = 6.8 Hz, 1H), 3.49 (d, J = 5.9 Hz, 2H), 3.16 (s, 1H), 3.10 (t, J = 6.1 Hz, 3H), 2.24-2.18 (m, 2H), 1.84-1.74 (m, 1H).

34 1H NMR (400 MHz, DMSO-d6) δ 9.19 (s, 2H), 8.90 (s, 1H), 8.68 (s, 1H), 7.97 (d, J = 7.6 Hz, 1H), 7.67 (ddd, J = 11.5, 7.7, 1.7 Hz, 2H), 7.62-7.58 (m, 1H), 7.58-7.51 (m, 1H), 7.48 (dd, J = 7.5, 1.8 Hz, 1H), 7.46-7.38 (m, 2H), 7.27 (s, 1H), 4.42 (s, 2H), 4.24 (s, 2H), 4.00 (s, 3H), 3.90 (d, J = 6.2 Hz, 1H), 2.93 (t, J = 6.1 Hz, 2H), 2.29-2.14 (m, 3H), 1.87-1.75 (m, 1H).

35 1H NMR (400 MHz, DMSO-d6) δ 9.32 (s, 2H), 8.94 (s, 1H), 8.71 (s, 1H), 8.17 (d, J = 7.8 Hz, 1H), 7.98 (d, J = 7.6 Hz, 1H), 7.71 (d, J = 7.6 Hz, 1H), 7.63-7.56 (m, 3H), 7.52 (d, J = 7.6 Hz, 1H), 7.42 (d, J = 7.6 Hz, 1H), 4.53 (s, 2H), 4.24 (s, 2H), 3.91 (q, J = 6.8 Hz, 1H), 3.56 (s, 2H), 3.11 (d, J = 6.6 Hz, 2H), 2.20 (td, J = 13.2, 12.6, 8.4 Hz, 3H), 1.81 (q, J = 7.6 Hz, 1H).

36 1H NMR (400 MHz, DMSO-d6) δ 9.33 (s, 2H), 8.91 (s, 1H), 8.68 (s, 1H), 8.18-8.11 (m, 1H), 7.97 (d, J = 7.7 Hz, 1H), 7.71 (d, J = 7.6 Hz, 1H), 7.65-7.56 (m, 3H), 7.52 (d, J = 7.6 Hz, 1H), 7.42 (d, J = 7.6 Hz, 1H), 4.44 (s, 2H), 4.24 (s, 2H), 4.00 (s, 3H), 3.90 (d, J = 6.4 Hz. 1H), 3.18 (d, J = 6.8 Hz, 3H), 3.10 (s, 1H), 2.20 (td, J = 12.3, 8.3 Hz. 3H), 1.81 (d, J = 6.7 Hz, 1H).

Biological Example 1

PD-1/PD-L1 & CTLA/CD80 Biochemical Protein-Protein Interaction Assay

Compounds were tested in biochemical protein-protein interaction assays to determine if they can specifically block the interaction between the extracellular domains of PD-1/PD-L1 or CTLA/CD80. Binding of the protein pairs is measured using a bead based Amplified Luminescent Proximity Homogeneous Assay (ALPHA) platform. Binding of each protein pair results in proximity of the donor and acceptor beads which leads to an increase in ALPHA signal. Disruption of the protein-protein interaction with a test compound results in a decrease in ALPHA signal. Assays are performed in 25 mM Hepes (pH 7.4), 150 mM NaCl, 3.4 mM EDTA, 0.005% Tween 20, and 0.01% BSA. Final protein concentration in the assays were 0.3 nM (His tagged PD-L1), 2.5 nM (biotinylated Fc-PD-1), 1 nM (His tagged CTLA4) and 1 nM (biotinylated CD80). After an assay reaction time of 60 minutes at 25° C., binding was measured with addition of 20 μg/mL ALPHA assay acceptor beads (anti-His coated) and 20 g/mL ALPHA assay donor beads (streptavidin coated). $IC_{50}$ values were calculated from the fit of the dose-response curves to a four-parameter equation. Representative data are shown below in Table 3.

TABLE 3

| No | IC$_{50}$ PD-L1-PD1 (nM) |
|---|---|
| 1 | 0.064 |
| 2 | 0.064 |
| 3 | 0.064 |
| 4 | 0.064 |
| 5 | 0.136 |
| 6 | 0.427 |
| 7 | 0.955 |
| 8 | 0.293 |
| 9 | 0.126 |
| 10 | 0.187 |
| 11 | 0.686 |
| 12 | 0.17 |
| 13 | 0.147 |
| 14 | 0.064 |
| 15 | 0.064 |
| 16 | 0.09 |
| 17 | 0.174 |
| 18 | 0.158 |
| 19 | 0.064 |
| 20 | 0.064 |
| 21 | 0.23 |
| 22 | 0.151 |
| 23 | 0.318 |
| 24 | 0.086 |
| 25 | 0.064 |
| 26 | 0.064 |
| 27 | 0.312 |
| 28 | 0.367 |
| 29 | 0.368 |
| 30 | 0.247 |
| 31 | 0.431 |
| 32 | 1.135 |
| 33 | 1.042 |
| 34 | 1.129 |
| 35 | 0.814 |
| 36 | 0.588 |

The above data shows that compounds of the present disclosure are generally effective at blocking the PD-1/PD-L1 interaction.

PD-1/PD-L1 NFAT Reporter Assay

Compounds were tested in a functional co-culture reporter assay in which TCR-mediated NFAT activity is inhibited by the engagement of PD-1 with PD-L1. Blocking the PD-1/PD-L1 interaction impairs PD-1 mediated blunting of TCR signaling and significantly increases NFAT-mediated transcription of luciferase. CHO cells expressing surface-bound anti-CD3 antibodies and PD-L1 (artificial antigen presenting cells, aAPC-PD-L1) were first seeded overnight. Jurkat cells overexpressing PD-1 and expressing a luciferase construct under NFAT control are diluted in RPMI assay medium (RPMI 1640 with 2% FBS), mixed with compounds, and immediately seeded on the monolayer of aAPC-PD-L1. The co-culture is then incubated for 6 hrs at 37° C. Luciferase activity is assessed by adding the ONE-Glo reagent and measuring luminescence with a plate reader. EC$_{50}$ values are calculated from the fit of the dose-response curves to a four-parameter equation (Table 4).

PD-L1/PD-L1 Dimerization Biochemical Protein-Protein Interaction Assay

Compounds were tested in biochemical protein-protein interaction assays to determine if they can specifically dimerize the extracellular domains of PD-L1. Dimerization of the proteins (His-tagged PD-L1 and FLAG-tagged PD-L1) is measured using a bead based Amplified Luminescent Proximity Homogeneous Assay (ALPHA) platform. Compound induced dimerization of PD-L1 results in proximity of the donor and acceptor beads which leads to an increase in ALPHA signal. Assays are performed in 25 mM Hepes (pH 7.4), 150 mM NaCl, 3.4 mM EDTA, 0.005% Tween 20, and 0.01% BSA. Final protein concentration in the assays were 0.5 nM (His tagged PD-L1) and 0.5 nM (FLAG tagged PD-L1). After an assay reaction time of 2 hours at 25° C., 20 µg/mL (final assay concentration) ALPHA assay acceptor beads (anti-His coated) were added and incubated for 60 minutes at 25° C. Binding was measured following a final 60 minute incubation with 40 µg/mL (final assay concentration) ALPHA assay donor beads (anti-FLAG coated). AC$_{50}$ values were calculated from the fit of the dose-response curves to a four-parameter equation (Table 4).

TABLE 4

| No | AC$_{50}$ PDL1 Dimer 1 nM | EC$_{50}$ NFAT Luciferase |
|---|---|---|
| 1 | 135.32 | 1264 |
| 2 | 23.023 | 3254 |
| 3 | 76.92 | 123 |
| 4 | 86.471 | 90 |
| 5 | 57.031 | 134 |
| 6 | 300.5 | 170 |
| 7 | 75.008 | 142 |
| 8 | 42.871 | 90 |
| 9 | 63.839 | 173 |
| 10 | 249.19 | 103 |
| 11 | 599.1 | 178 |
| 12 | 55.259 | 165 |
| 13 | 26.868 | 90 |
| 14 | 10.675 | 69 |
| 15 | 7.471 | 59 |
| 16 | 30.877 | 102 |
| 17 | 31.605 | 128 |
| 18 | 54.88 | 73 |
| 19 | 11.409 | 70 |
| 20 | 20.816 | 95 |
| 21 | 28.289 | 166 |
| 22 | 37.696 | 87 |
| 23 | 271.73 | 202 |
| 24 | 41.259 | 184 |
| 25 | 53.503 | 108 |
| 26 | 48.876 | 174 |
| 27 | 30.553 | 155 |
| 28 | 39.72 | 161 |
| 29 | 31.514 | 200 |
| 30 | 690.32 | 148 |
| 31 | 314.38 | 674 |
| 32 | 180.95 | 288 |
| 33 | 144.57 | 170 |
| 34 | 174.15 | 163 |
| 35 | 281.09 | 105 |
| 36 | 255.9 | 142 |

The invention claimed is:
1. A compound of Formula (I):

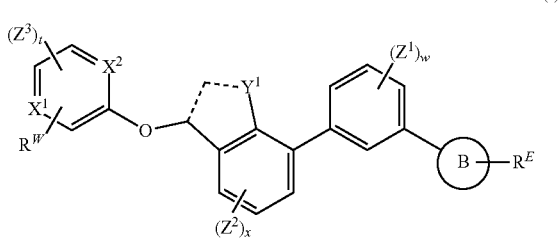

(I)

or a pharmaceutically acceptable salt thereof, wherein:
$X^1$ is N, CH, or $CZ^3$;
$X^2$ is N, CH, or $CZ^3$;
$Y^1$ is O, NH, or $CH_2$ and the dashed lines (---) are single bonds, or $Y^1$ is halo or —$C_{1-6}$ alkyl and the dashed lines (---) are absent;
ring B is

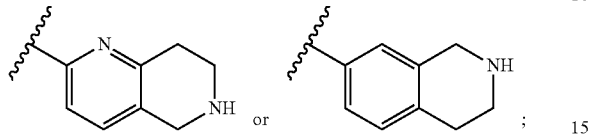

w is 0, 1, or 2;
each $Z^1$ is independently halo, —$OR^a$, —$NO_2$, cyano, —$NR^aR^b$, —$N_3$, —$S(O)_2R^a$, —$C_{1-6}$ alkyl, —$C_{1-6}$ haloalkyl, —$C_{2-6}$ alkenyl, —$C_{2-6}$ alkynyl, —O—$C_{1-6}$ alkyl, —O—$C_{1-6}$ haloalkyl, —$C_{3-8}$ cycloalkyl, or —$C_{1-6}$ alkyl$C_{3-8}$ cycloalkyl; and
wherein each alkyl, alkenyl, alkynyl, and cycloalkyl is optionally substituted with 1 to 4 groups independently selected from oxo, —$NO_2$, —$N_3$, —$OR^a$, halo, and cyano;
x is 0, 1, or 2;
each $Z^2$ is independently halo, —$OR^a$, —$NO_2$, cyano, —$NR^aR^b$, —$N_3$, —$S(O)_2R^a$, —$C_{1-6}$ alkyl, —$C_{1-6}$ haloalkyl, —$C_{2-6}$ alkenyl, —$C_{2-6}$ alkynyl, —O—$C_{1-6}$ alkyl, —O—$C_{1-6}$ haloalkyl, —$C_{3-8}$ cycloalkyl, or —$C_{1-6}$ alkyl$C_{3-8}$ cycloalkyl; and
wherein each alkyl, alkenyl, alkynyl, and cycloalkyl is optionally substituted with 1 to 4 groups independently selected from oxo, —$NO_2$, —$N_3$, —$OR^a$, halo, and cyano;
t is 0, 1, or 2;
each $Z^3$ is independently halo, —$OR^a$, —$N_3$, —$NO_2$, cyano, —$NR^1R^2$, —$S(O)_2R^a$, —$S(O)_2NR^aR^b$, —$NR^aS(O)_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aS(O)_2NR^aR^b$, —$C(O)NR^aS(O)_2NR^aR^b$, —$C_{1-6}$ alkyl, —$C_{2-6}$ alkenyl, —$C_{2-6}$ alkynyl, —O—$C_{1-6}$ alkyl, —$C_{1-6}$ cyanoalkyl, —$C_{1-6}$ haloalkyl, —O—$C_{1-6}$ cyanoalkyl, —O—$C_{1-6}$ haloalkyl, —$C_{3-8}$ cycloalkyl, —$C_{1-6}$ alkyl$C_{3-8}$ cycloalkyl, aryl, heteroaryl, heterocyclyl, or $R^N$; and
wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —O—$C_{1-6}$ cyanoalkyl, —$C(O)NR^aR^b$, $NR^aC(O)R^a$, —$NR^aC(O)OR^a$, —$S(O)_2R^a$, —$NR^aS(O)_2R^b$, —$S(O)_2NR^aR^b$, —$NR^aS(O)_2NR^aR^b$, —$C(O)NR^aS(O)_2NR^aR^b$, and —$C_{3-8}$ cycloalkyl;
$R^N$ is independently —$C_{1-6}$ alkyl$NR^1R^2$, —$OC_{1-6}$ alkyl$NR^1R^2$, —$C_{1-6}$ alkyl-O—$C_{1-6}$ alkyl$NR^1R^2$, —$NR^aC_{1-6}$ alkyl$NR^1R^2$, —$C_{1-6}$ alkyl$C(O)NR^1R^2$, —O—$C_{1-6}$ alkyl$C(O)NR^1R^2$, —O—$C_{1-6}$ alkyl$C(O)OR^1$, $SC_{1-6}$ alkyl$NR^1R^2$, —$C_{1-6}$ alkyl$OR^a$, or

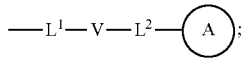

wherein:
$L^1$ is independently a bond, —O—, —$NR^a$—, —S—, —S(O)—, or —$S(O)_2$—;
V is independently selected from a bond, $C_{1-6}$ alkyl, $C_{2-6}$ alkenyl, and $C_{2-6}$ alkynyl;
wherein each alkyl, alkenyl, or alkynyl is optionally independently substituted with —$OR^a$, halo, cyano, —$NR^aR^b$, or —$C_{3-8}$ cycloalkyl;
$L^2$ is independently a bond, —O—, —$NR^a$—, —S—, —S(O)—, or —$S(O)_2$—;
ring A is independently cycloalkyl, aryl, heteroaryl, or heterocyclyl;
wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$ alkenyl, —$C_{2-6}$ alkynyl, —O—$C_{1-6}$ haloalkyl, —$NR^aR^b$, —$C(O)R^a$, —$C(O)OR^a$, —O—$C_{1-6}$ cyanoalkyl, —$C(O)NR^aR^b$, —$NR^aC(O)R^a$, —$NR^aC(O)OR^a$, —$C(O)N(R^a)OR^b$, —$S(O)_2R^a$, —$S(O)_2NR^aR^b$, —$NR^aS(O)_2R^b$, —$NR^aS(O)_2NR^aR^b$, —$C(O)NR^aS(O)_2NR^aR^b$, —$C_{3-8}$ cycloalkyl, and —$C_{1-6}$ alkyl$C_{3-8}$ cycloalkyl; and
wherein the alkyl, alkenyl, or alkynyl group is optionally independently substituted with —$OR^a$, halo, cyano, —$NR^aR^b$, or —$C_{3-8}$ cycloalkyl;
$R^E$ is hydrogen, halo, —OH, —$NR^1C(O)NR^1R^2$, —$C_{1-6}$ alkyl$OC(O)NR^1R^2$, —$C_{1-6}$ alkyl$NR^1C(O)R^2$, —CN, —$C_{1-9}$ alkyl, —$C_{2-6}$ alkenyl, —$C_{2-6}$ alkynyl, —$C_{1-8}$ haloalkyl, $C_{1-8}$ alkoxy, or $C_{3-15}$ cycloalkyl;
$R^W$ is —$NR^1R^2$, —$C_{1-6}$ alkyl$NR^1R^2$, —O—$C_{1-6}$ alkyl$NR^1R^2$, —$C_{1-6}$alkyl-O—$C_{1-6}$ alkyl$NR^1R^2$, —$NR^a$—$C_{1-6}$alkyl$NR^1R^2$, —$C_{1-6}$ alkyl$N^+R^1R^2R^3$, —S—$C_{1-6}$ alkyl$NR^1R^2$, —$C(O)NR^1R^2$, —$S(O)_2R^a$, —$(CH_2)_uS(O)_2NR^1R^2$, —$(CH_2)_uNR^aS(O)_2NR^aR^b$, —$S(O)_2NR^aC_{1-6}$alkyl$NR^1R^2$, —$NR^aS(O)_2C_{1-6}$alkyl$NR^1R^2$, —$(CH_2)_uC(O)NR^aS(O)_2NR^aR^b$, —$(CH_2)^+R^1R^2O^-$; —$(CH_2)_uP^+R^bR^cR^d$, —$(CH_2)_uP^+R^cR^dO^-$, —$(CH_2)_uP^+O[NR^aR^b][NR^cR^d]$, —$(CH_2)_uNR^aP(O)(OR^c)_2$, —$(CH_2)_uCH_2OP(O)(OR^c)(OR^d)$, —$(CH_2)_uOP(O)(OR^c)(OR^d)$, —$(CH_2)_uOP(O)(NR^aR^b)(OR^a)$, or

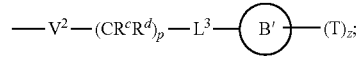

wherein:
$V^2$ is independently a bond, —O—, —$NR^a$—, —S—, —S(O)—, —$S(O)_2$—, —$C(O)NR^a$—, —$NR^aC(O)$—, —$S(O)_2NR^1$—, or —$NR^aS(O)_2$—;
$L^3$ is independently a bond, —O—, —$NR^a$—, —S—, —S(O)—, —$S(O)_2$—, —$C(O)NR^a$—, —$NR^aC(O)$—, —$S(O)_2NR^1$—, or —$NR^aS(O)_2$—;
ring B' is independently cycloalkyl, aryl, heteroaryl, or heterocyclyl;
T is independently hydrogen, —$OR^a$, —$(CH_2)_qNR^1R^2$, —$(CH_2)_qNR^aC(O)R^e$, or —$(CH_2)_qC(O)R^e$;
p is independently 0, 1, 2, 3, 4, or 5;
q is independently 0, 1, 2, 3, 4, or 5;
u is 0, 1, 2, 3, or 4;
z is 0, 1, 2, or 3; and
wherein the alkyl, cycloalkyl, aryl, heteroaryl, or heterocyclyl of $R^E$ or $R^W$ is optionally substituted with 1 to 3 substituents independently selected from the group consisting of —$NR^aR^b$, halo, cyano, oxo, —$OR^a$, —$C_{1-6}$ alkyl, —C$_{1-6}$haloalkyl, —C$_{1-6}$ cyanoalkyl, —C$_{1-6}$ alkylNR$^a$R$^b$, —C$_{1-6}$hydroxyalkyl, —C$_{3-8}$ cycloalkyl, and —C$_{1-3}$ alkylC$_{3-8}$ cycloalkyl;
   provided that at least one of V$^2$, L$^3$, ring B', and T contains a nitrogen atom;
each R$^1$ is independently selected from hydrogen, —C$_{1-8}$ alkyl, —C$_{2-6}$ alkenyl, —C$_{2-6}$ alkynyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{1-6}$ alkylC(O)OR$^a$, —C$_{2-6}$ alkenylC(O)OR$^a$, —S(O)$_2$R$^a$, —S(O)$_2$NR$^a$R$^b$, —C(O)NR$^a$S(O)$_2$R$^a$, and —C$_{1-6}$ alkylC$_{3-8}$ cycloalkyl;
   wherein each alkyl, alkenyl, cycloalkyl, aryl, heteroaryl, or heterocyclyl is optionally substituted with 1 to 4 groups independently selected from —OR$^a$, cyano, halo, C$_{1-6}$ alkyl, —C$_{1-6}$alkylOR$^a$, —C$_{1-6}$cyanoalkyl, —C$_{1-6}$haloalkyl, C$_{3-8}$cycloalkyl, —C$_{1-3}$ alkylC$_{3-8}$ cycloalkyl, —C(O)R$^a$, —C$_{1-6}$ alkylC(O)R$^a$, —C(O)OR$^a$, —C$_{1-6}$ alkylC(O)OR$^a$, —NR$^a$R$^b$, —OC(O)NR$^a$R$^b$, NR$^a$C(O)OR$^b$, —C$_{1-6}$ alkylNR$^a$R$^b$, —C(O)NR$^a$R$^b$, —C$_{1-6}$alkylC(O)NR$^a$R$^b$, —S(O)$_2$R$^a$, —C$_{1-6}$ alkylS(O)$_2$R$^a$, —S(O)$_2$NR$^a$R$^b$, —C$_{1-6}$ alkylS(O)$_2$NR$^a$R$^b$, —C(O)NR$^a$S(O)$_2$R$^b$, —C$_{1-6}$ alkylC(O)NR$^a$S(O)$_2$R$^b$, —NR$^a$C(O)R$^b$, and —C$_{1-6}$ alkylNR$^a$C(O)R$^b$;
each R$^2$ is independently selected from hydrogen, —C$_{1-6}$ alkyl, —C$_{2-6}$ alkenyl, —C$_{2-6}$ alkynyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{2-6}$ alkyl-OR$^a$, —C$_{1-6}$ alkylC(O)OR$^a$, and —C$_{2-6}$ alkenylC(O)OR$^a$;
   wherein each alkyl, alkenyl, alkynyl, cycloalkyl, aryl, heteroaryl, or heterocyclyl is optionally substituted with 1 to 4 groups independently selected from —OR$^a$, cyano, halo, —C$_{1-6}$ alkyl, —C$_{1-6}$alkylOR$^a$, —C$_{1-6}$cyanoalkyl, —C$_{1-6}$haloalkyl, —C$_{3-8}$cycloalkyl, —C$_{1-3}$ alkylC$_{3-8}$ cycloalkyl, —C(O)R$^a$, —C$_{1-6}$ alkylC(O)R$^a$, —C(O)OR$^a$, —C$_{1-6}$ alkylC(O)OR$^a$, —NR$^a$R$^b$, —C$_{1-6}$ alkylNR$^a$R$^b$, —C(O)NR$^a$R$^b$, C$_{1-6}$ alkylC(O)NR$^a$R$^b$, —S(O)$_2$R$^a$, —C$_{1-6}$alkylS(O)$_2$R$^a$, —S(O)$_2$NR$^a$R$^b$, —C$_{1-6}$alkylS(O)$_2$NR$^a$R$^b$, —C(O)NR$^a$S(O)$_2$R$^b$, and —NR$^a$C(O)R$^b$;
or R$^1$ and R$^2$ combine to form a heterocyclyl optionally substituted with 1 to 3 groups independently selected from oxo, —C$_{1-6}$ alkyl, —C$_{3-8}$ cycloalkyl, —C$_{2-6}$ alkenyl, —C$_{2-6}$ alkynyl, —OR$^a$, —C(O)OR$^a$, —C$_{1-6}$cyanoalkyl, —C$_{1-6}$alkylOR$^a$, —C$_{1-6}$haloalkyl, —C$_{1-3}$ alkylC$_{3-8}$ cycloalkyl, —C(O)R$^a$, —C$_{1-6}$ alkylC(O)R$^a$, —C$_{1-6}$ alkylC(O)OR$^a$, —NR$^a$R$^b$, —C$_{1-6}$ alkylNR$^a$R$^b$, —C(O)NR$^a$R$^b$, —C$_{1-6}$ alkylC(O)NR$^a$R$^b$, —S(O)$_2$R$^a$, —C$_{1-6}$ alkylS(O)$_2$R$^a$, —S(O)$_2$NR$^a$R$^b$, —C(O)N=S(O)R$^a$NR$^a$R$^b$, —C(O)N=S(O)R$^a$NR$^a$C(O)R$^b$, and —C$_{1-6}$ alkylS(O)$_2$NR$^a$R$^b$;
each R$^3$ is independently hydrogen, —C$_{1-6}$ alkyl, —C$_{2-6}$ alkenyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{2-6}$ alkyl-OR$^a$, —C$_{1-6}$ alkylC(O)OR$^a$, or —C$_{2-6}$ alkenylC(O)OR$^a$;
each R$^a$ is independently selected from hydrogen, —C$_{1-6}$ alkyl, —C$_{1-6}$ cyanoalkyl, —C$_{1-6}$ haloalkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl;
each R$^b$ is independently selected from hydrogen, —C$_{1-6}$ alkyl, —C$_{1-6}$ cyanoalkyl, —C$_{1-6}$ haloalkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl;
or R$^a$ and R$^b$ may combine together to form a heterocyclyl optionally substituted with 1 to 4 groups independently selected from —OR$^f$, cyano, halo, —C$_{1-6}$ alkylOR$^f$, —C$_{1-6}$ cyanoalkyl, —C$_{1-6}$ haloalkyl, —C$_{3-8}$ cycloalkyl, —C$_{1-3}$ alkylC$_{3-8}$ cycloalkyl, —C(O)R$^f$, —C$_{1-6}$ alkylC(O)R$^f$, —C(O)OR$^f$, —C$_{1-6}$ alkylC(O)OR$^f$, —NR$^f$R$^g$, —C$_{1-6}$ alkylNR$^f$R$^g$, —C(O)NR$^f$R$^g$, —C$_{1-6}$ alkylC(O)NR$^f$R$^g$, —S(O)$_2$R$^f$, —C$_{1-6}$alkylS(O)$_2$R$^f$, —S(O)$_2$NR$^f$R$^g$, —C$_{1-6}$alkylS(O)$_2$NR$^f$R$^g$, —C(O)NR$^f$S(O)$_2$R$^g$, and —NR$^f$C(O)R$^g$;
each R$^c$ is independently selected from hydrogen, —OH, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl;
each R$^d$ is independently selected from hydrogen, —C$_{1-6}$ alkyl, —C$_3$-C$_8$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl;
each R$^e$ is independently selected from hydrogen, —C$_{1-6}$ alkyl, —O—C$_{1-6}$ alkyl, —C$_{3-8}$ cycloalkyl, aryl, heteroaryl, heterocyclyl, —O—C$_{3-8}$ cycloalkyl, —O-aryl, —O-heteroaryl, —O-heterocyclyl, —C$_{1-3}$ alkylC$_{3-8}$ cycloalkyl, —C$_{1-6}$ alkylaryl, —C$_{1-6}$ alkylheteroaryl, —NR$^f$R$^g$, —C$_{1-6}$ alkylNR$^f$R$^g$, —C(O)NR$^f$R$^g$, —C$_{1-6}$ alkylC(O)NR$^f$R$^g$, —NHS(O)$_2$R$^f$, —C$_{1-6}$ alkylS(O)$_2$R$^f$, and —C$_{1-6}$ alkyl S(O)$_2$NR$^f$R$^g$;
each R$^f$ is independently selected from hydrogen, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl; and
each R$^g$ is independently selected from hydrogen, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl.

2. A compound of Formula (II):

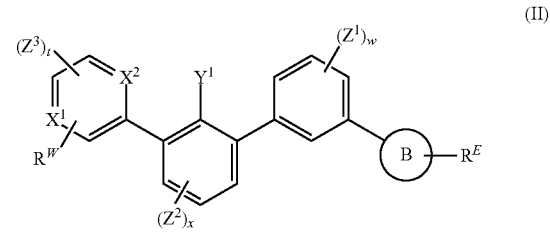

or a pharmaceutically acceptable salt thereof, wherein:
X$^1$ is N, CH, or CZ$^3$;
X$^2$ is N, CH, or CZ$^3$;
Y$^1$ is halo or —C$_{1-6}$ alkyl;
ring B is

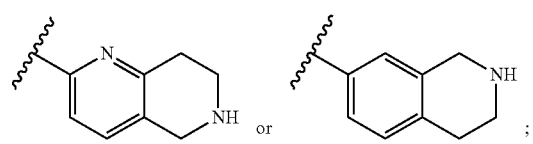 [SMILES: *c1ccc2c(n1)CCNC2 ; *c1ccc2c(c1)CNCC2]

w is 0, 1, or 2;
each Z$^1$ is independently halo, —OR$^a$, —NO$_2$, cyano, —NR$^a$R$^b$, —N$_3$, —S(O)$_2$R$^a$, —C$_{1-6}$ alkyl, —C$_{1-6}$ haloalkyl, —C$_{2-6}$ alkenyl, —C$_{2-6}$ alkynyl, —O—C$_{1-6}$ alkyl, —O—C$_{1-6}$ haloalkyl, —C$_{3-8}$ cycloalkyl, or —C$_{1-6}$ alkylC$_{3-8}$ cycloalkyl; and
   wherein each alkyl, alkenyl, alkynyl, and cycloalkyl is optionally substituted with 1 to 4 groups independently selected from oxo, —NO$_2$, —N$_3$, —OR$^a$, halo, and cyano;

x is 0, 1, or 2;
each $Z^2$ is independently halo, —$OR^a$, —$NO_2$, cyano, —$NR^aR^b$, —$N_3$, —$S(O)_2R^a$, —$C_{1-6}$ alkyl, —$C_{1-6}$ haloalkyl, —$C_{2-6}$ alkenyl, —$C_{2-6}$ alkynyl, —O—$C_{1-6}$ alkyl, —O—$C_{1-6}$ haloalkyl, —$C_{3-8}$ cycloalkyl, or —$C_{1-6}$ alkyl$C_{3-8}$ cycloalkyl; and
  wherein each alkyl, alkenyl, alkynyl, and cycloalkyl is optionally substituted with 1 to 4 groups independently selected from oxo, —$NO_2$, —$N_3$, —$OR^a$, halo, and cyano;
t is 0, 1, or 2;
each $Z^3$ is independently halo, —$OR^a$, —$N_3$, —$NO_2$, cyano, —$NR^1R^2$, —$S(O)_2R^a$, —$S(O)_2NR^aR^b$, —$NR^aS(O)_2R^a$, —$NR^aC(O)R^a$, —$C(O)R^a$, —$C(O)OR^a$, —$C(O)NR^aR^b$, —$NR^aC(O)OR^a$, —$NR^aC(O)NR^1R^2$, —$OC(O)NR^aR^b$, —$NR^aS(O)_2NR^aR^b$, —$C(O)NR^aS(O)_2NR^aR^b$, —$C_{1-6}$ alkyl, —$C_{2-6}$ alkenyl, —$C_{2-6}$ alkynyl, —O—$C_{1-6}$ alkyl, —$C_{1-6}$ cyanoalkyl, —$C_{1-6}$haloalkyl, —O—$C_{1-6}$ cyanoalkyl, —O—$C_{1-6}$haloalkyl, —$C_{3-8}$ cycloalkyl, —$C_{1-6}$ alkyl$C_{3-8}$ cycloalkyl, aryl, heteroaryl, heterocyclyl, or $R^N$; and
  wherein the alkyl, alkenyl, alkynyl, $C_{3-8}$ cycloalkyl, aryl, heteroaryl, or heterocyclyl group is optionally substituted with 1 to 4 groups independently selected from oxo, —$NO_2$, —$N_3$, —$OR^a$, halo, cyano, —$NR^aR^b$, —$C(O)R^a$, —$C(O)OR^a$, —O—$C_{1-6}$ cyanoalkyl, —$C(O)NR^aR^b$, —$NR^aC(O)R^a$, —$NR^aC(O)OR^a$, —$S(O)_2R^a$, —$NR^aS(O)_2R^b$, —$S(O)_2NR^aR^b$, —$NR^aS(O)_2NR^aR^b$, —$C(O)NR^aS(O)_2NR^aR^b$, and —$C_{3-8}$ cycloalkyl;
$R^N$ is independently —$C_{1-6}$ alkylNR$^1$R$^2$, —$OC_{1-6}$ alkylNR$^1$R$^2$, —$C_{1-6}$ alkyl-O—$C_{1-6}$ alkylNR$^1$R$^2$, —$NR^aC_{1-6}$ alkylNR$^1$R$^2$, —$C_{1-6}$ alkylC(O)NR$^1$R$^2$, —O—$C_{1-6}$ alkylC(O)NR$^1$R$^2$, O—$C_{1-6}$ alkylC(O)OR$^1$, —$SO_{1-6}$ alkylNR$^1$R$^2$, —$C_{1-6}$ alkylOR$^a$, or

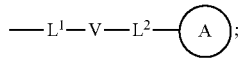

wherein:
$L^1$ is independently a bond, —O—, —$NR^a$—, —S—, —S(O)—, or —$S(O)_2$—;
V is independently selected from a bond, $C_{1-6}$ alkyl, $C_{2-6}$ alkenyl, and $C_{2-6}$ alkynyl;
  wherein each alkyl, alkenyl, or alkynyl is optionally independently substituted with —$OR^a$, halo, cyano, —$NR^aR^b$, or —$C_{3-8}$ cycloalkyl;
$L^2$ is independently a bond, —O—, —$NR^a$—, —S—, —S(O)—, or —$S(O)_2$—;
ring A is independently cycloalkyl, aryl, heteroaryl, or heterocyclyl;
  wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$ alkenyl, —$C_{2-6}$ alkynyl, —O—$C_{1-6}$ haloalkyl, —$NR^aR^b$, —$C(O)R^a$, —$C(O)OR^a$, —O—$C_{1-6}$ cyanoalkyl, —$C(O)NR^aR^b$, —$NR^aC(O)R^a$, —$NR^aC(O)OR^a$, —$C(O)N(R^a)OR^b$, —$S(O)_2R^a$, —$S(O)_2NR^aR^b$, —$NR^aS(O)_2R^b$, —$NR^aS(O)_2NR^aR^b$, —$C(O)NR^aS(O)_2NR^aR^b$, —$C_{3-8}$ cycloalkyl, and —$C_{1-6}$ alkyl$C_{3-8}$ cycloalkyl; and
    wherein the alkyl, alkenyl, or alkynyl group is optionally independently substituted with —$OR^a$, halo, cyano, —$NR^aR^b$, or —$C_{3-8}$ cycloalkyl;

$R^E$ is hydrogen, halo, —OH, —$NR^1C(O)NR^1R^2$, —$C_{1-6}$ alkylOC(O)NR$^1$R$^2$, —$C_{1-6}$ alkylNR$^1$C(O)R$^2$, —CN, —$C_{1-9}$ alkyl, —$C_{2-6}$ alkenyl, —$C_{2-6}$ alkynyl, —$C_{1-8}$ haloalkyl, $C_{1-8}$ alkoxy, or $C_{3-8}$ cycloalkyl;
$R^W$ is —$NR^3R^2$, —$C_{1-6}$ alkylNR$^1$R$^2$, —O—$C_{1-6}$ alkylNR$^1$R$^2$, —$C_{1-6}$ alkyl-O—$C_{1-6}$ alkylNR$^1$R$^2$, —$NR^a$—$C_{1-6}$alkylNR$^1$R$^2$, —$C_{1-6}$ alkylN$^+$R$^1$R$^2$R$^3$, —S—$C_{1-6}$ alkyl NR$^1$R$^2$, —$C(O)NR^1R^2$, —$S(O)_2R^a$, —$(CH_2)_uS(O)_2NR^1R^2$, —$(CH_2)_uNR^aS(O)_2NR^aR^b$, —$S(O)_2NR^aC_{1-6}$ alkylNR$^1$R$^2$, —$NR^aS(O)_2C_{1-6}$ alkylNR$^1$R$^2$, —$(CH_2)_uC(O)NR^aS(O)_2NR^aR^b$, —$(CH_2)_uN^+R^1R^2O^-$, —$(CH_2)_uP^+R^cR^cR^d$, —$(CH_2)_u$ P$^+$R$^c$R$^d$O$^-$, —$(CH_2)_uP^+O[NR^aR^b][NR^cR^d]$, —$(CH_2)_uNR^cP(O)(OR^c)_2$, —$(CH_2)_uCH_2OP(O)(OR^c)$ (OR$^d$), —$(CH_2)_uOP(O)(OR^c)(OR^d)$, —$(CH_2)_uOP(O)$ (NR$^a$R$^b$)(OR$^a$), or

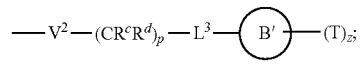

wherein:
$V^2$ is independently a bond, —O—, —$NR^a$—, —S—, —S(O)—, —$S(O)_2$—, —$C(O)NR^a$—, —$NR^aC(O)$—, —$S(O)_2NR^1$—, or —$NR^aS(O)_2$—;
$L^3$ is independently a bond, —O—, —$NR^a$—, —S—, —S(O)—, —$S(O)_2$—, —$C(O)NR^a$—, —$NR^aC(O)$—, —$S(O)_2NR^1$—, or —$NR^aS(O)_2$—;
ring B' is independently cycloalkyl, aryl, heteroaryl, or heterocyclyl;
T is independently hydrogen, —$OR^a$, —$(CH_2)_qNR^1R^2$, —$(CH_2)_qNR^aC(O)R^e$, or —$(CH_2)_qC(O)R^e$;
p is independently 0, 1, 2, 3, 4, or 5;
q is independently 0, 1, 2, 3, 4, or 5;
u is 0, 1, 2, 3, or 4;
z is 0, 1, 2, or 3; and
  wherein the alkyl, cycloalkyl, aryl, heteroaryl, or heterocyclyl of $R^E$ or $R^W$ is optionally substituted with 1 to 3 substituents independently selected from the group consisting of —$NR^aR^b$, halo, cyano, oxo, —$OR^a$, —$C_{1-6}$ alkyl, —$C_{1-6}$haloalkyl, —$C_{1-6}$ cyanoalkyl, —$C_{1-6}$ alkylNR$^a$R$^b$, —$C_{1-6}$hydroxyalkyl, —$C_{3-8}$ cycloalkyl, and —$C_{1-3}$ alkyl$C_{3-8}$ cycloalkyl;
  provided that at least one of $V^2$, $L^3$, ring B', and T contains a nitrogen atom;
each $R^1$ is independently selected from hydrogen, —$C_{1-8}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —$C_{1-6}$ alkylheterocyclyl, —$C_{1-6}$ alkylC(O)OR$^a$, —$C_{2-6}$ alkenylC(O)OR$^a$, —$S(O)_2R^a$, —$S(O)_2NR^aR^b$, —$C(O)NR^aS(O)_2R^a$, and —$C_{1-6}$ alkyl$C_{3-8}$ cycloalkyl;
  wherein each alkyl, alkenyl, cycloalkyl, aryl, heteroaryl, or heterocyclyl is optionally substituted with 1 to 4 groups independently selected from —$OR^a$, cyano, halo, —$C_{1-6}$ alkyl, —$C_{1-6}$alkylOR$^a$, —$C_{1-6}$cyanoalkyl, —$C_{1-6}$haloalkyl, $C_{3-8}$cycloalkyl, —$C_{1-3}$ alkyl$C_{3-8}$ cycloalkyl, —$C(O)R^a$, —$C_{1-6}$alkylC(O)R$^a$, —C(O) OR$^a$, —$C_{1-6}$alkylC(O)OR$^a$, —$NR^aR^b$, —OC(O) NR$^a$R$^b$, $NR^aC(O)OR^b$, —$C_{1-6}$alkylNR$^a$R$^b$, —C(O) NR$^a$R$^b$, —$C_{1-6}$alkylC(O)NR$^a$R$^b$, —$S(O)_2R^a$, —$C_{1-6}$alkylS(O)$_2$R$^a$, —$S(O)_2NR^aR^b$, —$C_{1-6}$ alkylS(O)$_2$NR$^a$R$^b$, —$C(O)NR^aS(O)_2R^b$, —$C_{1-6}$ alkylC(O)NR$^a$S(O)$_2$R$^b$, —$NR^aC(O)R^b$, and —$C_{1-6}$ alkylNR$^a$C(O)R$^b$;
each $R^2$ is independently selected from hydrogen, —$C_{1-6}$ alkyl, —$C_{2-6}$ alkenyl, —$C_{2-6}$ alkynyl, —$C_{3-6}$ cycloalkyl, aryl, heteroaryl, heterocyclyl, —$C_{1-6}$ alkylaryl, —$C_{1-6}$ alkylheteroaryl, —C$_{1-6}$ alkylheterocyclyl, —C$_{2-6}$ alkyl-OR$^a$, —C$_{1-6}$ alkylC(O)OR$^a$, and —C$_{2-6}$ alkenylC(O)OR$^a$;
  wherein each alkyl, alkenyl, alkynyl, cycloalkyl, aryl, heteroaryl, or heterocyclyl is optionally substituted with 1 to 4 groups independently selected from —OR$^a$, cyano, halo, —C$_{1-6}$alkyl, —C$_{1-6}$alkylOR$^a$, —C$_{1-6}$cyanoalkyl, —C$_{1-6}$haloalkyl, —C$_{3-8}$cycloalkyl, —C$_{1-3}$ alkylC$_{3-8}$ cycloalkyl, —C(O)R$^a$, —C$_{1-6}$ alkylC(O)R$^a$, —C(O)OR$^a$, —C$_{1-6}$ alkylC(O)OR$^a$, —NR$^a$R$^b$, —C$_{1-6}$ alkylNR$^a$R$^b$, —C(O)NR$^a$R$^b$, C$_{1-6}$ alkylC(O)NR$^a$R$^b$, —S(O)$_2$R$^a$, —C$_{1-6}$ alkylS(O)$_2$R$^a$, —S(O)$_2$NR$^a$R$^b$, —C$_{1-6}$ alkylS(O)$_2$NR$^a$R$^b$, —C(O)NR$^a$S(O)$_2$R$^b$, and —NR$^a$C(O)R$^b$;
or R$^1$ and R$^2$ combine to form a heterocyclyl optionally substituted with 1 to 3 groups independently selected from oxo, —C$_{1-6}$ alkyl, —C$_{3-8}$ cycloalkyl, —C$_{2-6}$ alkenyl, —C$_{2-6}$ alkynyl, —OR$^a$, —C(O)OR$^a$, —C$_{1-6}$cyanoalkyl, —C$_{1-6}$ alkylOR$^a$, —C$_{1-6}$haloalkyl, —C$_{1-3}$ alkylC$_{3-8}$ cycloalkyl, —C(O)R$^a$, —C$_{1-6}$ alkylC(O)R$^a$, —C$_{1-6}$ alkylC(O)OR$^a$, —NR$^a$R$^b$, —C$_{1-6}$ alkylNR$^a$R$^b$, —C(O)NR$^a$R$^b$, —C$_{1-6}$ alkylC(O)NR$^a$R$^b$, —S(O)$_2$R$^a$, —C$_{1-6}$ alkylS(O)$_2$R$^a$, —S(O)$_2$NR$^a$R$^b$, —C(O)N=S(O)R$^a$NR$^a$R$^b$, —C(O)N=S(O)R$^a$NR$^a$C(O)R$^b$, and —C$_{1-6}$ alkylS(O)$_2$NR$^a$R$^b$;
each R$^3$ is independently hydrogen, —C$_{1-6}$ alkyl, —C$_{2-6}$ alkenyl, —C$_{3-6}$ cycloalkyl, aryl, heteroaryl, heterocyclyl, —C$_{1-6}$ alkylaryl, —C$_{1-6}$ alkylheteroaryl, —C$_{1-6}$ alkylheterocyclyl, —C$_{2-6}$ alkyl-OR$^a$, —C$_{1-6}$ alkylC(O)OR$^a$, or —C$_{2-6}$ alkenylC(O)OR$^a$;
each R$^a$ is independently selected from hydrogen, —C$_{1-6}$ alkyl, —C$_{1-6}$ cyanoalkyl, —C$_{1-6}$ haloalkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl;
each R$^b$ is independently selected from hydrogen, —C$_{1-6}$ alkyl, —C$_{1-6}$ cyanoalkyl, —C$_{1-6}$ haloalkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl;
or R$^a$ and R$^b$ may combine together to form a heterocyclyl optionally substituted with 1 to 4 groups independently selected from —OR$^f$, cyano, halo, —C$_{1-6}$ alkylOR$^f$, —C$_{1-6}$ cyanoalkyl, —C$_{1-6}$ haloalkyl, —C$_{3-8}$ cycloalkyl, —C$_{1-3}$ alkylC$_{3-8}$ cycloalkyl, —C(O)R$^f$, —C$_{1-6}$ alkylC(O)R$^f$, —C(O)OR$^f$, —C$_{1-6}$ alkylC(O)OR$^f$, —NR$^f$R$^g$, —C$_{1-6}$ alkylNR$^f$R$^g$, —C(O)NR$^f$R$^g$, —C$_{1-6}$ alkylC(O)NR$^f$R$^g$, —S(O)$_2$R$^f$, —C$_{1-6}$alkylS(O)$_2$R$^f$, —S(O)$_2$NR$^f$R$^g$, —C$_{1-6}$alkylS(O)$_2$NR$^f$R$^g$, —C(O)NR$^f$S(O)$_2$R$^g$, and —NR$^f$C(O)R$^g$;
each R$^c$ is independently selected from hydrogen, —OH, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl;
each R$^d$ is independently selected from hydrogen, —C$_{1-6}$ alkyl, —C$_3$-C$_8$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl;
each R$^e$ is independently selected from hydrogen, —C$_{1-6}$ alkyl, —O—C$_{1-6}$ alkyl, —C$_{3-8}$ cycloalkyl, aryl, heteroaryl, heterocyclyl, —O—C$_{3-8}$ cycloalkyl, —O-aryl, —O-heteroaryl, —O-heterocyclyl, —C$_{1-3}$ alkylC$_{3-8}$ cycloalkyl, —C$_{1-6}$ alkylaryl, —C$_{1-6}$ alkylheteroaryl, —NR$^f$R$^g$, —C$_{1-6}$ alkylNR$^f$R$^g$, —C(O)NR$^f$R$^g$, —C$_{1-6}$ alkylC(O)NR$^f$R$^g$, —NHS(O)$_2$R$^f$, —C$_{1-6}$ alkylS(O)$_2$R$^f$, and —C$_{1-6}$ alkyl S(O)$_2$ NR$^f$R$^g$;
each R$^f$ is independently selected from hydrogen, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl; and each R$^g$ is independently selected from hydrogen, —C$_{1-6}$ alkyl, —C$_{3-8}$ cycloalkyl, aryl, heteroaryl, heterocyclyl, —C$_{1-3}$ alkylC$_{3-8}$ cycloalkyl, —C$_{1-6}$ alkylaryl, —C$_{1-6}$ alkylheteroaryl, and —C$_{1-6}$ alkylheterocyclyl.

3. The compound of claim 1, wherein Z$^1$ and Z$^2$ are each independently hydrogen, halo, —NH$_2$, —OH, cyano, —C$_{1-6}$ alkyl, —C$_{2-6}$ alkenyl, —C$_{2-6}$ alkynyl, —C$_{1-6}$ haloalkyl, or —O—C$_{1-6}$ alkyl.

4. The compound of claim 1, wherein Z$^1$ and Z$^2$ are each independently hydrogen, halo, or —C$_{1-6}$ alkyl.

5. The compound of claim 1, represented by Formula (IA):

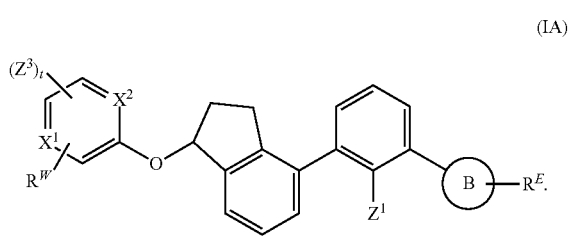

(IA)

6. The compound of claim 1, represented by Formula (IB):

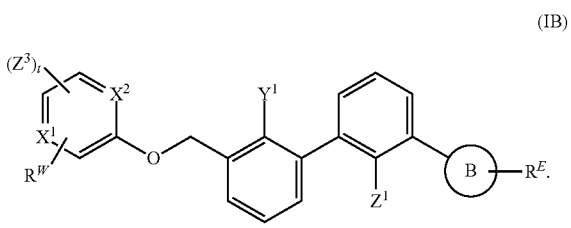

(IB)

7. The compound of claim 2, represented by Formula (IIA)

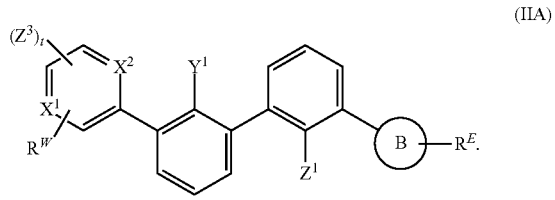

(IIA)

8. The compound of claim 1, represented by Formula (IA-c):

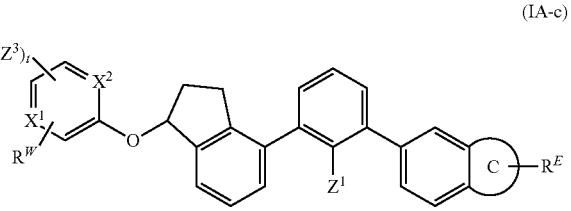

(IA-c)

wherein ring C is

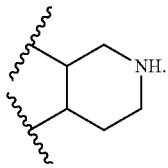 [SMILES: *C1CCNCC1*]

9. The compound of claim 1, represented by Formula (IB-c):

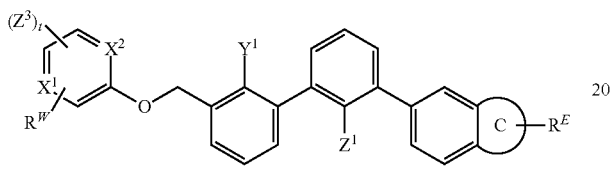
(IB-c)

wherein ring C is

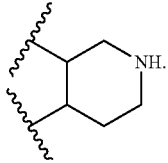 [SMILES: *C1CCNCC1*]

10. The compound of claim 2, represented by Formula (IIA-c):

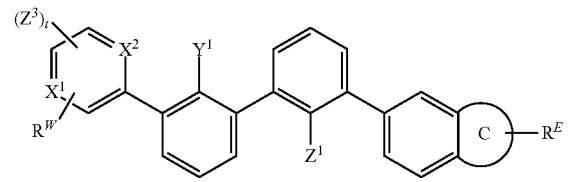
(IIA-c)

wherein ring C is

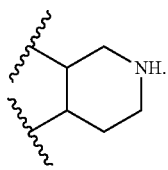 [SMILES: *C1CCNCC1*]

11. The compound of claim 1, wherein $Z^1$ is hydrogen, halo, or —$C_{1-6}$ alkyl.

12. The compound of claim 1, wherein t is 1.

13. The compound of claim 1, wherein $Z^3$ is hydrogen, halo, —OH, cyano, —$C_{1-6}$ alkyl, —$C_{2-6}$ alkenyl, —$C_{2-6}$ alkynyl, —$C_{1-6}$ haloalkyl, —O—$C_{1-6}$ alkyl or —$C_{3-8}$ cycloalkyl.

14. The compound of claim 1, wherein $R^E$ is hydrogen, —OH, —$NR^1C(O)NR^1R^2$, —$C_{1-6}$alkylOC(O)$NR^1R^2$, or —$C_{1-6}$ alkyl$NR^1C(O)R^2$.

15. The compound of claim 1, wherein $R^E$ is hydrogen.

16. The compound of claim 1, wherein each $Z^1$ is independently halo.

17. The compound of claim 1, wherein $Z^3$ is halo, —$C_{1-6}$ alkyl, —$C_{1-6}$ haloalkyl, —O—$C_{1-6}$ cyanoalkyl, —O—$C_{1-6}$ haloalkyl, or —O—$C_{1-6}$ alkyl.

18. The compound of claim 1, wherein $Z^3$ is of the formula:

V is independently selected from a bond, $C_{1-6}$ alkyl, $C_{2-6}$ alkenyl, and
$C_{2-6}$ alkynyl;
wherein each alkyl, alkenyl, or alkynyl is optionally independently substituted with —$OR^a$, halo, cyano, —$NR^aR^b$, or —$C_{3-8}$ cycloalkyl; and
ring A is independently cycloalkyl, aryl, heteroaryl, or heterocyclyl;
wherein each cycloalkyl, aryl, heteroaryl, or heterocyclyl is optionally substituted with 1 to 4 groups independently selected from oxo, —$NO_2$, —$N_3$, —$OR^a$, halo, cyano, —$C_{1-6}$ alkyl, —$C_{1-6}$ haloalkyl, —$C_{2-6}$ alkenyl, —$C_{2-6}$ alkynyl, —O—$C_{1-6}$ haloalkyl, $NR^aR^b$, —$C(O)R^a$, —$C(O)OR^a$, —O—$C_{1-6}$ alkylCN, —$C(O)NR^aR^b$, —$NR^aC(O)R^a$, —$NR^aC(O)OR^a$, —$C(O)N(R^a)OR^b$, —$S(O)_2R^a$, —$S(O)_2NR^aR^b$, —$NR^aS(O)_2R^b$, —$NR^aS(O)_2NR^aR^b$, —$C(O)NR^aS(O)_2NR^aR^b$, —$C_{3-8}$ cycloalkyl, and —$C_{1-6}$alkyl$C_{3-8}$ cycloalkyl.

19. The compound of claim 1, wherein $R^W$ is —$C_{1-6}$ alkyl$NR^1R^2$, where $R^1$ and $R^2$ combine to form a heterocyclyl optionally substituted with 1 to 3 groups independently selected from oxo, —$C_{1-6}$ alkyl, —$C_{3-8}$ cycloalkyl, —$C_{2-6}$ alkenyl, —$C_{2-6}$ alkynyl, —$OR^a$, —$C(O)OR^a$, —$C_{1-6}$cyanoalkyl, —$C_{1-6}$ alkyl$OR^a$, —$C_{1-6}$ haloalkyl, —$C_{1-3}$ alkyl$C_{3-8}$ cycloalkyl, —$C(O)R^a$, —$C_{1-6}$ alkylC(O)$R^a$, —$C_{1-6}$ alkylC(O)$OR^a$, —$NR^aR^b$, —$C_{1-6}$ alkyl$NR^aR^b$, —$C(O)NR^aR^b$, —$C_{1-6}$ alkylC(O)$NR^aR^b$, —$S(O)_2R^a$, —$C_{1-6}$ alkylS(O)$_2R^a$, —$S(O)_2NR^aR^b$, —$C(O)N=S(O)R^aNR^aR^b$, —$C(O)N=S(O)R^aNR^aC(O)R^b$, and —$C_{1-6}$ alkylS(O)$_2NR^aR^b$; or —$C_{1-6}$ alkyl$NR^1R^2$, where $R^1$ is hydrogen and $R^2$ is —$C_{1-6}$ alkylheteroaryl or —$C_{1-6}$ alkylheterocyclyl.

20. The compound of claim 1, wherein $R^W$ is —$C_{1-6}$ alkyl$NR^1R^2$.

21. The compound of claim 1, wherein $R^E$ is hydrogen and $R^W$ is —$C_{1-6}$ alkyl$NR^bR^2$.

22. The compound of claim 20, wherein $R^1$ and $R^2$ combine to form a heterocyclyl optionally substituted with 1 to 3 groups independently selected from oxo, —$C_{1-6}$ alkyl, —$C_{3-8}$ cycloalkyl, —$C_{2-6}$ alkenyl, —$C_{2-6}$ alkynyl, —$OR^a$, —$C(O)OR^a$, —$C_{1-6}$ cyanoalkyl, —$C_{1-6}$alkyl$OR^a$, —$C_{1-6}$ haloalkyl, —$C_{1-3}$ alkyl$C_{3-8}$cycloalkyl, —$C(O)R^a$, —$C_{1-6}$ alkylC(O)$R^a$, —$C_{1-6}$alkylC(O)$OR^a$, —$NR^aR^b$, —$C_{1-6}$ alkyl$NR^aR^b$, —$C(O)NR^aR^b$, —$C_{1-6}$alkylC(O)$NR^aR^b$, —$S(O)_2R^a$, —$C_{1-6}$ alkylS(O)$_2R^a$, —$S(O)_2NR^aR^b$, —$C(O)N=S(O)R^aNR^aR^b$, —$C(O)N=S(O)R^aNR^aC(O)R^b$, and —$C_{1-6}$ alkylS(O)$_2NR^aR^b$.

23. The compound of claim 1, wherein $R^1$ is hydrogen and $R^2$ is —$C_{1-6}$ alkylheteroaryl.

24. The compound of claim 1, wherein R¹ is hydrogen and R² is —C$_{1-6}$ alkylheterocyclyl.
25. A compound, or a pharmaceutically acceptable salt thereof, selected from:
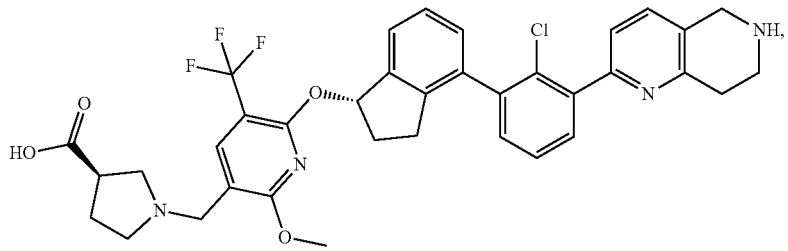
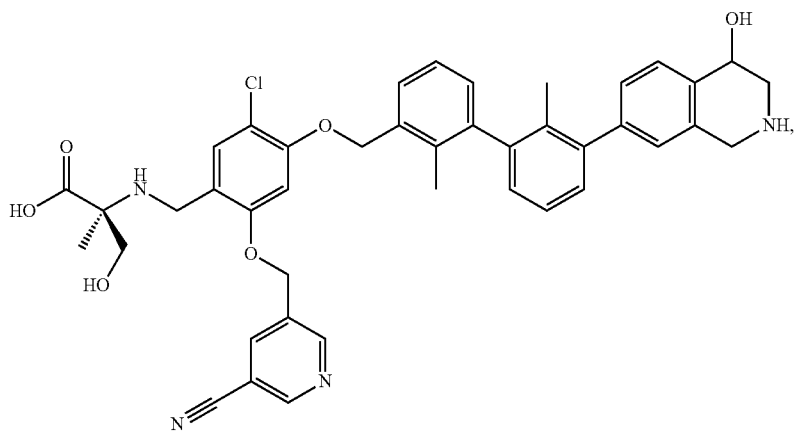
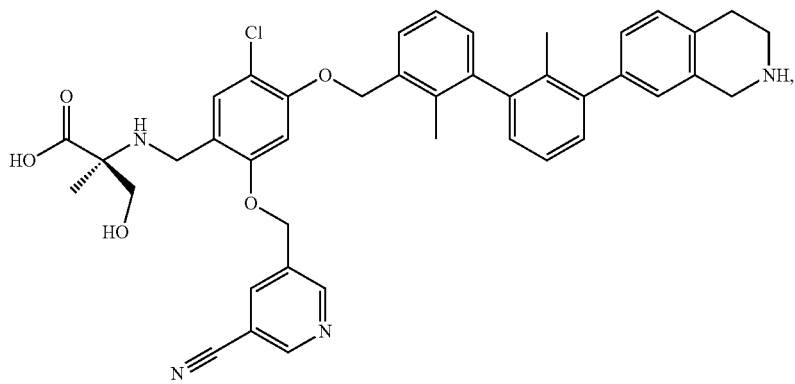
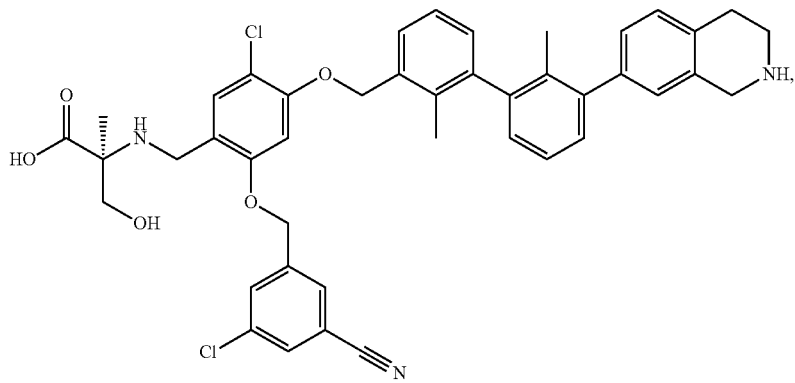

-continued
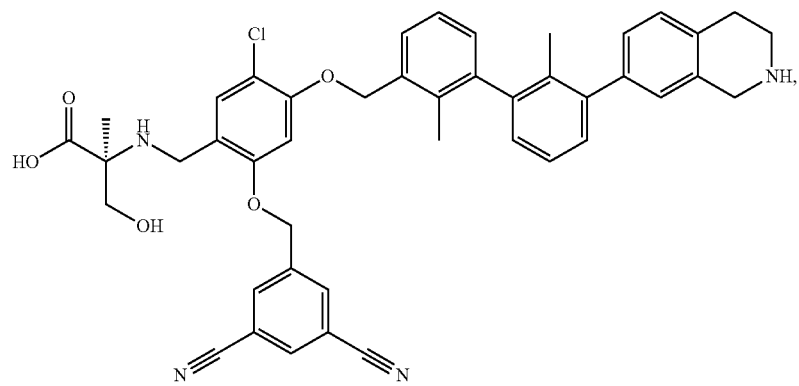
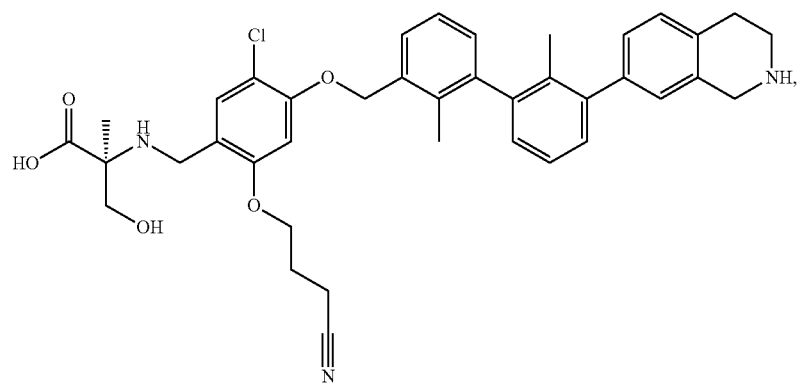
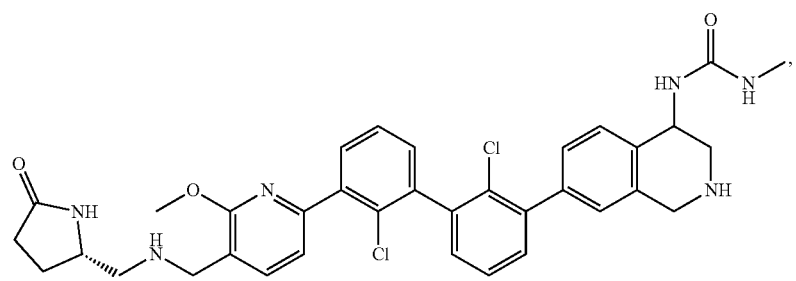
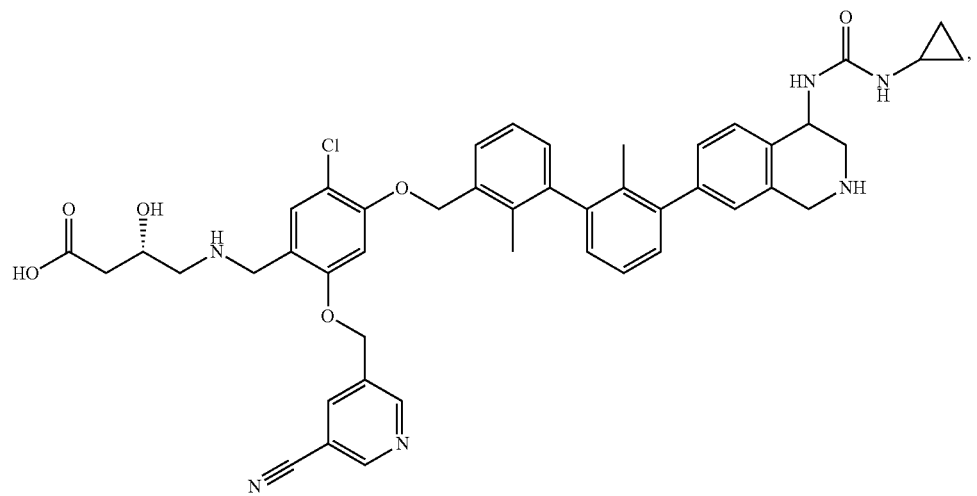

-continued
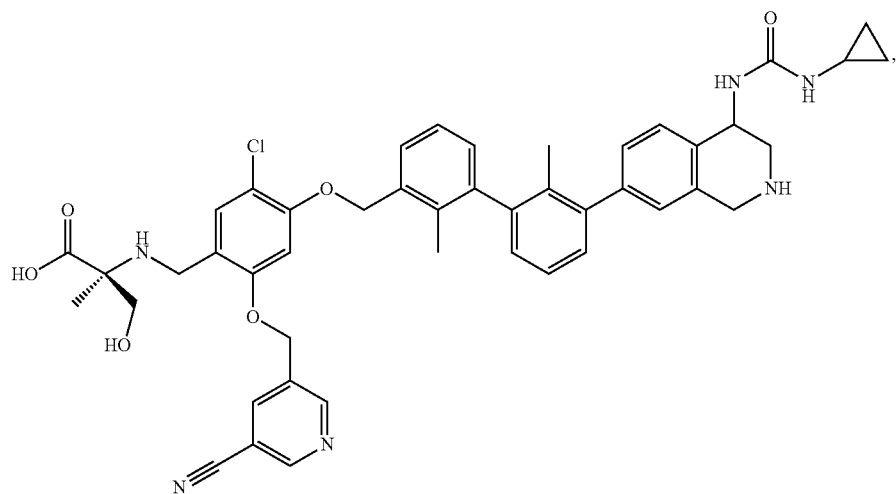
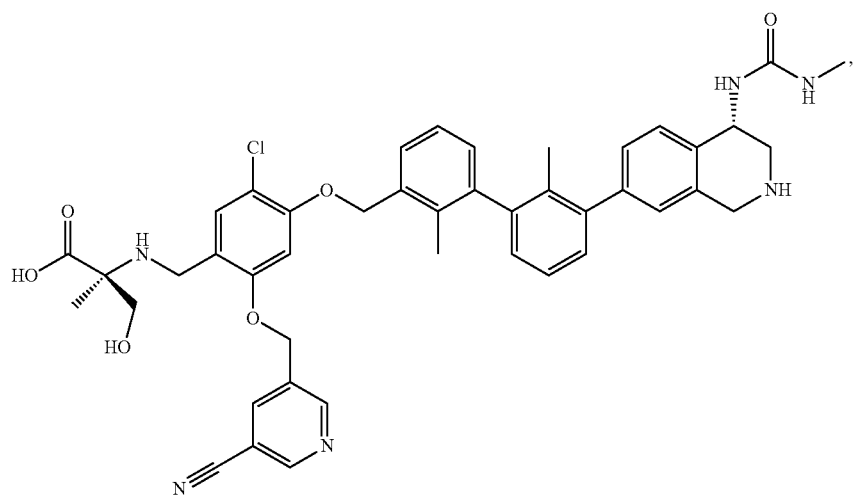
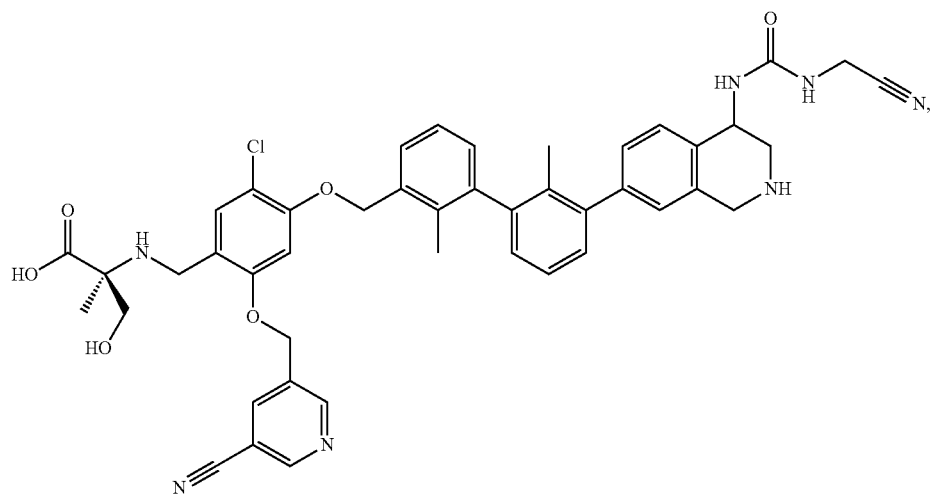

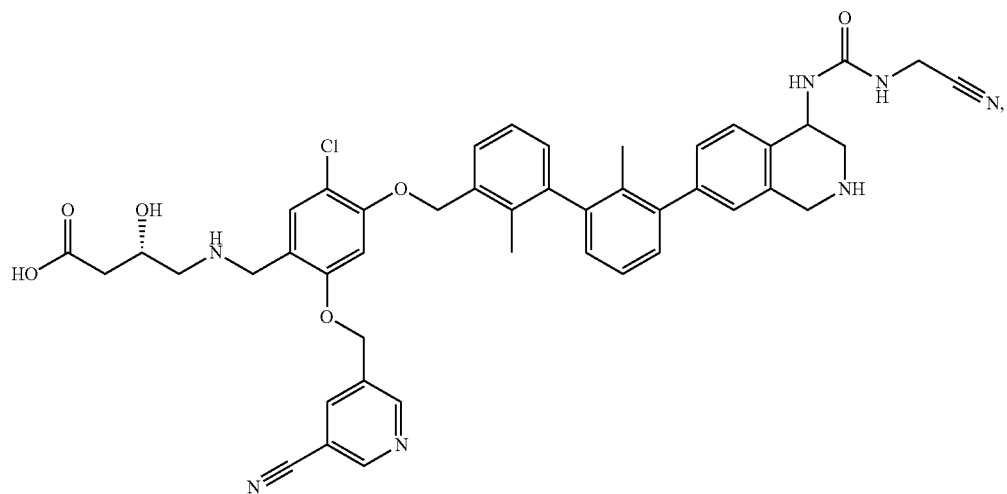
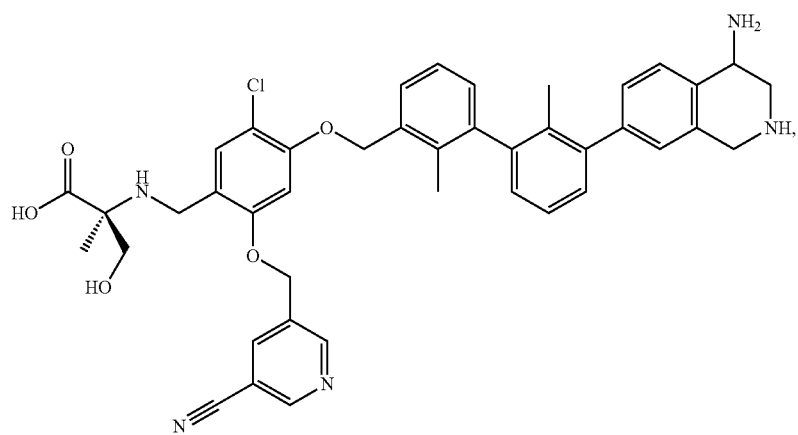
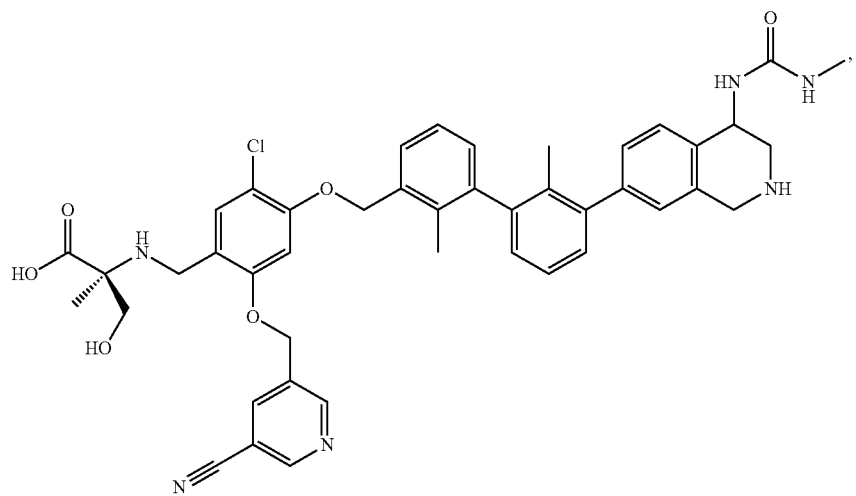

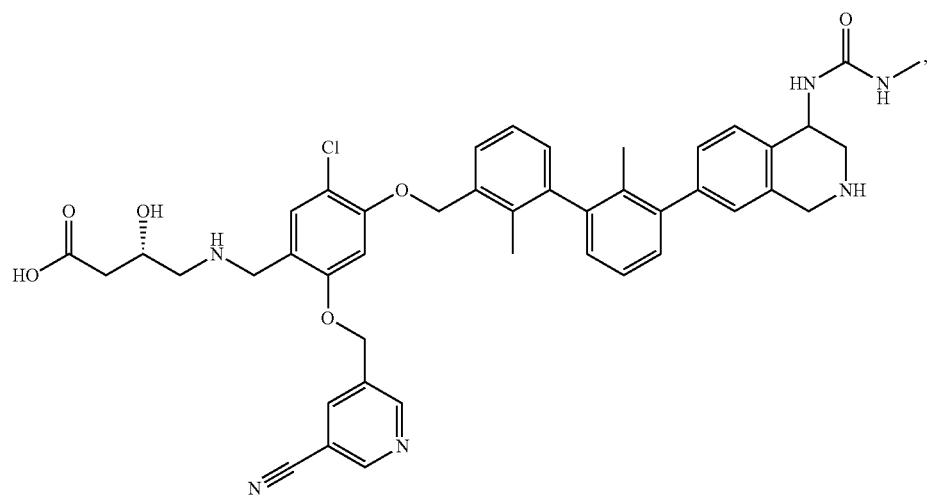
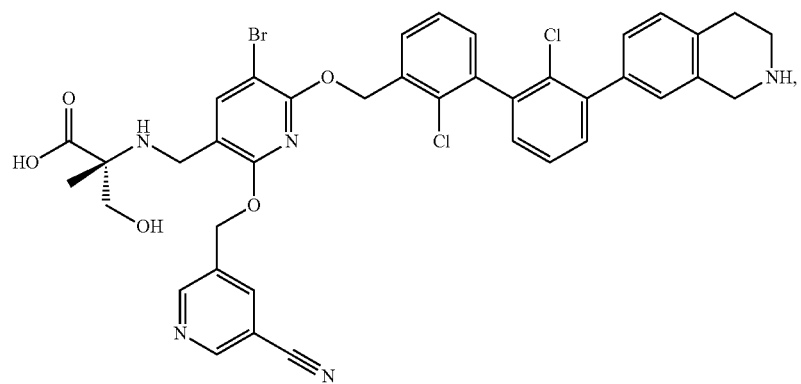
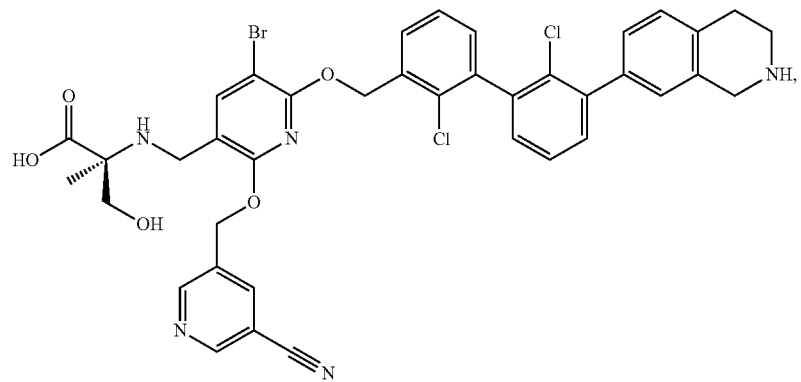

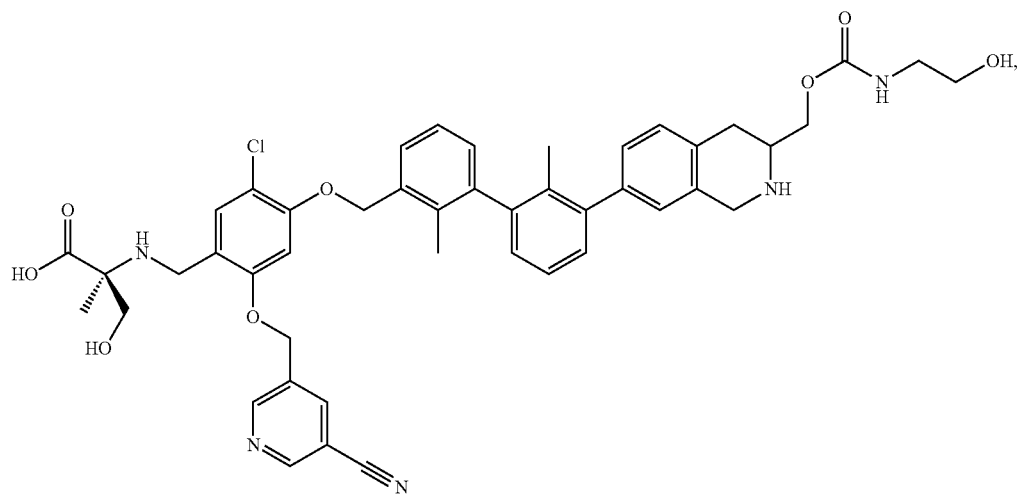
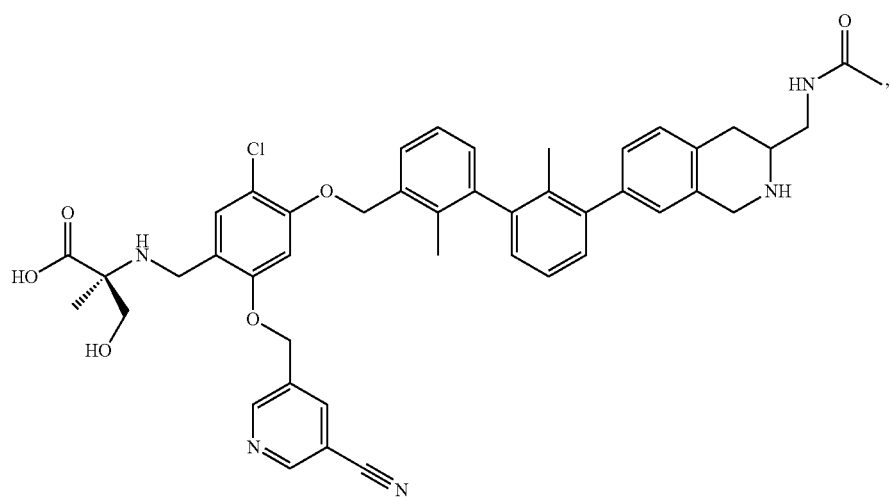
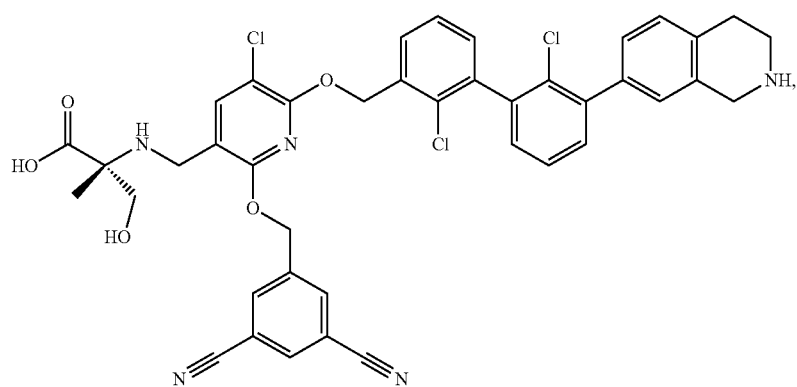

-continued

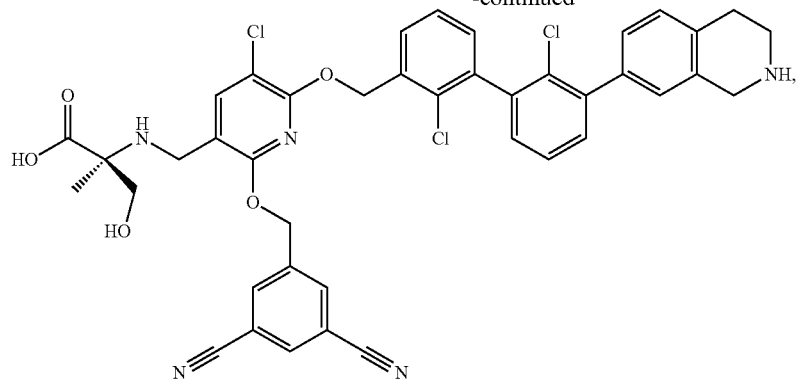

and

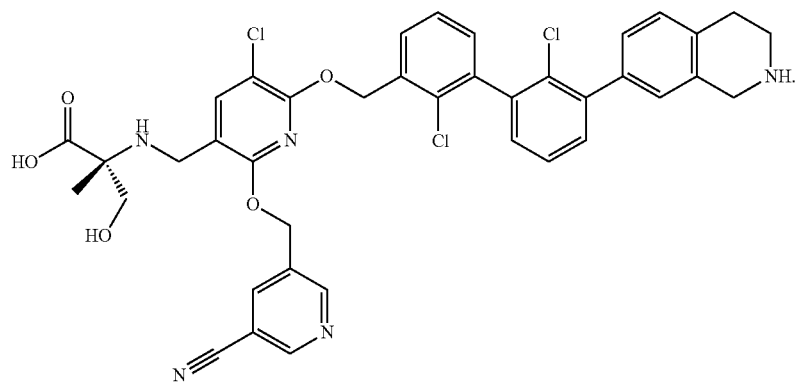 [SMILES: C[C@](CO)(NCc1cc(Cl)c(OCc2cccc(-c3cccc(-c4ccc5c(c4)CNCC5)c3Cl)c2Cl)nc1OCc1cncc(C#N)c1)C(=O)O]

26. A pharmaceutical composition comprising a compound according to claim 1, or a pharmaceutically acceptable salt thereof, and at least one pharmaceutically acceptable excipient.

27. The pharmaceutical composition according to claim 26, further comprising at least one additional anticancer agent.

28. The pharmaceutical composition according to claim 27, wherein the additional anticancer agent is rituxan, doxorubicin, gemcitabine, nivolumab, pembrolizumab, atezolizumab, or ipilimumab.

\* \* \* \* \*